United States Patent
Chiba et al.

(10) Patent No.: US 8,232,377 B2
(45) Date of Patent: Jul. 31, 2012

(54) METHOD FOR HIGH-LEVEL SECRETORY PRODUCTION OF PROTEIN

(75) Inventors: Yasunori Chiba, Ibaraki (JP); Yoshifumi Jigami, Ibaraki (JP); Kosuke Kuroda, Gunma (JP); Kazuo Kobayashi, Gunma (JP); Kimihisa Ichikawa, Tokyo (JP); Koichi Nonaka, Fukushima (JP); Takeshi Suzuki, Fukushima (JP)

(73) Assignees: National Institute of Advanced Industrial Science and Technology, Tokyo (JP); Kyowa Hakko Kirin Co., Ltd., Tokyo (JP); Daiichi Sankyo Company, Limited, Tokyo (JP)

( * ) Notice: Subject to any disclaimer, the term of this patent is extended or adjusted under 35 U.S.C. 154(b) by 449 days.

(21) Appl. No.: 12/300,926

(22) PCT Filed: May 16, 2007

(86) PCT No.: PCT/JP2007/060478
§ 371 (c)(1),
(2), (4) Date: Mar. 3, 2009

(87) PCT Pub. No.: WO2007/132949

PCT Pub. Date: Nov. 22, 2007

(65) Prior Publication Data

US 2009/0191587 A1    Jul. 30, 2009

(30) Foreign Application Priority Data

May 16, 2006    (JP) .................. 2006-136993

(51) Int. Cl.
    *C07H 21/04*    (2006.01)
    *C07K 1/00*    (2006.01)
    *C12N 15/00*    (2006.01)
(52) U.S. Cl. .............. 536/23.1; 530/350; 435/320.1
(58) Field of Classification Search .............. None
    See application file for complete search history.

(56) References Cited

U.S. PATENT DOCUMENTS

| 5,714,377 A | 2/1998 | Tanner et al. |
| 2002/0068325 A1 | 6/2002 | Ng et al. |
| 2005/0265988 A1* | 12/2005 | Choi et al. .............. 424/94.61 |

FOREIGN PATENT DOCUMENTS

| JP | 8-500975 A | 2/1996 |
| JP | 8-509867 A | 10/1996 |
| JP | 2005-515749 A | 6/2005 |
| WO | 94/26873 A1 | 11/1994 |

(Continued)

OTHER PUBLICATIONS

Guo et al., Protein tolerance to random amino acid change, 2004, Proc. Natl. Acad. Sci. USA 101: 9205-9210.*

(Continued)

*Primary Examiner* — Alexander Kim
(74) *Attorney, Agent, or Firm* — Sughrue Mion, PLLC

(57) ABSTRACT

This invention provides a means for enabling high-level secretory production of proteins, in particular proteins having complicated structures such as antibodies, in host cells such as yeast cells. The invention also provides transformed yeast cells having the activated HAC1 gene and the RRBP1 gene and a method for enabling high-level secretory production of foreign proteins using such transformed host cells by inhibiting O-sugar chain formation indigenous to host cells such as yeast cells.

32 Claims, 20 Drawing Sheets

FOREIGN PATENT DOCUMENTS

| WO | 99/01565 A1 | 1/1999 |
|---|---|---|
| WO | WO 01/72783 A2 | 10/2001 |
| WO | 2004/111194 A2 | 12/2004 |
| WO | WO/2005/106010 | * 10/2005 |

OTHER PUBLICATIONS

Lazar et al., Transforming Growth Factor α: Mutation of Aspartic Acid 47 and Leucine 48 Results in Different Biological Activity, 1988, Mol. Cell. Biol. 8:1247-1252.*

Hill et al., Functional Analysis of conserved Histidines in ADP-Glucose Pyrophosphorylase from *Escherichia coli*, 1998, Biochem. Biophys. Res. Comm. 244:573-577.*

Wacey et al., Disentangling the perturbational effects of amino acid substitutions in the DNA-binding domain of p53., Hum Genet, 1999, vol. 104, pp. 15-22.*

Becker et al., Expression of the 180-kD Ribosome Receptor Induces Membrane Proliferation and Increased Secretory Activity in Yeast., JCB, 1999, vol. 146, pp. 273-284.*

Hamiaux et al., The BPTI decamer observed in acidic pH crystal forms pre-exists as a stable species in solution., J Mol Biol., Mar. 31, 2000; vol. 297 (3), pp. 697-712.*

Definition of gene (last viewed on Apr. 26, 2011).*

Valkonen et al., Effects of Inactivation and Constitutive Expression of the Unfolded-Protein Response Pathway on Protein Production in the Yeast *Saccharomyces cerevisiae*., Appl Environ Microbiol, Apr. 2003, vol. 69, pp. 2065-2072.*

Sharma et al., Partial purification of a mannosyltransferase involved in the O-mannosylation of glycoproteins from *Saccharomyces cerevisiae*., Glycobiology, 1991, vol. 1, pp. 367-373.*

Orchard et al., Rhodanine-3-acetic acid derivatives as inhibitors of fungal protein mannosyl transferase 1 (PMT1)., Bioorganic & Medicinal Chemistry Letters, 2004, vol. 14, pp. 3975-3978.*

Cox et al., A novel mechanism for regulating activity of a transcription factor that controls the unfolded protein response., Cell. Nov. 1, 1996;87(3):391-404.*

Valkonen et al., Improvement of Foreign-Protein Production in *Aspergillus niger* var. *awamori* by Constitutive Induction of the Unfolded-Protein Response, Appl Environ Microbiol., Dec. 2003, vol. 69(12), pp. 6979-6986.*

Mari Valkonen, Functional studies of the secretory pathway of filamentous fungi. The effect of unfolded protein response on protein production, VTT Publication 505, Nov. 21, 2003, pp. 1-116.*

Frank Becker et al., "Expression of the 180-kD Ribosome Receptor Induces Membrane Proliferation and Increased Secretory Activity in Yeast", The Journal of Cell Biology, vol. 146, No. 2, Jul. 26, 1999, pp. 273-284.

Database DDBJ/EMBL/GenBank [online], Accession No. Q5AA52, http://www.ncbi.nlm.nih.gov/entrez/viewer. fcgi?74656449:CAGE_DDBJ:503330 May 10, 2005 uploaded, J. Dungan et al., Definition: Hypothetical protein HAC1, retrieved on Aug. 7, 2007.

Hiroshi Nojima et al., "Hac1: A novel yeast bZIP protein binding to the CRE motif is a multicopy suppressor for cdc10 mutant of *Schizosaccharomyces pombe*", Nucleic Acids Research, 1994, vol. 22, No. 24 5279-5288.

European Extended Search Report issued in EP 07743912.3 on Oct. 30, 2009.

Mari Valkonen et al., "Improvement of Foreign-Protein Production in *Aspergillus niger* var. *awamori* by Constitutive Induction of the Unfolded-Protein Response", Applied and Environmental Microbiology, 2003, 69(12): 6979-6986.

Maureen Hyde et al., "Induction of secretory pathway components in yeast is associated with increased stability of their mRNA", The Journal of Cell Biology, 2002, 156(6):993-1001.

Michael G. Orchard et al., "Rhodanine-3-acetic acid derivatives as inhibitors of fungal protein mannosyl transferase 1 (PMT1)", Bioorganic & Medicinal Chemistry Letters, 2004, 14: 3975-3978.

Japanese Patent Office Action issued in corresponding JP Application No. 2008-515609 on Mar. 13, 2012.

* cited by examiner

Fig. 8
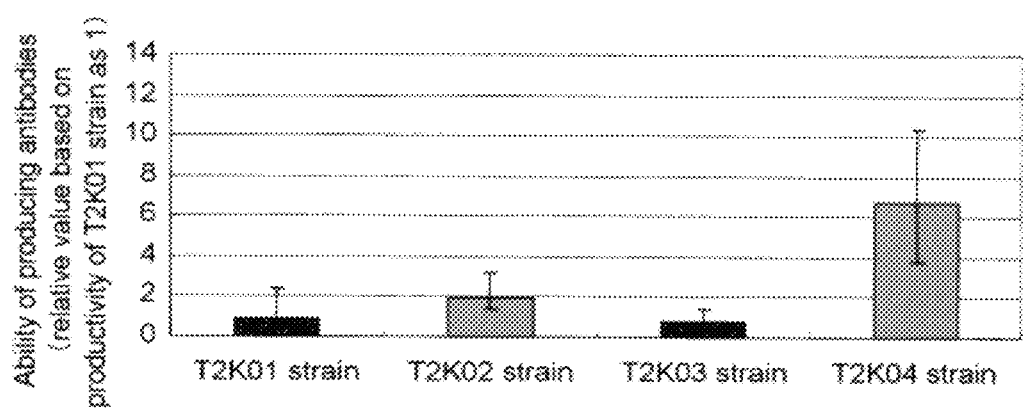
A
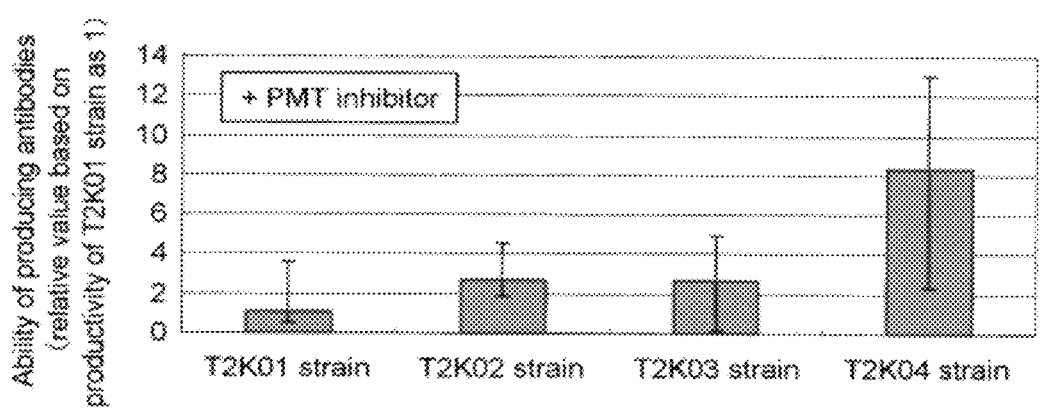
B
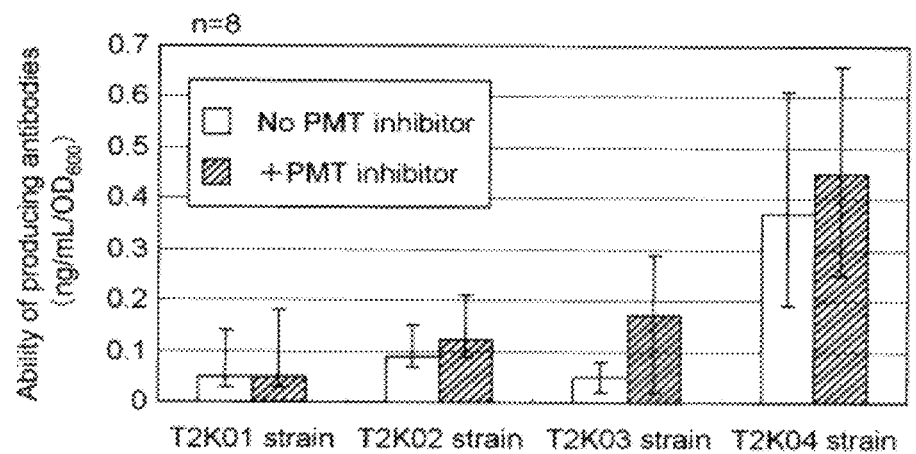
C

Fig. 16
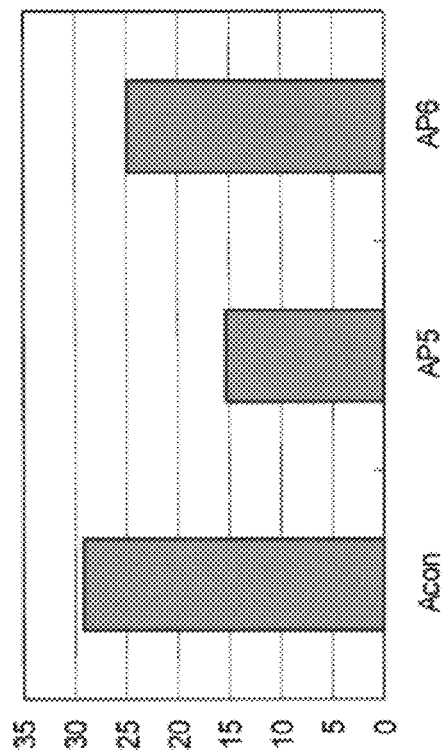
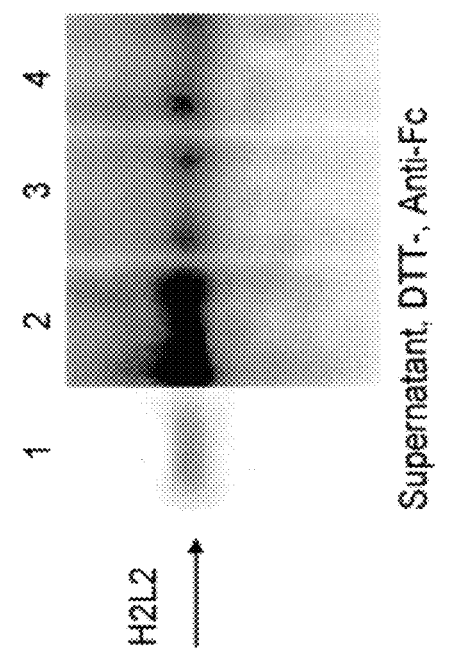

SEQUENCE LISTING

```
<160> NUMBER OF SEQ ID NOS: 124

<210> SEQ ID NO 1
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(2)
<223> OTHER INFORMATION: n is a, c, g, or t
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t
<220> FEATURE:
<221> NAME/KEY: misc_feature
<222> LOCATION: (20)..(20)
<223> OTHER INFORMATION: n is a, c, g, or t

<400> SEQUENCE: 1
gngtngaytt yaaygtnccn ttrga                                           25

<210> SEQ ID NO 2
<211> LENGTH: 26
<212> TYPE: DNA
<213> ORGANISM: Artificial Sequence
<220> FEATURE:
<223> OTHER INFORMATION: Synthetic oligonucleotide
<220> FEATURE:
```

```
<221> NAME/KEY: misc_feature
<222> LOCATION: (3)..(3)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t

<400> SEQUENCE: 2
gynacdccng gyaaytcytt dccytc                                          26

<210> SEQ ID NO 3
<211> LENGTH: 9046
<212> TYPE: DNA
<213> ORGANISM: Ogataea minuta
<220> FEATURE:
<221> NAME/KEY: CDS
<222> LOCATION: (4766)..(6016)

<400> SEQUENCE: 3
ggatcccgcc ctcgacggtt gttggtgcgg gataatgttc gttgatgagc caacttcgat      60
ttttgctgaa acgactgaga cagatccgac agacgaggtg tagttgcgga tcagattttg     120
catcactctg ctgtttcttt tgatgtgtct ttcgtcgtcc tggaaccccc aactcgatag     180
cagcgaaagg actttgtcgt ctcgctccac aagcgatagt tttggacgag ctagatatgg     240
attgacgtag cttcttgtcg aggtggcgga ctcttttttg atgtgggttt cggtaacgga     300
ttccgacttg gcatgtgatt caatcactcc ctcgtagtgg gacgacacca cgctcatgtt     360
gtcgtcgtcc tgttgtccgc tgaagtcaaa cggattgctt tttctgtcaa cggtgtcgac     420
gacagcgtca acgctcaaca gatctgagtc cacagtctcg acgctggaga cgtccgactc     480
atgaacagga tacctgaaat tcatctgggt cccaagaaac gtgtctgtgt gtgtctttct     540
gtgctgtctt ttcgtcattg cttgatattc cccctaaata gttatcacgt acggaactct     600
ggtaaaaaaa cctgatccgt ttcagatcaa ctacatttaa aatcaggttg ttcctccagc     660
cccggcggaa gctaagatg gctggttttt tcaatcagat ggtgaaatat taatttttt       720 gagccgcaac ccagccccag atccgaggct gtgcagcaga ttcggtcgat aaatgtacaa     780
cgactatgct aaatagggag tgaaaagcag caaaaaaaat gtcttagagg tagtaccttg     840
gttcttcaaa gacatggaat ttgtggtctc tgaccccatc tccatagaac atcgatggga     900
atcggaggtc tggatcaacg gtttcctcgt ctatccgctg ttgcgagtag ctttcgtcgt     960
agtctccatt ggagggtatg ataaatttac ccacctgaac ctcagtgtcg gtgatggacc    1020
cacgactgat ccgagcatac ccggttcttt tgagtttctt gtacaagatg tactcgcacc    1080
aacgatcgtc atcagtagcg tcgatatcgt gcattcctga cttgtcgctc acgtaggtgt    1140
tgtaattccc cttgaggggt tcggtcacca agtagctcaa caggatcatt ggcctttctg    1200
aactgcccat aatttcggaa acaccgagag attgtaaacg gcggtcctca acgtcctctt    1260
cttgtcccga atggaaaacg acaacgtcca cgagctctcc gtaacagtcc agagtagcgt    1320
ggatggcagg agccaattcg cccacaggag acggaagcaa gtgatgcgtg gaattgatga    1380
tcggaaactt ggacaaaagg gccgcacccc aggtatgttt cgttgggttc ggaccgaaat    1440
cggcgtacat gccgagttct tcggcaattc tttgggtgag atctctgttt cccatgatga    1500
ttctttgagt gtccgattct aataaaccca caacgtccaa ctccaggtct ttgatcaggt    1560
ctctcattct gtgctcagat gcccacatgt cgttatcgag accaaagtga atggtccaaa    1620
taccagccgt gacaagtctg gactggggat ggtagggtct tggttttcg aactggaatc    1680 tgttgaaagc gataaatccc gagagcagtg taaagaaaat gaggtaattt gtgattttt     1740
```

```
tcaacgacga cttcagtcgc tttgaatgcg aaacttcaga ctgcttgtag ttgaaaacaa    1800
gaccgcaaat catcagaact gaaacagaca ggatgatatc tgttctttct ctcaacaatg    1860
gtccaccggg aacaaaggca tatgcgacaa cccagacgtg agccaaagag agcactatgt    1920
caaacaggaa cgaaagacca aacactagag ccacgccgtc cactttggaa acctgatcaa    1980
aacaaacagg agtgatgaaa cacagccaga aagcgtatgc cagcccacca gcgtaactga    2040
tccagccgtt gaaatagtac aggaacaaag ctccgagaac tcccgcataa gtgacagact    2100
tgtaggaact ggaccggtag aatccgaaaa aggctcctag acacatgaaa atcaccgtca    2160
ccgcaccgtg gggaacaggg atcggcccgt tgataggata gccctcccat gtccacagaa    2220
caatggtaga agagtcggta agcatggcac taatcgagaa aatcagagat ccaaaaccca    2280
tggctgacag cataagagaa ggcttttgag tcttaagtgg gcctttctca gatacagtcc    2340
cctgtggtag cttttgtgaaa gctgcagctg tcaatccgac aactagaccg gtgaggttcc    2400
acccaccggt gtcgctgttc atgatgggcc aaataggatt attggtccag aacgcaaact    2460
tggcgagact ggacagaatg agccccattg taaacgaggt tgcaaacgtt ttcgtagcca    2520
gttgatcatt cagtttgcca atggcagcca cttcggtact taaggcaatg gttgcgaacg    2580
aaacagccgc gccaataacc atcaatctgc aggcagggtc taccaccaag taagccccca    2640
caccgaacaa acaggtgagc gttctagcga cttgaggacg ttttgtgaaa aacagcttca    2700
cctttggaac tgccaagaca aacggagtca atagaaggac acagactgcc tcgtatcccg    2760
agattcccat gtaccacagc gggaagtacc agatacagag gaacaatgag gagtagacag    2820
accagaaaac gaaccaattg atggtgtcga cagtgagttg ccagaaagag ctgctgaact    2880
gagtcgactt cggtaatagc ttcccgctgg aggttgggc cgaggaactt gaagtgccgt    2940
ttattctgtc ttgaatgagc ttgatgtcga aattggcact gaaaaattcg tctcttgttg    3000
ctgaaggtct gagctcgatg atcaggtctt tgaagtccaa gatggaccag gcatcaaagc    3060
caacatcaag aaagatcaac gcccattcgc agtatgcgta gtaagaataa gctcccttga    3120
cgtgatgaac cttgtgctgg ataaaaagat acaccagagg gacaagtgca ccaaaaaatg    3180
tccatgcggt gtacttcctg gctcttctga tcctggaccg tggtggggac agcttggtga    3240
tagcgaggtc ccacgggata gtcaggacaa tgtaggagat cataaacaca tcgtgcgcgt    3300
cgtgatcatc cgtagaagta atataaaccc agcctccaca cgtgatggtt ctgatgaagc    3360
ccgatatcag ggcaagttta gggtacactg aattggcctt gtgcagacga acatacgtta    3420
gtagcagtag taagaaccga ggaccagctg taagcgcgat caaaatctgg aagattgacc    3480
gttcaggata tctgtcacca atggtggccg agacactcgg gaaccactcg tctggatacc    3540
cataatactc gttctcaacg attttgtaaa aatggagcca gcacccaaca gccaaggcag    3600
ctaaaaaggc agagagcgag cacacagagt gtgcgatcgc aatggcctgt gagttcaacc    3660
gcactagagg ctgcgagttg ggcccgtctg gaactgccat gatgataaat tgcgagcaaa    3720
ttgggtgaac atcagcacta aagcgacttg ttcccatcag aatctttaaa aacaacacct    3780 gaaatgacg ttttcagaga tcaggtgtaa gggtgtttgc ttggaaaaac acgaggaaaa    3840 gagcttggc tgggaacacc cgtacaccgg atctagctcc tggctgcggg atctggattt    3900
aggaaaaaaa caaaacgcac gaatgagctt tgtcgccttt agcagagggt agaggtgata    3960
cactagacag caagagattg gaaaatggcg ggtaagtcgg ctgttgatga aatcttgatg    4020
acaactactg acatggaaca gaaatcaaag agaaacctga atttagaaag tcgccagacg    4080
tttcgttcga cgagattgat tacagagacc cgcttgctct aaaaaaggca caggagtcga    4140
```

-continued

```
tgctgagaga gcagttcatc agaattgagg ttctgaaggt ggtgagaaaa gcgctagaga    4200
attgctggag ggtgaacggg cccaacggac acgaagagtg ccgggacctg ccgacaagt    4260 acctagacat gctgccaaac tcccgggccc agggatacat gggataccaa agaaacgacc    4320
cgtccaaata ggctggctgc ggctggctgc ggctggctgc agaccgaccg caaaccaact    4380
gcaggcttgt tgtaggctga ttatttattg actatttatt gaatatttat tgcaccactt    4440
gtgtgttccc cttgaccatg cgtcgatcga cgcgcgaggc ttaggaagcc cggagcgggg    4500
aattcacgtg gtgtacgggt gtggaggtct agcacccgag ttttcggaga ggcagatgat    4560
gcatctccgg ggagtgtcag gcaaggagga atgggcagat cgacgaaga aagggatata    4620 aaatgttata tttgcacttg tttttgtgaa tatcagcacc caaacaaaat aagacaactt    4680
atcagtttct taagtattac aagtgagtaa ttgtcaacca gcacagctgt cgtagtgtaa    4740
acactaacgc cgcatagaac tagca atg tcg tta tcc agc aag ctg tca gtt     4792
                              Met Ser Leu Ser Ser Lys Leu Ser Val
                               1               5 aag gac ttg gac gtc tcg ggc aag aga gtg ttc ata aga gtg gac ttc     4840
Lys Asp Leu Asp Val Ser Gly Lys Arg Val Phe Ile Arg Val Asp Phe
 10              15                  20                  25 aat gtt cca ttg gac gga gac aag atc acc aac aac caa aga att gtc     4888
Asn Val Pro Leu Asp Gly Asp Lys Ile Thr Asn Asn Gln Arg Ile Val
             30                  35                  40 gct gct ttg cca acc att cag tac gtt ctt gag aac aag cca aag gtg     4936
Ala Ala Leu Pro Thr Ile Gln Tyr Val Leu Glu Asn Lys Pro Lys Val
         45                  50                  55 gtt gtt ttg gcc tcc cac ttg ggc aga ccc aac gga gag aag aac ctc     4984
Val Val Leu Ala Ser His Leu Gly Arg Pro Asn Gly Glu Lys Asn Leu
     60                  65                  70 aag tac aca ttg aag cct gtc gcc aag gaa ctg gag act ctt ttg ggc     5032
Lys Tyr Thr Leu Lys Pro Val Ala Lys Glu Leu Glu Thr Leu Leu Gly
 75                  80                  85 cag aaa gtg acc ttc ttg gac gac tgt gtt ggt tct gag gtc gaa tct     5080
Gln Lys Val Thr Phe Leu Asp Asp Cys Val Gly Ser Glu Val Glu Ser
 90                  95                 100                 105 acc gtc aac tct gcc cct gct ggc tcg gtg att ttg cta gaa aat ttg     5128
Thr Val Asn Ser Ala Pro Ala Gly Ser Val Ile Leu Leu Glu Asn Leu
             110                 115                 120 aga ttc cac att gag gag gaa ggc tcg aaa aag act tca gag gga aaa     5176
Arg Phe His Ile Glu Glu Glu Gly Ser Lys Lys Thr Ser Glu Gly Lys
         125                 130                 135 gtt aag gct tcc aaa gag gac gtt gaa aaa ttc aga aag caa ctc act     5224
Val Lys Ala Ser Lys Glu Asp Val Glu Lys Phe Arg Lys Gln Leu Thr
     140                 145                 150 gct ctg gct gat gtc tac gtt aac gac gct ttc ggt act gct cac aga     5272
Ala Leu Ala Asp Val Tyr Val Asn Asp Ala Phe Gly Thr Ala His Arg
 155                 160                 165 gcc cac tcc tcc atg gtc ggt ttc gag ctc gag gac aga gct gct ggc     5320
Ala His Ser Ser Met Val Gly Phe Glu Leu Glu Asp Arg Ala Ala Gly
170                 175                 180                 185 ttc ctg atg gcc aag gag ctg gag tac ttc tcc aag gct ctg gag aac     5368
Phe Leu Met Ala Lys Glu Leu Glu Tyr Phe Ser Lys Ala Leu Glu Asn
             190                 195                 200 ccg gtg aga ccg ttt ttg gct atc ctt ggt ggt gca aag gtg tct gac     5416
Pro Val Arg Pro Phe Leu Ala Ile Leu Gly Gly Ala Lys Val Ser Asp
         205                 210                 215 aaa att cag ctg att gac aat ttg ctc gac aag gtc gat ctc ttg att     5464
Lys Ile Gln Leu Ile Asp Asn Leu Leu Asp Lys Val Asp Leu Leu Ile
     220                 225                 230
```

```
gtc ggt gga gga atg gcc ttc act ttc aac aag gtg ttg aac gac atg      5512
Val Gly Gly Gly Met Ala Phe Thr Phe Asn Lys Val Leu Asn Asp Met
    235                 240                 245 aag atc ggt aag tct ttg ttc gac gag act gga gct gag att gtt cca      5560
Lys Ile Gly Lys Ser Leu Phe Asp Glu Thr Gly Ala Glu Ile Val Pro
250                 255                 260                 265 aag ctc gtg gag aag gcc aag aag aac ggc gtc aag atc gtt ttg cca      5608
Lys Leu Val Glu Lys Ala Lys Lys Asn Gly Val Lys Ile Val Leu Pro
                270                 275                 280 gtg gac ttt gtc act gcc gat gcg ttc tcg cca gat gcc aag gtt ggc      5656
Val Asp Phe Val Thr Ala Asp Ala Phe Ser Pro Asp Ala Lys Val Gly
            285                 290                 295 tac gcc acc ctt gag gag ggt att gcc gac gat ttg caa ggt ctg gac      5704
Tyr Ala Thr Leu Glu Glu Gly Ile Ala Asp Asp Leu Gln Gly Leu Asp
        300                 305                 310 ggt ggt gaa aag acc cgt aag ctg ttt gcc gac acc atc gcg cag gcc      5752
Gly Gly Glu Lys Thr Arg Lys Leu Phe Ala Asp Thr Ile Ala Gln Ala
    315                 320                 325 aag acc atc gtc tgg aac ggt cca cct ggt gtg ttt gag ttc gag agc      5800
Lys Thr Ile Val Trp Asn Gly Pro Pro Gly Val Phe Glu Phe Glu Ser
330                 335                 340                 345 ttt gcc agc ggt acc aag tcg atg ttg caa gct tgt gtc gag tct gcc      5848
Phe Ala Ser Gly Thr Lys Ser Met Leu Gln Ala Cys Val Glu Ser Ala
                350                 355                 360 cag gcc gga aac acc gtt att atc ggt ggt gga gac act gcc acc gtg      5896
Gln Ala Gly Asn Thr Val Ile Ile Gly Gly Gly Asp Thr Ala Thr Val
            365                 370                 375 gca aag aag ttt ggc ggt gcc gac aag ctg tcc cac gtt tcc act gga      5944
Ala Lys Lys Phe Gly Gly Ala Asp Lys Leu Ser His Val Ser Thr Gly
        380                 385                 390 gga ggt gct tcc ctg gaa ttg ttg gag ggt aag gag ctt cct ggt gtt      5992
Gly Gly Ala Ser Leu Glu Leu Leu Glu Gly Lys Glu Leu Pro Gly Val
    395                 400                 405 gct gct ttg aag agc aag act gct taggtgggat ttgcgtgatc tacgtagtgg     6046
Ala Ala Leu Lys Ser Lys Thr Ala
410                 415 ttattttgt agttagtttg actgtctaga aatactcttt gcacagcccc aaataaatta     6106
cactgccgtg aaattcatga gaaaaagta ccaaagataa acaggggaga agtgatcgg      6166
gtgttccctc ttgtgtgatc cagtcgtgaa cagtactgat caccacccca gatgactaaa    6226
cacaggcgca aaaacattcc actgacttac atcacacaga gcctagacaa ttccaggacc    6286
aatcagggtt cttcgtttga taaggctcta gtgaacaaac acaaacaaca cagatcaaag    6346
actcacaatt ctgtcaaatt ggccagtcta accaagtctt acttgtctgc caagccggtc    6406
caggcaacaa agagcccaac agttgacaaa atcaccaaaa ggatcaaccg aaagtcccac    6466
tcgaccaaga aaatcgaccc tgtcgcctct ttctcagggc cctgggggct tcttaccggc    6526
caacttaacg actatttaac gtcgattcgc tcaatgaact ctgttttgga ttacgaccag    6586
cccttgacca cggctcagaa gtcgtcgtcg tcgattttgg acatcaaacc gatttcagac    6646
catttgaacg tggtcaggtt cgcagagctc gatagcgtga tgctgggctc gttccaaaac    6706
cacccagtca gactcaaggc tggcgaccaa attcacattg agacgatta ctacaatgtt     6766
ccgtacaacg gaaagtatct cagatgttac tatcgatggt ttaaagtgat atgaggtata    6826
tacaggatgc cgactagacg gtgaactgtt cgcgcagttg agagtactgg ctggaacggt    6886
ccggatcaca cttttccaac agttgcgaca caaatggtcc gtgcacagtt ttttccagag    6946
tgtttgaaat actcaacaaa ggcatgtact cgtccaggaa ctccttgcac atggtggcat    7006
```

```
cgcctttcac tgccaggaat tgaagagcaa ccagcgacgg ggtcaaatct tcccgtttca    7066
atgcaccgtc aaggactttc ttcatgtaca cccagttgtt gcggttggca aaaatggtga    7126
ggaaaacaac atccaatctg aacgaaatt gggcagcagc caggtcgtgt tcgaacattc     7186
gggtggacag ttggtacagc ttgtgaacca ttggagagta cttgaagctg taattagggt    7246
ctgcagttag cgaaccgatc gtaaggaagt tttcgttatc gatctgcgag cccgagatga    7306
ctaatagagg tattagtttt tgaacgtcct ccgttgacaa aacagggtta taagtgttga    7366
gaatccggaa gatacgtgcg tatctcttgt tgaacacctc cgcctctgtc tctactgatt    7426
tgtgaaattc agacgactgt agcacgagat caatatatct gaacacctcg tcaacagtaa    7486
cgggtttccc gttggcttgc atggctttga aatggttctc gatcttgttc agagggtaag    7546
tggctgggtc cttcaaatgc agtgttttta aagcctcaaa tcgctggttg tagttctccg    7606
aggttaagag ttccggtcta aaagcgctcg agctcgcttg ggtggtgtag agatgtagcc    7666
ggttcagctg caaaatagtt tgaagattcg agatcctcgg ccgggcagtg tgatagtatc    7726
tgatcccggc aaagatatcg tcgttgtagc cacggtcact tctggctgga actttgtct     7786 tctctttcga ccacaggttc tccaagcaca tgacttctct tctctccgcg gtcagaaagt    7846
ggacgtaaat gttatcgatt ttgcagtcca tcatcatcca ggtatttgct gaggccccgt    7906
aatcattgct ggcgtacgaa ggggctctct tacccttttt caacagtctt ctgtgatact    7966
tggctagctg gccactgctc agaagaccgtt ctgccagagg gatggttttc agagtgtgtt    8026
tgatgaaaag attgagctcc gccgtagctt tctggagatg cttcgaactc tttcctgttc    8086
caatgatcat gaagtcggcg atctcttggg ctccttcgtt gacctctgcc ccggtgctat    8146
cgcgcaagtc gaacagggcc agatcggtca ttcccagctt ctccgcgata aactcgagaa    8206
ctggctgcaa gctggccgga gagttgggcg gaagatccgg aatctgaatc tgtctaggct    8266
gcgaggccaa atccgcagac tcttcagctc tcatgtacca cgggagagct gccgttttga    8326
cttcttggtg gctgactgga actgacgaga agtcggcgac cagttgctgg gaactggcag    8386
cgttgtgagg gaagaagccg ctccgaaggg cgcggggcac aggacgcgac accgacaca    8446 accgacaccg tctccacatt atggctgtat ttggaaaaga ttgagtagtc gatagtttct    8506
gcaaaagctt tagcaaacaa caaacacgcg acgtttgaag acagtttttt ggcagcttcg    8566
atctgtcgat agttcagtgg tgatctcagt ggtcgtttcg tctaccttga atctctcacc    8626
ccagatgttg tctctgtgtg aagttttttgt gaattttttca tctttctttt tactcgattt    8686
tttcctcttc cacgtcgata gtcgcgagac gccttgcgac gcgccgtttt aatttcccaa    8746
aatttgcaca aacaaaagat aaaaacagga ctgtcgattt gggttttgtg ggaacagaaa    8806
agaggaaccg tttgaacaat aaagcaacgg tcctccaaaa tcatcctcta ccactcattc    8866
tcaacacgtg accatcggga acaagttctg gagctctctt caaaccgcga ctcaacatag    8926
tgttttgtgc caggcccgta tttactata aggtgccct caagaaccat tagttcgtgc     8986
tacttgcctc cgatttgtgc ttcctaacgg tgtttcaaca atcatgacag gccgggatcc    9046
```

<210> SEQ ID NO 4
<211> LENGTH: 417
<212> TYPE: PRT
<213> ORGANISM: Ogataea minuta

<400> SEQUENCE: 4

Met Ser Leu Ser Ser Lys Leu Ser Val Lys Asp Leu Asp Val Ser Gly
 1               5                  10                  15

Lys Arg Val Phe Ile Arg Val Asp Phe Asn Val Pro Leu Asp Gly Asp
                20                  25                  30

Lys Ile Thr Asn Asn Gln Arg Ile Val Ala Ala Leu Pro Thr Ile Gln
            35                  40                  45

Tyr Val Leu Glu Asn Lys Pro Lys Val Val Leu Ala Ser His Leu
        50                  55                  60

Gly Arg Pro Asn Gly Glu Lys Asn Leu Lys Tyr Thr Leu Lys Pro Val
65                  70                  75                  80

Ala Lys Glu Leu Glu Thr Leu Leu Gly Gln Lys Val Thr Phe Leu Asp
                85                  90                  95

Asp Cys Val Gly Ser Glu Val Glu Ser Thr Val Asn Ser Ala Pro Ala
            100                 105                 110

Gly Ser Val Ile Leu Leu Glu Asn Leu Arg Phe His Ile Glu Glu Glu
        115                 120                 125

Gly Ser Lys Lys Thr Ser Glu Gly Lys Val Lys Ala Ser Lys Glu Asp
    130                 135                 140

Val Glu Lys Phe Arg Lys Gln Leu Thr Ala Leu Ala Asp Val Tyr Val
145                 150                 155                 160

Asn Asp Ala Phe Gly Thr Ala His Arg Ala His Ser Ser Met Val Gly
                165                 170                 175

Phe Glu Leu Glu Asp Arg Ala Ala Gly Phe Leu Met Ala Lys Glu Leu
            180                 185                 190

Glu Tyr Phe Ser Lys Ala Leu Glu Asn Pro Val Arg Pro Phe Leu Ala
        195                 200                 205

Ile Leu Gly Gly Ala Lys Val Ser Asp Lys Ile Gln Leu Ile Asp Asn
    210                 215                 220

Leu Leu Asp Lys Val Asp Leu Leu Ile Val Gly Gly Gly Met Ala Phe
225                 230                 235                 240

Thr Phe Asn Lys Val Leu Asn Asp Met Lys Ile Gly Lys Ser Leu Phe
                245                 250                 255

Asp Glu Thr Gly Ala Glu Ile Val Pro Lys Leu Val Glu Lys Ala Lys
            260                 265                 270

Lys Asn Gly Val Lys Ile Val Leu Pro Val Asp Phe Val Thr Ala Asp
        275                 280                 285

Ala Phe Ser Pro Asp Ala Lys Val Gly Tyr Ala Thr Leu Glu Glu Gly
    290                 295                 300

Ile Ala Asp Asp Leu Gln Gly Leu Asp Gly Gly Glu Lys Thr Arg Lys
305                 310                 315                 320

Leu Phe Ala Asp Thr Ile Ala Gln Ala Lys Thr Ile Val Trp Asn Gly
                325                 330                 335

Pro Pro Gly Val Phe Glu Phe Glu Ser Phe Ala Ser Gly Thr Lys Ser
            340                 345                 350

Met Leu Gln Ala Cys Val Glu Ser Ala Gln Ala Gly Asn Thr Val Ile
        355                 360                 365

Ile Gly Gly Gly Asp Thr Ala Thr Val Ala Lys Lys Phe Gly Gly Ala
    370                 375                 380

Asp Lys Leu Ser His Val Ser Thr Gly Gly Gly Ala Ser Leu Glu Leu
385                 390                 395                 400

Leu Glu Gly Lys Glu Leu Pro Gly Val Ala Ala Leu Lys Ser Lys Thr
                405                 410                 415

Ala

<210> SEQ ID NO 5
<211> LENGTH: 42

```
<212> TYPE: DNA
<213> ORGANISM: Artificial Sequence
<220> FEATURE:
<223> OTHER INFORMATION: Synthetic oligonucleotide

<400> SEQUENCE: 5
aagcttgaca atgtaggaga tcataaacac atcgtgcgcg tc                          42

<210> SEQ ID NO 6
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 6
ggatccagat ctcatatgac tagttgctag ttctatgcgg cgttagtgtt tacactacga      60
cagct                                                                   65

<210> SEQ ID NO 7
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 7
ggatccgtgg gatttgcgtg atctacgtag tggttatttt                            40

<210> SEQ ID NO 8
<211> LENGTH: 42
<212> TYPE: DNA
<213> ORGANISM: Artificial Sequence
<220> FEATURE:
<223> OTHER INFORMATION: Synthetic oligonucleotide

<400> SEQUENCE: 8
ggtaccgcag tgaaaggcga tgccaccatg tgcaaggagt tc                          42

<210> SEQ ID NO 9
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 9
actagtatga gatttccttc aattt                                             25

<210> SEQ ID NO 10
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 10
gtcgacatga gatttccttc aattt                                             25

<210> SEQ ID NO 11
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 11
```
agcttcagcc tctcttttat ctagaga                                      27

<210> SEQ ID NO 12
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 12
tctctagata aaagagaggc tgaagctcag ctgcagctgc aggagtc                47

<210> SEQ ID NO 13
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 13
ccagatctgg atcctcattt acccggagac agggagagg                         39

<210> SEQ ID NO 14
<211> LENGTH: 47
<212> TYPE: DNA
<213> ORGANISM: Artificial Sequence
<220> FEATURE:
<223> OTHER INFORMATION: Synthetic oligonucleotide

<400> SEQUENCE: 14
tctctagata aaagagaggc tgaagctgaa attgtgttga cacagtc                47

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 15
aaagggccct caacactctc ccctgttgaa gctct                             35

<210> SEQ ID NO 16
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 16
atgacttcct tttcagcacc gcatc                                        25

<210> SEQ ID NO 17
<211> LENGTH: 23
<212> TYPE: DNA
<213> ORGANISM: Artificial Sequence
<220> FEATURE:
<223> OTHER INFORMATION: Synthetic oligonucleotide

<400> SEQUENCE: 17
caaaattgca agcaagttaa ccg                                          23

<210> SEQ ID NO 18
<211> LENGTH: 1431
<212> TYPE: DNA
<213> ORGANISM: Ogataea minuta

<400> SEQUENCE: 18

```
atgacttcct tttcagcacc gcatcaacac cagtctattc cgtcggatgt tcctgtcgga      60
acgcttcctc ctagaaagag ggcgaagacc gacgaagaga aggagcaacg cagggttgag     120
cggattctca gaaataggag agccgcccac gcgtcgaggg aaaagaaaag aagacatgtt     180
gaacatctcg agacgtatgt gagtggcctg gagtcctcgc ttgcgattta cgagttgaat     240
caatccaaac tgcaaacgat acagtcgact ctcatatctt tgttgacgga gcacgggatc     300
gaatactctg gtattgactt ctcaatccaa gcaacaacaa aagtcagcaa gcctgacggg     360
ctcgacttga cacagacgaa tcctaccaaa aaacaaaaga gtttctcaaa gtcactttca     420
aaaaaaatgg gttcttcctc tagcatgaag atgtcggaac tcccatctcc tagcttcgac     480
gaggacgtct cttcggatga agacgacgat cttgaagatg acgagggagc agaaattgtc     540
gaggaatcgc caatgacgta tttggaccct ccggatccaa aagcgaacta caaaaagaga     600
aaggctgaag aagcttatat ttctccacct ggctcgacct ccccttccaa attgaagttg     660
gaggaagacg agctgatttt gaagcaagag tacagcaatt tgtttgacga cacggaagac     720
tttttctcta ctgagaagtc ttgcagtttg gagttgttca acaaggcga ctctccttcg     780
gaatcattca tcaaacagga agacgatata ctgaaaatac ctgaggctgt tttcaactca     840
gaagaatatc atttgaatcc agtggaggac ctctgtgctt taatagcgt gcatcatcca     900
gcagtgatga ttgtatgatt tattgaaaag gcatctcaat aacattgaaa cagtgagatt     960
tccaaacaag aattgtacaa acgtgacatc atcaaaggta aaatcagaaa aaagttcttt    1020
tttcagggt atttgtttgt tcttctttct gattttaccg tagttacgtt ttgtctgttt     1080
tttgaggaag tccaagctct tcgagcgttt catgtcggtt tattgcagat gttcgttttg    1140
gtccgcagca ccattatcag cgggggtcgt taacacttca tttgaattcg atgatttctt    1200
gtcatgagga agatagtcta cttggtttta tttagttgga atttggtgtc attgtttgat    1260
gaggggatg gaggtttgat caatcggttt caagttctct ttcgatgaga ttaatttgtt    1320
accgtctatg agttagatcc tgacccttgg tgagcttcgg aaaaaagttt gaagttcagc    1380
ctggttccat gccacgcgtg tttggttacg gttaacttgc ttgcaatttt g             1431
```

<210> SEQ ID NO 19
<211> LENGTH: 1187
<212> TYPE: DNA
<213> ORGANISM: Ogataea minuta

<400> SEQUENCE: 19

```
atgacttcct tttcagcacc gcatcaacac cagtctattc cgtcggatgt tcctgtcgga      60
acgcttcctc ctagaaagag ggcgaagacc gacgaagaga aggagcaacg cagggttgag     120
cggattctca gaaataggag agccgcccac gcgtcgaggg aaaagaaaag aagacatgtt     180
gaacatctcg agacgtatgt gagtggcctg gagtcctcgc ttgcgattta cgagttgaat     240
caatccaaac tgcaaacgat acagtcgact ctcatatctt tgttgacgga gcacgggatc     300
gaatactctg gtattgactt ctcaatccaa gcaacaacaa aagtcagcaa gcctgacggg     360
ctcgacttga cacagacgaa tcctaccaaa aaacaaaaga gtttctcaaa gtcactttca     420
aaaaaaatgg gttcttcctc tagcatgaag atgtcggaac tcccatctcc tagcttcgac     480
gaggacgtct cttcggatga agacgacgat cttgaagatg acgagggagc agaaattgtc     540
gaggaatcgc caatgacgta tttggaccct ccggatccaa aagcgaacta caaaaagaga     600
aaggctgaag aagcttatat ttctccacct ggctcgacct ccccttccaa attgaagttg     660
```

```
gaggaagacg agctgatttt gaagcaagag tacagcaatt tgtttgacga cacggaagac    720 ttttttctcta ctgagaagtc ttgcagtttg gagttgttca acaaggcga ctctccttcg    780 gaatcattca tcaaacagga agacgatata ctgaaaatac ctgaggctgt tttcaactca    840
gaagaatatc atttgaatcc agtggaggac ctctgtgctt taatagcgt gcatcatcca     900 gcagcaccat tatcagcggg ggtcgttaac acttcatttg aattcgatga tttcttgtca    960
tgaggaagat agtctacttg gttttattta gttggaattt ggtgtcattg tttgatgagg    1020
gggatggagg tttgatcaat cggtttcaag ttctctttcg atgagattaa tttgttaccg    1080
tctatgagtt agatcctgac ccttggtgag cttcggaaaa aagtttgaag ttcagcctgg    1140
ttccatgcca cgcgtgtttg gttacggtta acttgcttgc aattttg                  1187

<210> SEQ ID NO 20
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 20
gactagtatg acttcctttt cagcaccg                                       28

<210> SEQ ID NO 21
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 21
cagatcttca tgacaagaaa tcatcgaat                                      29

<210> SEQ ID NO 22
<211> LENGTH: 963
<212> TYPE: DNA
<213> ORGANISM: Ogataea minuta
<220> FEATURE:
<221> NAME/KEY: CDS
<222> LOCATION: (1)..(963)

<400> SEQUENCE: 22 atg act tcc ttt tca gca ccg cat caa cac cag tct att ccg tcg gat    48
Met Thr Ser Phe Ser Ala Pro His Gln His Gln Ser Ile Pro Ser Asp
 1               5                  10                  15 gtt cct gtc gga acg ctt cct cct aga aag agg gcg aag acc gac gaa    96
Val Pro Val Gly Thr Leu Pro Pro Arg Lys Arg Ala Lys Thr Asp Glu
             20                  25                  30 gag aag gag caa cgc agg gtt gag cgg att ctc aga aat agg aga gcc    144
Glu Lys Glu Gln Arg Arg Val Glu Arg Ile Leu Arg Asn Arg Arg Ala
         35                  40                  45 gcc cac gcg tcg agg gaa aag aaa aga aga cat gtt gaa cat ctc gag   192
Ala His Ala Ser Arg Glu Lys Lys Arg Arg His Val Glu His Leu Glu
     50                  55                  60 acg tat gtg agt ggc ctg gag tcc tcg ctt gcg att tac gag ttg aat   240
Thr Tyr Val Ser Gly Leu Glu Ser Ser Leu Ala Ile Tyr Glu Leu Asn
 65                  70                  75                  80 caa tcc aaa ctg caa acg ata cag tcg act ctc ata tct ttg ttg acg   288
Gln Ser Lys Leu Gln Thr Ile Gln Ser Thr Leu Ile Ser Leu Leu Thr
                 85                  90                  95 gag cac ggg atc gaa tac tct ggt att gac ttc tca atc caa gca aca   336
Glu His Gly Ile Glu Tyr Ser Gly Ile Asp Phe Ser Ile Gln Ala Thr
```

```
         100                 105                 110
aca aaa gtc agc aag cct gac ggg ctc gac ttg aca cag acg aat cct    384
Thr Lys Val Ser Lys Pro Asp Gly Leu Asp Leu Thr Gln Thr Asn Pro
        115                 120                 125 acc aaa aaa caa aag agt ttc tca aag tca ctt tca aaa aaa atg ggt    432
Thr Lys Lys Gln Lys Ser Phe Ser Lys Ser Leu Ser Lys Lys Met Gly
130                 135                 140 tct tcc tct agc atg aag atg tcg gaa ctc cca tct cct agc ttc gac    480
Ser Ser Ser Ser Met Lys Met Ser Glu Leu Pro Ser Pro Ser Phe Asp
145                 150                 155                 160 gag gac gtc tct tcg gat gaa gac gac gat ctt gaa gat gac gag gga    528
Glu Asp Val Ser Ser Asp Glu Asp Asp Asp Leu Glu Asp Asp Glu Gly
                165                 170                 175 gca gaa att gtc gag gaa tcg cca atg acg tat ttg gac ctt ccg gat    576
Ala Glu Ile Val Glu Glu Ser Pro Met Thr Tyr Leu Asp Leu Pro Asp
            180                 185                 190 cca aaa gcg aac tac aaa aag aga aag gct gaa gaa gct tat att tct    624
Pro Lys Ala Asn Tyr Lys Lys Arg Lys Ala Glu Glu Ala Tyr Ile Ser
        195                 200                 205 cca cct ggc tcg acc tcc cct tcc aaa ttg aag ttg gag gaa gac gag    672
Pro Pro Gly Ser Thr Ser Pro Ser Lys Leu Lys Leu Glu Glu Asp Glu
210                 215                 220 ctg att ttg aag caa gag tac agc aat ttg ttt gac gac acg gaa gac    720
Leu Ile Leu Lys Gln Glu Tyr Ser Asn Leu Phe Asp Asp Thr Glu Asp
225                 230                 235                 240 ttt ttc tct act gag aag tct tgc agt ttg gag ttg ttc aaa caa ggc    768
Phe Phe Ser Thr Glu Lys Ser Cys Ser Leu Glu Leu Phe Lys Gln Gly
                245                 250                 255 gac tct cct tcg gaa tca ttc atc aaa cag gaa gac gat ata ctg aaa    816
Asp Ser Pro Ser Glu Ser Phe Ile Lys Gln Glu Asp Asp Ile Leu Lys
            260                 265                 270 ata cct gag gct gtt ttc aac tca gaa gaa tat cat ttg aat cca gtg    864
Ile Pro Glu Ala Val Phe Asn Ser Glu Glu Tyr His Leu Asn Pro Val
        275                 280                 285 gag gac ctc tgt gct ttt aat agc gtg cat cat cca gca gca cca tta    912
Glu Asp Leu Cys Ala Phe Asn Ser Val His His Pro Ala Ala Pro Leu
        290                 295                 300 tca gcg ggg gtc gtt aac act tca ttt gaa ttc gat gat ttc ttg tca    960
Ser Ala Gly Val Val Asn Thr Ser Phe Glu Phe Asp Asp Phe Leu Ser
305                 310                 315                 320 tga                                                                 963
```

<210> SEQ ID NO 23
<211> LENGTH: 320
<212> TYPE: PRT
<213> ORGANISM: Ogataea minuta

<400> SEQUENCE: 23

Met Thr Ser Phe Ser Ala Pro His Gln His Gln Ser Ile Pro Ser Asp
1               5                   10                  15

Val Pro Val Gly Thr Leu Pro Pro Arg Lys Arg Ala Lys Thr Asp Glu
            20                  25                  30

Glu Lys Glu Gln Arg Arg Val Glu Arg Ile Leu Arg Asn Arg Arg Ala
        35                  40                  45

Ala His Ala Ser Arg Glu Lys Lys Arg Arg His Val Glu His Leu Glu
    50                  55                  60

Thr Tyr Val Ser Gly Leu Glu Ser Ser Leu Ala Ile Tyr Glu Leu Asn
65                  70                  75                  80

Gln Ser Lys Leu Gln Thr Ile Gln Ser Thr Leu Ile Ser Leu Leu Thr

```
                    85                  90                  95
Glu His Gly Ile Glu Tyr Ser Gly Ile Asp Phe Ser Ile Gln Ala Thr
                100                 105                 110

Thr Lys Val Ser Lys Pro Asp Gly Leu Asp Leu Thr Gln Thr Asn Pro
            115                 120                 125

Thr Lys Lys Gln Lys Ser Phe Ser Lys Ser Leu Ser Lys Lys Met Gly
        130                 135                 140

Ser Ser Ser Ser Met Lys Met Ser Glu Leu Pro Ser Pro Ser Phe Asp
145                 150                 155                 160

Glu Asp Val Ser Asp Glu Asp Asp Leu Glu Asp Asp Glu Gly
                165                 170                 175

Ala Glu Ile Val Glu Glu Ser Pro Met Thr Tyr Leu Asp Leu Pro Asp
            180                 185                 190

Pro Lys Ala Asn Tyr Lys Lys Arg Lys Ala Glu Glu Ala Tyr Ile Ser
        195                 200                 205

Pro Pro Gly Ser Thr Ser Pro Ser Lys Leu Lys Leu Glu Glu Asp Glu
    210                 215                 220

Leu Ile Leu Lys Gln Glu Tyr Ser Asn Leu Phe Asp Asp Thr Glu Asp
225                 230                 235                 240

Phe Phe Ser Thr Glu Lys Ser Cys Ser Leu Glu Leu Phe Lys Gln Gly
                245                 250                 255

Asp Ser Pro Ser Glu Ser Phe Ile Lys Gln Asp Asp Ile Leu Lys
            260                 265                 270

Ile Pro Glu Ala Val Phe Asn Ser Glu Glu Tyr His Leu Asn Pro Val
        275                 280                 285

Glu Asp Leu Cys Ala Phe Asn Ser Val His His Pro Ala Ala Pro Leu
    290                 295                 300

Ser Ala Gly Val Val Asn Thr Ser Phe Glu Phe Asp Asp Phe Leu Ser
305                 310                 315                 320
```

<210> SEQ ID NO 24
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 24
atacaataca aagtcgagac tagtatggat atttacgaca ctcaaacctt     50

<210> SEQ ID NO 25
<211> LENGTH: 50
<212> TYPE: DNA
<213> ORGANISM: Artificial Sequence
<220> FEATURE:
<223> OTHER INFORMATION: Synthetic oligonucleotide

<400> SEQUENCE: 25
tctatccaca cggatcagat cttcagacag aggtgccctc ctttgagctg     50

<210> SEQ ID NO 26
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 26
ggaattcatg agatttcctt caat     24

<210> SEQ ID NO 27
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 27
ctccaccagc tgtacttctc ttttctcgag agata                35

<210> SEQ ID NO 28
<211> LENGTH: 35
<212> TYPE: DNA
<213> ORGANISM: Artificial Sequence
<220> FEATURE:
<223> OTHER INFORMATION: Synthetic oligonucleotide

<400> SEQUENCE: 28
tatctctcga gaaaagagaa gtacagctgg tggag                35

<210> SEQ ID NO 29
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 29
ggtcgactca tttacccggg gacag                25

<210> SEQ ID NO 30
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 30
tgggtcatct gaatgtctct tttctcgaga gata                34

<210> SEQ ID NO 31
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 31
tatctctcga gaaaagagac attcagatga ccca                34

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 32
ggtcgaccta acactctccc ctgt                24

<210> SEQ ID NO 33
<211> LENGTH: 26
<212> TYPE: DNA
<213> ORGANISM: Artificial Sequence
<220> FEATURE:
<223> OTHER INFORMATION: Synthetic oligonucleotide -continued

```
<400> SEQUENCE: 33
ggagctcatg gaaatgactg attttg                                          26

<210> SEQ ID NO 34
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 34
gaattcaaac ctgactgcgc ttctggatta cgccaattgt caag                      44

<210> SEQ ID NO 35
<211> LENGTH: 44
<212> TYPE: DNA
<213> ORGANISM: Artificial Sequence
<220> FEATURE:
<223> OTHER INFORMATION: Synthetic oligonucleotide

<400> SEQUENCE: 35
cttgacaatt ggcgtaatcc agaagcgcag tcaggtttga attc                      44

<210> SEQ ID NO 36
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 36
gcccgggtca tgaagtgatg aagaaatc                                        28

<210> SEQ ID NO 37
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 37
gggtaccatg gatatttacg acactc                                          26

<210> SEQ ID NO 38
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 38
gtctagatca gacagaggtg ccctcc                                          26

<210> SEQ ID NO 39
<211> LENGTH: 717
<212> TYPE: DNA
<213> ORGANISM: Saccharomyces cerevisiae
<220> FEATURE:
<221> NAME/KEY: CDS
<222> LOCATION: (1)..(717)

<400> SEQUENCE: 39 atg gaa atg act gat ttt gaa cta act agt aat tcg caa tcg aac ttg      48
Met Glu Met Thr Asp Phe Glu Leu Thr Ser Asn Ser Gln Ser Asn Leu
 1               5                  10                  15 gct atc cct acc aac ttc aag tcg act ctg cct cca agg aaa aga gcc      96
```

```
     Ala Ile Pro Thr Asn Phe Lys Ser Thr Leu Pro Pro Arg Lys Arg Ala
                      20                  25                  30 aag aca aaa gag gaa aag gaa cag cga agg atc gag cgt att ttg aga      144
Lys Thr Lys Glu Glu Lys Glu Gln Arg Arg Ile Glu Arg Ile Leu Arg
             35                  40                  45 aac aga aga gct gct cac cag agc aga gag aaa aaa aga cta cat ctg      192
Asn Arg Arg Ala Ala His Gln Ser Arg Glu Lys Lys Arg Leu His Leu
 50                  55                  60 cag tat ctc gag aga aaa tgt tct ctt ttg gaa aat tta ctg aac agc      240
Gln Tyr Leu Glu Arg Lys Cys Ser Leu Leu Glu Asn Leu Leu Asn Ser
 65                  70                  75                  80 gtc aac ctt gaa aaa ctg gct gac cac gaa gac gcg ttg act tgc agc      288
Val Asn Leu Glu Lys Leu Ala Asp His Glu Asp Ala Leu Thr Cys Ser
                 85                  90                  95 cac gac gct ttt gtt gct tct ctt gac gag tac agg gat ttc cag agc      336
His Asp Ala Phe Val Ala Ser Leu Asp Glu Tyr Arg Asp Phe Gln Ser
            100                 105                 110 acg agg ggc gct tca ctg gac acc agg gcc agt tcg cac tcg tcg tct      384
Thr Arg Gly Ala Ser Leu Asp Thr Arg Ala Ser Ser His Ser Ser Ser
        115                 120                 125 gat acg ttc aca cct tca cct ctg aac tgt aca atg gag cct gcg act      432
Asp Thr Phe Thr Pro Ser Pro Leu Asn Cys Thr Met Glu Pro Ala Thr
130                 135                 140 ttg tcg ccc aag agt atg cgc gat tcc gcg tcg gac caa gag act tca      480
Leu Ser Pro Lys Ser Met Arg Asp Ser Ala Ser Asp Gln Glu Thr Ser
145                 150                 155                 160 tgg gag ctg cag atg ttt aag acg gaa aat gta cca gag tcg acg acg      528
Trp Glu Leu Gln Met Phe Lys Thr Glu Asn Val Pro Glu Ser Thr Thr
                165                 170                 175 cta cct gcc gta gac aac aac aat ttg ttt gat gcg gtg gcc tcg ccg      576
Leu Pro Ala Val Asp Asn Asn Asn Leu Phe Asp Ala Val Ala Ser Pro
            180                 185                 190 ttg gca gac cca ctc tgc gac gat ata gcg gga aac agt cta ccc ttt      624
Leu Ala Asp Pro Leu Cys Asp Asp Ile Ala Gly Asn Ser Leu Pro Phe
        195                 200                 205 gac aat tca att gat ctt gac aat tgg cgt aat cca gaa gcg cag tca      672
Asp Asn Ser Ile Asp Leu Asp Asn Trp Arg Asn Pro Glu Ala Gln Ser
    210                 215                 220 ggt ttg aat tca ttt gaa ttg aat gat ttc ttc atc act tca tga         717
Gly Leu Asn Ser Phe Glu Leu Asn Asp Phe Phe Ile Thr Ser
225                 230                 235

<210> SEQ ID NO 40
<211> LENGTH: 238
<212> TYPE: PRT
<213> ORGANISM: Saccharomyces cerevisiae

<400> SEQUENCE: 40

Met Glu Met Thr Asp Phe Glu Leu Thr Ser Asn Ser Gln Ser Asn Leu
 1               5                  10                  15

Ala Ile Pro Thr Asn Phe Lys Ser Thr Leu Pro Pro Arg Lys Arg Ala
                 20                  25                  30

Lys Thr Lys Glu Glu Lys Glu Gln Arg Arg Ile Glu Arg Ile Leu Arg
             35                  40                  45

Asn Arg Arg Ala Ala His Gln Ser Arg Glu Lys Lys Arg Leu His Leu
 50                  55                  60

Gln Tyr Leu Glu Arg Lys Cys Ser Leu Leu Glu Asn Leu Leu Asn Ser
 65                  70                  75                  80

Val Asn Leu Glu Lys Leu Ala Asp His Glu Asp Ala Leu Thr Cys Ser
                 85                  90                  95
```

```
His Asp Ala Phe Val Ala Ser Leu Asp Glu Tyr Arg Asp Phe Gln Ser
            100                 105                 110

Thr Arg Gly Ala Ser Leu Asp Thr Arg Ala Ser Ser His Ser Ser Ser
        115                 120                 125

Asp Thr Phe Thr Pro Ser Pro Leu Asn Cys Thr Met Glu Pro Ala Thr
    130                 135                 140

Leu Ser Pro Lys Ser Met Arg Asp Ser Ala Ser Asp Gln Glu Thr Ser
145                 150                 155                 160

Trp Glu Leu Gln Met Phe Lys Thr Glu Asn Val Pro Glu Ser Thr Thr
                165                 170                 175

Leu Pro Ala Val Asp Asn Asn Leu Phe Asp Ala Val Ala Ser Pro
                180                 185                 190

Leu Ala Asp Pro Leu Cys Asp Asp Ile Ala Gly Asn Ser Leu Pro Phe
                195                 200                 205

Asp Asn Ser Ile Asp Leu Asp Asn Trp Arg Asn Pro Glu Ala Gln Ser
        210                 215                 220

Gly Leu Asn Ser Phe Glu Leu Asn Asp Phe Phe Ile Thr Ser
225                 230                 235

<210> SEQ ID NO 41
<211> LENGTH: 1356
<212> TYPE: DNA
<213> ORGANISM: Trichoderma reesei
<220> FEATURE:
<221> NAME/KEY: CDS
<222> LOCATION: (1)..(1356)

<400> SEQUENCE: 41 atg gcg ttc cag cag tcg tct ccc ctc gtc aag ttt gag gcc tct ccc      48
Met Ala Phe Gln Gln Ser Ser Pro Leu Val Lys Phe Glu Ala Ser Pro
  1               5                  10                  15 gcc gaa tcc ttc ctc tcc gcc ccc ggc gac aac ttc aca tcc ctc ttc      96
Ala Glu Ser Phe Leu Ser Ala Pro Gly Asp Asn Phe Thr Ser Leu Phe
                 20                  25                  30 gcc gac tca aca ccc tca aca ctt aac cct cgg gac atg atg acc cct     144
Ala Asp Ser Thr Pro Ser Thr Leu Asn Pro Arg Asp Met Met Thr Pro
             35                  40                  45 gac agc gtc gcc gac atc gac tct cgc ctg tcc gtc atc ccc gaa tca     192
Asp Ser Val Ala Asp Ile Asp Ser Arg Leu Ser Val Ile Pro Glu Ser
         50                  55                  60 cag gac gcg gaa gat gac gaa tca cac tcc aca tcc gct acc gca ccc     240
Gln Asp Ala Glu Asp Asp Glu Ser His Ser Thr Ser Ala Thr Ala Pro
 65                  70                  75                  80 tct acc tca gaa aag aag ccc gtc aag aag agg aaa tca tgg ggc cag     288
Ser Thr Ser Glu Lys Lys Pro Val Lys Lys Arg Lys Ser Trp Gly Gln
                 85                  90                  95 gtt ctt cct gag ccc aag acc aac ctc cct cct cga aaa cgt gca aag     336
Val Leu Pro Glu Pro Lys Thr Asn Leu Pro Pro Arg Lys Arg Ala Lys
                100                 105                 110 acg gaa gat gaa aag gag cag cgc cgc gtc gag cgt gtt ctc cgc aac     384
Thr Glu Asp Glu Lys Glu Gln Arg Arg Val Glu Arg Val Leu Arg Asn
            115                 120                 125 cgc cgc gcc gcg cag tcc tcg cgc gag cgc aag agg ctc gag gtc gag     432
Arg Arg Ala Ala Gln Ser Ser Arg Glu Arg Lys Arg Leu Glu Val Glu
        130                 135                 140 gct ctc gag aag cgc aac aag gag ctc gag acg ctc ctc atc aac gtc     480
Ala Leu Glu Lys Arg Asn Lys Glu Leu Glu Thr Leu Leu Ile Asn Val
145                 150                 155                 160 cag aag acc aac ctg atc ctc gtc gag gag ctc aac cgc ttc cga cgc     528
```

| | | |
|---|---|---|
| Gln Lys Thr Asn Leu Ile Leu Val Glu Glu Leu Asn Arg Phe Arg Arg<br>165 170 175 | | |
| agc tca ggc gtc gtc acc cgc tcg tcc tcc ccc ctc gac tct ctc cag<br>Ser Ser Gly Val Val Thr Arg Ser Ser Ser Pro Leu Asp Ser Leu Gln<br>180 185 190 | | 576 |
| gac agc atc act ctc tcc cag caa ctc ttt ggc tcg cgg gat ggc caa<br>Asp Ser Ile Thr Leu Ser Gln Gln Leu Phe Gly Ser Arg Asp Gly Gln<br>195 200 205 | | 624 |
| acc atg tcc aac ccc gag cag tcc ttg atg gac cag atc atg aga tct<br>Thr Met Ser Asn Pro Glu Gln Ser Leu Met Asp Gln Ile Met Arg Ser<br>210 215 220 | | 672 |
| gcc gct aac cct acc gtt aac ccg gcc tct ctt tcc ccc tcc ctc ccc<br>Ala Ala Asn Pro Thr Val Asn Pro Ala Ser Leu Ser Pro Ser Leu Pro<br>225 230 235 240 | | 720 |
| ccc atc tcg gac aag gag ttc cag acc aag gag gag gac gag gaa cag<br>Pro Ile Ser Asp Lys Glu Phe Gln Thr Lys Glu Glu Asp Glu Glu Gln<br>245 250 255 | | 768 |
| gcc gac gaa gat gaa gag atg gag cag aca tgg cac gag acc aaa gaa<br>Ala Asp Glu Asp Glu Glu Met Glu Gln Thr Trp His Glu Thr Lys Glu<br>260 265 270 | | 816 |
| gcc gcc gcc gcc aag gag aag aac agc aag cag tcc cgc gtc tcc act<br>Ala Ala Ala Ala Lys Glu Lys Asn Ser Lys Gln Ser Arg Val Ser Thr<br>275 280 285 | | 864 |
| gat tcg aca caa cgt cct gca gtg tca atc ggt gga gat gcc gct gtc<br>Asp Ser Thr Gln Arg Pro Ala Val Ser Ile Gly Gly Asp Ala Ala Val<br>290 295 300 | | 912 |
| cct gtc ttc tca gac gac gcc ggc gca aac tgc ctt ggc ctg gac cct<br>Pro Val Phe Ser Asp Asp Ala Gly Ala Asn Cys Leu Gly Leu Asp Pro<br>305 310 315 320 | | 960 |
| gtt cat cag gat gat ggt cct ttc agc atc ggc cat tct ttc ggc ctg<br>Val His Gln Asp Asp Gly Pro Phe Ser Ile Gly His Ser Phe Gly Leu<br>325 330 335 | | 1008 |
| tca gcg gcc ctt gat gca gat cgc tat ctc ctc gaa agc caa ctt ctc<br>Ser Ala Ala Leu Asp Ala Asp Arg Tyr Leu Leu Glu Ser Gln Leu Leu<br>340 345 350 | | 1056 |
| gct tcg ccc aac gcc tca act gtt gac gac gat tat ctg gct ggt gac<br>Ala Ser Pro Asn Ala Ser Thr Val Asp Asp Asp Tyr Leu Ala Gly Asp<br>355 360 365 | | 1104 |
| tct gcc gcc tgc ttc acg aat cct ctc ccc tcc gac tac gac ttc gac<br>Ser Ala Ala Cys Phe Thr Asn Pro Leu Pro Ser Asp Tyr Asp Phe Asp<br>370 375 380 | | 1152 |
| atc aac gac ttc ctc aca gac gac gca aac cac gcc gcc tat gac att<br>Ile Asn Asp Phe Leu Thr Asp Asp Ala Asn His Ala Ala Tyr Asp Ile<br>385 390 395 400 | | 1200 |
| gtg gca gcg agc aac tat gcc gct gcg gac cgc gag ctc gac ctc gag<br>Val Ala Ala Ser Asn Tyr Ala Ala Ala Asp Arg Glu Leu Asp Leu Glu<br>405 410 415 | | 1248 |
| atc cac gac cct gag aat cag atc cct tcg cga cat tct atc cag cag<br>Ile His Asp Pro Glu Asn Gln Ile Pro Ser Arg His Ser Ile Gln Gln<br>420 425 430 | | 1296 |
| ccc cag tct ggc gcg tcc tct cat gga tgc gac gat ggc ggc att gcg<br>Pro Gln Ser Gly Ala Ser Ser His Gly Cys Asp Asp Gly Gly Ile Ala<br>435 440 445 | | 1344 |
| gtt ggt gtc tga<br>Val Gly Val<br>450 | | 1356 |

<210> SEQ ID NO 42
<211> LENGTH: 451
<212> TYPE: PRT
<213> ORGANISM: Trichoderma reesei

<400> SEQUENCE: 42

```
Met Ala Phe Gln Gln Ser Ser Pro Leu Val Lys Phe Glu Ala Ser Pro
 1               5                  10                  15

Ala Glu Ser Phe Leu Ser Ala Pro Gly Asp Asn Phe Thr Ser Leu Phe
             20                  25                  30

Ala Asp Ser Thr Pro Ser Thr Leu Asn Pro Arg Asp Met Met Thr Pro
         35                  40                  45

Asp Ser Val Ala Asp Ile Asp Ser Arg Leu Ser Val Ile Pro Glu Ser
     50                  55                  60

Gln Asp Ala Glu Asp Glu Ser His Ser Thr Ser Ala Thr Ala Pro
 65                  70                  75                  80

Ser Thr Ser Glu Lys Lys Pro Val Lys Arg Lys Ser Trp Gly Gln
             85                  90                  95

Val Leu Pro Glu Pro Lys Thr Asn Leu Pro Pro Arg Lys Arg Ala Lys
            100                 105                 110

Thr Glu Asp Glu Lys Glu Gln Arg Val Glu Arg Val Leu Arg Asn
            115                 120                 125

Arg Arg Ala Ala Gln Ser Ser Arg Glu Arg Lys Arg Leu Glu Val Glu
130                 135                 140

Ala Leu Glu Lys Arg Asn Lys Glu Leu Glu Thr Leu Leu Ile Asn Val
145                 150                 155                 160

Gln Lys Thr Asn Leu Ile Leu Val Glu Glu Leu Asn Arg Phe Arg Arg
                165                 170                 175

Ser Ser Gly Val Val Thr Arg Ser Ser Pro Leu Asp Ser Leu Gln
            180                 185                 190

Asp Ser Ile Thr Leu Ser Gln Gln Leu Phe Gly Ser Arg Asp Gly Gln
            195                 200                 205

Thr Met Ser Asn Pro Glu Gln Ser Leu Met Asp Gln Ile Met Arg Ser
        210                 215                 220

Ala Ala Asn Pro Thr Val Asn Pro Ala Ser Leu Ser Pro Ser Leu Pro
225                 230                 235                 240

Pro Ile Ser Asp Lys Glu Phe Gln Thr Lys Glu Glu Asp Glu Glu Gln
                245                 250                 255

Ala Asp Glu Asp Glu Glu Met Glu Gln Thr Trp His Glu Thr Lys Glu
            260                 265                 270

Ala Ala Ala Ala Lys Glu Lys Asn Ser Lys Gln Ser Arg Val Ser Thr
        275                 280                 285

Asp Ser Thr Gln Arg Pro Ala Val Ser Ile Gly Gly Asp Ala Ala Val
    290                 295                 300

Pro Val Phe Ser Asp Asp Ala Gly Ala Asn Cys Leu Gly Leu Asp Pro
305                 310                 315                 320

Val His Gln Asp Asp Gly Pro Phe Ser Ile Gly His Ser Phe Gly Leu
                325                 330                 335

Ser Ala Ala Leu Asp Ala Asp Arg Tyr Leu Leu Glu Ser Gln Leu Leu
            340                 345                 350

Ala Ser Pro Asn Ala Ser Thr Val Asp Asp Tyr Leu Ala Gly Asp
        355                 360                 365

Ser Ala Ala Cys Phe Thr Asn Pro Leu Pro Ser Asp Tyr Asp Phe Asp
370                 375                 380

Ile Asn Asp Phe Leu Thr Asp Ala Asn His Ala Ala Tyr Asp Ile
385                 390                 395                 400

Val Ala Ala Ser Asn Tyr Ala Ala Ala Asp Arg Glu Leu Asp Leu Glu
                405                 410                 415
```

```
Ile His Asp Pro Glu Asn Gln Ile Pro Ser Arg His Ser Ile Gln Gln
            420                 425                 430

Pro Gln Ser Gly Ala Ser Ser His Gly Cys Asp Asp Gly Ile Ala
        435                 440                 445

Val Gly Val
    450

<210> SEQ ID NO 43
<211> LENGTH: 1053
<212> TYPE: DNA
<213> ORGANISM: Aspergillus nidulans
<220> FEATURE:
<221> NAME/KEY: CDS
<222> LOCATION: (1)..(1053)

<400> SEQUENCE: 43 atg aaa tca gca gac cgg ttt tcg cca gtg aaa atg gag gac gct ttc     48
Met Lys Ser Ala Asp Arg Phe Ser Pro Val Lys Met Glu Asp Ala Phe
  1               5                  10                  15 gca aac tct ttg cct act acc ccg tca ttg gag gtt cct gtg ctc act     96
Ala Asn Ser Leu Pro Thr Thr Pro Ser Leu Glu Val Pro Val Leu Thr
             20                  25                  30 gtc tcc ccg gct gac aca tct ctt cgg acg aag aat gtg gtg gct cag    144
Val Ser Pro Ala Asp Thr Ser Leu Arg Thr Lys Asn Val Val Ala Gln
         35                  40                  45 aca aag cct gag gag aag aag cca gcg aag aaa aga aag tcc tgg ggc    192
Thr Lys Pro Glu Glu Lys Lys Pro Ala Lys Lys Arg Lys Ser Trp Gly
     50                  55                  60 cag gaa tta cca gtt ccc aag aca aac tta cct cca aga aaa cgc gct    240
Gln Glu Leu Pro Val Pro Lys Thr Asn Leu Pro Pro Arg Lys Arg Ala
 65                  70                  75                  80 aag aca gaa gat gag aaa gag cag cgc cgg att gag cga gtt ctt cgc    288
Lys Thr Glu Asp Glu Lys Glu Gln Arg Arg Ile Glu Arg Val Leu Arg
                 85                  90                  95 aac cgc gca gcc gca caa acc tct cgc gag cgc aag aga ctt gaa atg    336
Asn Arg Ala Ala Ala Gln Thr Ser Arg Glu Arg Lys Arg Leu Glu Met
            100                 105                 110 gag aag tta gaa agc gag aag att gat atg gaa caa caa aac cag ttc    384
Glu Lys Leu Glu Ser Glu Lys Ile Asp Met Glu Gln Gln Asn Gln Phe
        115                 120                 125 ctt ctt cag cgt ctc gcc cag atg gag gct gag aac aac cgt tta agt    432
Leu Leu Gln Arg Leu Ala Gln Met Glu Ala Glu Asn Asn Arg Leu Ser
    130                 135                 140 cag caa gtt gct cag cta tcc gcg gag gtt cgg gga tcc cgc cac agc    480
Gln Gln Val Ala Gln Leu Ser Ala Glu Val Arg Gly Ser Arg His Ser
145                 150                 155                 160 act cca act tcc agt tcc ccc gcg tca gtt tcg cca act ctc aca ccg    528
Thr Pro Thr Ser Ser Ser Pro Ala Ser Val Ser Pro Thr Leu Thr Pro
                165                 170                 175 act ctt ttt aag cag gaa ggg gat gag gtt cct ctg gac cgc atc cct    576
Thr Leu Phe Lys Gln Glu Gly Asp Glu Val Pro Leu Asp Arg Ile Pro
            180                 185                 190 ttt cca act ccc tcc gtg acc gac tac tcc cca act ctt aag cct tca    624
Phe Pro Thr Pro Ser Val Thr Asp Tyr Ser Pro Thr Leu Lys Pro Ser
        195                 200                 205 tct ctg gct gag tcc ccc gat ttg aca caa cat cct gca gtg tca gtc    672
Ser Leu Ala Glu Ser Pro Asp Leu Thr Gln His Pro Ala Val Ser Val
    210                 215                 220 ggc ggg ctc gaa gga gat gaa agt gcc ctc acg ctt ttc gac ctc gga    720
Gly Gly Leu Glu Gly Asp Glu Ser Ala Leu Thr Leu Phe Asp Leu Gly
225                 230                 235                 240
```

```
gcc agc att aag cat gag cct aca cat gac ctt aca gct cct ctt tct      768
Ala Ser Ile Lys His Glu Pro Thr His Asp Leu Thr Ala Pro Leu Ser
                245                 250                 255 gac gat gac ttc cgc cgc cta ttc aac ggt gat tca tcc ctt gag tca      816
Asp Asp Asp Phe Arg Arg Leu Phe Asn Gly Asp Ser Ser Leu Glu Ser
            260                 265                 270 gat tct tca ctc ctt gaa gac ggg ttc gcc ttt gac gtt ctc gac tca      864
Asp Ser Ser Leu Leu Glu Asp Gly Phe Ala Phe Asp Val Leu Asp Ser
        275                 280                 285 gga gat tta tca gca ttt cca ttt gat tct atg gtt gat ttt gac acc      912
Gly Asp Leu Ser Ala Phe Pro Phe Asp Ser Met Val Asp Phe Asp Thr
    290                 295                 300 gag cct gtc acc ctc gaa gat ctc gag caa acc aac ggc ctt tcg gat      960
Glu Pro Val Thr Leu Glu Asp Leu Glu Gln Thr Asn Gly Leu Ser Asp
305                 310                 315                 320 tca gct tct tgc aag gct gct agc ttg caa ccc agc cat ggc gcg tcc     1008
Ser Ala Ser Cys Lys Ala Ala Ser Leu Gln Pro Ser His Gly Ala Ser
                325                 330                 335 act tcg cga tgc gac ggg cag ggc att gca gct ggc agt gcg tga         1053
Thr Ser Arg Cys Asp Gly Gln Gly Ile Ala Ala Gly Ser Ala
                340                 345                 350
```

<210> SEQ ID NO 44
<211> LENGTH: 350
<212> TYPE: PRT
<213> ORGANISM: Aspergillus nudulans

<400> SEQUENCE: 44

```
Met Lys Ser Ala Asp Arg Phe Ser Pro Val Lys Met Glu Asp Ala Phe
 1               5                  10                  15

Ala Asn Ser Leu Pro Thr Thr Pro Ser Leu Glu Val Pro Val Leu Thr
                20                  25                  30

Val Ser Pro Ala Asp Thr Ser Leu Arg Thr Lys Asn Val Val Ala Gln
            35                  40                  45

Thr Lys Pro Glu Glu Lys Lys Pro Ala Lys Lys Arg Lys Ser Trp Gly
        50                  55                  60

Gln Glu Leu Pro Val Pro Lys Thr Asn Leu Pro Arg Lys Arg Ala
 65                 70                  75                  80

Lys Thr Glu Asp Glu Lys Glu Gln Arg Ile Glu Arg Val Leu Arg
                85                  90                  95

Asn Arg Ala Ala Ala Gln Thr Ser Arg Glu Arg Lys Arg Leu Glu Met
            100                 105                 110

Glu Lys Leu Glu Ser Glu Lys Ile Asp Met Glu Gln Gln Asn Gln Phe
        115                 120                 125

Leu Leu Gln Arg Leu Ala Gln Met Glu Ala Glu Asn Asn Arg Leu Ser
    130                 135                 140

Gln Gln Val Ala Gln Leu Ser Ala Glu Val Arg Gly Ser Arg His Ser
145                 150                 155                 160

Thr Pro Thr Ser Ser Ser Pro Ala Ser Val Ser Pro Thr Leu Thr Pro
                165                 170                 175

Thr Leu Phe Lys Gln Glu Gly Asp Glu Val Pro Leu Asp Arg Ile Pro
            180                 185                 190

Phe Pro Thr Pro Ser Val Thr Asp Tyr Ser Pro Thr Leu Lys Pro Ser
        195                 200                 205

Ser Leu Ala Glu Ser Pro Asp Leu Thr Gln His Pro Ala Val Ser Val
    210                 215                 220

Gly Gly Leu Glu Gly Asp Glu Ser Ala Leu Thr Leu Phe Asp Leu Gly
```

```
                225                 230                 235                 240
Ala Ser Ile Lys His Glu Pro Thr His Asp Leu Thr Ala Pro Leu Ser
                    245                 250                 255
Asp Asp Asp Phe Arg Arg Leu Phe Asn Gly Asp Ser Ser Leu Glu Ser
                260                 265                 270
Asp Ser Ser Leu Leu Glu Asp Gly Phe Ala Phe Asp Val Leu Asp Ser
            275                 280                 285
Gly Asp Leu Ser Ala Phe Pro Phe Asp Ser Met Val Asp Phe Asp Thr
        290                 295                 300
Glu Pro Val Thr Leu Glu Asp Leu Glu Gln Thr Asn Gly Leu Ser Asp
305                 310                 315                 320
Ser Ala Ser Cys Lys Ala Ala Ser Leu Gln Pro Ser His Gly Ala Ser
                325                 330                 335
Thr Ser Arg Cys Asp Gly Gln Gly Ile Ala Ala Gly Ser Ala
                340                 345                 350

<210> SEQ ID NO 45
<211> LENGTH: 5468
<212> TYPE: DNA
<213> ORGANISM: Homo sapiens
<220> FEATURE:
<221> NAME/KEY: CDS
<222> LOCATION: (285)..(4967)

<400> SEQUENCE: 45
ggtatcgata agcttgatgg agcggacggc agacggggcg gcggcgtca gggtcgcagc      60 gtctacagct gctcggggc ggtttcttgg cggaggcttg gccggctcct ctctcccggc     120
tccgcggcgg ctgcgaaggc ggcggctcct gccctctcgc tttccctctc gcgtctctgg    180
ctgcagaaag aagcttccgg ttctgaggtc ctggaggtgc catttccctc tctgttgaag    240
caaaggccgg ggcagacctc ctagtgaaag gaaagcaagc cagg atg gat att tac     296
                                                Met Asp Ile Tyr
                                                  1 gac act caa acc ttg ggg gtt gtg gtc ttt gga gga ttc atg gtt gtt      344
Asp Thr Gln Thr Leu Gly Val Val Val Phe Gly Gly Phe Met Val Val
  5              10                  15                  20 tct gcc att ggc atc ttc ctg gtg tcg act ttc tcc atg aag gaa acg      392
Ser Ala Ile Gly Ile Phe Leu Val Ser Thr Phe Ser Met Lys Glu Thr
                25                  30                  35 tca tat gaa gaa gcc cta gcc aac cag cgc aag gag atg gcg aaa act      440
Ser Tyr Glu Glu Ala Leu Ala Asn Gln Arg Lys Glu Met Ala Lys Thr
            40                  45                  50 cac cac cag aaa gtc gag aag aaa aag aag gag aaa aca gtg gag aag      488
His His Gln Lys Val Glu Lys Lys Lys Lys Glu Lys Thr Val Glu Lys
        55                  60                  65 aaa gga aag acc aag aaa aag gaa gag aaa cct aat ggg aag ata cct      536
Lys Gly Lys Thr Lys Lys Lys Glu Glu Lys Pro Asn Gly Lys Ile Pro
   70                  75                  80 gat cat gat cca gcc ccc aat gtg act gtc ctc ctt cga gaa cca gtg      584
Asp His Asp Pro Ala Pro Asn Val Thr Val Leu Leu Arg Glu Pro Val
85                  90                  95                 100 cgg gct cct gct gtg gct gtg gct cca acc cca gtg cag ccc ccc att      632
Arg Ala Pro Ala Val Ala Val Ala Pro Thr Pro Val Gln Pro Pro Ile
                105                 110                 115 atc gtt gct cct gtc gcc aca gtt cca gcc atg ccc cag gag aag ctg      680
Ile Val Ala Pro Val Ala Thr Val Pro Ala Met Pro Gln Glu Lys Leu
            120                 125                 130 gcc tcc tcc ccc aag gac aaa aag aag aag gag aaa aag gtg gca aaa      728
Ala Ser Ser Pro Lys Asp Lys Lys Lys Lys Glu Lys Lys Val Ala Lys
```

-continued

```
             135                 140                 145
gtg gaa cca gct gtc agc tct gta gtg aat tcc atc cag gtt ctc act    776
Val Glu Pro Ala Val Ser Ser Val Val Asn Ser Ile Gln Val Leu Thr
150                 155                 160 tcg aag gct gcc atc ttg gaa act gct ccc aag gag gtg ccg atg gtg    824
Ser Lys Ala Ala Ile Leu Glu Thr Ala Pro Lys Glu Val Pro Met Val
165                 170                 175                 180 gtg gtg ccc cca gtg ggt gcc aag ggc aac aca cca gcc act ggc act    872
Val Val Pro Pro Val Gly Ala Lys Gly Asn Thr Pro Ala Thr Gly Thr
                185                 190                 195 act cag ggc aaa aag gcg gag ggg act cag aat caa agc aaa aag gct    920
Thr Gln Gly Lys Lys Ala Glu Gly Thr Gln Asn Gln Ser Lys Lys Ala
        200                 205                 210 gaa gga gcc cca aac cag ggc aga aag gca gag gga acc cca aac cag    968
Glu Gly Ala Pro Asn Gln Gly Arg Lys Ala Glu Gly Thr Pro Asn Gln
                215                 220                 225 ggc aaa aag aca gag gga acc cca aac caa ggg aaa aag gca gag gga   1016
Gly Lys Lys Thr Glu Gly Thr Pro Asn Gln Gly Lys Lys Ala Glu Gly
        230                 235                 240 acc cca aac caa ggc aaa aag gca gaa gga acc cca aac caa ggc aaa   1064
Thr Pro Asn Gln Gly Lys Lys Ala Glu Gly Thr Pro Asn Gln Gly Lys
245                 250                 255                 260 aag gcg gag ggg gcc cag aac cag ggt aaa aag gta gat aca acc cca   1112
Lys Ala Glu Gly Ala Gln Asn Gln Gly Lys Lys Val Asp Thr Thr Pro
                265                 270                 275 aac cag ggg aaa aag gtg gag ggg gcc cca acc cag ggc aga aag gcc   1160
Asn Gln Gly Lys Lys Val Glu Gly Ala Pro Thr Gln Gly Arg Lys Ala
        280                 285                 290 gag ggg gct cag aac cag gcc aaa aag gta gaa ggg gcc cag aac cag   1208
Glu Gly Ala Gln Asn Gln Ala Lys Lys Val Glu Gly Ala Gln Asn Gln
                295                 300                 305 ggc aaa aag gca gag ggg gcc cag aat cag ggc aaa aag gga gag ggg   1256
Gly Lys Lys Ala Glu Gly Ala Gln Asn Gln Gly Lys Lys Gly Glu Gly
        310                 315                 320 gcc cag aac cag ggc aag aag gcc gag ggg gcc cag aat cag ggc aag   1304
Ala Gln Asn Gln Gly Lys Lys Ala Glu Gly Ala Gln Asn Gln Gly Lys
325                 330                 335                 340 aag gcc gag ggg gcc cag aat cag ggc aag aag gcc gag ggg gcc cag   1352
Lys Ala Glu Gly Ala Gln Asn Gln Gly Lys Lys Ala Glu Gly Ala Gln
                345                 350                 355 aat cag ggc aag aag gcc gag ggg gcc cag aat cag ggc aag aag gct   1400
Asn Gln Gly Lys Lys Ala Glu Gly Ala Gln Asn Gln Gly Lys Lys Ala
        360                 365                 370 gag ggg gct cag aac cag ggc aaa aag gcc gag ggg gct cag aac cag   1448
Glu Gly Ala Gln Asn Gln Gly Lys Lys Ala Glu Gly Ala Gln Asn Gln
                375                 380                 385 ggc aaa aaa gta gaa ggg gcc cag aac cag ggc aag aag gct gag ggt   1496
Gly Lys Lys Val Glu Gly Ala Gln Asn Gln Gly Lys Lys Ala Glu Gly
        390                 395                 400 gcc cag aac cag ggc aaa aag gcc gag ggg gcc cag aat cag ggc aaa   1544
Ala Gln Asn Gln Gly Lys Lys Ala Glu Gly Ala Gln Asn Gln Gly Lys
405                 410                 415                 420 aag gcc gag ggg gcc cag aac cag ggc aag aag gca gag ggg gcc cag   1592
Lys Ala Glu Gly Ala Gln Asn Gln Gly Lys Lys Ala Glu Gly Ala Gln
                425                 430                 435 aac cag ggc aag aag gcc gag ggg gcc cag aac cag gac aag aag gcc   1640
Asn Gln Gly Lys Lys Ala Glu Gly Ala Gln Asn Gln Asp Lys Lys Ala
        440                 445                 450 gag ggg gcc cag aac cag ggc agg aag gcc gag ggg gcc cag aac cag   1688
Glu Gly Ala Gln Asn Gln Gly Arg Lys Ala Glu Gly Ala Gln Asn Gln
```

-continued

```
                455                 460                 465
ggc agg aag gcc gag ggg gcc cag aac cag ggc aag aag gcc gag ggg    1736
Gly Arg Lys Ala Glu Gly Ala Gln Asn Gln Gly Lys Lys Ala Glu Gly
    470                 475                 480 gcc ccg aac cag ggc aag aag gcc gag ggg gcc ccg aac cag ggc aag    1784
Ala Pro Asn Gln Gly Lys Lys Ala Glu Gly Ala Pro Asn Gln Gly Lys
485                 490                 495                 500 aag gcc gag ggg acc ccg aac cag ggc aag aag gcc gag ggg acc ccg    1832
Lys Ala Glu Gly Thr Pro Asn Gln Gly Lys Lys Ala Glu Gly Thr Pro
                505                 510                 515 aac cag ggc aag aag gcc gag ggg acc ccg aac cag ggc aag aag gcc    1880
Asn Gln Gly Lys Lys Ala Glu Gly Thr Pro Asn Gln Gly Lys Lys Ala
            520                 525                 530 gag ggg gcc cag aac cag ggc aag aag gcc gag ggg gcc cag aac cag    1928
Glu Gly Ala Gln Asn Gln Gly Lys Lys Ala Glu Gly Ala Gln Asn Gln
        535                 540                 545 ggc aag aag gcc gag ggg acc ccg aac cag ggc aag aag gcc gag ggg    1976
Gly Lys Lys Ala Glu Gly Thr Pro Asn Gln Gly Lys Lys Ala Glu Gly
    550                 555                 560 gcc cag aac cag ggc aag aag gcc gag ggg gcc cag aac cag ggc aag    2024
Ala Gln Asn Gln Gly Lys Lys Ala Glu Gly Ala Gln Asn Gln Gly Lys
565                 570                 575                 580 aag gcc gag ggg gcc cag aac cag ggc aag aag gcc gag ggg gcc cag    2072
Lys Ala Glu Gly Ala Gln Asn Gln Gly Lys Lys Ala Glu Gly Ala Gln
                585                 590                 595 aac cag ggc aag aag gcc gag ggg gcc cag aac cag ggc aag aag gcc    2120
Asn Gln Gly Lys Lys Ala Glu Gly Ala Gln Asn Gln Gly Lys Lys Ala
            600                 605                 610 gag ggt gct cag aac cag ggc aaa aaa gta gaa ggg gcc cag aac cag    2168
Glu Gly Ala Gln Asn Gln Gly Lys Lys Val Glu Gly Ala Gln Asn Gln
        615                 620                 625 ggc aag aag gct gag ggg gcc cag aac cag ggc aag aag gcc gag ggg    2216
Gly Lys Lys Ala Glu Gly Ala Gln Asn Gln Gly Lys Lys Ala Glu Gly
    630                 635                 640 gct cag aac cag ggc aaa aag gcc gag gga gcc cag aac cag ggc caa    2264
Ala Gln Asn Gln Gly Lys Lys Ala Glu Gly Ala Gln Asn Gln Gly Gln
645                 650                 655                 660 aaa gga gag gga gcc cag aat cag ggt aaa aag aca gaa ggg gct cag    2312
Lys Gly Glu Gly Ala Gln Asn Gln Gly Lys Lys Thr Glu Gly Ala Gln
                665                 670                 675 ggc aaa aag gca gaa agg agt ccc aac caa ggc aaa aaa gga gag gga    2360
Gly Lys Lys Ala Glu Arg Ser Pro Asn Gln Gly Lys Lys Gly Glu Gly
            680                 685                 690 gct ccc atc cag ggc aaa aag gca gat tcg gtt gct aat cag ggc aca    2408
Ala Pro Ile Gln Gly Lys Lys Ala Asp Ser Val Ala Asn Gln Gly Thr
        695                 700                 705 aag gta gag ggt att aca aac cag ggg aaa aaa gca gaa ggg tcc ccc    2456
Lys Val Glu Gly Ile Thr Asn Gln Gly Lys Lys Ala Glu Gly Ser Pro
    710                 715                 720 agt gaa ggc aaa aag gca gaa ggg tcc ccc aac caa ggc aaa aag gca    2504
Ser Glu Gly Lys Lys Ala Glu Gly Ser Pro Asn Gln Gly Lys Lys Ala
725                 730                 735                 740 gac gca gct gcc aat cag ggt aaa aag aca gag tca gct tct gtc cag    2552
Asp Ala Ala Ala Asn Gln Gly Lys Lys Thr Glu Ser Ala Ser Val Gln
                745                 750                 755 ggc aga aat aca gat gtg gcc cag agc cca gag gca cca aag caa gag    2600
Gly Arg Asn Thr Asp Val Ala Gln Ser Pro Glu Ala Pro Lys Gln Glu
            760                 765                 770 gct cct gcc aag aag aag tct ggt tca aag aaa aaa ggt gag cct ggg    2648
Ala Pro Ala Lys Lys Lys Ser Gly Ser Lys Lys Lys Gly Glu Pro Gly
```

|  |  |
|---|---|
| 775 780 785 | |
| ccc cca gat gcc gac ggc cct ctc tac ctc ccc tac aag acg ctg gtc<br>Pro Pro Asp Ala Asp Gly Pro Leu Tyr Leu Pro Tyr Lys Thr Leu Val<br>790 795 800 | 2696 |
| tcc acg gtt ggg agc atg gtg ttc aac gag ggc gag gcc cag cgg ctc<br>Ser Thr Val Gly Ser Met Val Phe Asn Glu Gly Glu Ala Gln Arg Leu<br>805 810 815 820 | 2744 |
| atc gag atc ctg tct gag aag gct ggc atc att cag gac acc tgg cac<br>Ile Glu Ile Leu Ser Glu Lys Ala Gly Ile Ile Gln Asp Thr Trp His<br>825 830 835 | 2792 |
| aag gcc act cag aag ggt gac cct gtg gcg att ctg aaa cgc cag ctg<br>Lys Ala Thr Gln Lys Gly Asp Pro Val Ala Ile Leu Lys Arg Gln Leu<br>840 845 850 | 2840 |
| gaa gag aag gaa aaa ctg ctg gcc aca gaa cag gaa gat gcg gct gtc<br>Glu Glu Lys Glu Lys Leu Leu Ala Thr Glu Gln Glu Asp Ala Ala Val<br>855 860 865 | 2888 |
| gcc aag agc aaa ctg agg gag ctc aac aag gag atg gca gca gaa aag<br>Ala Lys Ser Lys Leu Arg Glu Leu Asn Lys Glu Met Ala Ala Glu Lys<br>870 875 880 | 2936 |
| gcc aaa gca gca gcc ggg gag gcc aaa gtg aaa aag cag ctg gtg gcc<br>Ala Lys Ala Ala Ala Gly Glu Ala Lys Val Lys Lys Gln Leu Val Ala<br>885 890 895 900 | 2984 |
| cgg gag cag gag atc acg gct gtg cag gca cgc atg cag gcc agc tac<br>Arg Glu Gln Glu Ile Thr Ala Val Gln Ala Arg Met Gln Ala Ser Tyr<br>905 910 915 | 3032 |
| cgg gag cac gtg aag gag gtg cag cag ctg cag ggc aag atc cgg act<br>Arg Glu His Val Lys Glu Val Gln Gln Leu Gln Gly Lys Ile Arg Thr<br>920 925 930 | 3080 |
| ctt cag gag cag ctg gag aat ggc ccc aac acg cag ctg gcc cgc ctg<br>Leu Gln Glu Gln Leu Glu Asn Gly Pro Asn Thr Gln Leu Ala Arg Leu<br>935 940 945 | 3128 |
| cag cag gag aac tcc atc ctg cgg gat gcc ttg aac cag gcc acg agc<br>Gln Gln Glu Asn Ser Ile Leu Arg Asp Ala Leu Asn Gln Ala Thr Ser<br>950 955 960 | 3176 |
| cag gtg gag agc aag cag aac gca gag ctg gcc aag ctt cgg cag gag<br>Gln Val Glu Ser Lys Gln Asn Ala Glu Leu Ala Lys Leu Arg Gln Glu<br>965 970 975 980 | 3224 |
| ctc agc aag gtc agc aaa gag ctg gtg gag aag tca gag gct gtg cgg<br>Leu Ser Lys Val Ser Lys Glu Leu Val Glu Lys Ser Glu Ala Val Arg<br>985 990 995 | 3272 |
| caa gat gag cag cag cgg aaa gct ctg gaa gcc aag gca gct gcc ttc<br>Gln Asp Glu Gln Gln Arg Lys Ala Leu Glu Ala Lys Ala Ala Ala Phe<br>1000 1005 1010 | 3320 |
| gag aag cag gtc ctg cag ctg cag gcg tcc cac agg gag agt gag gag<br>Glu Lys Gln Val Leu Gln Leu Gln Ala Ser His Arg Glu Ser Glu Glu<br>1015 1020 1025 | 3368 |
| gcc ctg cag aag cgc ctg gac gag gtc agc cgg gag ctg tgc cac acg<br>Ala Leu Gln Lys Arg Leu Asp Glu Val Ser Arg Glu Leu Cys His Thr<br>1030 1035 1040 | 3416 |
| cag agc agc cac gcc agc ctc cgg gcg gat gcc gag aag gcc cag gag<br>Gln Ser Ser His Ala Ser Leu Arg Ala Asp Ala Glu Lys Ala Gln Glu<br>1045 1050 1055 1060 | 3464 |
| caa cag cag cag atg gcc gag ctg cac agc aag tta cag tcc tcc gag<br>Gln Gln Gln Gln Met Ala Glu Leu His Ser Lys Leu Gln Ser Ser Glu<br>1065 1070 1075 | 3512 |
| gcg gag gtg cgc agc aaa tgc gag gag ctg agt ggc ctc cac ggg cag<br>Ala Glu Val Arg Ser Lys Cys Glu Glu Leu Ser Gly Leu His Gly Gln<br>1080 1085 1090 | 3560 |
| ctc cag gag gcc agg gcg gag aac tcc cag ctc aca gag aga atc cgt<br>Leu Gln Glu Ala Arg Ala Glu Asn Ser Gln Leu Thr Glu Arg Ile Arg | 3608 |

```
                    1095              1100              1105
tcc att gag gcc ctg ctg gag gcg ggc cag gcg cgg gat gcc cag gac      3656
Ser Ile Glu Ala Leu Leu Glu Ala Gly Gln Ala Arg Asp Ala Gln Asp
        1110              1115              1120 gtc cag gcc agc cag gcg gag gct gac cag cag cag act cgc ctc aag      3704
Val Gln Ala Ser Gln Ala Glu Ala Asp Gln Gln Gln Thr Arg Leu Lys
1125              1130              1135              1140 gag ctg gag tcc cag gtg tcg ggt ctg gag aag gag gcc atc gag ctc      3752
Glu Leu Glu Ser Gln Val Ser Gly Leu Glu Lys Glu Ala Ile Glu Leu
                    1145              1150              1155 agg gag gcc gtc gag cag cag aaa gtg aag aac aat gac ctc cgg gag      3800
Arg Glu Ala Val Glu Gln Gln Lys Val Lys Asn Asn Asp Leu Arg Glu
            1160              1165              1170 aag aac tgg aag gcc atg gag gca ctg gcc acg gcc gag cag gcc tgc      3848
Lys Asn Trp Lys Ala Met Glu Ala Leu Ala Thr Ala Glu Gln Ala Cys
        1175              1180              1185 aag gag aag ctg cac tcc ctg acc cag gcc aag gag gaa tcg gag aag      3896
Lys Glu Lys Leu His Ser Leu Thr Gln Ala Lys Glu Glu Ser Glu Lys
    1190              1195              1200 cag ctc tgt ctg att gag gcg cag acc atg gag gcc ctg ctg gct ctg      3944
Gln Leu Cys Leu Ile Glu Ala Gln Thr Met Glu Ala Leu Leu Ala Leu
1205              1210              1215              1220 ctc cca gaa ctc tct gtc ttg gca caa cag aat tac acc gag tgg ctg      3992
Leu Pro Glu Leu Ser Val Leu Ala Gln Gln Asn Tyr Thr Glu Trp Leu
                    1225              1230              1235 cag gat ctc aaa gag aaa ggc ccc acg ctg ctg aag cac ccg cca gct      4040
Gln Asp Leu Lys Glu Lys Gly Pro Thr Leu Leu Lys His Pro Pro Ala
            1240              1245              1250 ccc gcg gag ccc tcc tcg gac ctg gcc tcc aag ttg agg gag gcc gag      4088
Pro Ala Glu Pro Ser Ser Asp Leu Ala Ser Lys Leu Arg Glu Ala Glu
        1255              1260              1265 gag acg cag agc aca ctg cag gcc gag tgt gac cag tac cgc agc atc      4136
Glu Thr Gln Ser Thr Leu Gln Ala Glu Cys Asp Gln Tyr Arg Ser Ile
    1270              1275              1280 ctg gcg gag acg gag ggc atg ctc aga gac ctg cag aag agc gtg gag      4184
Leu Ala Glu Thr Glu Gly Met Leu Arg Asp Leu Gln Lys Ser Val Glu
1285              1290              1295              1300 gag gag gag cag gtg tgg agg gcc aag gtg ggc gcc gca gag gag gag      4232
Glu Glu Glu Gln Val Trp Arg Ala Lys Val Gly Ala Ala Glu Glu Glu
                    1305              1310              1315 ctc cag aag tcc cgg gtc aca gtg aag cat ctc gaa gag att gta gag      4280
Leu Gln Lys Ser Arg Val Thr Val Lys His Leu Glu Glu Ile Val Glu
            1320              1325              1330 aag cta aaa gga gaa ctt gaa agt tcg gac cag gtg agg gag cac acg      4328
Lys Leu Lys Gly Glu Leu Glu Ser Ser Asp Gln Val Arg Glu His Thr
        1335              1340              1345 ttg cat ttg gag gca gag ctg gaa aag cac atg gcg gcc gcc agc gcc      4376
Leu His Leu Glu Ala Glu Leu Glu Lys His Met Ala Ala Ala Ser Ala
    1350              1355              1360 gag tgc cag aac tac gcc aag gag gtg gca ggg ctg agg caa ctt ctc      4424
Glu Cys Gln Asn Tyr Ala Lys Glu Val Ala Gly Leu Arg Gln Leu Leu
1365              1370              1375              1380 cta gaa tct caa tct cag ctc gat gcc gcc aag agc gaa gcc cag aaa      4472
Leu Glu Ser Gln Ser Gln Leu Asp Ala Ala Lys Ser Glu Ala Gln Lys
                    1385              1390              1395 cag agc gat gag ctt gcc ctg gtc agg cag cag ttg agt gaa atg aag      4520
Gln Ser Asp Glu Leu Ala Leu Val Arg Gln Gln Leu Ser Glu Met Lys
            1400              1405              1410 agc cac gta gag gat ggt gac ata gct ggg gcc cca gct tcc tcc cca      4568
Ser His Val Glu Asp Gly Asp Ile Ala Gly Ala Pro Ala Ser Ser Pro
```

```
                   1415                  1420                  1425
gag gcg ccc cca gcc gag cag gac ccc gtt cag ctg aag acg cag ctg        4616
Glu Ala Pro Pro Ala Glu Gln Asp Pro Val Gln Leu Lys Thr Gln Leu
            1430                    1435                1440 gag tgg aca gaa gcc atc ctg gag gat gag cag aca cag cgg cag aag        4664
Glu Trp Thr Glu Ala Ile Leu Glu Asp Glu Gln Thr Gln Arg Gln Lys
1445                    1450                    1455                1460 ctc acg gcc gag ttt gag gag gct cag acc tcg gca tgt cgg tta caa        4712
Leu Thr Ala Glu Phe Glu Glu Ala Gln Thr Ser Ala Cys Arg Leu Gln
                    1465                    1470                1475 gaa gaa ttg gag aag ctc cgc aca gcc ggc ccc cta gag tct tca gaa        4760
Glu Glu Leu Glu Lys Leu Arg Thr Ala Gly Pro Leu Glu Ser Ser Glu
                1480                    1485                1490 aca gag gag gcc tca cag ctg aag gag aga cta gaa aaa gag aag aag        4808
Thr Glu Glu Ala Ser Gln Leu Lys Glu Arg Leu Glu Lys Glu Lys Lys
            1495                    1500                1505 tta aca agt gac ctg ggg cgc gcc gcc acg aga ctg cag gag ctt ctg        4856
Leu Thr Ser Asp Leu Gly Arg Ala Ala Thr Arg Leu Gln Glu Leu Leu
        1510                    1515                1520 aag acg acc cag gag cag ctg gca agg gag aag gac acg gtg aag aag        4904
Lys Thr Thr Gln Glu Gln Leu Ala Arg Glu Lys Asp Thr Val Lys Lys
1525                    1530                    1535                1540 ctg cag gaa cag ctg gaa aag gca gag gac ggc agc agc tca aag gag        4952
Leu Gln Glu Gln Leu Glu Lys Ala Glu Asp Gly Ser Ser Ser Lys Glu
                    1545                    1550                1555 ggc acc tct gtc tga gtttcctctt tggaaaaaga agttactgtt caacttacca       5007
Gly Thr Ser Val
            1560 aaatgcctta cacattcctt acaaataaac caaccaacct acacagcgtt atccaggccc     5067 aacttccggt actccgagag aagccatgag agacaagtct cttagagcca cagaagtaga     5127 ccttccagag ccccagtttg taaatgaacc tgtgtcacat ttgataaaca ctatcctggg     5187 cgcagccccg ggccaccgcc gagtgacgcc aaagccctgg ttgactctga cagccccgtg     5247 ggtgtgtggg aggccgggcg ctctggggtc tgtctgtcag tgcaatcgtt tagtgttttt     5307 tcagtggggc ggggcgggaa gcgggtggga ccgggcagcc agttctcaaa ggctgtgggg     5367 ccgactggag gccacagccc ctcaccccta gacgttgcca accagaactg acgtgtgacc     5427 tcctgggtgt tgatgccatt aaaaccaacg ttggtgcccg g                         5468

<210> SEQ ID NO 46
<211> LENGTH: 1560
<212> TYPE: PRT
<213> ORGANISM: Homo sapiens

<400> SEQUENCE: 46

Met Asp Ile Tyr Asp Thr Gln Thr Leu Gly Val Val Phe Gly Gly
1               5                   10                  15

Phe Met Val Val Ser Ala Ile Gly Ile Phe Leu Val Ser Thr Phe Ser
                20                  25                  30

Met Lys Glu Thr Ser Tyr Glu Glu Ala Leu Ala Asn Gln Arg Lys Glu
            35                  40                  45

Met Ala Lys Thr His His Gln Lys Val Glu Lys Lys Lys Glu Lys
        50                  55                  60

Thr Val Glu Lys Lys Gly Lys Thr Lys Lys Glu Glu Lys Pro Asn
65                  70                  75                  80

Gly Lys Ile Pro Asp His Asp Pro Ala Pro Asn Val Thr Val Leu Leu
                85                  90                  95
```

```
Arg Glu Pro Val Arg Ala Pro Ala Val Ala Val Ala Pro Thr Pro Val
            100                 105                 110

Gln Pro Pro Ile Ile Val Ala Pro Val Ala Thr Val Pro Ala Met Pro
        115                 120                 125

Gln Glu Lys Leu Ala Ser Ser Pro Lys Asp Lys Lys Lys Glu Lys
    130                 135                 140

Lys Val Ala Lys Val Glu Pro Ala Val Ser Ser Val Val Asn Ser Ile
145                 150                 155                 160

Gln Val Leu Thr Ser Lys Ala Ala Ile Leu Glu Thr Ala Pro Lys Glu
                165                 170                 175

Val Pro Met Val Val Pro Pro Val Gly Ala Lys Gly Asn Thr Pro
            180                 185                 190

Ala Thr Gly Thr Thr Gln Gly Lys Lys Ala Glu Gly Thr Gln Asn Gln
            195                 200                 205

Ser Lys Lys Ala Glu Gly Ala Pro Asn Gln Gly Arg Lys Ala Glu Gly
    210                 215                 220

Thr Pro Asn Gln Gly Lys Lys Thr Glu Gly Thr Pro Asn Gln Gly Lys
225                 230                 235                 240

Lys Ala Glu Gly Thr Pro Asn Gln Gly Lys Lys Ala Glu Gly Thr Pro
            245                 250                 255

Asn Gln Gly Lys Lys Ala Glu Gly Ala Gln Asn Gln Gly Lys Lys Val
            260                 265                 270

Asp Thr Thr Pro Asn Gln Gly Lys Lys Val Glu Gly Ala Pro Thr Gln
    275                 280                 285

Gly Arg Lys Ala Glu Gly Ala Gln Asn Gln Ala Lys Lys Val Glu Gly
    290                 295                 300

Ala Gln Asn Gln Gly Lys Lys Ala Glu Gly Ala Gln Asn Gln Gly Lys
305                 310                 315                 320

Lys Gly Glu Gly Ala Gln Asn Gln Gly Lys Lys Ala Glu Gly Ala Gln
            325                 330                 335

Asn Gln Gly Lys Lys Ala Glu Gly Ala Gln Asn Gln Gly Lys Lys Ala
            340                 345                 350

Glu Gly Ala Gln Asn Gln Gly Lys Lys Ala Glu Gly Ala Gln Asn Gln
            355                 360                 365

Gly Lys Lys Ala Glu Gly Ala Gln Asn Gln Gly Lys Lys Ala Glu Gly
    370                 375                 380

Ala Gln Asn Gln Gly Lys Lys Val Glu Gly Ala Gln Asn Gln Gly Lys
385                 390                 395                 400

Lys Ala Glu Gly Ala Gln Asn Gln Gly Lys Lys Ala Glu Gly Ala Gln
            405                 410                 415

Asn Gln Gly Lys Lys Ala Glu Gly Ala Gln Asn Gln Gly Lys Lys Ala
            420                 425                 430

Glu Gly Ala Gln Asn Gln Gly Lys Lys Ala Glu Gly Ala Gln Asn Gln
            435                 440                 445

Asp Lys Lys Ala Glu Gly Ala Gln Asn Gln Gly Arg Lys Ala Glu Gly
    450                 455                 460

Ala Gln Asn Gln Gly Arg Lys Ala Glu Gly Ala Gln Asn Gln Gly Lys
465                 470                 475                 480

Lys Ala Glu Gly Ala Pro Asn Gln Gly Lys Lys Ala Glu Gly Ala Pro
            485                 490                 495

Asn Gln Gly Lys Lys Ala Glu Gly Thr Pro Asn Gln Gly Lys Lys Ala
            500                 505                 510

Glu Gly Thr Pro Asn Gln Gly Lys Lys Ala Glu Gly Thr Pro Asn Gln
            515                 520                 525
```

```
Gly Lys Lys Ala Glu Gly Ala Gln Asn Gln Gly Lys Lys Ala Glu Gly
    530                 535                 540

Ala Gln Asn Gln Gly Lys Lys Ala Glu Gly Thr Pro Asn Gln Gly Lys
545                 550                 555                 560

Lys Ala Glu Gly Ala Gln Asn Gln Gly Lys Lys Ala Glu Gly Ala Gln
                565                 570                 575

Asn Gln Gly Lys Lys Ala Glu Gly Ala Gln Asn Gln Gly Lys Lys Ala
            580                 585                 590

Glu Gly Ala Gln Asn Gln Gly Lys Lys Ala Glu Gly Ala Gln Asn Gln
        595                 600                 605

Gly Lys Lys Ala Glu Gly Ala Gln Asn Gln Gly Lys Lys Val Glu Gly
    610                 615                 620

Ala Gln Asn Gln Gly Lys Lys Ala Glu Gly Ala Gln Asn Gln Gly Lys
625                 630                 635                 640

Lys Ala Glu Gly Ala Gln Asn Gln Gly Lys Lys Ala Glu Gly Ala Gln
                645                 650                 655

Asn Gln Gly Gln Lys Gly Glu Gly Ala Gln Asn Gln Gly Lys Lys Thr
            660                 665                 670

Glu Gly Ala Gln Gly Lys Lys Ala Glu Arg Ser Pro Asn Gln Gly Lys
        675                 680                 685

Lys Gly Glu Gly Ala Pro Ile Gln Gly Lys Lys Ala Asp Ser Val Ala
    690                 695                 700

Asn Gln Gly Thr Lys Val Glu Gly Ile Thr Asn Gln Gly Lys Lys Ala
705                 710                 715                 720

Glu Gly Ser Pro Ser Glu Gly Lys Lys Ala Glu Gly Ser Pro Asn Gln
                725                 730                 735

Gly Lys Lys Ala Asp Ala Ala Asn Gln Gly Lys Lys Thr Glu Ser
            740                 745                 750

Ala Ser Val Gln Gly Arg Asn Thr Asp Val Ala Gln Ser Pro Glu Ala
        755                 760                 765

Pro Lys Gln Glu Ala Pro Ala Lys Lys Ser Gly Ser Lys Lys Lys
    770                 775                 780

Gly Glu Pro Gly Pro Pro Asp Ala Asp Gly Pro Leu Tyr Leu Pro Tyr
785                 790                 795                 800

Lys Thr Leu Val Ser Thr Val Gly Ser Met Val Phe Asn Glu Gly Glu
                805                 810                 815

Ala Gln Arg Leu Ile Glu Ile Leu Ser Glu Lys Ala Gly Ile Ile Gln
            820                 825                 830

Asp Thr Trp His Lys Ala Thr Gln Lys Gly Asp Pro Val Ala Ile Leu
        835                 840                 845

Lys Arg Gln Leu Glu Glu Lys Glu Lys Leu Leu Ala Thr Glu Gln Glu
    850                 855                 860

Asp Ala Ala Val Ala Lys Ser Lys Leu Arg Glu Leu Asn Lys Glu Met
865                 870                 875                 880

Ala Ala Glu Lys Ala Lys Ala Ala Gly Glu Ala Lys Val Lys Lys
                885                 890                 895

Gln Leu Val Ala Arg Glu Gln Glu Ile Thr Ala Val Gln Ala Arg Met
            900                 905                 910

Gln Ala Ser Tyr Arg Glu His Val Lys Glu Val Gln Leu Gln Gly
        915                 920                 925

Lys Ile Arg Thr Leu Gln Glu Gln Leu Glu Asn Gly Pro Asn Thr Gln
    930                 935                 940

Leu Ala Arg Leu Gln Gln Glu Asn Ser Ile Leu Arg Asp Ala Leu Asn
```

-continued

```
                945                 950                 955                 960
Gln Ala Thr Ser Gln Val Glu Ser Lys Gln Asn Ala Glu Leu Ala Lys
                    965                 970                 975
Leu Arg Gln Glu Leu Ser Lys Val Ser Lys Glu Leu Val Glu Lys Ser
                    980                 985                 990
Glu Ala Val Arg Gln Asp Glu Gln Arg Lys Ala Leu Glu Ala Lys
                995                1000                1005
Ala Ala Ala Phe Glu Lys Gln Val Leu Gln Leu Gln Ala Ser His Arg
            1010                1015                1020
Glu Ser Glu Glu Ala Leu Gln Lys Arg Leu Asp Glu Val Ser Arg Glu
1025                1030                1035                1040
Leu Cys His Thr Gln Ser Ser His Ala Ser Leu Arg Ala Asp Ala Glu
                1045                1050                1055
Lys Ala Gln Glu Gln Gln Gln Met Ala Glu Leu His Ser Lys Leu
                1060                1065                1070
Gln Ser Ser Glu Ala Glu Val Arg Ser Lys Cys Glu Glu Leu Ser Gly
            1075                1080                1085
Leu His Gly Gln Leu Gln Glu Ala Arg Ala Glu Asn Ser Gln Leu Thr
        1090                1095                1100
Glu Arg Ile Arg Ser Ile Glu Ala Leu Leu Glu Ala Gly Gln Ala Arg
1105                1110                1115                1120
Asp Ala Gln Asp Val Gln Ala Ser Gln Ala Glu Ala Asp Gln Gln Gln
                1125                1130                1135
Thr Arg Leu Lys Glu Leu Glu Ser Gln Val Ser Gly Leu Glu Lys Glu
                1140                1145                1150
Ala Ile Glu Leu Arg Glu Ala Val Glu Gln Gln Lys Val Lys Asn Asn
                1155                1160                1165
Asp Leu Arg Glu Lys Asn Trp Lys Ala Met Glu Ala Leu Ala Thr Ala
        1170                1175                1180
Glu Gln Ala Cys Lys Glu Lys Leu His Ser Leu Thr Gln Ala Lys Glu
1185                1190                1195                1200
Glu Ser Glu Lys Gln Leu Cys Leu Ile Glu Ala Gln Thr Met Glu Ala
                1205                1210                1215
Leu Leu Ala Leu Leu Pro Glu Leu Ser Val Leu Ala Gln Gln Asn Tyr
            1220                1225                1230
Thr Glu Trp Leu Gln Asp Leu Lys Glu Lys Gly Pro Thr Leu Leu Lys
            1235                1240                1245
His Pro Pro Ala Pro Ala Glu Pro Ser Ser Asp Leu Ala Ser Lys Leu
        1250                1255                1260
Arg Glu Ala Glu Glu Thr Gln Ser Thr Leu Gln Ala Glu Cys Asp Gln
1265                1270                1275                1280
Tyr Arg Ser Ile Leu Ala Glu Thr Glu Gly Met Leu Arg Asp Leu Gln
            1285                1290                1295
Lys Ser Val Glu Glu Glu Gln Val Trp Arg Ala Lys Val Gly Ala
            1300                1305                1310
Ala Glu Glu Glu Leu Gln Lys Ser Arg Val Thr Val Lys His Leu Glu
        1315                1320                1325
Glu Ile Val Glu Lys Leu Lys Gly Glu Leu Glu Ser Ser Asp Gln Val
        1330                1335                1340
Arg Glu His Thr Leu His Leu Glu Ala Glu Leu Glu Lys His Met Ala
1345                1350                1355                1360
Ala Ala Ser Ala Glu Cys Gln Asn Tyr Ala Lys Glu Val Ala Gly Leu
            1365                1370                1375
```

```
                      -continued

Arg Gln Leu Leu Leu Glu Ser Gln Ser Gln Leu Asp Ala Ala Lys Ser
            1380                1385                1390

Glu Ala Gln Lys Gln Ser Asp Glu Leu Ala Leu Val Arg Gln Gln Leu
        1395                1400                1405

Ser Glu Met Lys Ser His Val Glu Asp Gly Asp Ile Ala Gly Ala Pro
    1410                1415                1420

Ala Ser Ser Pro Glu Ala Pro Pro Ala Glu Gln Asp Pro Val Gln Leu
1425                1430                1435                1440

Lys Thr Gln Leu Glu Trp Thr Glu Ala Ile Leu Glu Asp Glu Gln Thr
                1445                1450                1455

Gln Arg Gln Lys Leu Thr Ala Glu Phe Glu Gly Ala Gln Thr Ser Ala
            1460                1465                1470

Cys Arg Leu Gln Glu Glu Leu Glu Lys Leu Arg Thr Ala Gly Pro Leu
        1475                1480                1485

Glu Ser Ser Glu Thr Glu Glu Ala Ser Gln Leu Lys Glu Arg Leu Glu
    1490                1495                1500

Lys Glu Lys Lys Leu Thr Ser Asp Leu Gly Arg Ala Ala Thr Arg Leu
1505                1510                1515                1520

Gln Glu Leu Leu Lys Thr Thr Gln Glu Gln Leu Ala Arg Glu Lys Asp
                1525                1530                1535

Thr Val Lys Lys Leu Gln Glu Gln Leu Glu Lys Ala Glu Asp Gly Ser
            1540                1545                1550

Ser Ser Lys Glu Gly Thr Ser Val
        1555                1560

<210> SEQ ID NO 47
<211> LENGTH: 5425
<212> TYPE: DNA
<213> ORGANISM: Canis familiaris
<220> FEATURE:
<221> NAME/KEY: CDS
<222> LOCATION: (244)..(4848)

<400> SEQUENCE: 47
gaggcagaaa gtgccacgac tccacacgcg cgcacgcagc cagcgagcgg ccggagcgga    60
cggcggacgg ggcggacggc ggtggggtcg cggcgcctgc agctgctcgg ggcggcttct   120
cggcggaggc tcggccggct cctctctccc ggctccgcgg cggcggcggc ggcggcggcg   180
gctcctgccc tttcgctctc cctcccgcgt ctccggctgc aggtaaaggg aaagcaagcc   240 agg atg gat att tac gac act cag acc ttg ggg gtt atg gta ttc ggt    288
    Met Asp Ile Tyr Asp Thr Gln Thr Leu Gly Val Met Val Phe Gly
    1               5                   10                  15 gga ttc atg gtc gtt tct gcc atc ggc atc ttc ctg gtg tca acc ttt    336
Gly Phe Met Val Val Ser Ala Ile Gly Ile Phe Leu Val Ser Thr Phe
                20                  25                  30 tcc atg aag gag acg tca tat gaa gaa gcc cta gcc aac cag cgc aag    384
Ser Met Lys Glu Thr Ser Tyr Glu Glu Ala Leu Ala Asn Gln Arg Lys
            35                  40                  45 gag atg gca aaa act cac cac cag aaa gta gag aag aaa aag aag gag    432
Glu Met Ala Lys Thr His His Gln Lys Val Glu Lys Lys Lys Lys Glu
        50                  55                  60 aaa aca gtg gag aag aaa gga aaa acc aag aaa aag gaa gag aaa cct    480
Lys Thr Val Glu Lys Lys Gly Lys Thr Lys Lys Lys Glu Glu Lys Pro
    65                  70                  75 aac ggg aag ata cct gac cat gag cca gcc ccc aat gtg acc atc ctt    528
Asn Gly Lys Ile Pro Asp His Glu Pro Ala Pro Asn Val Thr Ile Leu
80                  85                  90                  95 ctc aaa gac cca gtg agg gca ccc gca gtg ccc gtg gct cca act ccg    576
```

```
                    Leu Lys Asp Pro Val Arg Ala Pro Ala Val Pro Val Ala Pro Thr Pro
                                    100                 105                 110 gtc cag cct cct gtg gtc att gcc cct gta gcc aca gta cca gcc atg         624
Val Gln Pro Pro Val Val Ile Ala Pro Val Ala Thr Val Pro Ala Met
            115                 120                 125 ccc caa gag aag ttg gcc cct tct cct aag gac aaa aag aaa aag gag         672
Pro Gln Glu Lys Leu Ala Pro Ser Pro Lys Asp Lys Lys Lys Lys Glu
            130                 135                 140 aaa aaa gtg gca aag gtg gaa cca gca gtc agt tct gta gtg aat tcc         720
Lys Lys Val Ala Lys Val Glu Pro Ala Val Ser Ser Val Val Asn Ser
        145                 150                 155 gtc caa gtt ctt gcc tcc aag gct gcc atc tta gaa act gct ccc aag         768
Val Gln Val Leu Ala Ser Lys Ala Ala Ile Leu Glu Thr Ala Pro Lys
160                 165                 170                 175 gag gtg cct atg gtg gtt gtg ccc cca gtg ggt gcc aag gcc ggt acc         816
Glu Val Pro Met Val Val Val Pro Pro Val Gly Ala Lys Ala Gly Thr
                    180                 185                 190 cca gcc acc agc act gca cag ggc aaa aag gca gag gga gcc cag aac         864
Pro Ala Thr Ser Thr Ala Gln Gly Lys Lys Ala Glu Gly Ala Gln Asn
                195                 200                 205 cag agc aga aag gca gag gga gcc ccc aac cag ggc aaa aag gca gag         912
Gln Ser Arg Lys Ala Glu Gly Ala Pro Asn Gln Gly Lys Lys Ala Glu
            210                 215                 220 ggg gcc ctc aac caa ggc aaa aag gca gag ggg gcc cag aat cag ggc         960
Gly Ala Leu Asn Gln Gly Lys Lys Ala Glu Gly Ala Gln Asn Gln Gly
        225                 230                 235 aaa aag gta gaa gtg gcc cca aac caa ggc aaa aag gca gag ggg ggc        1008
Lys Lys Val Glu Val Ala Pro Asn Gln Gly Lys Lys Ala Glu Gly Gly
240                 245                 250                 255 cag aat cag ggc aaa aag gta gaa ggg gcc cag aat cag ggc aaa aag        1056
Gln Asn Gln Gly Lys Lys Val Glu Gly Ala Gln Asn Gln Gly Lys Lys
                    260                 265                 270 gca gaa gga acc cca aac cag ggc aaa aag gca gaa ggg gcc ccc aac        1104
Ala Glu Gly Thr Pro Asn Gln Gly Lys Lys Ala Glu Gly Ala Pro Asn
                275                 280                 285 caa ggc aaa aag aca gat ggg gct ccc aac cag ggc aaa aag tca gaa        1152
Gln Gly Lys Lys Thr Asp Gly Ala Pro Asn Gln Gly Lys Lys Ser Glu
            290                 295                 300 gga gct cca aac cag ggc aaa aag gca gag ggg gcc cag aat cag ggc        1200
Gly Ala Pro Asn Gln Gly Lys Lys Ala Glu Gly Ala Gln Asn Gln Gly
305                 310                 315 aaa aag gta gaa gtg gcc cca aac caa ggc aaa aag gca gag ggg ggc        1248
Lys Lys Val Glu Val Ala Pro Asn Gln Gly Lys Lys Ala Glu Gly Gly
320                 325                 330                 335 cag aat cag ggc aaa aag gta gaa ggg gcc cag aat cag ggc aaa aag        1296
Gln Asn Gln Gly Lys Lys Val Glu Gly Ala Gln Asn Gln Gly Lys Lys
                    340                 345                 350 gca gaa gga acc cca aac cag ggc aaa aag gca gaa ggg gcc ccc aac        1344
Ala Glu Gly Thr Pro Asn Gln Gly Lys Lys Ala Glu Gly Ala Pro Asn
                355                 360                 365 caa ggc aaa aag aca gat ggg gct ccc aac cag ggc aaa aag tca gaa        1392
Gln Gly Lys Lys Thr Asp Gly Ala Pro Asn Gln Gly Lys Lys Ser Glu
            370                 375                 380 gga gct cca aac cag ggc aaa aaa gta gag ggg gcc cag aat caa ggc        1440
Gly Ala Pro Asn Gln Gly Lys Lys Val Glu Gly Ala Gln Asn Gln Gly
385                 390                 395 aaa aag gta gag ggg gtg cag aat cag ggc aaa aaa gcc gaa gga gca        1488
Lys Lys Val Glu Gly Val Gln Asn Gln Gly Lys Lys Ala Glu Gly Ala
400                 405                 410                 415 cag aat cag ggc aaa aag gca gaa ggg acc tcc agc cag ggt aga aaa        1536
```

|     |     |     |     |     |     |     |     |     |     |     |     |     |      |
| --- | --- | --- | --- | --- | --- | --- | --- | --- | --- | --- | --- | --- | ---- |
| Gln | Asn | Gln | Gly | Lys | Lys | Ala | Glu | Gly | Thr | Ser | Ser | Gln | Gly | Arg | Lys |
|     |     |     |     | 420 |     |     |     |     | 425 |     |     |     |     | 430 |     |

| gag | gag | ggg | acc | cca | aac | ctg | ggc | aaa | aag | gca | gag | ggg | agc | ccc | aat | 1584 |
| --- | --- | --- | --- | --- | --- | --- | --- | --- | --- | --- | --- | --- | --- | --- | --- | ---- |
| Glu | Glu | Gly | Thr | Pro | Asn | Leu | Gly | Lys | Lys | Ala | Glu | Gly | Ser | Pro | Asn |      |
|     |     |     | 435 |     |     |     |     | 440 |     |     |     |     | 445 |     |     |      |

| cag | ggc | aaa | aag | gtg | gaa | gtg | gtt | cag | aac | cag | agc | aaa | aag | gta | gag | 1632 |
| Gln | Gly | Lys | Lys | Val | Glu | Val | Val | Gln | Asn | Gln | Ser | Lys | Lys | Val | Glu |      |
|     |     | 450 |     |     |     |     | 455 |     |     |     |     | 460 |     |     |     |      |

| gga | gcc | ccc | aac | cag | ggc | aaa | aaa | gca | gag | ggg | tct | cag | aac | cag | ggc | 1680 |
| Gly | Ala | Pro | Asn | Gln | Gly | Lys | Lys | Ala | Glu | Gly | Ser | Gln | Asn | Gln | Gly |      |
|     | 465 |     |     |     |     | 470 |     |     |     |     | 475 |     |     |     |     |      |

| aaa | aag | aca | gaa | ggg | gcc | tcc | aac | caa | ggc | aaa | aag | gtg | gat | ggg | gct | 1728 |
| Lys | Lys | Thr | Glu | Gly | Ala | Ser | Asn | Gln | Gly | Lys | Lys | Val | Asp | Gly | Ala |      |
| 480 |     |     |     |     | 485 |     |     |     |     | 490 |     |     |     |     | 495 |      |

| cag | aac | cag | ggc | aaa | aag | gca | gag | gga | gcc | ccc | aac | cag | ggt | aaa | aag | 1776 |
| Gln | Asn | Gln | Gly | Lys | Lys | Ala | Glu | Gly | Ala | Pro | Asn | Gln | Gly | Lys | Lys |      |
|     |     |     | 500 |     |     |     |     | 505 |     |     |     |     | 510 |     |     |      |

| gta | gag | ggg | gct | cag | aac | cag | ggc | aaa | aag | gca | gag | ggg | acc | ccc | aac | 1824 |
| Val | Glu | Gly | Ala | Gln | Asn | Gln | Gly | Lys | Lys | Ala | Glu | Gly | Thr | Pro | Asn |      |
|     |     |     | 515 |     |     |     |     | 520 |     |     |     |     | 525 |     |     |      |

| cag | ggt | aaa | aag | gca | gag | ggg | gct | cag | aac | cag | ggc | aaa | aag | gca | gag | 1872 |
| Gln | Gly | Lys | Lys | Ala | Glu | Gly | Ala | Gln | Asn | Gln | Gly | Lys | Lys | Ala | Glu |      |
|     |     | 530 |     |     |     |     | 535 |     |     |     |     | 540 |     |     |     |      |

| ggg | gct | ccc | aac | cag | ggc | aaa | aag | gca | gag | ggg | gct | ccc | aac | cag | ggc | 1920 |
| Gly | Ala | Pro | Asn | Gln | Gly | Lys | Lys | Ala | Glu | Gly | Ala | Pro | Asn | Gln | Gly |      |
|     | 545 |     |     |     |     | 550 |     |     |     |     | 555 |     |     |     |     |      |

| aaa | aag | gca | gag | ggg | gct | ccc | aac | cag | ggc | aaa | aag | gca | gag | ggg | gct | 1968 |
| Lys | Lys | Ala | Glu | Gly | Ala | Pro | Asn | Gln | Gly | Lys | Lys | Ala | Glu | Gly | Ala |      |
| 560 |     |     |     |     | 565 |     |     |     |     | 570 |     |     |     |     | 575 |      |

| ccc | aac | cag | ggc | aaa | aag | gca | gag | gcg | gct | ccc | aac | cag | ggc | aaa | aag | 2016 |
| Pro | Asn | Gln | Gly | Lys | Lys | Ala | Glu | Ala | Ala | Pro | Asn | Gln | Gly | Lys | Lys |      |
|     |     |     | 580 |     |     |     |     | 585 |     |     |     |     | 590 |     |     |      |

| gca | gag | ggg | gct | ccc | aac | cag | ggc | aaa | aag | gca | gag | ggg | gct | ccc | aac | 2064 |
| Ala | Glu | Gly | Ala | Pro | Asn | Gln | Gly | Lys | Lys | Ala | Glu | Gly | Ala | Pro | Asn |      |
|     |     | 595 |     |     |     |     | 600 |     |     |     |     | 605 |     |     |     |      |

| cag | ggc | aaa | aag | gca | gag | gcg | gct | ccc | aac | cag | ggc | aaa | aag | gca | gag | 2112 |
| Gln | Gly | Lys | Lys | Ala | Glu | Ala | Ala | Pro | Asn | Gln | Gly | Lys | Lys | Ala | Glu |      |
|     |     |     | 610 |     |     |     |     | 615 |     |     |     |     | 620 |     |     |      |

| ggg | gct | ccc | aac | cag | ggc | aaa | aag | gca | gag | ggg | gct | ccc | aac | cag | ggc | 2160 |
| Gly | Ala | Pro | Asn | Gln | Gly | Lys | Lys | Ala | Glu | Gly | Ala | Pro | Asn | Gln | Gly |      |
|     | 625 |     |     |     |     | 630 |     |     |     |     | 635 |     |     |     |     |      |

| aaa | aag | gca | gag | ggg | gct | ccc | aac | cag | ggc | aaa | aag | gca | gag | ggg | gcc | 2208 |
| Lys | Lys | Ala | Glu | Gly | Ala | Pro | Asn | Gln | Gly | Lys | Lys | Ala | Glu | Gly | Ala |      |
| 640 |     |     |     |     | 645 |     |     |     |     | 650 |     |     |     |     | 655 |      |

| cag | aat | cag | ggc | aaa | aag | gca | gag | ggg | gct | ccc | aac | cag | ggt | aaa | aag | 2256 |
| Gln | Asn | Gln | Gly | Lys | Lys | Ala | Glu | Gly | Ala | Pro | Asn | Gln | Gly | Lys | Lys |      |
|     |     |     | 660 |     |     |     |     | 665 |     |     |     |     | 670 |     |     |      |

| gca | gat | ttg | gtt | gct | aat | caa | ggc | aca | aag | gca | gag | ggt | gtt | gca | ggc | 2304 |
| Ala | Asp | Leu | Val | Ala | Asn | Gln | Gly | Thr | Lys | Ala | Glu | Gly | Val | Ala | Gly |      |
|     |     |     | 675 |     |     |     |     | 680 |     |     |     |     | 685 |     |     |      |

| cag | ggg | aaa | aaa | gca | gag | ggg | gcc | ccc | aat | caa | ggc | aaa | aag | gga | gaa | 2352 |
| Gln | Gly | Lys | Lys | Ala | Glu | Gly | Ala | Pro | Asn | Gln | Gly | Lys | Lys | Gly | Glu |      |
|     |     | 690 |     |     |     |     | 695 |     |     |     |     | 700 |     |     |     |      |

| gga | acc | cca | aac | cag | ggc | aaa | aag | tca | gaa | gga | tct | ccc | aac | cag | ggc | 2400 |
| Gly | Thr | Pro | Asn | Gln | Gly | Lys | Lys | Ser | Glu | Gly | Ser | Pro | Asn | Gln | Gly |      |
|     | 705 |     |     |     |     | 710 |     |     |     |     | 715 |     |     |     |     |      |

| aaa | aag | gtg | gat | gcg | tct | gcc | aat | cag | agt | aaa | agg | gca | gag | tca | gct | 2448 |
| Lys | Lys | Val | Asp | Ala | Ser | Ala | Asn | Gln | Ser | Lys | Arg | Ala | Glu | Ser | Ala |      |
| 720 |     |     |     |     | 725 |     |     |     |     | 730 |     |     |     |     | 735 |      |

| cct | atc | caa | ggc | aaa | aat | gca | gat | atg | gtc | cag | agc | caa | gag | gca | cca | 2496 |

```
                                    -continued

Pro Ile Gln Gly Lys Asn Ala Asp Met Val Gln Ser Gln Glu Ala Pro
            740                 745                 750 aag caa gag gct cct gca aag aag aaa tct ggt tca aag aag aaa ggt    2544
Lys Gln Glu Ala Pro Ala Lys Lys Lys Ser Gly Ser Lys Lys Lys Gly
                755                 760                 765 gag cct ggg cct cca gac tct gac agc cct ctc tac ctc ccc tac aag    2592
Glu Pro Gly Pro Pro Asp Ser Asp Ser Pro Leu Tyr Leu Pro Tyr Lys
            770                 775                 780 acg ctg gtc tcc aca gtt gga agc atg gta ttc aac gag ggt gag gcc    2640
Thr Leu Val Ser Thr Val Gly Ser Met Val Phe Asn Glu Gly Glu Ala
        785                 790                 795 cag cgg ctc att gag atc ctg tcc gag aag gct ggt gtc att caa gac    2688
Gln Arg Leu Ile Glu Ile Leu Ser Glu Lys Ala Gly Val Ile Gln Asp
800                 805                 810                 815 acc tgg cat aag gct act cag aag ggt gac ccc gtg gcg att ctg aag    2736
Thr Trp His Lys Ala Thr Gln Lys Gly Asp Pro Val Ala Ile Leu Lys
                820                 825                 830 cgc cag cta gaa gag aag gag aag ctg ctg gcc aca gag cag gag gac    2784
Arg Gln Leu Glu Glu Lys Glu Lys Leu Leu Ala Thr Glu Gln Glu Asp
            835                 840                 845 gcg gct gtt gcg aag agc aaa ctg agg gag gtg aat aag gag ctg gca    2832
Ala Ala Val Ala Lys Ser Lys Leu Arg Glu Val Asn Lys Glu Leu Ala
        850                 855                 860 gca gaa aag gct aag gca gca gcg ggg gag gcc aag gtg aag aag cag    2880
Ala Glu Lys Ala Lys Ala Ala Ala Gly Glu Ala Lys Val Lys Lys Gln
865                 870                 875 ctg gtg gcc cgg gag cag gag atc aca gcc gtg cag gcg cgc atc gaa    2928
Leu Val Ala Arg Glu Gln Glu Ile Thr Ala Val Gln Ala Arg Ile Glu
880                 885                 890                 895 gcc agc tac cgg gag cat gtg aag gag gtg cag cag ctg cag ggc aag    2976
Ala Ser Tyr Arg Glu His Val Lys Glu Val Gln Gln Leu Gln Gly Lys
                900                 905                 910 atc cgg acc ctt cag gag cag ttg gag aac ggc ccc aac aca cag ctg    3024
Ile Arg Thr Leu Gln Glu Gln Leu Glu Asn Gly Pro Asn Thr Gln Leu
            915                 920                 925 gcc cgt ctg cag cag gaa aat tcc atc ctg agg gat gcc ttg aac cag    3072
Ala Arg Leu Gln Gln Glu Asn Ser Ile Leu Arg Asp Ala Leu Asn Gln
        930                 935                 940 gcc acg agc cag gtg gag agc aag cag aac acc gag ctg gcc aag ctc    3120
Ala Thr Ser Gln Val Glu Ser Lys Gln Asn Thr Glu Leu Ala Lys Leu
945                 950                 955 cgg cag gag ctc agc aag gtc agc aag gag ctg gtg gag aaa tca gag    3168
Arg Gln Glu Leu Ser Lys Val Ser Lys Glu Leu Val Glu Lys Ser Glu
                960                 965                 970                 975 gct gcg cgg cag gag gaa cag cag cga aag gcc ctg gag acc aaa aca    3216
Ala Ala Arg Gln Glu Glu Gln Gln Arg Lys Ala Leu Glu Thr Lys Thr
            980                 985                 990 gcc gcc ttg gag aag cag gtc cta cag ctg caa gca tct cac aag gag    3264
Ala Ala Leu Glu Lys Gln Val Leu Gln Leu Gln Ala Ser His Lys Glu
        995                 1000                1005 agt gag gag gcc ctg cag aag cgc ctg gac gag gtc agc cgg gag cta    3312
Ser Glu Glu Ala Leu Gln Lys Arg Leu Asp Glu Val Ser Arg Glu Leu
1010                1015                1020 tgc cgc tcc cag acc agc cat gcc agc ctg cgg gcg gat gcc gag aag    3360
Cys Arg Ser Gln Thr Ser His Ala Ser Leu Arg Ala Asp Ala Glu Lys
                1025                1030                1035 gcc cag gag cag cag cag cag atg gct gag ctg cac agc aaa ctt cag    3408
Ala Gln Glu Gln Gln Gln Gln Met Ala Glu Leu His Ser Lys Leu Gln
1040                1045                1050                1055 tcc tcc gag gcg gag gtg aaa agc aag tct gag gag ctg agt ggt ctc    3456
Ser Ser Glu Ala Glu Val Lys Ser Lys Ser Glu Glu Leu Ser Gly Leu
```

-continued

```
            Ser Ser Glu Ala Glu Val Lys Ser Lys Ser Glu Gly Leu
                    1060                1065            1070 cat ggg cag ctc aag gag gcc agg gcc gag aac tca cag ctc atg gag      3504
His Gly Gln Leu Lys Glu Ala Arg Ala Glu Asn Ser Gln Leu Met Glu
                    1075                1080            1085 aga atc cgg tcc atc gag gcc ctg ctg gag gcg ggc cag gcc cgg gac      3552
Arg Ile Arg Ser Ile Glu Ala Leu Leu Glu Ala Gly Gln Ala Arg Asp
                1090                1095            1100 acc cag gat gcc cag gcc agc cga gcg gag cat cag gcc cgc ctc aag      3600
Thr Gln Asp Ala Gln Ala Ser Arg Ala Glu His Gln Ala Arg Leu Lys
            1105                1110            1115 gag cta gag tcc cag gtg tgg tgc ctg gag aag gag gcc acc gag ctc      3648
Glu Leu Glu Ser Gln Val Trp Cys Leu Glu Lys Glu Ala Thr Glu Leu
1120                1125            1130                1135 aag gag gct gtt gag cag cag aaa gtg aag aac aac gac ctc cga gag      3696
Lys Glu Ala Val Glu Gln Gln Lys Val Lys Asn Asn Asp Leu Arg Glu
                    1140                1145            1150 aag aac tgg aag gcc atg gag gct ctg gcc tcg gcc gag aga gcc tgc      3744
Lys Asn Trp Lys Ala Met Glu Ala Leu Ala Ser Ala Glu Arg Ala Cys
                    1155                1160            1165 gag gag aag ctc cgc tcc tta acc cag gcc aag gag gaa tcc gag aag      3792
Glu Glu Lys Leu Arg Ser Leu Thr Gln Ala Lys Glu Glu Ser Glu Lys
                1170                1175            1180 cag ctc agc ctg acg gag gcc cag acc aag gag gcc ctg ctg gcc ctg      3840
Gln Leu Ser Leu Thr Glu Ala Gln Thr Lys Glu Ala Leu Leu Ala Leu
            1185                1190            1195 ttg ccg gct ctc tcc agc tca gcc ccc cag agt tac acc gag tgg ctg      3888
Leu Pro Ala Leu Ser Ser Ser Ala Pro Gln Ser Tyr Thr Glu Trp Leu
1200                1205            1210                1215 cag gaa ctc cga gag aag ggc ccg gag ctg ctg aag cag cgg ccg gct      3936
Gln Glu Leu Arg Glu Lys Gly Pro Glu Leu Leu Lys Gln Arg Pro Ala
                    1220                1225            1230 gac aca gat ccg tcc tcg gac ctg gct tcc aag ctg agg gag gct gag      3984
Asp Thr Asp Pro Ser Ser Asp Leu Ala Ser Lys Leu Arg Glu Ala Glu
                    1235                1240            1245 gag acc cag aac aat ctg cag gcc gag tgt gac cag tac cgc acc atc      4032
Glu Thr Gln Asn Asn Leu Gln Ala Glu Cys Asp Gln Tyr Arg Thr Ile
                1250                1255            1260 ctg gca gag acg gag ggc atg ctc aaa gac ctg cag aag agt gtg gag      4080
Leu Ala Glu Thr Glu Gly Met Leu Lys Asp Leu Gln Lys Ser Val Glu
            1265                1270            1275 gag gag gag cag gtg tgg aag gcc aaa gtg agc gcc acg gag gag gag      4128
Glu Glu Glu Gln Val Trp Lys Ala Lys Val Ser Ala Thr Glu Glu Glu
1280                1285            1290                1295 ctt cag aag tca cgg gtc aca gtg aaa cat ctc gaa gac att gta gag      4176
Leu Gln Lys Ser Arg Val Thr Val Lys His Leu Glu Asp Ile Val Glu
                    1300                1305            1310 aag cta aaa gga gaa ctt gaa agt tca gag cag gtg agg gag cac acc      4224
Lys Leu Lys Gly Glu Leu Glu Ser Ser Glu Gln Val Arg Glu His Thr
                    1315                1320            1325 tca cat ctg gaa gca gag ctg gag aag cac atg gca gct gcc agc gct      4272
Ser His Leu Glu Ala Glu Leu Glu Lys His Met Ala Ala Ala Ser Ala
                1330                1335            1340 gag tgc cag agc tac gcc aag gag gtg gcg ggg ttg agg caa ctt tta      4320
Glu Cys Gln Ser Tyr Ala Lys Glu Val Ala Gly Leu Arg Gln Leu Leu
            1345                1350            1355 tta gag tct cag tct cag ctg gat gca gcc aag agt gaa gcc cag aaa      4368
Leu Glu Ser Gln Ser Gln Leu Asp Ala Ala Lys Ser Glu Ala Gln Lys
1360                1365            1370                1375 caa agc aat gag ctc gcc ctg gtc agg cag cag ttg agt gag atg aag      4416
```

```
              Gln Ser Asn Glu Leu Ala Leu Val Arg Gln Gln Leu Ser Glu Met Lys
                      1380                1385                1390 agc cac gta gag gat ggt gac gta gct ggg tcc cca gct gcc ccc cca              4464
Ser His Val Glu Asp Gly Asp Val Ala Gly Ser Pro Ala Ala Pro Pro
            1395                1400                1405 gca gag cag gac cct gtc gag ctg aag gcg cag ctg gag cgg aca gag              4512
Ala Glu Gln Asp Pro Val Glu Leu Lys Ala Gln Leu Glu Arg Thr Glu
1410                1415                1420 gcc acc ctg gag gac gag cag gcg ctg cgg agg aag ctc acg gcc gag              4560
Ala Thr Leu Glu Asp Glu Gln Ala Leu Arg Arg Lys Leu Thr Ala Glu
        1425                1430                1435 ttc cag gag gct cag agc tct gcg tgc cgg ctc cag gcc gag ctg gag              4608
Phe Gln Glu Ala Gln Ser Ser Ala Cys Arg Leu Gln Ala Glu Leu Glu
1440                1445                1450                1455 aag ctc cgc agc aca ggg ccc ctg gag tct tca gca gca gag gag gcc              4656
Lys Leu Arg Ser Thr Gly Pro Leu Glu Ser Ser Ala Ala Glu Glu Ala
                1460                1465                1470 aca cag ctg aag gag aga cta gaa aaa gag aag aaa cta acc agt gac              4704
Thr Gln Leu Lys Glu Arg Leu Glu Lys Glu Lys Lys Leu Thr Ser Asp
            1475                1480                1485 ctg gga cat gct gcc acc aaa ttg cag gag ctt ttg aag acc acc cag              4752
Leu Gly His Ala Ala Thr Lys Leu Gln Glu Leu Leu Lys Thr Thr Gln
        1490                1495                1500 gag cag ctg gca aag gag aga gac aca gtg aag aag ttg cag gag cag              4800
Glu Gln Leu Ala Lys Glu Arg Asp Thr Val Lys Lys Leu Gln Glu Gln
1505                1510                1515 ttg gac aaa aca gac gac agc agc tca aag gag ggc act tct gtc tga              4848
Leu Asp Lys Thr Asp Asp Ser Ser Ser Lys Glu Gly Thr Ser Val
1520                1525                1530 gtctgctctt cgggaaaaga agttcccatt caacttacca aaatgcctta cacattcctt           4908
acaaataaat aaaccaacca acacaccgtt atccaggccc aacctccagt agctctgaga           4968
gaagccatga gagactctta gaatcacaga aatagacctt ccagaccct tgtttgtaaa           5028 agaacctttg tcacatttga taaacactat tccccaggac cagccctgga ccaccaccga           5088
gcagacgcca aagcccttac cagctctgtg acagacccca gggtatgtgc tggggaggcc           5148
gggacgctgg gtatctgtat gtcaatcagt gcaattgttt tcttcccctg ggttggggt           5208 caggaggcga gcggcctggt ggtgagtctc cagggctgtg gagcagactg gaggggccca           5268
gccagccggg gaggcagcag cctctcaccc ccgggggaag ttgccagcaa gaactgatgt           5328
gtgacttcct ggatgttaat gccattaaaa ccaacattgt tgcccggcaa aaaaaaaaa           5388 aaaaaaaaaa aaaaaaaaaa aaaaaaaaaa aaaaaaa                                   5425

<210> SEQ ID NO 48
<211> LENGTH: 1534
<212> TYPE: PRT
<213> ORGANISM: Canis familiaris

<400> SEQUENCE: 48

Met Asp Ile Tyr Asp Thr Gln Thr Leu Gly Val Met Val Phe Gly Gly
  1               5                  10                  15

Phe Met Val Val Ser Ala Ile Gly Ile Phe Leu Val Ser Thr Phe Ser
                 20                  25                  30

Met Lys Glu Thr Ser Tyr Glu Glu Ala Leu Ala Asn Gln Arg Lys Glu
             35                  40                  45

Met Ala Lys Thr His His Gln Lys Val Glu Lys Lys Lys Glu Lys
         50                  55                  60

Thr Val Glu Lys Lys Gly Lys Thr Lys Lys Lys Glu Glu Lys Pro Asn
```

```
                65                  70                  75                  80
Gly Lys Ile Pro Asp His Glu Pro Ala Pro Asn Val Thr Ile Leu Leu
                    85                  90                  95
Lys Asp Pro Val Arg Ala Pro Val Pro Val Ala Pro Thr Pro Val
                100                 105                 110
Gln Pro Pro Val Val Ile Ala Pro Val Ala Thr Val Pro Ala Met Pro
                115                 120                 125
Gln Glu Lys Leu Ala Pro Ser Pro Lys Asp Lys Lys Lys Glu Lys
                130                 135                 140
Lys Val Ala Lys Val Glu Pro Ala Val Ser Ser Val Val Asn Ser Val
145                 150                 155                 160
Gln Val Leu Ala Ser Lys Ala Ala Ile Leu Glu Thr Ala Pro Lys Glu
                165                 170                 175
Val Pro Met Val Val Pro Pro Val Gly Ala Lys Ala Gly Thr Pro
                180                 185                 190
Ala Thr Ser Thr Ala Gln Gly Lys Lys Ala Glu Gly Ala Gln Asn Gln
                195                 200                 205
Ser Arg Lys Ala Glu Gly Ala Pro Asn Gln Gly Lys Ala Glu Gly
    210                 215                 220
Ala Leu Asn Gln Gly Lys Lys Ala Glu Gly Ala Gln Asn Gln Gly Lys
225                 230                 235                 240
Lys Val Glu Val Ala Pro Asn Gln Gly Lys Ala Glu Gly Gly Gln
                245                 250                 255
Asn Gln Gly Lys Lys Val Glu Gly Ala Gln Asn Gln Gly Lys Lys Ala
            260                 265                 270
Glu Gly Thr Pro Asn Gln Gly Lys Ala Glu Gly Ala Pro Asn Gln
            275                 280                 285
Gly Lys Lys Thr Asp Gly Ala Pro Asn Gln Gly Lys Lys Ser Glu Gly
        290                 295                 300
Ala Pro Asn Gln Gly Lys Lys Ala Glu Gly Ala Gln Asn Gln Gly Lys
305                 310                 315                 320
Lys Val Glu Val Ala Pro Asn Gln Gly Lys Ala Glu Gly Gly Gln
                325                 330                 335
Asn Gln Gly Lys Lys Val Glu Gly Ala Gln Asn Gln Gly Lys Lys Ala
            340                 345                 350
Glu Gly Thr Pro Asn Gln Gly Lys Ala Glu Gly Ala Pro Asn Gln
            355                 360                 365
Gly Lys Lys Thr Asp Gly Ala Pro Asn Gln Gly Lys Lys Ser Glu Gly
        370                 375                 380
Ala Pro Asn Gln Gly Lys Lys Val Glu Gly Ala Gln Asn Gln Gly Lys
385                 390                 395                 400
Lys Val Glu Gly Val Gln Asn Gln Gly Lys Lys Ala Glu Gly Ala Gln
                405                 410                 415
Asn Gln Gly Lys Lys Ala Glu Gly Thr Ser Ser Gln Gly Arg Lys Glu
            420                 425                 430
Glu Gly Thr Pro Asn Leu Gly Lys Lys Ala Glu Gly Ser Pro Asn Gln
            435                 440                 445
Gly Lys Lys Val Glu Val Gln Asn Gln Ser Lys Lys Val Glu Gly
    450                 455                 460
Ala Pro Asn Gln Gly Lys Lys Ala Glu Gly Ser Gln Asn Gln Gly Lys
465                 470                 475                 480
Lys Thr Glu Gly Ala Ser Asn Gln Gly Lys Lys Val Asp Gly Ala Gln
                485                 490                 495
```

```
Asn Gln Gly Lys Lys Ala Glu Gly Ala Pro Asn Gln Gly Lys Lys Val
                500                 505                 510
Glu Gly Ala Gln Asn Gln Gly Lys Lys Ala Glu Gly Thr Pro Asn Gln
                515                 520                 525
Gly Lys Lys Ala Glu Gly Ala Gln Asn Gln Gly Lys Lys Ala Glu Gly
                530                 535                 540
Ala Pro Asn Gln Gly Lys Lys Ala Glu Gly Ala Pro Asn Gln Gly Lys
545                 550                 555                 560
Lys Ala Glu Gly Ala Pro Asn Gln Gly Lys Lys Ala Glu Gly Ala Pro
                565                 570                 575
Asn Gln Gly Lys Lys Ala Glu Ala Pro Asn Gln Gly Lys Lys Ala
                580                 585                 590
Glu Gly Ala Pro Asn Gln Gly Lys Lys Ala Glu Gly Ala Pro Asn Gln
                595                 600                 605
Gly Lys Lys Ala Glu Ala Ala Pro Asn Gln Gly Lys Lys Ala Glu Gly
                610                 615                 620
Ala Pro Asn Gln Gly Lys Lys Ala Glu Gly Ala Pro Asn Gln Gly Lys
625                 630                 635                 640
Lys Ala Glu Gly Ala Pro Asn Gln Gly Lys Lys Ala Glu Gly Ala Gln
                645                 650                 655
Asn Gln Gly Lys Lys Ala Glu Gly Ala Pro Asn Gln Gly Lys Lys Ala
                660                 665                 670
Asp Leu Val Ala Asn Gln Gly Thr Lys Ala Glu Gly Val Ala Gly Gln
                675                 680                 685
Gly Lys Lys Ala Glu Gly Ala Pro Asn Gln Gly Lys Lys Gly Glu Gly
                690                 695                 700
Thr Pro Asn Gln Gly Lys Lys Ser Glu Gly Ser Pro Asn Gln Gly Lys
705                 710                 715                 720
Lys Val Asp Ala Ser Ala Asn Gln Ser Lys Arg Ala Glu Ser Ala Pro
                725                 730                 735
Ile Gln Gly Lys Asn Ala Asp Met Val Gln Ser Gln Glu Ala Pro Lys
                740                 745                 750
Gln Glu Ala Pro Ala Lys Lys Ser Gly Ser Lys Lys Lys Gly Glu
                755                 760                 765
Pro Gly Pro Pro Asp Ser Asp Ser Pro Leu Tyr Leu Pro Tyr Lys Thr
770                 775                 780
Leu Val Ser Thr Val Gly Ser Met Val Phe Asn Glu Gly Glu Ala Gln
785                 790                 795                 800
Arg Leu Ile Glu Ile Leu Ser Glu Lys Ala Gly Val Ile Gln Asp Thr
                805                 810                 815
Trp His Lys Ala Thr Gln Lys Gly Asp Pro Val Ala Ile Leu Lys Arg
                820                 825                 830
Gln Leu Glu Glu Lys Glu Lys Leu Leu Ala Thr Glu Gln Glu Asp Ala
                835                 840                 845
Ala Val Ala Lys Ser Lys Leu Arg Glu Val Asn Lys Glu Leu Ala Ala
                850                 855                 860
Glu Lys Ala Lys Ala Ala Ala Gly Glu Ala Lys Val Lys Lys Gln Leu
865                 870                 875                 880
Val Ala Arg Glu Gln Glu Ile Thr Ala Val Gln Ala Arg Ile Glu Ala
                885                 890                 895
Ser Tyr Arg Glu His Val Lys Glu Val Gln Gln Leu Gln Gly Lys Ile
                900                 905                 910
Arg Thr Leu Gln Glu Gln Leu Glu Asn Gly Pro Asn Thr Gln Leu Ala
                915                 920                 925
```

```
Arg Leu Gln Gln Glu Asn Ser Ile Leu Arg Asp Ala Leu Asn Gln Ala
            930                 935                 940

Thr Ser Gln Val Glu Ser Lys Gln Asn Thr Glu Leu Ala Lys Leu Arg
945                 950                 955                 960

Gln Glu Leu Ser Lys Val Ser Lys Glu Leu Val Glu Lys Ser Glu Ala
            965                 970                 975

Ala Arg Gln Glu Glu Gln Arg Lys Ala Leu Glu Thr Lys Thr Ala
            980                 985                 990

Ala Leu Glu Lys Gln Val Leu Gln Leu Gln Ala Ser His Lys Glu Ser
            995                 1000                1005

Glu Glu Ala Leu Gln Lys Arg Leu Asp Glu Val Ser Arg Glu Leu Cys
            1010                1015                1020

Arg Ser Gln Thr Ser His Ala Ser Leu Arg Ala Asp Ala Glu Lys Ala
1025                1030                1035                1040

Gln Glu Gln Gln Gln Gln Met Ala Glu Leu His Ser Lys Leu Gln Ser
            1045                1050                1055

Ser Glu Ala Glu Val Lys Ser Lys Ser Glu Glu Leu Ser Gly Leu His
            1060                1065                1070

Gly Gln Leu Lys Glu Ala Arg Ala Glu Asn Ser Gln Leu Met Glu Arg
            1075                1080                1085

Ile Arg Ser Ile Glu Ala Leu Leu Glu Ala Gly Gln Ala Arg Asp Thr
            1090                1095                1100

Gln Asp Ala Gln Ala Ser Arg Ala Glu His Gln Ala Arg Leu Lys Glu
1105                1110                1115                1120

Leu Glu Ser Gln Val Trp Cys Leu Glu Lys Glu Ala Thr Glu Leu Lys
            1125                1130                1135

Glu Ala Val Glu Gln Gln Lys Val Lys Asn Asn Asp Leu Arg Glu Lys
            1140                1145                1150

Asn Trp Lys Ala Met Glu Ala Leu Ala Ser Ala Glu Arg Ala Cys Glu
            1155                1160                1165

Glu Lys Leu Arg Ser Leu Thr Gln Ala Lys Glu Glu Ser Glu Lys Gln
            1170                1175                1180

Leu Ser Leu Thr Glu Ala Gln Thr Lys Glu Ala Leu Leu Ala Leu Leu
1185                1190                1195                1200

Pro Ala Leu Ser Ser Ser Ala Pro Gln Ser Tyr Thr Glu Trp Leu Gln
            1205                1210                1215

Glu Leu Arg Glu Lys Gly Pro Glu Leu Leu Lys Gln Arg Pro Ala Asp
            1220                1225                1230

Thr Asp Pro Ser Ser Asp Leu Ala Ser Lys Leu Arg Glu Ala Glu Glu
            1235                1240                1245

Thr Gln Asn Asn Leu Gln Ala Glu Cys Asp Gln Tyr Arg Thr Ile Leu
            1250                1255                1260

Ala Glu Thr Glu Gly Met Leu Lys Asp Leu Gln Lys Ser Val Glu Glu
1265                1270                1275                1280

Glu Glu Gln Val Trp Lys Ala Lys Val Ser Ala Thr Glu Glu Glu Leu
            1285                1290                1295

Gln Lys Ser Arg Val Thr Val Lys His Leu Glu Asp Ile Val Glu Lys
            1300                1305                1310

Leu Lys Gly Glu Leu Glu Ser Ser Glu Gln Val Arg Glu His Thr Ser
            1315                1320                1325

His Leu Glu Ala Glu Leu Glu Lys His Met Ala Ala Ser Ala Glu
            1330                1335                1340

Cys Gln Ser Tyr Ala Lys Glu Val Ala Gly Leu Arg Gln Leu Leu Leu
```

```
                1345                1350                1355                1360
Glu Ser Gln Ser Gln Leu Asp Ala Ala Lys Ser Glu Ala Gln Lys Gln
                1365                1370                1375

Ser Asn Glu Leu Ala Leu Val Arg Gln Gln Leu Ser Glu Met Lys Ser
            1380                1385                1390

His Val Glu Asp Gly Asp Val Ala Gly Ser Pro Ala Ala Pro Pro Ala
        1395                1400                1405

Glu Gln Asp Pro Val Glu Leu Lys Ala Gln Leu Glu Arg Thr Glu Ala
    1410                1415                1420

Thr Leu Glu Asp Glu Gln Ala Leu Arg Arg Lys Leu Thr Ala Glu Phe
1425                1430                1435                1440

Gln Glu Ala Gln Ser Ser Ala Cys Arg Leu Gln Ala Glu Leu Glu Lys
                1445                1450                1455

Leu Arg Ser Thr Gly Pro Leu Glu Ser Ser Ala Ala Glu Glu Ala Thr
            1460                1465                1470

Gln Leu Lys Glu Arg Leu Glu Lys Glu Lys Leu Thr Ser Asp Leu
        1475                1480                1485

Gly His Ala Ala Thr Lys Leu Gln Glu Leu Leu Lys Thr Thr Gln Glu
    1490                1495                1500

Gln Leu Ala Lys Glu Arg Asp Thr Val Lys Lys Leu Gln Glu Gln Leu
1505                1510                1515                1520

Asp Lys Thr Asp Asp Ser Ser Ser Lys Glu Gly Thr Ser Val
                1525                1530

<210> SEQ ID NO 49
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 49
ctcaagggcc tggagactac g                                              21

<210> SEQ ID NO 50
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 50
cgggattccc gagtcgctca cc                                             22

<210> SEQ ID NO 51
<211> LENGTH: 1416
<212> TYPE: DNA
<213> ORGANISM: Artificial Sequence
<220> FEATURE:
<223> OTHER INFORMATION: Synthetic polynucleotide

<400> SEQUENCE: 51
tctagaatgt tgttgcaagc cttcttgttc ttgttggctg gtttcgctgc taagatttcc      60
gctcaattgc agttgcaaga gtccggtcca ggattggtta agccatccga gaccttgtcc     120
ttgacctgta ccgtttccgg tggttccatc atctccaagt cctcctactg gggatggatc     180
agacaaccac caggaaaggg tttggagtgg atcggttcca tctactactc cggttccacc     240
ttctacaacc catccttgaa gtccagagtt accatctccg ttgacacctc caagaaccaa     300
ttctccttga agttgtcctc cgttaccgct gctgacaccg ctgtttacta ctgtgctaga     360
```

-continued

```
ttgaccgttg ctgagttcga ctactggggt caaggaacct tggttaccgt ttcctccgct      420
tccaccaagg gtccatccgt tttcccattg gctccatcct ccaagtccac ctccggtgga      480
accgctgctt tgggttgttt ggtcaaggac tacttcccag agccagtcac cgtttcctgg      540
aactccggtg ctttgacctc cggtgttcac accttcccag ctgttttgca atcctccggt      600
ttgtactcct tgtcctccgt cgttaccgtt ccatcctcct ccttgggtac tcaaacctac      660
atctgcaacg tcaaccacaa gccatccaac accaaggttg acaagaaggt tgagccaaag      720
tcctgtgaca agacccacac ctgtccacca tgtccagctc cagagttgtt gggtggtcct      780
tctgttttct tgttcccacc aaagccaaag gacaccttga tgatctccag aaccccagag      840
gttacctgtg ttgtcgttga cgtttcccac gaggacccag aggttaagtt caactggtac      900
gttgacggtg ttgaggttca aacgctaag accaagccaa gagaggagca atacaactcc      960
acctacagag ttgttccgt cttgaccgtt ttgcaccaag actggttgaa cggaaaggag     1020
tacaagtgca aggtttccaa caaggctttg ccagctccaa tcgaaaagac catctccaag     1080
gctaagggtc aaccaagaga gccacaagtt tacaccttgc caccatccag agatgagttg     1140
accaagaacc aagtttcctt gacctgcttg gtcaagggtt tctacccatc cgacatcgct     1200
gttgagtggg agtccaacgg tcaaccagag aacaactaca agaccacccc accagttttg     1260
gactccgacg gttccttctt cttgtactcc aagttgaccg ttgacaagtc cagatggcaa     1320
caaggtaacg ttttctcctg ctccgttatg cacgaggctt tgcacaacca ctacacccaa     1380
aagtccttgt ccttgtcccc aggtaagtaa ggatcc                                1416
```

<210> SEQ ID NO 52
<211> LENGTH: 1416
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (7)..(1410)

<400> SEQUENCE: 52

```
tctaga atg ttg ttg caa gcc ttc ttg ttc ttg ttg gct ggt ttc gct         48
       Met Leu Leu Gln Ala Phe Leu Phe Leu Leu Ala Gly Phe Ala
         1               5                  10 gct aag att tcc gct caa ttg cag ttg caa gag tcc ggt cca gga ttg        96
Ala Lys Ile Ser Ala Gln Leu Gln Leu Gln Glu Ser Gly Pro Gly Leu
 15                  20                  25                  30 gtt aag cca tcc gag acc ttg tcc ttg acc tgt acc gtt tcc ggt ggt       144
Val Lys Pro Ser Glu Thr Leu Ser Leu Thr Cys Thr Val Ser Gly Gly
                 35                  40                  45 tcc atc atc tcc aag tcc tcc tac tgg gga tgg atc aga caa cca cca       192
Ser Ile Ile Ser Lys Ser Ser Tyr Trp Gly Trp Ile Arg Gln Pro Pro
             50                  55                  60 gga aag ggt ttg gag tgg atc ggt tcc atc tac tac tcc ggt tcc acc       240
Gly Lys Gly Leu Glu Trp Ile Gly Ser Ile Tyr Tyr Ser Gly Ser Thr
 65                  70                  75 ttc tac aac cca tcc ttg aag tcc aga gtt acc atc tcc gtt gac acc       288
Phe Tyr Asn Pro Ser Leu Lys Ser Arg Val Thr Ile Ser Val Asp Thr
             80                  85                  90 tcc aag aac caa ttc tcc ttg aag ttg tcc tcc gtt acc gct gct gac       336
Ser Lys Asn Gln Phe Ser Leu Lys Leu Ser Ser Val Thr Ala Ala Asp
 95                 100                 105                 110 acc gct gtt tac tac tgt gct aga ttg acc gtt gct gag ttc gac tac       384
Thr Ala Val Tyr Tyr Cys Ala Arg Leu Thr Val Ala Glu Phe Asp Tyr
```

```
            115                 120                 125
tgg ggt caa gga acc ttg gtt acc gtt tcc tcc gct tcc acc aag ggt      432
Trp Gly Gln Gly Thr Leu Val Thr Val Ser Ser Ala Ser Thr Lys Gly
            130                 135                 140 cca tcc gtt ttc cca ttg gct cca tcc tcc aag tcc acc tcc ggt gga      480
Pro Ser Val Phe Pro Leu Ala Pro Ser Ser Lys Ser Thr Ser Gly Gly
            145                 150                 155 acc gct gct ttg ggt tgt ttg gtc aag gac tac ttc cca gag cca gtc      528
Thr Ala Ala Leu Gly Cys Leu Val Lys Asp Tyr Phe Pro Glu Pro Val
            160                 165                 170 acc gtt tcc tgg aac tcc ggt gct ttg acc tcc ggt gtt cac acc ttc      576
Thr Val Ser Trp Asn Ser Gly Ala Leu Thr Ser Gly Val His Thr Phe
175                     180                 185                 190 cca gct gtt ttg caa tcc tcc ggt ttg tac tcc ttg tcc tcc gtc gtt      624
Pro Ala Val Leu Gln Ser Ser Gly Leu Tyr Ser Leu Ser Ser Val Val
                195                 200                 205 acc gtt cca tcc tcc tcc ttg ggt act caa acc tac atc tgc aac gtc      672
Thr Val Pro Ser Ser Ser Leu Gly Thr Gln Thr Tyr Ile Cys Asn Val
            210                 215                 220 aac cac aag cca tcc aac acc aag gtt gac aag aag gtt gag cca aag      720
Asn His Lys Pro Ser Asn Thr Lys Val Asp Lys Lys Val Glu Pro Lys
            225                 230                 235 tcc tgt gac aag acc cac acc tgt cca cca tgt cca gct cca gag ttg      768
Ser Cys Asp Lys Thr His Thr Cys Pro Pro Cys Pro Ala Pro Glu Leu
240                 245                 250 ttg ggt ggt cct tct gtt ttc ttg ttc cca cca aag cca aag gac acc      816
Leu Gly Gly Pro Ser Val Phe Leu Phe Pro Pro Lys Pro Lys Asp Thr
255                 260                 265                 270 ttg atg atc tcc aga acc cca gag gtt acc tgt gtt gtc gtt gac gtt      864
Leu Met Ile Ser Arg Thr Pro Glu Val Thr Cys Val Val Val Asp Val
                275                 280                 285 tcc cac gag gac cca gag gtt aag ttc aac tgg tac gtt gac ggt gtt      912
Ser His Glu Asp Pro Glu Val Lys Phe Asn Trp Tyr Val Asp Gly Val
            290                 295                 300 gag gtt cac aac gct aag acc aag cca aga gag gag caa tac aac tcc      960
Glu Val His Asn Ala Lys Thr Lys Pro Arg Glu Glu Gln Tyr Asn Ser
            305                 310                 315 acc tac aga gtt gtt tcc gtc ttg acc gtt ttg cac caa gac tgg ttg     1008
Thr Tyr Arg Val Val Ser Val Leu Thr Val Leu His Gln Asp Trp Leu
            320                 325                 330 aac gga aag gag tac aag tgc aag gtt tcc aac aag gct ttg cca gct     1056
Asn Gly Lys Glu Tyr Lys Cys Lys Val Ser Asn Lys Ala Leu Pro Ala
335                 340                 345                 350 cca atc gaa aag acc atc tcc aag gct aag ggt caa cca aga gag cca     1104
Pro Ile Glu Lys Thr Ile Ser Lys Ala Lys Gly Gln Pro Arg Glu Pro
                355                 360                 365 caa gtt tac acc ttg cca cca tcc aga gat gag ttg acc aag aac caa     1152
Gln Val Tyr Thr Leu Pro Pro Ser Arg Asp Glu Leu Thr Lys Asn Gln
            370                 375                 380 gtt tcc ttg acc tgc ttg gtc aag ggt ttc tac cca tcc gac atc gct     1200
Val Ser Leu Thr Cys Leu Val Lys Gly Phe Tyr Pro Ser Asp Ile Ala
            385                 390                 395 gtt gag tgg gag tcc aac ggt caa cca gag aac aac tac aag acc acc     1248
Val Glu Trp Glu Ser Asn Gly Gln Pro Glu Asn Asn Tyr Lys Thr Thr
            400                 405                 410 cca cca gtt ttg gac tcc gac ggt tcc ttc ttc ttg tac tcc aag ttg     1296
Pro Pro Val Leu Asp Ser Asp Gly Ser Phe Phe Leu Tyr Ser Lys Leu
415                 420                 425                 430 acc gtt gac aag tcc aga tgg caa caa ggt aac gtt ttc tcc tgc tcc     1344
Thr Val Asp Lys Ser Arg Trp Gln Gln Gly Asn Val Phe Ser Cys Ser
```

```
                 435               440               445
gtt atg cac gag gct ttg cac aac cac tac acc caa aag tcc ttg tcc       1392
Val Met His Glu Ala Leu His Asn His Tyr Thr Gln Lys Ser Leu Ser
            450                 455                 460 ttg tcc cca ggt aag taa ggatcc                                        1416
Leu Ser Pro Gly Lys
        465
```

<210> SEQ ID NO 53
<211> LENGTH: 714
<212> TYPE: DNA
<213> ORGANISM: Artificial Sequence
<220> FEATURE:
<223> OTHER INFORMATION: Synthetic polynucleotide

<400> SEQUENCE: 53

```
tctagaatgt tgttgcaagc cttcttgttc ttgttggctg gtttcgctgc taagatttcc      60
gctgagatcg ttttgaccca atccccagct accttgtcct tgtccccagg tgagagagcc    120
accttgtcct gtagagcttc ccaatccgtt tcctccttct tggcttggta ccaacaaaag    180
ccaggtcaag ccccaagatt gttgatctac gacgcttcca acagagctac cggtatccca    240
gctagattct ccggttccgg ttccggaacc gacttcacct tgaccatctc ctccttggag    300
ccagaggact cgctgtttta ctactgccaa caaagatcca actggccatt gaccttcggt    360
ccaggtacta aggttgacat caagagaacc gttgctgctc catccgtttt catcttccca    420
ccatccgacg agcaattgaa gtccggtact gcttccgttg tttgcttgtt gaacaacttc    480
tacccaagag aggctaaggt tcaatggaag gttgacaacg ctttgcaatc cggtaactcc    540
caagagtccg ttaccgagca agactccaag gactccacct actccttgtc ctccaccttg    600
accttgtcca aggctgacta cgagaagcac aaggtttacg cttgtgaggt tacccaccaa    660
ggtttgtcct ccccagttac caagtccttc aacagaggtg agtgctaagg atcc           714
```

<210> SEQ ID NO 54
<211> LENGTH: 714
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (7)..(708)

<400> SEQUENCE: 54

```
tctaga atg ttg ttg caa gcc ttc ttg ttc ttg ttg gct ggt ttc gct        48
        Met Leu Leu Gln Ala Phe Leu Phe Leu Leu Ala Gly Phe Ala
          1               5                  10 gct aag att tcc gct gag atc gtt ttg acc caa tcc cca gct acc ttg       96
Ala Lys Ile Ser Ala Glu Ile Val Leu Thr Gln Ser Pro Ala Thr Leu
 15                  20                  25                  30 tcc ttg tcc cca ggt gag aga gcc acc ttg tcc tgt aga gct tcc caa     144
Ser Leu Ser Pro Gly Glu Arg Ala Thr Leu Ser Cys Arg Ala Ser Gln
                 35                  40                  45 tcc gtt tcc tcc ttc ttg gct tgg tac caa caa aag cca ggt caa gcc     192
Ser Val Ser Ser Phe Leu Ala Trp Tyr Gln Gln Lys Pro Gly Gln Ala
             50                  55                  60 cca aga ttg ttg atc tac gac gct tcc aac aga gct acc ggt atc cca     240
Pro Arg Leu Leu Ile Tyr Asp Ala Ser Asn Arg Ala Thr Gly Ile Pro
         65                  70                  75 gct aga ttc tcc ggt tcc ggt tcc gga acc gac ttc acc ttg acc atc     288
Ala Arg Phe Ser Gly Ser Gly Ser Gly Thr Asp Phe Thr Leu Thr Ile
     80                  85                  90
```

| | | | | | | | | | | | | | | | |
|---|---|---|---|---|---|---|---|---|---|---|---|---|---|---|---|
| tcc | tcc | ttg | gag | cca | gag | gac | ttc | gct | gtt | tac | tac | tgc | caa | caa | aga |
| Ser | Ser | Leu | Glu | Pro | Glu | Asp | Phe | Ala | Val | Tyr | Tyr | Cys | Gln | Gln | Arg |
| 95 | | | | 100 | | | | | 105 | | | | | 110 | |

336

| tcc | aac | tgg | cca | ttg | acc | ttc | ggt | cca | ggt | act | aag | gtt | gac | atc | aag |
|---|---|---|---|---|---|---|---|---|---|---|---|---|---|---|---|
| Ser | Asn | Trp | Pro | Leu | Thr | Phe | Gly | Pro | Gly | Thr | Lys | Val | Asp | Ile | Lys |
| | | | 115 | | | | | 120 | | | | | 125 | | |

384

| aga | acc | gtt | gct | gct | cca | tcc | gtt | ttc | atc | ttc | cca | cca | tcc | gac | gag |
|---|---|---|---|---|---|---|---|---|---|---|---|---|---|---|---|
| Arg | Thr | Val | Ala | Ala | Pro | Ser | Val | Phe | Ile | Phe | Pro | Pro | Ser | Asp | Glu |
| | 130 | | | | | 135 | | | | | 140 | | | | |

432

| caa | ttg | aag | tcc | ggt | act | gct | tcc | gtt | gtt | tgc | ttg | ttg | aac | aac | ttc |
|---|---|---|---|---|---|---|---|---|---|---|---|---|---|---|---|
| Gln | Leu | Lys | Ser | Gly | Thr | Ala | Ser | Val | Val | Cys | Leu | Leu | Asn | Asn | Phe |
| | | 145 | | | | | 150 | | | | | 155 | | | |

480

| tac | cca | aga | gag | gct | aag | gtt | caa | tgg | aag | gtt | gac | aac | gct | ttg | caa |
|---|---|---|---|---|---|---|---|---|---|---|---|---|---|---|---|
| Tyr | Pro | Arg | Glu | Ala | Lys | Val | Gln | Trp | Lys | Val | Asp | Asn | Ala | Leu | Gln |
| 160 | | | | | 165 | | | | | 170 | | | | | |

528

| tcc | ggt | aac | tcc | caa | gag | tcc | gtt | acc | gag | caa | gac | tcc | aag | gac | tcc |
|---|---|---|---|---|---|---|---|---|---|---|---|---|---|---|---|
| Ser | Gly | Asn | Ser | Gln | Glu | Ser | Val | Thr | Glu | Gln | Asp | Ser | Lys | Asp | Ser |
| 175 | | | | | 180 | | | | | 185 | | | | | 190 |

576

| acc | tac | tcc | ttg | tcc | tcc | acc | ttg | acc | ttg | tcc | aag | gct | gac | tac | gag |
|---|---|---|---|---|---|---|---|---|---|---|---|---|---|---|---|
| Thr | Tyr | Ser | Leu | Ser | Ser | Thr | Leu | Thr | Leu | Ser | Lys | Ala | Asp | Tyr | Glu |
| | | | | 195 | | | | | 200 | | | | | 205 | |

624

| aag | cac | aag | gtt | tac | gct | tgt | gag | gtt | acc | cac | caa | ggt | ttg | tcc | tcc |
|---|---|---|---|---|---|---|---|---|---|---|---|---|---|---|---|
| Lys | His | Lys | Val | Tyr | Ala | Cys | Glu | Val | Thr | His | Gln | Gly | Leu | Ser | Ser |
| | | 210 | | | | | 215 | | | | | 220 | | | |

672

| cca | gtt | acc | aag | tcc | ttc | aac | aga | ggt | gag | tgc | taa | ggatcc | | | |
|---|---|---|---|---|---|---|---|---|---|---|---|---|---|---|---|
| Pro | Val | Thr | Lys | Ser | Phe | Asn | Arg | Gly | Glu | Cys | | | | | |
| | | 225 | | | | | 230 | | | | | | | | |

714

<210> SEQ ID NO 55
<211> LENGTH: 1437
<212> TYPE: DNA
<213> ORGANISM: Artificial Sequence
<220> FEATURE:
<223> OTHER INFORMATION: Synthetic polynucleotide

<400> SEQUENCE: 55

| | | | | |
|---|---|---|---|---|
| tctagaatgt tgggtaagaa cgacccaatg tgcttggtct tggtcttgtt gggttttgacc | | | | 60 |
| gctttgttgg gtatctgtca aggacaattg cagttgcaag agtccggtcc aggattggtt | | | | 120 |
| aagccatccg agaccttgtc cttgacctgt accgtttccg gtggttccat catctccaag | | | | 180 |
| tcctcctact ggggatggat cagacaacca ccaggaaagg gtttggagtg gatcggttcc | | | | 240 |
| atctactact ccggttccac cttctacaac ccatccttga gtccagagt accatctcc | | | | 300 |
| gttgacacct ccaagaacca attctccttg aagttgtcct ccgttaccgc tgctgacacc | | | | 360 |
| gctgtttact actgtgctag attgaccgtt gctgagttcg actactgggg tcaaggaacc | | | | 420 |
| ttggttaccg tttcctccgc ttccaccaag ggtccatccg ttttcccatt ggctccatcc | | | | 480 |
| tccaagtcca cctccggtgg aaccgctgct ttgggttgtt tggtcaagga ctacttccca | | | | 540 |
| gagccagtca ccgtttcctg aactccggt gctttgacct ccgtgttca caccttccca | | | | 600 |
| gctgttttgc aatcctccgg tttgtactcc ttgtcctccg tcgttaccgt tccatcctcc | | | | 660 |
| tccttgggta ctcaaaccta catctgcaac gtcaaccaca agccatccaa caccaaggtt | | | | 720 |
| gacaagaagg ttgagccaaa gtcctgtgac aagacccaca cctgtccacc atgtccagct | | | | 780 |
| ccagagttgt gggtggtcc ttctgttttc ttgttcccac aaagccaaa ggacaccttg | | | | 840 |
| atgatctcca gaaccccaga ggttacctgt gttgtcgttg acgtttccca cgaggaccca | | | | 900 |
| gaggttaagt tcaactggta cgttgacggt gttgaggttc acaacgctaa gaccaagcca | | | | 960 |
| agagaggagc aatacaactc cacctacaga gttgtttccg tcttgaccgt tttgcaccaa | | | | 1020 |

```
gactggttga acggaaagga gtacaagtgc aaggtttcca acaaggcttt gccagctcca      1080
atcgaaaaga ccatctccaa ggctaagggt caaccaagag agccacaagt ttacaccttg      1140
ccaccatcca gagatgagtt gaccaagaac caagtttcct tgacctgctt ggtcaagggt      1200
ttctacccat ccgacatcgc tgttgagtgg gagtccaacg gtcaaccaga gaacaactac      1260
aagaccaccc caccagtttt ggactccgac ggttccttct tcttgtactc caagttgacc      1320
gttgacaagt ccagatggca acaaggtaac gttttctcct gctccgttat gcacgaggct      1380
ttgcacaacc actacaccca aaagtccttg tccttgtccc caggtaagta aggatcc        1437

<210> SEQ ID NO 56
<211> LENGTH: 1437
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (7)..(1431)

<400> SEQUENCE: 56 tctaga atg ttg ggt aag aac gac cca atg tgc ttg gtc ttg gtc ttg        48
       Met Leu Gly Lys Asn Asp Pro Met Cys Leu Val Leu Val Leu
       1               5                  10 ttg ggt ttg acc gct ttg ttg ggt atc tgt caa gga caa ttg cag ttg        96
Leu Gly Leu Thr Ala Leu Leu Gly Ile Cys Gln Gly Gln Leu Gln Leu
15                  20                  25                  30 caa gag tcc ggt cca gga ttg gtt aag cca tcc gag acc ttg tcc ttg       144
Gln Glu Ser Gly Pro Gly Leu Val Lys Pro Ser Glu Thr Leu Ser Leu
                35                  40                  45 acc tgt acc gtt tcc ggt ggt tcc atc atc tcc aag tcc tcc tac tgg       192
Thr Cys Thr Val Ser Gly Gly Ser Ile Ile Ser Lys Ser Ser Tyr Trp
            50                  55                  60 gga tgg atc aga caa cca cca gga aag ggt ttg gag tgg atc ggt tcc       240
Gly Trp Ile Arg Gln Pro Pro Gly Lys Gly Leu Glu Trp Ile Gly Ser
        65                  70                  75 atc tac tac tcc ggt tcc acc ttc tac aac cca tcc ttg aag tcc aga       288
Ile Tyr Tyr Ser Gly Ser Thr Phe Tyr Asn Pro Ser Leu Lys Ser Arg
    80                  85                  90 gtt acc atc tcc gtt gac acc tcc aag aac caa ttc tcc ttg aag ttg       336
Val Thr Ile Ser Val Asp Thr Ser Lys Asn Gln Phe Ser Leu Lys Leu
95                  100                 105                 110 tcc tcc gtt acc gct gct gac acc gct gtt tac tac tgt gct aga ttg       384
Ser Ser Val Thr Ala Ala Asp Thr Ala Val Tyr Tyr Cys Ala Arg Leu
                115                 120                 125 acc gtt gct gag ttc gac tac tgg ggt caa gga acc ttg gtt acc gtt       432
Thr Val Ala Glu Phe Asp Tyr Trp Gly Gln Gly Thr Leu Val Thr Val
            130                 135                 140 tcc tcc gct tcc acc aag ggt cca tcc gtt ttc cca ttg gct cca tcc       480
Ser Ser Ala Ser Thr Lys Gly Pro Ser Val Phe Pro Leu Ala Pro Ser
        145                 150                 155 tcc aag tcc acc tcc ggt gga acc gct gct ttg ggt tgt ttg gtc aag       528
Ser Lys Ser Thr Ser Gly Gly Thr Ala Ala Leu Gly Cys Leu Val Lys
    160                 165                 170 gac tac ttc cca gag cca gtc acc gtt tcc tgg aac tcc ggt gct ttg       576
Asp Tyr Phe Pro Glu Pro Val Thr Val Ser Trp Asn Ser Gly Ala Leu
175                 180                 185                 190 acc tcc ggt gtt cac acc ttc cca gct gtt ttg caa tcc tcc ggt ttg       624
Thr Ser Gly Val His Thr Phe Pro Ala Val Leu Gln Ser Ser Gly Leu
                195                 200                 205
```

```
tac tcc ttg tcc tcc gtc gtt acc gtt cca tcc tcc ttg ggt act        672
Tyr Ser Leu Ser Ser Val Val Thr Val Pro Ser Ser Leu Gly Thr
            210                 215                 220 caa acc tac atc tgc aac gtc aac cac aag cca tcc aac acc aag gtt    720
Gln Thr Tyr Ile Cys Asn Val Asn His Lys Pro Ser Asn Thr Lys Val
        225                 230                 235 gac aag aag gtt gag cca aag tcc tgt gac aag acc cac acc tgt cca    768
Asp Lys Lys Val Glu Pro Lys Ser Cys Asp Lys Thr His Thr Cys Pro
    240                 245                 250 cca tgt cca gct cca gag ttg ttg ggt ggt cct tct gtt ttc ttg ttc    816
Pro Cys Pro Ala Pro Glu Leu Leu Gly Gly Pro Ser Val Phe Leu Phe
255                 260                 265                 270 cca cca aag cca aag gac acc ttg atg atc tcc aga acc cca gag gtt    864
Pro Pro Lys Pro Lys Asp Thr Leu Met Ile Ser Arg Thr Pro Glu Val
                275                 280                 285 acc tgt gtt gtc gtt gac gtt tcc cac gag gac cca gag gtt aag ttc    912
Thr Cys Val Val Val Asp Val Ser His Glu Asp Pro Glu Val Lys Phe
            290                 295                 300 aac tgg tac gtt gac ggt gtt gag gtt cac aac gct aag acc aag cca    960
Asn Trp Tyr Val Asp Gly Val Glu Val His Asn Ala Lys Thr Lys Pro
        305                 310                 315 aga gag gag caa tac aac tcc acc tac aga gtt gtt tcc gtc ttg acc    1008
Arg Glu Glu Gln Tyr Asn Ser Thr Tyr Arg Val Val Ser Val Leu Thr
    320                 325                 330 gtt ttg cac caa gac tgg ttg aac gga aag gag tac aag tgc aag gtt    1056
Val Leu His Gln Asp Trp Leu Asn Gly Lys Glu Tyr Lys Cys Lys Val
335                 340                 345                 350 tcc aac aag gct ttg cca gct cca atc gaa aag acc atc tcc aag gct    1104
Ser Asn Lys Ala Leu Pro Ala Pro Ile Glu Lys Thr Ile Ser Lys Ala
                355                 360                 365 aag ggt caa cca aga gag cca caa gtt tac acc ttg cca cca tcc aga    1152
Lys Gly Gln Pro Arg Glu Pro Gln Val Tyr Thr Leu Pro Pro Ser Arg
            370                 375                 380 gat gag ttg acc aag aac caa gtt tcc ttg acc tgc ttg gtc aag ggt    1200
Asp Glu Leu Thr Lys Asn Gln Val Ser Leu Thr Cys Leu Val Lys Gly
        385                 390                 395 ttc tac cca tcc gac atc gct gtt gag tgg gag tcc aac ggt caa cca    1248
Phe Tyr Pro Ser Asp Ile Ala Val Glu Trp Glu Ser Asn Gly Gln Pro
    400                 405                 410 gag aac aac tac aag acc acc cca cca gtt ttg gac tcc gac ggt tcc    1296
Glu Asn Asn Tyr Lys Thr Thr Pro Pro Val Leu Asp Ser Asp Gly Ser
415                 420                 425                 430 ttc ttc ttg tac tcc aag ttg acc gtt gac aag tcc aga tgg caa caa    1344
Phe Phe Leu Tyr Ser Lys Leu Thr Val Asp Lys Ser Arg Trp Gln Gln
                435                 440                 445 ggt aac gtt ttc tcc tgc tcc gtt atg cac gag gct ttg cac aac cac    1392
Gly Asn Val Phe Ser Cys Ser Val Met His Glu Ala Leu His Asn His
            450                 455                 460 tac acc caa aag tcc ttg tcc ttg tcc cca ggt aag taa ggatcc         1437
Tyr Thr Gln Lys Ser Leu Ser Leu Ser Pro Gly Lys
        465                 470

<210> SEQ ID NO 57
<211> LENGTH: 735
<212> TYPE: DNA
<213> ORGANISM: Artificial Sequence
<220> FEATURE:
<223> OTHER INFORMATION: Synthetic polynucleotide

<400> SEQUENCE: 57
tctagaatgt tgggtaagaa cgacccaatg tgcttggtct tggtcttgtt gggtttgacc     60
```

```
gctttgttgg gtatctgtca aggagagatc gttttgaccc aatccccagc taccttgtcc    120
ttgtccccag gtgagagagc caccttgtcc tgtagagctt cccaatccgt ttcctccttc    180
ttggcttggt accaacaaaa gccaggtcaa gccccaagat tgttgatcta cgacgcttcc    240
aacagagcta ccggtatccc agctagattc tccggttccg gttccggaac cgacttcacc    300
ttgaccatct cctccttgga gccagaggac ttcgctgttt actactgcca acaaagatcc    360
aactggccat tgaccttcgg tccaggtact aaggttgaca tcaagagaac cgttgctgct    420
ccatccgttt tcatcttccc accatccgac gagcaattga agtccggtac tgcttccgtt    480
gtttgcttgt tgaacaactt ctacccaaga gaggctaagg ttcaatggaa ggttgacaac    540
gctttgcaat ccggtaactc ccaagagtcc gttaccgagc aagactccaa ggactccacc    600
tactccttgt cctccacctt gaccttgtcc aaggctgact acgagaagca caaggtttac    660
gcttgtgagg ttacccacca aggtttgtcc tccccagtta ccaagtcctt caacagaggt    720
gagtgctaag gatcc                                                    735
```

```
<210> SEQ ID NO 58
<211> LENGTH: 735
<212> TYPE: DNA
<213> ORGANISM: Artificial Sequence
<220> FEATURE:
<223> OTHER INFORMATION: Synthetic polynucleotide
<220> FEATURE:
<221> NAME/KEY: CDS
<222> LOCATION: (7)..(729)

<400> SEQUENCE: 58 tctaga atg ttg ggt aag aac gac cca atg tgc ttg gtc ttg gtc ttg         48
       Met Leu Gly Lys Asn Asp Pro Met Cys Leu Val Leu Val Leu
       1               5                   10 ttg ggt ttg acc gct ttg ttg ggt atc tgt caa gga gag atc gtt ttg        96
Leu Gly Leu Thr Ala Leu Leu Gly Ile Cys Gln Gly Glu Ile Val Leu
15                  20                  25                  30 acc caa tcc cca gct acc ttg tcc ttg tcc cca ggt gag aga gcc acc       144
Thr Gln Ser Pro Ala Thr Leu Ser Leu Ser Pro Gly Glu Arg Ala Thr
                35                  40                  45 ttg tcc tgt aga gct tcc caa tcc gtt tcc tcc ttc ttg gct tgg tac       192
Leu Ser Cys Arg Ala Ser Gln Ser Val Ser Ser Phe Leu Ala Trp Tyr
            50                  55                  60 caa caa aag cca ggt caa gcc cca aga ttg ttg atc tac gac gct tcc       240
Gln Gln Lys Pro Gly Gln Ala Pro Arg Leu Leu Ile Tyr Asp Ala Ser
65                  70                  75 aac aga gct acc ggt atc cca gct aga ttc tcc ggt tcc ggt tcc gga       288
Asn Arg Ala Thr Gly Ile Pro Ala Arg Phe Ser Gly Ser Gly Ser Gly
            80                  85                  90 acc gac ttc acc ttg acc atc tcc tcc ttg gag cca gag gac ttc gct       336
Thr Asp Phe Thr Leu Thr Ile Ser Ser Leu Glu Pro Glu Asp Phe Ala
95                  100                 105                 110 gtt tac tac tgc caa caa aga tcc aac tgg cca ttg acc ttc ggt cca       384
Val Tyr Tyr Cys Gln Gln Arg Ser Asn Trp Pro Leu Thr Phe Gly Pro
                115                 120                 125 ggt act aag gtt gac atc aag aga acc gtt gct gct cca tcc gtt ttc       432
Gly Thr Lys Val Asp Ile Lys Arg Thr Val Ala Ala Pro Ser Val Phe
            130                 135                 140 atc ttc cca cca tcc gac gag caa ttg aag tcc ggt act gct tcc gtt       480
Ile Phe Pro Pro Ser Asp Glu Gln Leu Lys Ser Gly Thr Ala Ser Val
145                 150                 155 gtt tgc ttg ttg aac aac ttc tac cca aga gag gct aag gtt caa tgg       528
Val Cys Leu Leu Asn Asn Phe Tyr Pro Arg Glu Ala Lys Val Gln Trp
            160                 165                 170
```

```
aag gtt gac aac gct ttg caa tcc ggt aac tcc caa gag tcc gtt acc        576
Lys Val Asp Asn Ala Leu Gln Ser Gly Asn Ser Gln Glu Ser Val Thr
175                 180                 185                 190 gag caa gac tcc aag gac tcc acc tac tcc ttg tcc tcc acc ttg acc        624
Glu Gln Asp Ser Lys Asp Ser Thr Tyr Ser Leu Ser Ser Thr Leu Thr
                195                 200                 205 ttg tcc aag gct gac tac gag aag cac aag gtt tac gct tgt gag gtt        672
Leu Ser Lys Ala Asp Tyr Glu Lys His Lys Val Tyr Ala Cys Glu Val
            210                 215                 220 acc cac caa ggt ttg tcc tcc cca gtt acc aag tcc ttc aac aga ggt        720
Thr His Gln Gly Leu Ser Ser Pro Val Thr Lys Ser Phe Asn Arg Gly
        225                 230                 235 gag tgc taa ggatcc                                                     735
Glu Cys
    240

<210> SEQ ID NO 59
<211> LENGTH: 37
<212> TYPE: DNA
<213> ORGANISM: Artificial Sequence
<220> FEATURE:
<223> OTHER INFORMATION: Synthetic oligonucleotide

<400> SEQUENCE: 59
atagaactag caactagatg aaaaagcctg aactcac                               37

<210> SEQ ID NO 60
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 60
caaatcccac ggatcactat tcctttgccc tcggac                                36

<210> SEQ ID NO 61
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 61
aattcgagct cggtacaggg atacatggga taccaaag                              38

<210> SEQ ID NO 62
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 62
gaggatcccc gggtaccagg gtcgattttc ttggtcga                              38

<210> SEQ ID NO 63
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 63
atgcccgtag attcttctca taagacagc                                        29
```

<210> SEQ ID NO 64
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 64
caaagtcatt taaatcaaat gcattagcgg                                    30

<210> SEQ ID NO 65
<211> LENGTH: 1220
<212> TYPE: DNA
<213> ORGANISM: Pichia pastoris

<400> SEQUENCE: 65
atgcccgtag attcttctca taagacagct agcccacttc cacctcgtaa aagagcaaag    60
acggaagaag aaaaggagca gcgtcgagtg aacgtatcc tacgtaatag gagagcggcc    120
catgcttcca gagagaagaa acgaagacac gttgaatttc tggaaaacca cgtcgtcgac    180
ctggaatctg cacttcaaga atcagccaaa gccactaaca agttgaaaga atacaagat    240 atcattgttt caaggttgga agccttaggt ggtaccgtct cagatttgga tttaacagtt    300
ccggaagtcg atttttccaa atcttctgat ttggaaccca tgtctgatct ctcaacttct    360
tcgaaatcgg agaaagcatc tacatccact cgcagatctt tgactgagga tctggacgaa    420
gatgacgtcg ctgaatatga cgacgaagaa gaggacgaag agttaccag gaaaatgaaa    480 gtcttaaacg acaaaaacaa gagcacatct atcaagcagg agaagttgaa tgaacttcca    540
tctcctttgt catccgattt ttcagacgta gatgaagaaa agtcaactct cacacattta    600
aagttgcaac agcaacaaca acaaccagta gacaattatg tttctactcc tttgagtctt    660
ccggaggatt cagttgattt tattaaccca ggtaacttaa aaatagagtc cgatgagaac    720
ttcttgttga gttcaaatac tttacaaata aaacacgaaa atgacaccga ctacattact    780
acagctccat caggttccat caatgatttt tttaattctt atgacattag cgagtcgaat    840
cggttgcatc atccagcagt gatgacggat tcatctttac acattacagc aggctccatc    900
ggcttttcct cttttgattg gggggggaa agttctgtag cagggaggcg cagttcagtt    960
ggcacatatc agttgacatg catagcgatc aggtgattgc tcttgttaac tggtatgcca    1020
agtcaaccgt tttcggcgta cctactactc tactttaact cttgaattga gatgaaacaa    1080
tcgcccttgt tcgagacgcg tagttaattt aagatgaatc aatttgcaac aaaagaacaa    1140
acgaaaaaga taacagcaaa cttaagtttc gtggtctgca gcaccattta ccgctaatgc    1200
atttgattta aatgactttg                                               1220

<210> SEQ ID NO 66
<211> LENGTH: 898
<212> TYPE: DNA
<213> ORGANISM: Pichia pastoris

<400> SEQUENCE: 66
atgcccgtag attcttctca taagacagct agcccacttc cacctcgtaa aagagcaaag    60
acggaagaag aaaaggagca gcgtcgagtg aacgtatcc tacgtaatag gagagcggcc    120
catgcttcca gagagaagaa acgaagacac gttgaatttc tggaaaacca cgtcgtcgac    180
ctggaatctg cacttcaaga atcagccaaa gccactaaca agttgaaaga atacaagat    240 atcattgttt caaggttgga agccttaggt ggtaccgtct cagatttgga tttaacagtt    300

```
ccggaagtcg attttcccaa atcttctgat ttggaaccca tgtctgatct ctcaacttct    360
tcgaaatcgg agaaagcatc tacatccact cgcagatctt tgactgagga tctggacgaa    420
gatgacgtcg ctgaatatga cgacgaagaa gaggacgaag agttacccag gaaaatgaaa    480
gtcttaaacg acaaaaacaa gagcacatct atcaagcagg agaagttgaa tgaacttcca    540
tctcctttgt catccgattt ttcagacgta gatgaagaaa agtcaactct cacacattta    600
aagttgcaac agcaacaaca acaaccagta gacaattatg tttctactcc tttgagtctt    660
ccggaggatt cagttgattt tattaaccca ggtaacttaa aaatagagtc cgatgagaac    720
ttcttgttga gttcaaatac tttacaaata aaacacgaaa atgacaccga ctacattact    780
acagctccat caggttccat caatgatttt tttaattctt atgacattag cgagtcgaat    840
cggttgcatc atccagcagc accatttacc gctaatgcat ttgatttaaa tgactttg     898
```

<210> SEQ ID NO 67
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 67

```
gactagtatg cccgtagatt cttctcata                                       29
```

<210> SEQ ID NO 68
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 68

```
cagatctcta ttcctggaag aatacaaagt                                      30
```

<210> SEQ ID NO 69
<211> LENGTH: 915
<212> TYPE: DNA
<213> ORGANISM: Pichia pastoris

<400> SEQUENCE: 69

```
atgcccgtag attcttctca taagacagct agcccacttc cacctcgtaa aagagcaaag    60
acggaagaag aaaaggagca gcgtcgagtg gaacgtatcc tacgtaatag agagcggcc    120 catgcttcca gagagaagaa acgaagacac gttgaatttc tggaaaacca cgtcgtcgac    180
ctggaatctg cacttcaaga atcagccaaa gccactaaca agttgaaaga atacaaagat    240
atcattgttt caaggttgga agccttaggt ggtaccgtct cagatttgga tttaacagtt    300
ccggaagtcg attttcccaa atcttctgat ttggaaccca tgtctgatct ctcaacttct    360
tcgaaatcgg agaaagcatc tacatccact cgcagatctt tgactgagga tctggacgaa    420
gatgacgtcg ctgaatatga cgacgaagaa gaggacgaag agttacccag gaaaatgaaa    480
gtcttaaacg acaaaaacaa gagcacatct atcaagcagg agaagttgaa tgaacttcca    540
tctcctttgt catccgattt ttcagacgta gatgaagaaa agtcaactct cacacattta    600
aagttgcaac agcaacaaca acaaccagta gacaattatg tttctactcc tttgagtctt    660
ccggaggatt cagttgattt tattaaccca ggtaacttaa aaatagagtc cgatgagaac    720
ttcttgttga gttcaaatac tttacaaata aaacacgaaa atgacaccga ctacattact    780
acagctccat caggttccat caatgatttt tttaattctt atgacattag cgagtcgaat    840
```

-continued

```
cggttgcatc atccagcagc accatttacc gctaatgcat ttgatttaaa tgactttgta      900
ttcttccagg aatag                                                       915
```

<210> SEQ ID NO 70
<211> LENGTH: 304
<212> TYPE: PRT
<213> ORGANISM: Pichia pastoris

<400> SEQUENCE: 70

```
Met Pro Val Asp Ser Ser His Lys Thr Ala Ser Pro Leu Pro Pro Arg
  1               5                  10                  15

Lys Arg Ala Lys Thr Glu Glu Lys Glu Gln Arg Arg Val Glu Arg
             20                  25                  30

Ile Leu Arg Asn Arg Arg Ala Ala His Ala Ser Arg Glu Lys Lys Arg
         35                  40                  45

Arg His Val Glu Phe Leu Glu Asn His Val Val Asp Leu Glu Ser Ala
     50                  55                  60

Leu Gln Glu Ser Ala Lys Ala Thr Asn Lys Leu Lys Glu Ile Gln Asp
 65                  70                  75                  80

Ile Ile Val Ser Arg Leu Glu Ala Leu Gly Gly Thr Val Ser Asp Leu
                 85                  90                  95

Asp Leu Thr Val Pro Glu Val Asp Phe Pro Lys Ser Ser Asp Leu Glu
            100                 105                 110

Pro Met Ser Asp Leu Ser Thr Ser Ser Lys Ser Glu Lys Ala Ser Thr
        115                 120                 125

Ser Thr Arg Arg Ser Leu Thr Glu Asp Leu Asp Glu Asp Val Ala
    130                 135                 140

Glu Tyr Asp Asp Glu Glu Glu Asp Glu Glu Leu Pro Arg Lys Met Lys
145                 150                 155                 160

Val Leu Asn Asp Lys Asn Lys Ser Thr Ser Ile Lys Gln Glu Lys Leu
                165                 170                 175

Asn Glu Leu Pro Ser Pro Leu Ser Ser Asp Phe Ser Asp Val Asp Glu
            180                 185                 190

Glu Lys Ser Thr Leu Thr His Leu Lys Leu Gln Gln Gln Gln Gln
        195                 200                 205

Pro Val Asp Asn Tyr Val Ser Thr Pro Leu Ser Leu Pro Glu Asp Ser
    210                 215                 220

Val Asp Phe Ile Asn Pro Gly Asn Leu Lys Ile Glu Ser Asp Glu Asn
225                 230                 235                 240

Phe Leu Leu Ser Ser Asn Thr Leu Gln Ile Lys His Glu Asn Asp Thr
                245                 250                 255

Asp Tyr Ile Thr Thr Ala Pro Ser Gly Ser Ile Asn Asp Phe Asn
            260                 265                 270

Ser Tyr Asp Ile Ser Glu Ser Asn Arg Leu His His Pro Ala Ala Pro
        275                 280                 285

Phe Thr Ala Asn Ala Phe Asp Leu Asn Asp Phe Val Phe Phe Gln Glu
    290                 295                 300
```

<210> SEQ ID NO 71
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 71

```
gtctagaatg gaaatgactg attttgaact                                       30

<210> SEQ ID NO 72
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 72
cggatcctca tgaagtgatg aagaaatcat                                       30

<210> SEQ ID NO 73
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 73
atggcgggca aaaatcagaa atctagcgcg                                       30

<210> SEQ ID NO 74
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 74
ttacaactcg tctttgacta gaggcgggga                                       30

<210> SEQ ID NO 75
<211> LENGTH: 2520
<212> TYPE: DNA
<213> ORGANISM: Ogataea minuta

<400> SEQUENCE: 75
atggcgggca aaaatcagaa atctagcgcg accaccgctc agtcgttgag gggcgacacc       60
acaacagaac tcgtgttgca aaagggggaag ttgaggacct atatcaaaac agagttgtca    120
gaggacacat tgagccacag ggtactgaac acgacgagcg agaagttgtt gttggtgttg    180
ctgacagttt ttgctgccgt gattcgtttc cgcagtctca gcttccctga ctcagtggta    240
tttgacgagg ttcactttgg aggatttgcc agaaaataca tcctgggaaa cttcttcatg    300
gatgttcatc cgccattggc caaactgtta tttgctgcgg ttggatacct aggcggattc    360
aagggtgatt tgagtttgc gtctattggt gacaagttcc cgacctctgt tccatatgtt    420
ctgatgagaa aaatgagtgc gctcctcagt gttggaacag tggttctcat gtacttaacc    480
ttgcgggcct cgggctgcaa gccaatcgtc tcgtttctca ccgcctcttt gctggtggtc    540
gagagtgcca atgtgaccat ctccagatac attctgctgg actctccttt gatctttttc    600
attgctggct cagtctactc cttgaagaag gtccagatct acaaaccata ctcgttcgag    660
tggatcaaat ccctgtttgc aacaggagtt tgcctgggac ttgcgttctc gtccaaatgg    720
gttggtctat tcactgtggc ctgggtcggt gcctgcagcg tgatcagtct gtggtttcag    780
attggcgatc tgtccgtcaa gcccaagtca attgttaccc aggcggtcgc caaggtgtcc    840
gttttgctcg gagtccctgc catttttgtac ttggttttct tctacctcca cctctcgttc    900
ctcaaccacg agggagacgg tgctgccttc ctctcttctg ccttcagagt gtccttcgac    960
gacactaatg tccctgtgtc caccttggca gacgttggag ttggctcggt cgtcactatc   1020
```

-continued

```
agacatctca acaccaacgg aggctacttg cactcccaca accatttgta tgaaggagga    1080
tcgggacaac agcaaatcac tctgtaccca catctggacg agaacaataa atggaagatt    1140
gagctctaca acgttactga ggaacctacc gaatttgagc caattacaga cggaacaaag    1200
atcagattga acacacatt cacctccaga agattgcatt cccacgacgt gagaccggca    1260
gtcagcgaga tagactggca aaatgaggct tcctgctacg ggtacgagga ctttgaagga    1320
gatgccaacg acgatttcgt tgttgagatt gtggacagtt tgtctgctcc tggcgactcc    1380
agaacacaag tgaaagccat ccataccgtg ttcagattga ggcacgcaat gaccggttgt    1440
tatctgttct cccacgagac caagttgcca aaatggggat ttgaacaaca ggaggtcaca    1500
tgtgccaccc aaggtatcaa acctctctcc tactggtacg tggagcaaaa tgagaaccca    1560
ttccttgatg cggaaaccgc tgaaatcgcc gcttatccgc agctcacttt ccttcaaaaa    1620
ttcactgaat tgcacaagag gatgtggaaa atcaacaaga gtctgaacgc tccacacact    1680
tacgagtcga gaccagagtc ctggcctgtt ctgtccagag gtatttctta ctggagagat    1740
ggagacagac aggtctattt gcttggaaac ccaattgtgt ggtggctagc ctcttttatc    1800
ttccttccgt tcggcttcta cgttatcgct cagcttttga gatggcaatt gggtgctgac    1860
ttgggggata actcggctgt tttcaattac agtatcacca catttgagtt ccttttggga    1920
tggttcattc attactatcc atccttcctc atggagagac agctctttt gcaccactac    1980
atcccagccc tctactttgg tatttggca ttgggacaaa cgttcgaggt gctgtactct    2040
cacgtcctca aaggcaagaa attcctctcg atggccctct tcggcttgct cttcgccagc    2100
gcaggataca tgtttgttca gagatcctcc atcatctacg gatccgcctg ggacaaacag    2160
agctgtgagg cttccaagct gctttcaagc tgggactatg attgcagcat ctacccagag    2220
actttgtttg cttcttccgc atcaattgcg gagccaaagc agactcaggc gccaaagatc    2280
aactttgacg aggcattgaa cgtggacctg gaacccggct acgacaattc acagtttgtt    2340
gagagcattt atgaaacgtc taacgacgaa aaaaaccaag cagagaacgt tgttcaagag    2400
accccctcgtg acaacggcgc cgactccgtt ccagcgacg attcaacagt cggtgaggcc    2460
gtccctgacg atctcaagac aaatggagag tccccgcctc tagtcaaaga cgagttgtaa    2520
```

<210> SEQ ID NO 76
<211> LENGTH: 839
<212> TYPE: PRT
<213> ORGANISM: Ogataea minuta

<400> SEQUENCE: 76

```
Met Ala Gly Lys Asn Gln Lys Ser Ser Ala Thr Thr Ala Gln Ser Leu
  1               5                  10                  15

Arg Gly Asp Thr Thr Thr Glu Leu Val Leu Gln Lys Gly Lys Leu Arg
             20                  25                  30

Thr Tyr Ile Lys Thr Glu Leu Ser Glu Asp Thr Leu Ser His Arg Val
         35                  40                  45

Leu Asn Thr Thr Ser Glu Lys Leu Leu Leu Val Leu Leu Thr Val Phe
     50                  55                  60

Ala Ala Val Ile Arg Phe Arg Ser Leu Ser Phe Pro Asp Ser Val Val
 65                  70                  75                  80

Phe Asp Glu Val His Phe Gly Gly Phe Ala Arg Lys Tyr Ile Leu Gly
                 85                  90                  95

Asn Phe Phe Met Asp Val His Pro Pro Leu Ala Lys Leu Leu Phe Ala
                100                 105                 110

Ala Val Gly Tyr Leu Gly Gly Phe Lys Gly Asp Phe Glu Phe Ala Ser
```

-continued

```
              115                 120                 125
Ile Gly Asp Lys Phe Pro Thr Ser Val Pro Tyr Val Leu Met Arg Glu
130                 135                 140
Met Ser Ala Leu Leu Ser Val Gly Thr Val Val Leu Met Tyr Leu Thr
145                 150                 155                 160
Leu Arg Ala Ser Gly Cys Lys Pro Ile Val Ser Phe Leu Thr Ala Ser
                165                 170                 175
Leu Leu Val Val Glu Ser Ala Asn Val Thr Ile Ser Arg Tyr Ile Leu
                180                 185                 190
Leu Asp Ser Pro Leu Ile Phe Phe Ile Ala Gly Ser Val Tyr Ser Leu
                195                 200                 205
Lys Lys Val Gln Ile Tyr Lys Pro Tyr Ser Phe Glu Trp Ile Lys Ser
210                 215                 220
Leu Phe Ala Thr Gly Val Cys Leu Gly Leu Ala Phe Ser Ser Lys Trp
225                 230                 235                 240
Val Gly Leu Phe Thr Val Ala Trp Val Gly Ala Cys Ser Val Ile Ser
                245                 250                 255
Leu Trp Phe Gln Ile Gly Asp Leu Ser Val Lys Pro Lys Ser Ile Val
                260                 265                 270
Thr Gln Ala Val Ala Lys Val Ser Val Leu Leu Gly Val Pro Ala Ile
                275                 280                 285
Leu Tyr Leu Val Phe Phe Tyr Leu His Leu Ser Phe Leu Asn His Glu
                290                 295                 300
Gly Asp Gly Ala Ala Phe Leu Ser Ser Ala Phe Arg Val Ser Phe Asp
305                 310                 315                 320
Asp Thr Asn Val Pro Val Ser Thr Leu Ala Asp Val Gly Val Gly Ser
                325                 330                 335
Val Val Thr Ile Arg His Leu Asn Thr Asn Gly Gly Tyr Leu His Ser
                340                 345                 350
His Asn His Leu Tyr Glu Gly Gly Ser Gly Gln Gln Ile Thr Leu
                355                 360                 365
Tyr Pro His Leu Asp Glu Asn Asn Lys Trp Lys Ile Glu Leu Tyr Asn
370                 375                 380
Val Thr Glu Glu Pro Thr Glu Phe Glu Pro Ile Thr Asp Gly Thr Lys
385                 390                 395                 400
Ile Arg Leu Lys His Thr Phe Thr Ser Arg Arg Leu His Ser His Asp
                405                 410                 415
Val Arg Pro Ala Val Ser Glu Ile Asp Trp Gln Asn Glu Ala Ser Cys
                420                 425                 430
Tyr Gly Tyr Glu Asp Phe Glu Gly Asp Ala Asn Asp Phe Val Val
                435                 440                 445
Glu Ile Val Asp Ser Leu Ser Ala Pro Gly Asp Ser Arg Thr Gln Val
                450                 455                 460
Lys Ala Ile His Thr Val Phe Arg Leu Arg His Ala Met Thr Gly Cys
465                 470                 475                 480
Tyr Leu Phe Ser His Glu Thr Lys Leu Pro Lys Trp Gly Phe Glu Gln
                485                 490                 495
Gln Glu Val Thr Cys Ala Thr Gln Gly Ile Lys Pro Leu Ser Tyr Trp
                500                 505                 510
Tyr Val Glu Gln Asn Glu Asn Pro Phe Leu Asp Ala Glu Thr Ala Glu
                515                 520                 525
Ile Ala Ala Tyr Pro Gln Leu Thr Phe Leu Gln Lys Phe Thr Glu Leu
530                 535                 540
```

His Lys Arg Met Trp Lys Ile Asn Lys Ser Leu Asn Ala Pro His Thr
545                 550                 555                 560

Tyr Glu Ser Arg Pro Glu Ser Trp Pro Val Leu Ser Arg Gly Ile Ser
            565                 570                 575

Tyr Trp Arg Asp Gly Asp Arg Gln Val Tyr Leu Leu Gly Asn Pro Ile
        580                 585                 590

Val Trp Trp Leu Ala Ser Phe Ile Phe Leu Pro Phe Gly Phe Tyr Val
    595                 600                 605

Ile Ala Gln Leu Leu Arg Trp Gln Leu Gly Ala Asp Leu Gly Asp Asn
610                 615                 620

Ser Ala Val Phe Asn Tyr Ser Ile Thr Thr Phe Glu Phe Leu Leu Gly
625                 630                 635                 640

Trp Phe Ile His Tyr Tyr Pro Ser Phe Leu Met Glu Arg Gln Leu Phe
                645                 650                 655

Leu His His Tyr Ile Pro Ala Leu Tyr Phe Gly Ile Leu Ala Leu Gly
            660                 665                 670

Gln Thr Phe Glu Val Leu Tyr Ser His Val Leu Lys Gly Lys Lys Phe
        675                 680                 685

Leu Ser Met Ala Leu Phe Gly Leu Leu Phe Ala Ser Ala Gly Tyr Met
690                 695                 700

Phe Val Gln Arg Ser Ser Ile Ile Tyr Gly Ser Ala Trp Asp Lys Gln
705                 710                 715                 720

Ser Cys Glu Ala Ser Lys Leu Leu Ser Ser Trp Asp Tyr Asp Cys Ser
                725                 730                 735

Ile Tyr Pro Glu Thr Leu Phe Ala Ser Ala Ser Ile Ala Glu Pro
            740                 745                 750

Lys Gln Thr Gln Ala Pro Lys Ile Asn Phe Asp Glu Ala Leu Asn Val
        755                 760                 765

Asp Leu Glu Pro Gly Tyr Asp Asn Ser Gln Phe Val Glu Ser Ile Tyr
770                 775                 780

Glu Thr Ser Asn Asp Glu Lys Asn Gln Ala Glu Asn Val Val Gln Glu
785                 790                 795                 800

Thr Pro Arg Asp Asn Gly Ala Asp Ser Val Ser Ser Asp Asp Ser Thr
                805                 810                 815

Val Gly Glu Ala Val Pro Asp Asp Leu Lys Thr Asn Gly Glu Ser Pro
            820                 825                 830

Pro Leu Val Lys Asp Glu Leu
        835

<210> SEQ ID NO 77
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 77
atgggcgaac gtacgggcaa aagtgcgctc                                    30

<210> SEQ ID NO 78
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 78
ctaatcggaa attctccacg tgctcaagag                                    30

<210> SEQ ID NO 79
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 79
atggggccca aaataaagac cggcaagaaa                                          30

<210> SEQ ID NO 80
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 80
ctatttagca aaatgcagtt tgatgttgag                                          30

<210> SEQ ID NO 81
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 81
atggacgaga aaacatctc tggcttagaa                                           30

<210> SEQ ID NO 82
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 82
ctactcacta tagacggagc agtcgatcga                                          30

<210> SEQ ID NO 83
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 83
atgtccgagt cagagctgag aaaccgcaaa                                          30

<210> SEQ ID NO 84
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 84
ctaagctata cgccaggtgg aaacccagtt                                          30

<210> SEQ ID NO 85
<211> LENGTH: 2259
<212> TYPE: DNA
<213> ORGANISM: Ogataea minuta

<400> SEQUENCE: 85

-continued

```
atgggcgaac gtacgggcaa aagtgcgctc gaaaaggaac ccttgttgga aaacgatgag      60
tttacagaag atgaagtgaa ggcgaaacta gttgaattgg ccaccaagcc agagccggag     120
tccgaaatta cctctgtttg tcagtggtgg ttccgcaccg agacctggct ggcgccaatc     180
ttgttcactc ttctttcttt ctttgtcaga atgtacaaaa tcggaatcaa tcctcacgtt     240
gtttgggatg aagcccattt cggtaagttt ggatcctact atttgagaca cgaattttac     300
cacgatgtcc accctcctct tggaaaaatg cttgttggtc tctcaggata ccttgctgga     360
tacaatggtt cgtgggactt cccatctggc caggaatacc cggactacat tgactttgtc     420
aaaatgagat tattcaacgc gactttcagt gctctttgtg ttccaatcgc ctacttcacc     480
atgaaagaat ttggcttcaa cagaaaaacg acatggctct tcactttgat ggtgactttg     540
gaaacttcgt acactacgct tgccagattc attctgctgg actcgatgct tcttcttttt     600
accgtggcta ccgtgttctg tttcgccaga ttccacaacc aaaacagagt tgaatcaaac     660
tccttctcga gaaaatggtg gaaatggatt ttgttgactg gtatcaacat cggatgcacc     720
tgttcggtga aaatggttgg tcttttcgtc accaccttgg ttggtatcta cacggttgtc     780
gatctgtgga ctaagttcgg ccagctgagg aagaccatct ctgtaaagag atacattttc     840
cactgggcca ccagaatctt tgctctcatt atcattccat tgctgttttt tttgatctct     900
ttcaaagtcc acttcgacct gcttttcgga tccgtccag gagacgcgaa catgtcctcg     960
ttgttccagg ccaacctggt tggatccacc ctcatttccg ggccaagaga cgtcatgact    1020
ctcaactctg tcgtgactct caaaagtcag ggattgaccg tggtttgct ccattcccac     1080
gtgcagacct atcccgaagg ctcgaaccaa cagcaagtga ccacttactc gcacaaagat    1140
gcgaacaacg actggacttt tgagctggtc agagaagacg tcagaaactc cttcaccgaa    1200
cctcactacg tcgttgacgg aatggccgtc agacttgttc acaaatctac gggaagaaac    1260
ttgcacaccc acgagatccc tgctccagtg tccagttccc aatacgaagt ctccggttac    1320
ggtaacttga ccgttggcga ccgcaaagac aactggattg tggagattgc tgaccaatac    1380
ggcgacgagg acaagatcag attgcatccg ctgacctctt cattcagact cagatcggag    1440
ttgatgggtt gttacttggc cacaaccggt gtctctctgc cacagtgggg attcagacaa    1500
ggagaggttg tctgtatgca ctcgccattc aagagggaca agagaacatg gtggaacatt    1560
gaaaaccacg agaatccaga actgccaaac ccaccagaag acttcaaatt gccaaaaaca    1620
tctttcatca aggactttgt ccagctcaac atcgccatga tggccaccaa caacgcactg    1680
gtcccagatc cggaaaaaca ggacgatttg gcttctaaat tctggcaatg gccttcgttg    1740
aacgtcggta tcagactctg tggttgggga gacgacaatg tcaagtactt cttgattggt    1800
tctccggcca ctacttggac ctcgtcggtt tccatcgtgg tgtttgttgc aatggttgcc    1860
ttctacctgg tcagatggca gagacagatc gaggatttcc catccgactc gaagacacac    1920
tacaagagcg acaaactcaa cctgttcttg atgggaggag tctatccgtt cctgggttgg    1980
ttcctgcatt acatgccgtt ctgtatcatg ggcagagtca cttacgttca ccattacctc    2040
cctgcattgt actttgctat gattgtgatg tgctacactg ttcagtcctt cacgtccttc    2100
gccaacaaca aatacctcac cgctgttgtc tacttgtctc tctatgcact tgtgattggg    2160
ttctttgtgt ttttgcttcc tgtttcgttc ggtatggacg tccgaacgc agacttcaag    2220
tatctcagcc tcttgagcac gtggagaatt tccgattag                            2259
```

<210> SEQ ID NO 86
<211> LENGTH: 752

```
<212> TYPE: PRT
<213> ORGANISM: Ogataea minuta

<400> SEQUENCE: 86
```

| | | | | | | | | | | | | | | |
|---|---|---|---|---|---|---|---|---|---|---|---|---|---|---|
| Met | Gly | Glu | Arg | Thr | Gly | Lys | Ser | Ala | Leu | Glu | Lys | Glu | Pro | Leu | Leu |
| 1 | | | | 5 | | | | | 10 | | | | | 15 | |

Met Gly Glu Arg Thr Gly Lys Ser Ala Leu Glu Lys Glu Pro Leu Leu
1               5                   10                  15

Glu Asn Asp Glu Phe Thr Glu Asp Val Lys Ala Lys Leu Val Glu
            20                  25                  30

Leu Ala Thr Lys Pro Glu Pro Glu Ser Glu Ile Thr Ser Val Cys Gln
            35                  40                  45

Trp Trp Phe Arg Thr Glu Thr Trp Leu Ala Pro Ile Leu Phe Thr Leu
        50                  55                  60

Leu Ser Phe Phe Val Arg Met Tyr Lys Ile Gly Ile Asn Pro His Val
65                  70                  75                  80

Val Trp Asp Glu Ala His Phe Gly Lys Phe Gly Ser Tyr Tyr Leu Arg
                85                  90                  95

His Glu Phe Tyr His Asp Val His Pro Pro Leu Gly Lys Met Leu Val
                100                 105                 110

Gly Leu Ser Gly Tyr Leu Ala Gly Tyr Asn Gly Ser Trp Asp Phe Pro
            115                 120                 125

Ser Gly Gln Glu Tyr Pro Asp Tyr Ile Asp Phe Val Lys Met Arg Leu
130                 135                 140

Phe Asn Ala Thr Phe Ser Ala Leu Cys Val Pro Ile Ala Tyr Phe Thr
145                 150                 155                 160

Met Lys Glu Phe Gly Phe Asn Arg Lys Thr Thr Trp Leu Phe Thr Leu
                165                 170                 175

Met Val Thr Leu Glu Thr Ser Tyr Thr Thr Leu Ala Arg Phe Ile Leu
                180                 185                 190

Leu Asp Ser Met Leu Leu Phe Thr Val Ala Thr Val Phe Cys Phe
            195                 200                 205

Ala Arg Phe His Asn Gln Asn Arg Val Glu Ser Asn Ser Phe Ser Arg
            210                 215                 220

Lys Trp Trp Lys Trp Ile Leu Leu Thr Gly Ile Asn Ile Gly Cys Thr
225                 230                 235                 240

Cys Ser Val Lys Met Val Gly Leu Phe Val Thr Thr Leu Val Gly Ile
                245                 250                 255

Tyr Thr Val Val Asp Leu Trp Thr Lys Phe Gly Gln Leu Arg Lys Thr
                260                 265                 270

Ile Ser Val Lys Arg Tyr Ile Phe His Trp Ala Thr Arg Ile Phe Ala
            275                 280                 285

Leu Ile Ile Ile Pro Phe Ala Val Phe Leu Ile Ser Phe Lys Val His
290                 295                 300

Phe Asp Leu Leu Phe Gly Ser Gly Pro Gly Asp Ala Asn Met Ser Ser
305                 310                 315                 320

Leu Phe Gln Ala Asn Leu Val Gly Ser Thr Leu Ile Ser Gly Pro Arg
                325                 330                 335

Asp Val Met Thr Leu Asn Ser Val Thr Leu Lys Ser Gln Gly Leu
            340                 345                 350

Thr Gly Gly Leu Leu His Ser His Val Gln Thr Tyr Pro Glu Gly Ser
            355                 360                 365

Asn Gln Gln Gln Val Thr Thr Tyr Ser His Lys Asp Ala Asn Asn Asp
            370                 375                 380

Trp Thr Phe Glu Leu Val Arg Glu Asp Val Arg Asn Ser Phe Thr Glu
385                 390                 395                 400

-continued

```
Pro His Tyr Val Val Asp Gly Met Ala Val Arg Leu Val His Lys Ser
                405                 410                 415
Thr Gly Arg Asn Leu His Thr His Glu Ile Pro Ala Pro Val Ser Ser
            420                 425                 430
Ser Gln Tyr Glu Val Ser Gly Tyr Gly Asn Leu Thr Val Gly Asp Arg
        435                 440                 445
Lys Asp Asn Trp Ile Val Glu Ile Ala Asp Gln Tyr Gly Asp Glu Asp
    450                 455                 460
Lys Ile Arg Leu His Pro Leu Thr Ser Ser Phe Arg Leu Arg Ser Glu
465                 470                 475                 480
Leu Met Gly Cys Tyr Leu Ala Thr Thr Gly Val Ser Leu Pro Gln Trp
                485                 490                 495
Gly Phe Arg Gln Gly Glu Val Val Cys Met His Ser Pro Phe Lys Arg
            500                 505                 510
Asp Lys Arg Thr Trp Trp Asn Ile Glu Asn His Glu Asn Pro Glu Leu
        515                 520                 525
Pro Asn Pro Pro Glu Asp Phe Lys Leu Pro Lys Thr Ser Phe Ile Lys
    530                 535                 540
Asp Phe Val Gln Leu Asn Ile Ala Met Met Ala Thr Asn Asn Ala Leu
545                 550                 555                 560
Val Pro Asp Pro Glu Lys Gln Asp Asp Leu Ala Ser Lys Phe Trp Gln
                565                 570                 575
Trp Pro Ser Leu Asn Val Gly Ile Arg Leu Cys Gly Trp Gly Asp Asp
            580                 585                 590
Asn Val Lys Tyr Phe Leu Ile Gly Ser Pro Ala Thr Thr Trp Thr Ser
        595                 600                 605
Ser Val Ser Ile Val Val Phe Val Ala Met Val Ala Phe Tyr Leu Val
    610                 615                 620
Arg Trp Gln Arg Gln Ile Glu Asp Phe Pro Ser Asp Ser Lys Thr His
625                 630                 635                 640
Tyr Lys Ser Asp Lys Leu Asn Leu Phe Leu Met Gly Val Tyr Pro
                645                 650                 655
Phe Leu Gly Trp Phe Leu His Tyr Met Pro Phe Cys Ile Met Gly Arg
            660                 665                 670
Val Thr Tyr Val His His Tyr Leu Pro Ala Leu Tyr Phe Ala Met Ile
        675                 680                 685
Val Met Cys Tyr Thr Val Gln Ser Phe Thr Ser Phe Ala Asn Asn Lys
    690                 695                 700
Tyr Leu Thr Ala Val Val Tyr Leu Ser Leu Tyr Ala Leu Val Ile Gly
705                 710                 715                 720
Phe Phe Val Phe Leu Leu Pro Val Ser Phe Gly Met Asp Gly Pro Asn
                725                 730                 735
Ala Asp Phe Lys Tyr Leu Ser Leu Leu Ser Thr Trp Arg Ile Ser Asp
            740                 745                 750

<210> SEQ ID NO 87
<211> LENGTH: 2265
<212> TYPE: DNA
<213> ORGANISM: Ogataea minuta

<400> SEQUENCE: 87
atggggccca aaataaagac cggcaagaaa cccaatgcgg tggaatcagt ggttgttgac      60
aaaaagggga gtgtctcgtt ggagggcaag attgacaccc cagtcaagaa ctcctcgatc     120
gatccctcaa tggagatcta ctacaagctg acgaatacaa tgttgacgct tctggctttg     180
```

```
gccactagat tctactacat ctggtacccc aacgaggtgg tgttcgatga agttcacttt      240
ggaaagtttg cctcgtacta cttggagaga acctatttct tcgatctcca ccctccattc      300
gccaagctcc tcattgcctt cgttggctat ctggttggtt tcagtgggaa attcaagttt      360
gacaacatcg gggacagcta tatcacccac tctattccat acatcccgtt gcgtgcgctt      420
tctgctgttc tgggatccct gaccgtgccg ctcatgttct ccacgttgca agagtgtggt      480
tactcaattc caacgtgcgc ttttggtgcc ctgctggttg tgtttgacaa cgctcatgct      540
gccgagacta gattgattct gctcgacgct acgctgatct tctcggttgc agcttctgtg      600
tactgctacg tgagattcac aaagcaaaga caccagcctt ttaccgcaac ctggtacaag      660
tggttggttt tgaccggtgt ctcgttgtcc tgtgtcattt ccaccaaata cgtgggtgtt      720
ttcacctttg cctgcgttgg tgtggctgtg gtttgggact tgtgggagct tttggatatt      780
aagaagggcc tcacaattag agttttggct agacattttg tccacagagc catcggcctc      840
attttgctgc cgttcattat ttacttgggc tggttttaca tccactttgc cattctgacc      900
aaatcgggac cgggagatcc tttcatgagc gcagacttcc aagaaacttt gggagactct      960
cctctcacaa gagaagcaag agaggtcaac taccatgata tcataacggt caaacacaaa     1020
gacactgagt gtttattgca ctcgcatcct ttcaactatc cactacgtta cgatgacgga     1080
agaatttctt cgcaaggcca gcaggtgact tgtatgaaag attacacaga cgttaacaac     1140
tactgggaaa ttcttcctgc taaagcttct gacgaaactg tgaacctcgg tctcgctgtc     1200
aaacaaggag acactttcag attgagacac gttgagacag gcggatttttt actcactcat     1260 gacgttgctt ctcccctttt cccgaccaac gaggagttta ctgtcatgag cgctgaagaa     1320
gcggattcta caaggttcaa cgacactttg ttcagatttg atccgttcga caagaggaag     1380
aacgacgtgc tcaagaccaa ggcatccgtg gtcaaagttt ccacgttcc taccattgtc     1440 actatgtgga ctcacgatga tcagctactt ccagaatggg gcttcaacca acaggaggtc     1500
aacggaaaca aaaaggttgc ggactccgat aactactgga ctattgactc tatcattggt     1560
ttgtctggcg aaagagccaa gtacgttcca aaagaagtga aacgtttgcc attccttacc     1620
aaatggaaag agctgcaact cactatgttt gaacaaaaca caaattgag ttcgagccat     1680 ccatttgcat cccaacctga gtcatggcct ttgtcgttgt ccggtgtctc gttctggact     1740
aagaatgata cccgcgaaca aatctacttc attggaaatc ttttcggctg gtggttagaa     1800
gccggactgc ttctgtgtta cctaggaata ttgctggcag accaactcac gagacgcaga     1860
aatgtgactg tttttgagcac tagagccaga gctaggttgt acaaaaacat cggatttttc     1920
ttctgcggat gggccacccca ctacttccca ttcttcctca tgtcaagaca aaagttcctg     1980
catcattatt tgcctgcgca cctgctggct gcgctgtttt cggcgtcctt gttggaattc     2040 atttttcaccg ataacagaca cgaggagctc agggatccaa agataagtc tgagccagga     2100 aaggtcaact ggatcctata cctgtcgtgc ctgattctgc ttgtgacagt cttagttgga     2160
ttctacgtct tccttgctcc gttgacctac ggaaacgttt cattgacccc tgaagaagtc     2220
atcaagagac aaattctcaa catcaaactg cattttgcta aatag                     2265

<210> SEQ ID NO 88
<211> LENGTH: 754
<212> TYPE: PRT
<213> ORGANISM: Ogataea minuta

<400> SEQUENCE: 88

Met Gly Pro Lys Ile Lys Thr Gly Lys Lys Pro Asn Ala Val Glu Ser
 1               5                  10                  15
```

-continued

Val Val Val Asp Lys Gly Ser Val Ser Leu Glu Gly Lys Ile Asp
            20                  25                  30

Thr Pro Val Lys Asn Ser Ser Ile Asp Pro Ser Met Glu Ile Tyr Tyr
            35                  40                  45

Lys Leu Thr Asn Thr Met Leu Thr Leu Leu Ala Leu Ala Thr Arg Phe
    50                  55                  60

Tyr Tyr Ile Trp Tyr Pro Asn Glu Val Val Phe Asp Glu Val His Phe
65                  70                  75                  80

Gly Lys Phe Ala Ser Tyr Tyr Leu Glu Arg Thr Tyr Phe Phe Asp Leu
                85                  90                  95

His Pro Pro Phe Ala Lys Leu Leu Ile Ala Phe Val Gly Tyr Leu Val
            100                 105                 110

Gly Phe Ser Gly Lys Phe Lys Phe Asp Asn Ile Gly Asp Ser Tyr Ile
            115                 120                 125

Thr His Ser Ile Pro Tyr Ile Pro Leu Arg Ala Leu Ser Ala Val Leu
    130                 135                 140

Gly Ser Leu Thr Val Pro Leu Met Phe Ser Thr Leu Gln Glu Cys Gly
145                 150                 155                 160

Tyr Ser Ile Pro Thr Cys Ala Phe Gly Ala Leu Leu Val Val Phe Asp
                165                 170                 175

Asn Ala His Ala Ala Glu Thr Arg Leu Ile Leu Leu Asp Ala Thr Leu
            180                 185                 190

Ile Phe Ser Val Ala Ala Ser Val Tyr Cys Tyr Val Arg Phe Thr Lys
            195                 200                 205

Gln Arg His Gln Pro Phe Thr Ala Thr Trp Tyr Lys Trp Leu Val Leu
    210                 215                 220

Thr Gly Val Ser Leu Ser Cys Val Ile Ser Thr Lys Tyr Val Gly Val
225                 230                 235                 240

Phe Thr Phe Ala Cys Val Gly Val Ala Val Val Trp Asp Leu Trp Glu
                245                 250                 255

Leu Leu Asp Ile Lys Lys Gly Leu Thr Ile Arg Val Leu Ala Arg His
            260                 265                 270

Phe Val His Arg Ala Ile Gly Leu Ile Leu Leu Pro Phe Ile Ile Tyr
            275                 280                 285

Leu Gly Trp Phe Tyr Ile His Phe Ala Ile Leu Thr Lys Ser Gly Pro
    290                 295                 300

Gly Asp Pro Phe Met Ser Ala Asp Phe Gln Glu Thr Leu Gly Asp Ser
305                 310                 315                 320

Pro Leu Thr Arg Glu Ala Arg Glu Val Asn Tyr His Asp Ile Ile Thr
                325                 330                 335

Val Lys His Lys Asp Thr Glu Cys Leu Leu His Ser His Pro Phe Asn
            340                 345                 350

Tyr Pro Leu Arg Tyr Asp Asp Gly Arg Ile Ser Ser Gln Gly Gln Gln
            355                 360                 365

Val Thr Cys Met Lys Asp Tyr Thr Asp Val Asn Asn Tyr Trp Glu Ile
    370                 375                 380

Leu Pro Ala Lys Ala Ser Asp Glu Thr Val Asn Leu Gly Leu Ala Val
385                 390                 395                 400

Lys Gln Gly Asp Thr Phe Arg Leu Arg His Val Glu Thr Gly Gly Phe
                405                 410                 415

Leu Leu Thr His Asp Val Ala Ser Pro Leu Phe Pro Thr Asn Glu Glu
            420                 425                 430

Phe Thr Val Met Ser Ala Glu Glu Ala Asp Ser Thr Arg Phe Asn Asp

```
                435           440             445
Thr Leu Phe Arg Phe Asp Pro Phe Asp Lys Arg Lys Asn Asp Val Leu
450                 455                 460

Lys Thr Lys Ala Ser Val Val Lys Val Phe His Val Pro Thr Ile Val
465                 470                 475                 480

Thr Met Trp Thr His Asp Asp Gln Leu Leu Pro Glu Trp Gly Phe Asn
                    485                 490                 495

Gln Gln Glu Val Asn Gly Asn Lys Lys Val Ala Asp Ser Asp Asn Tyr
                500                 505                 510

Trp Thr Ile Asp Ser Ile Ile Gly Leu Ser Gly Glu Arg Ala Lys Tyr
                515                 520                 525

Val Pro Lys Glu Val Lys Arg Leu Pro Phe Leu Thr Lys Trp Lys Glu
530                 535                 540

Leu Gln Leu Thr Met Phe Glu Gln Asn Asn Lys Leu Ser Ser Ser His
545                 550                 555                 560

Pro Phe Ala Ser Gln Pro Glu Ser Trp Pro Leu Ser Leu Ser Gly Val
                565                 570                 575

Ser Phe Trp Thr Lys Asn Asp Thr Arg Glu Gln Ile Tyr Phe Ile Gly
                580                 585                 590

Asn Leu Phe Gly Trp Trp Leu Glu Ala Gly Leu Leu Leu Cys Tyr Leu
                595                 600                 605

Gly Ile Leu Leu Ala Asp Gln Leu Thr Arg Arg Asn Val Thr Val
610                 615                 620

Leu Ser Thr Arg Ala Arg Ala Arg Leu Tyr Lys Asn Ile Gly Phe Phe
625                 630                 635                 640

Phe Cys Gly Trp Ala Thr His Tyr Phe Pro Phe Phe Leu Met Ser Arg
                645                 650                 655

Gln Lys Phe Leu His His Tyr Leu Pro Ala His Leu Leu Ala Ala Leu
                660                 665                 670

Phe Ser Ala Ser Leu Leu Glu Phe Ile Phe Thr Asp Asn Arg His Glu
                675                 680                 685

Glu Leu Arg Asp Pro Lys Asp Lys Ser Glu Pro Gly Lys Val Asn Trp
690                 695                 700

Ile Leu Tyr Leu Ser Cys Leu Ile Leu Leu Val Thr Val Leu Val Gly
705                 710                 715                 720

Phe Tyr Val Phe Leu Ala Pro Leu Thr Tyr Gly Asn Val Ser Leu Thr
                725                 730                 735

Pro Glu Glu Val Ile Lys Arg Gln Ile Leu Asn Ile Lys Leu His Phe
                740                 745                 750

Ala Lys

<210> SEQ ID NO 89
<211> LENGTH: 2199
<212> TYPE: DNA
<213> ORGANISM: Ogataea minuta

<400> SEQUENCE: 89
atggacgaga aaacatctct tggcttagaa cgcctaggca ccggcccaga gttcacactc     60
gtgcagggcc cgagacgcaa ctacctccgt ctgccggaaa aggcggggct tccaagccgc    120
actagaaagg agaagctcca ggttctgtgc gtcattctgc tcgcgctcac cacgagactc    180
gtctctctga accatccgtc gtcggtcgtc tacgacgagc taactaccgg aaacatcgtc    240
aacaactacc tccatggaca ctattttgtc gatgcagatc ctccttttgt caaaattcta    300
tacactgctg tcgcccaaat atcgcagtac acgggcgcgt tccaattcca ctctgctggc    360
```

```
cagtcgtatc tgaacgaaga cctcgagccg gagttcccat acgtggcact ccgggtgttc    420
agcggcctct gcagcgtggc aaccgttctc ctggcataca aaactctcag agccacggga    480
gtcagacacc tgattgctct gttcggcgcc tttctgattg cactagaagg ctcgatgatt    540
acgcaatcaa gattttcat gcaaacggct cacgtcgtgt tcttcaccgg cttggccgtt     600
ggaatgtcca aaacgtcaga cctgtttgaa ccctcgagcg caaaatggct caaacacacc    660
gcagcggccg gcctcggcgt ggcgtttcta atttcgtccg cgtggtcggg tcttttcacg    720
gctgtttggt tggttctcgt caccctgaga gagtctggt acctcaccgg cgacgttacg     780
acaaatccaa gaaccacgtt cctcagatac gcgcttcccc gctttgctct tattgttgcg    840
gcgccagtgg ccttctacct gtgggtgttc aaagtgcatc tggacttgct tccagtggct    900
ggtcccggct acccgttcat gtccgcggag ttccagcacg gctggtcgg cacccatctc     960
aacaacatt ctgccgaagt ctcgtatggc tccacagttt ccattagaca cttgcacacg    1020
gggaagtacc tgcactccga gaacaaaacg taccctaaaa caggacacca gcgggtcacc   1080
acattcggcg accaggactt caacaacctg ttttacgtcg agatgagggt caagtccgaa   1140
cgcggcgagc tcgcacggaa agtcaaagct gtcgagagcg cagacaaat acgtcttttc    1200
cacaatgcca cccagaagta cctgtttatc gacccggaca caagcctcc tctctccgag    1260
acagactata caaggaagt gagcacgttt ggaaacgctt cctgggtggg cgagaactac    1320
ctcaacttcg agcttctgct tgccccgggc ttctccaaga ccgaggtggg caagaaaaga   1380
gtgcgggccg tcgagtctgt cttccagctg tacaacgtca agaacaagtg ctatctgctg   1440
gggaccgaga acaggcttcc gagctgggca gacggggaaa acgaggtcgt ttgcatcgag   1500
aaacctattt tcgaaagatc gttgtggtac ttgaaacca atctccacga caagttcacc    1560
cccgcacggg cccaggtcgc tttcaggcag cagacgttct gggacaagat tctcgaaatt   1620
cacaaagtca tggcagatct gctcgcacaa aacacccatg acgacgccaa cagcaccgct   1680
cctcgggatt ggttcttctt cagaaaggga atcaggtact gggcagaaag tcaggccatg   1740
gtatatctca ctgggaaccc ggttgtctac tcgttgacgg cgctaggcac tgtgggattc   1800
ttggtgttca aactcggtca tctatgttcg ttcaacccga ataagtcgcc agactactcc   1860
agcgacttcc tcaagttcga ctaccacgct caggaatttc ttctcggata cctgctgaac   1920
tggcttcctc acgcgctttc aaagacaaac acatacgtgt tcgagtacca gccggcgttg   1980
tacttcggtg ttcttctgtc ctgtcagtcg ctagagtacc tggcctccaa gaacctgaag   2040
ctgtgctatg tgtttgcggc cgcggttgca ctgctcacag cagctttctt ccgtttgtcg   2100
gcaccgttga tgtacggact gaagtggcag gagttgtact cgtcgctgt ttcaacagct    2160
gccagacagt cgatcgactg ctccgtctat agtgagtag                          2199
```

<210> SEQ ID NO 90  
<211> LENGTH: 732  
<212> TYPE: PRT  
<213> ORGANISM: Ogataea minuta

<400> SEQUENCE: 90

Met Asp Glu Lys Asn Ile Ser Gly Leu Glu Arg Leu Gly Thr Gly Pro
1               5                   10                  15

Glu Phe Thr Leu Val Gln Gly Pro Arg Arg Asn Tyr Leu Arg Leu Pro
            20                  25                  30

Glu Lys Ala Gly Leu Pro Ser Arg Thr Arg Lys Glu Lys Leu Gln Val
        35                  40                  45

```
Leu Cys Val Ile Leu Leu Ala Leu Thr Thr Arg Leu Val Ser Leu Asn
 50                  55                  60

His Pro Ser Ser Val Val Tyr Asp Glu Leu Thr Gly Asn Ile Val
 65                  70                  75                  80

Asn Asn Tyr Leu His Gly His Tyr Phe Val Asp Ala Asp Pro Pro Phe
                 85                  90                  95

Val Lys Ile Leu Tyr Thr Ala Val Ala Gln Ile Ser Gln Tyr Thr Gly
             100                 105                 110

Ala Phe Gln Phe His Ser Ala Gly Gln Ser Tyr Leu Asn Glu Asp Leu
         115                 120                 125

Glu Pro Glu Phe Pro Tyr Val Ala Leu Arg Val Phe Ser Gly Leu Cys
 130                 135                 140

Ser Val Ala Thr Val Leu Leu Ala Tyr Lys Thr Leu Arg Ala Thr Gly
145                 150                 155                 160

Val Arg His Leu Ile Ala Leu Phe Gly Ala Phe Leu Ile Ala Leu Glu
                 165                 170                 175

Gly Ser Met Ile Thr Gln Ser Arg Phe Phe Met Gln Thr Ala His Val
             180                 185                 190

Val Phe Phe Thr Gly Leu Ala Val Gly Met Ser Lys Thr Ser Asp Leu
         195                 200                 205

Phe Glu Pro Ser Ser Ala Lys Trp Leu Lys His Thr Ala Ala Gly
 210                 215                 220

Leu Gly Val Ala Phe Leu Ile Ser Ser Ala Trp Ser Gly Leu Phe Thr
225                 230                 235                 240

Ala Val Trp Leu Val Leu Val Thr Leu Arg Arg Val Trp Tyr Leu Thr
                 245                 250                 255

Gly Asp Val Thr Thr Asn Pro Arg Thr Thr Phe Leu Arg Tyr Ala Leu
             260                 265                 270

Pro Arg Phe Ala Leu Ile Val Ala Ala Pro Val Ala Phe Tyr Leu Trp
         275                 280                 285

Val Phe Lys Val His Leu Asp Leu Leu Pro Val Ala Gly Pro Gly Tyr
 290                 295                 300

Pro Phe Met Ser Ala Glu Phe Gln His Gly Leu Val Gly Thr His Leu
305                 310                 315                 320

Asn Asn Ile Ser Ala Glu Val Ser Tyr Gly Ser Thr Val Ser Ile Arg
                 325                 330                 335

His Leu His Thr Gly Lys Tyr Leu His Ser Glu Asn Lys Thr Tyr Pro
             340                 345                 350

Lys Thr Gly His Gln Arg Val Thr Thr Phe Gly Asp Gln Asp Phe Asn
         355                 360                 365

Asn Leu Phe Tyr Val Glu Met Arg Val Lys Ser Glu Arg Gly Glu Leu
 370                 375                 380

Ala Arg Lys Val Lys Ala Val Glu Ser Gly Arg Gln Ile Arg Leu Phe
385                 390                 395                 400

His Asn Ala Thr Gln Lys Tyr Leu Phe Ile Asp Pro Asp Asn Lys Pro
                 405                 410                 415

Pro Leu Ser Glu Thr Asp Tyr Asn Lys Glu Val Ser Thr Phe Gly Asn
             420                 425                 430

Ala Ser Trp Val Gly Glu Asn Tyr Leu Asn Phe Glu Leu Leu Leu Ala
         435                 440                 445

Pro Gly Phe Ser Lys Thr Glu Val Gly Lys Lys Arg Val Arg Ala Val
 450                 455                 460

Glu Ser Val Phe Gln Leu Tyr Asn Val Lys Asn Lys Cys Tyr Leu Leu
465                 470                 475                 480
```

Gly Thr Glu Asn Arg Leu Pro Ser Trp Ala Asp Gly Glu Asn Glu Val
            485                 490                 495

Val Cys Ile Glu Lys Pro Ile Phe Glu Arg Ser Leu Trp Tyr Phe Glu
        500                 505                 510

Thr Asn Leu His Asp Lys Phe Thr Pro Ala Arg Ala Gln Val Ala Phe
            515                 520                 525

Arg Gln Gln Thr Phe Trp Asp Lys Ile Leu Glu Ile His Lys Val Met
530                 535                 540

Ala Asp Leu Leu Ala Gln Asn Thr His Asp Ala Asn Ser Thr Ala
545                 550                 555                 560

Pro Arg Asp Trp Phe Phe Arg Lys Gly Ile Arg Tyr Trp Ala Glu
                565                 570                 575

Ser Gln Ala Met Val Tyr Leu Thr Gly Asn Pro Val Val Tyr Ser Leu
            580                 585                 590

Thr Ala Leu Gly Thr Val Gly Phe Leu Val Phe Lys Leu Gly His Leu
        595                 600                 605

Cys Ser Phe Asn Pro Asn Lys Ser Pro Asp Tyr Ser Ser Asp Phe Leu
            610                 615                 620

Lys Phe Asp Tyr His Ala Gln Glu Phe Leu Leu Gly Tyr Leu Leu Asn
625                 630                 635                 640

Trp Leu Pro His Ala Leu Ser Lys Thr Asn Thr Tyr Val Phe Glu Tyr
                645                 650                 655

Gln Pro Ala Leu Tyr Phe Gly Val Leu Leu Ser Cys Gln Ser Leu Glu
            660                 665                 670

Tyr Leu Ala Ser Lys Asn Leu Lys Leu Cys Tyr Val Phe Ala Ala Ala
        675                 680                 685

Val Ala Leu Leu Thr Ala Ala Phe Phe Arg Leu Ser Ala Pro Leu Met
            690                 695                 700

Tyr Gly Leu Lys Trp Gln Glu Leu Tyr Cys Val Ala Val Ser Thr Ala
705                 710                 715                 720

Ala Arg Gln Ser Ile Asp Cys Ser Val Tyr Ser Glu
                725                 730

<210> SEQ ID NO 91
<211> LENGTH: 2241
<212> TYPE: DNA
<213> ORGANISM: Ogataea minuta

<400> SEQUENCE: 91
atgtccgagt cagagctgag aaaccgcaaa gctactctgg aactgcgtt tcaagatgag      60 tcgactggac cgaaagaaga gagtcacttg atcaaaaat cgttagccag aagagggtgg     120
gtccaactga tcaccacgta tgttgaacca gtggcaggtc cccttttctt cactgtcctg     180
gctgcgtatc tgagactcta tgatctcaaa gccaacaatc gagtggtctg ggacgaggct     240
cattttggca aatttggagc ccagtacttg agacacgaat tttaccacga cgtccatccg     300
ccgctgggga aaatgctgtg cggactgagc gagtatctgg caggctacaa tggcagttct     360
gagggtttca atttcgagag cggaaaagaa tatccggatc accttgacta tgcctcgatg     420
agatcgttcg ggacttggtt cagcactctg tcattcctg tctgctattt cacatgcaaa     480
tcgctcaatt tcaacctaca gaccaccat ctagttcga caatgtgctg tctggagaac     540
tcgtacattg cgctgggaaa gttcatactg ctggactcca tgctgatgtt gttcacgggg     600 actacgttt tctgtctcgt caaaacccac acgctgcggg cgcaggagtt ctccaccaga     660
tggactcttt ggatgtgtct gaccggagtt tcaactggct gtgtttgctc ggtgaaatgg     720

```
gtcggtctgt tgtcacgct acttgttgga gcatacacgg tgctagagct atggctgaaa      780
ttctggtcca aggagttcaa gacagccagg tacttgaaaa gctgggtttt cagagcagtg      840
agtctgatct tcatcccagc tctcgtttat ttgatattct tcaaggtaca tttctcgctc      900
ctgacccgga ccgggacggg agcgggctct tgtcgtctc tttaccaggc cagcatggag       960
gacgcggaca tcctggatta cccgagaaac gttgctattg gctcgcgcat cactctcaga     1020
tctcaaggcc cctcgcccag tcttttgcac tcgcaccagt ctgtctatcc cgcaggatcg     1080
gaacagtacc aggtgacaac ctacgggttc aaagactcca caacaacttt ctggtgaaa      1140
aaagcccgga cacctttcaa atatggagag ttcgtctcca acggcgacct gattcgactt     1200
cagcacgagc taacccgagg aaacctccat tctcacgcca tcaacggaca tgtttccaag     1260
cagttctggg aggtgagcgg gtacgaaaac gaggaaatcg gggacgacaa ggatgattgg     1320
gaggtgatta ttgcggagca gctcaaatct cctaactcga cctattcagc gctgcacgag     1380
tcgtccccag aattctaccg cacggtccac ccgatctcca ctagcttcaa gttgcgccac     1440
aaggttttag gctgctacct ggccaccaca gggcactcgt atccgacatg gggctttaaa     1500
caaggcgagg tgatctgtaa accggcggag tcgctcttga cccgctgga caaatcgacc      1560
tggtggaacg tcgagcttca cgacaacagc ggtctgaaag tagacccagg ctaccaatac     1620
ccccgtcccc ggttctttg ggactttctc tcgattcaaa tggccatgat ggcctcgaac      1680
aacgctttgg ttccagaccc gcacaaacag gacgatatag cctccagttg gtgggagtgg     1740
ccgacgttga acaggggct gaggatgtgc tcttggtctc acggggtggt gcggtactac       1800
ctcctgggaa atccgttttc tacgtggttc agcacttttt gcattggcgc tctgctggtg     1860
ctgatggctc gctggacgct cctctggcaa agacagatcc tcgttctcac cgaaaaccag     1920
gcctggactt taaccatgaa agccgttgtt ccgctcatgg ggtgggcttt ccactacctt     1980
ccattcgtcg tgatgggaag ggtgacgtat taccaccatt acatgccggc tttgtacttt     2040
gctttcttcg tgacgggctt tgtagtcgaa cattcggtcg ctcgtttcgg aggggtttac     2100
acgggaaagt tggtctatct agtactttgg ggctgtgtgt gctacagctt ctggctgttc     2160
agtccgcttt gtttggggat gcacggaatg acgtcgctct atcgtcatct caactgggtt     2220
tccacctggc gtatagctta g                                               2241
```

<210> SEQ ID NO 92
<211> LENGTH: 746
<212> TYPE: PRT
<213> ORGANISM: Ogataea minuta

<400> SEQUENCE: 92

Met Ser Glu Ser Glu Leu Arg Asn Arg Lys Ala Thr Leu Gly Thr Ala
1               5                   10                  15

Phe Gln Asp Glu Ser Thr Gly Pro Lys Glu Glu Ser His Leu Asp Gln
            20                  25                  30

Lys Ser Leu Ala Arg Arg Gly Trp Val Gln Leu Ile Thr Thr Tyr Val
        35                  40                  45

Glu Pro Val Ala Gly Pro Leu Phe Phe Thr Val Leu Ala Ala Tyr Leu
    50                  55                  60

Arg Leu Tyr Asp Leu Lys Ala Asn Asn Arg Val Val Trp Asp Glu Ala
65                  70                  75                  80

His Phe Gly Lys Phe Gly Ala Gln Tyr Leu Arg His Glu Phe Tyr His
                85                  90                  95

Asp Val His Pro Pro Leu Gly Lys Met Leu Cys Gly Leu Ser Glu Tyr

-continued

```
                100                 105                 110
Leu Ala Gly Tyr Asn Gly Ser Ser Glu Gly Phe Asn Phe Glu Ser Gly
            115                 120                 125
Lys Glu Tyr Pro Asp His Leu Asp Tyr Ala Ser Met Arg Ser Phe Gly
            130                 135                 140
Thr Trp Phe Ser Thr Leu Val Ile Pro Val Cys Tyr Phe Thr Cys Lys
145                 150                 155                 160
Ser Leu Asn Phe Asn Leu Gln Thr Thr Tyr Leu Val Ser Thr Met Cys
            165                 170                 175
Cys Leu Glu Asn Ser Tyr Ile Ala Leu Gly Lys Phe Ile Leu Leu Asp
            180                 185                 190
Ser Met Leu Met Leu Phe Thr Gly Thr Thr Phe Phe Cys Leu Val Lys
            195                 200                 205
Thr His Thr Leu Arg Ala Gln Glu Phe Ser Thr Arg Trp Thr Leu Trp
            210                 215                 220
Met Cys Leu Thr Gly Val Ser Thr Gly Cys Val Cys Ser Val Lys Trp
225                 230                 235                 240
Val Gly Leu Phe Val Thr Leu Val Gly Ala Tyr Thr Val Leu Glu
            245                 250                 255
Leu Trp Leu Lys Phe Trp Ser Lys Glu Phe Lys Thr Ala Arg Tyr Leu
            260                 265                 270
Lys Ser Trp Val Phe Arg Ala Val Ser Leu Ile Phe Ile Pro Ala Leu
            275                 280                 285
Val Tyr Leu Ile Phe Phe Lys Val His Phe Ser Leu Leu Thr Arg Thr
            290                 295                 300
Gly Thr Gly Ala Gly Ser Leu Ser Ser Leu Tyr Gln Ala Ser Met Glu
305                 310                 315                 320
Asp Ala Asp Ile Leu Asp Tyr Pro Arg Asn Val Ala Ile Gly Ser Arg
            325                 330                 335
Ile Thr Leu Arg Ser Gln Gly Pro Ser Pro Ser Leu Leu His Ser His
            340                 345                 350
Gln Ser Val Tyr Pro Ala Gly Ser Glu Gln Tyr Gln Val Thr Thr Tyr
            355                 360                 365
Gly Phe Lys Asp Ser Asn Asn Asn Phe Leu Val Lys Lys Ala Arg Thr
            370                 375                 380
Pro Phe Lys Tyr Gly Glu Phe Val Ser Asn Gly Asp Leu Ile Arg Leu
385                 390                 395                 400
Gln His Glu Leu Thr Arg Gly Asn Leu His Ser His Ala Ile Asn Gly
            405                 410                 415
His Val Ser Lys Gln Phe Trp Glu Val Ser Gly Tyr Gly Asn Glu Glu
            420                 425                 430
Ile Gly Asp Asp Lys Asp Trp Glu Val Ile Ile Ala Glu Gln Leu
            435                 440                 445
Lys Ser Pro Asn Ser Thr Tyr Ser Ala Leu His Glu Ser Ser Pro Glu
            450                 455                 460
Phe Tyr Arg Thr Val His Pro Ile Ser Thr Ser Phe Lys Leu Arg His
465                 470                 475                 480
Lys Val Leu Gly Cys Tyr Leu Ala Thr Thr Gly His Ser Tyr Pro Thr
            485                 490                 495
Trp Gly Phe Lys Gln Gly Glu Val Ile Cys Lys Pro Ala Glu Ser Leu
            500                 505                 510
Leu Asn Pro Leu Asp Lys Ser Thr Trp Trp Asn Val Glu Leu His Asp
            515                 520                 525
```

```
Asn Ser Gly Leu Lys Val Asp Pro Gly Tyr Gln Tyr Pro Arg Pro Arg
            530                 535                 540

Phe Phe Trp Asp Phe Leu Ser Ile Gln Met Ala Met Met Ala Ser Asn
545                 550                 555                 560

Asn Ala Leu Val Pro Asp Pro His Lys Gln Asp Asp Ile Ala Ser Ser
                565                 570                 575

Trp Trp Glu Trp Pro Thr Leu Lys Gln Gly Leu Arg Met Cys Ser Trp
            580                 585                 590

Ser His Gly Val Val Arg Tyr Tyr Leu Leu Gly Asn Pro Phe Ser Thr
            595                 600                 605

Trp Phe Ser Thr Phe Cys Ile Gly Ala Leu Leu Val Leu Met Ala Arg
            610                 615                 620

Trp Thr Leu Leu Trp Gln Arg Gln Ile Leu Val Leu Thr Glu Asn Gln
625                 630                 635                 640

Ala Trp Thr Leu Thr Met Lys Ala Val Val Pro Leu Met Gly Trp Ala
                645                 650                 655

Phe His Tyr Leu Pro Phe Val Val Met Gly Arg Val Thr Tyr Tyr His
            660                 665                 670

His Tyr Met Pro Ala Leu Tyr Phe Ala Phe Phe Val Thr Gly Phe Val
            675                 680                 685

Val Glu His Ser Val Ala Arg Phe Gly Gly Val Tyr Thr Gly Lys Leu
            690                 695                 700

Val Tyr Leu Val Leu Trp Gly Cys Val Cys Tyr Ser Phe Trp Leu Phe
705                 710                 715                 720

Ser Pro Leu Cys Leu Gly Met His Gly Met Thr Ser Leu Tyr Arg His
                725                 730                 735

Leu Asn Trp Val Ser Thr Trp Arg Ile Ala
                740                 745

<210> SEQ ID NO 93
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 93
caagcttgga cctacaacac gtccgaagaa                                      30

<210> SEQ ID NO 94
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 94
cggtaccggt ttgataccct gggtggcaca                                      30

<210> SEQ ID NO 95
<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 95
gaagcttact acataattcg tgtacgtgtt c                                    31

<210> SEQ ID NO 96
```

<211> LENGTH: 31
<212> TYPE: DNA
<213> ORGANISM: Artificial Sequence
<220> FEATURE:
<223> OTHER INFORMATION: Synthetic oligonucleotide

<400> SEQUENCE: 96
cggtaccgtc gccgtattgg tcagcaatct c                                    31

<210> SEQ ID NO 97
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 97
gtcatgagat ccaagctgat ccctcaatgg agatctact                            39

<210> SEQ ID NO 98
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 98
ggtgtgtggg ggatcgggat gcaaatggat ggctcgaac                            39

<210> SEQ ID NO 99
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 99
gacggtatcg ataagcttga tgcgcggcct tccgacctt                            39

<210> SEQ ID NO 100
<211> LENGTH: 39
<212> TYPE: DNA
<213> ORGANISM: Artificial Sequence
<220> FEATURE:
<223> OTHER INFORMATION: Synthetic oligonucleotide

<400> SEQUENCE: 100
ctggggaagc tcggatccgg ctcgaggtct tcgttcaga                            39

<210> SEQ ID NO 101
<211> LENGTH: 38
<212> TYPE: DNA
<213> ORGANISM: Artificial Sequence
<220> FEATURE:
<223> OTHER INFORMATION: Synthetic oligonucleotide

<400> SEQUENCE: 101
ctagttctag agcggcccag gtcgctttca ggcagcag                             38

<210> SEQ ID NO 102
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 102

-continued caccgcggtg gcggccaagc ttgggtaccg gctcgcgtag               40

<210> SEQ ID NO 103
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 103
gcagcccggg ggatccacga aaccacgtcc tact               34

<210> SEQ ID NO 104
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 104
ggggaagctc ggatcgactc atcttgaaac gca               33

<210> SEQ ID NO 105
<211> LENGTH: 33
<212> TYPE: DNA
<213> ORGANISM: Artificial Sequence
<220> FEATURE:
<223> OTHER INFORMATION: Synthetic oligonucleotide

<400> SEQUENCE: 105
agttctagag cggccttacc accattacat gcc               33

<210> SEQ ID NO 106
<211> LENGTH: 40
<212> TYPE: DNA
<213> ORGANISM: Artificial Sequence
<220> FEATURE:
<223> OTHER INFORMATION: Synthetic oligonucleotide

<400> SEQUENCE: 106
aattggagct ccaccgcggc cgcaacttac tcgacgctaa               40

<210> SEQ ID NO 107
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 107
gaacggcact ggtcaacttg gccat               25

<210> SEQ ID NO 108
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 108
cttcgtggcc gaggagcagg actga               25

<210> SEQ ID NO 109
<211> LENGTH: 23
<212> TYPE: DNA
<213> ORGANISM: Artificial Sequence
<220> FEATURE:

<223> OTHER INFORMATION: Synthetic oligonucleotide

<400> SEQUENCE: 109
gaattctagc cgagcatgag cta                                        23

<210> SEQ ID NO 110
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 110
cgttcagact cttgttgatt ttccac                                     26

<210> SEQ ID NO 111
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 111
gctgtgccac tgcacgcctc gactc                                      25

<210> SEQ ID NO 112
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 112
cttgtccctc ttgaatggcg agtg                                       24

<210> SEQ ID NO 113
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 113
ggaacacgcc aaacatcatg                                            20

<210> SEQ ID NO 114
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 114
cacaagcaga atcaggcac                                             19

<210> SEQ ID NO 115
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 115
cggtgacgac ttcgactagt cgag                                       24

<210> SEQ ID NO 116

```
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 116
cggtgctgtt ggcgtcgtca tgggtg                                          26

<210> SEQ ID NO 117
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 117
ggcgcgttcc aattccactc tgctg                                           25

<210> SEQ ID NO 118
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 118
cgacgagtcc tctcaccagg aggttg                                          26

<210> SEQ ID NO 119
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 119
tgtgggtgcg atcctgag                                                   18

<210> SEQ ID NO 120
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 120
gccgtcgttg gagcaaaact                                                 20

<210> SEQ ID NO 121
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 121
gcatgtgcca ctgctaaa                                                   18

<210> SEQ ID NO 122
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 122
```

```
gaccaacttt cccgtgtaa                                               19

<210> SEQ ID NO 123
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 123

Arg Val Asp Phe Asn Val Pro Leu Asp
                 5

<210> SEQ ID NO 124
<211> LENGTH: 9
<212> TYPE: PRT
<213> ORGANISM: Artificial Sequence
<220> FEATURE:
<223> OTHER INFORMATION: Synthetic oligopeptide

<400> SEQUENCE: 124

Glu Gly Lys Glu Leu Pro Gly Val Ala
  1               5
```

METHOD FOR HIGH-LEVEL SECRETORY PRODUCTION OF PROTEIN

TECHNICAL FIELD

The present invention relates to a method for high-level secretory production of a protein, mainly in yeast.

BACKGROUND ART

To date, production of proteins for pharmaceutical applications via gene recombination techniques has mainly involved the use of animal cells or *E. coli* cells as hosts. *E. coli* cells enable the production of target proteins at low cost; however, *E. coli* cells cannot undergo modification typified by sugar chain modification, and inactive proteins are produced in the inclusion bodies. This requires a process of solubilization, and thus, *E. coli* cells are not suitable for complicated procedures for protein production. In contrast, animal cells enable the production of target proteins as active proteins. Disadvantageously, however, use of animal cells would remarkably increase production costs in terms of equipment and material costs, due to time-consuming operations of breeding and culture of animal cells.

Among proteins, antibodies have been used as pharmaceutical products for a long time. Since they were derived from sources other than humans, antibodies against the administered antibodies were newly produced. Thus, such antibodies could not be administered more than once, and use thereof was restricted. In recent years, production of a humanized antibody in which an amino acid sequence other than the antigen-binding site has been substituted with a sequence derived from a human antibody became possible. Further, production of a human antibody-producing mouse into which a human antibody gene has been introduced became possible. Thus, application of antibodies as pharmaceutical products became extensive. At present, such antibodies are produced by cultured cells, such as CHO cells, into which genes encoding hybridomas or antibodies have been introduced. Such production, however, is problematic in terms of cost, productivity, safety, and the like.

In recent years, production of proteins for pharmaceutical applications has been attempted with the use of yeast, for the purpose of complementing the drawbacks described above. However, substantially no such attempts have been put to practical use. Regarding antibodies having complicated structures, in particular, there are examples of expression of Fab, a single stranded antibody (ScFv), or the like (Biosci. Biotechnol. Biochem., 64: 2138-2144, 2000). Productivity, however, is very low in terms of a full-length antibody (Proc. Natl. Acad. Sci. U.S.A., 85: 8678-8682, 1988). An example of antibody production with the use of yeast (*Pichia pastoris*) that produces a mammalian N-binding sugar chain was reported recently (Nature Biotechnology, 24: 210-215, 2006), although this report does not refer to the yield. Thus, high-level production of antibodies in yeast is difficult. Causes thereof are considered to be insufficient secretion ability of yeast, degradation caused by protease, or the like.

As a means for resolving such problems, a method involving the use of a protease deficient strain was proposed (Enzyme and Microbial Technology, 26: 671-677, 2000; Protein Expr. Purif., 20: 485-491, 2000, Biosci. Biotechnol. Biochem., 66: 628-631, 2002). The inventors have also developed a method of using a protease, which is a protease A (PEP4), protease B (PRB1), or yapsin (YPS1) gene deficient strain, to inhibit degradation of an antibody (WO 2003/091431). As a method for improving protein productivity via gene introduction, a method for improving ScFv productivity by allowing coexpression of parts of molecular chaperones that assist formation of 3-dimensional structures of proteins on the endoplasmic reticulum, such as BiP (KAR2)/PDI, was reported (Nat. Biotechnol. 16: 773-777, 1998), although this method merely produces a fragment of a single-stranded antibody.

Also, many inducible or constitutive promoters have been developed and used for producing foreign proteins. When genes encoding foreign proteins are allowed to express at high levels with the use of potent promoters in cells or when proteins that are less likely to fold are produced, however, aggregation occurs in the endoplasmic reticulum (ER) and resulting proteins may be sometimes accumulated in cells. Further, secretory proteins and membrane proteins are translated into proteins, incorporated into the endoplasmic reticulum immediately thereafter, subjected to a given modification, and then transferred to the Golgi apparatus. In such a case, unfolded proteins may be sometimes accumulated in the endoplasmic reticulum for some reason. This is referred to as "endoplasmic reticulum stress." Examples of causes for such endoplasmic reticulum stress include disturbance of modification (e.g., addition of a sugar chain or disulfide bond) that occurs in the endoplasmic reticulum and deteriorated transportation from the endoplasmic reticulum. Mammalian cells have an "unfold protein response (UPR)" mechanism as a means for reacting against such endoplasmic reticulum stress. For example, proteins accumulated in the endoplasmic reticulum are protected by inhibition of transcription, acceleration of folding induced by molecular chaperones, degradation of denatured proteins, or cell death via apoptosis.

As genes that regulate UPR, genes of IRE1α-XBP1, PERK-eIF-2α, and ATF6 animal cells are known. In case of yeast, Ire1p-Hac1p is the only gene that is known as such gene, and the Ire1p-Hac1p gene is associated with UPR by the mechanism shown below (see FIG. 1). First of all, Ire1p is generally bound to an antibody heavy chain binding protein (BiP). When an unfolded protein (UFP) is produced, however, BiP binds to such UFP. Ire1p dissociated from BiP is activated via autophosphorylation or dimerization, and it exhibits endonuclease activity. While the HAC1 gene is generally in an inactivated state, Ire1p having endonuclease activity subjects mRNA transcribed from the HAC1 gene to splicing and produces active Hac1p (Cell, 87: 405-413, 1996; Cell, 90: 1031-1039, 1997; the EMBO Journal, 18: 3119-3132, 1999). Such active Hac1p migrates to the nucleus, acts as a transcription factor, and promotes expression of genes encoding various proteins associated with a series of reactions referred to as UPR, e.g., associated sugar chain addition, protein folding, protein degradation (ER-associated degradation: ERAD), protein sorting, lipid metabolism, or the like (Cell, 101: 249-258, 2000).

Regarding an attempt to improve productivity of foreign proteins utilizing activated Hac1p, there is an example in which the gene encoding activated Hac1p of a filamentous bacterium, i.e., *Trichoderma reesei*, is introduced into *S. cerevisiae* to improve secretion of a heterogeneous protein, α-amylase, and an endogenous protein, i.e., invertase, (Appl. Environ. Microbiol. 69: 2065-2072, 2003). However, a single protein, α-amylase or invertase, has been known as a protein that is easily secreted, and improvement in the amount of production is as low as approximately two times the amount of production prior to the improvement. In recent years, it has been reported that an antibody fragment, Fab, was produced using *Pichia pastoris* in a strain into which the activated HAC1 gene had been solely introduced (Biotechnology and Bioengineering, 94: 353-361). Productivity improvement via introduction of the activated HAC1 gene is as low as approximately 1.3 times.

Meanwhile, an example in which the mammalian-derived RRBP1 (ribosome-binding protein1, ribosome receptor, p180 protein) gene is solely introduced into a yeast strain, so as to quintuple the amount of proteins (bovine pancreatic trypsin inhibitor (BPTI)) secreted is known (The Journal of Cell Biology, 146: 273-284, 1999). At first, the RRBP1 gene was isolated from a dog as a gene encoding a protein binding to the ribosome (Nature, 346: 540-544, 1990). RRBP1 has a molecular weight of 180 kDa and a special structure such that a sequence comprising 10 amino acid residues on the N-terminal side is repeated 54 times and this region is bound to a ribosome. RRBP1 is known to be involved in enlargement of membrane structure and in stabilization of mRNA (the Journal of Cell Biology, 130: 29-39, 1995; the Journal of Cell Biology, 156: 993-1001, 2002). A successful example in the aforementioned BPTI has a molecular weight of 6,500, which represents a very small peptide. Such results cannot always be applied to other high-molecular-weight proteins or protein aggregates composed of different proteins such as light-chain or heavy-chain of antibodies.

The protein O-mannosyltransferase (PMT) gene is known to be associated with formation of O-sugar chains that are inherent to yeast or mold. The PMT gene product is localized on the ER membrane and has activity of adding mannose to a hydroxyl residue of serine (Ser) or threonine (Thr) of a secretory protein (hereafter, such activity is referred to as PMT activity). Some proteins to which sugar chains had been added by PMT serve as primary components of the yeast strain wall as mannoproteins. When PMT activity is extremely lowered, the cell wall is known to become fragile and to affect the growth of cells.

Regarding the PMT genes, the existence of seven genes, i.e., PMT1, 2, 3, 4, 5, 6, and 7, is known in *Saccharomyces cerevisiae* (*S. cerevisiae*) (Biochim. Biophys. Acta., 1426: 297-307, 1999). The PMT gene is classified into three types; i.e., the PMT1 family, the PMT2 family, and the PMT4 family. It is known that PMT1p and PMT2p exhibit activity upon formation of heterodimers, and PMT4p exhibits activity upon formation of homodimers. Because of amino acid sequence homology and the like, it is said that PMT5p complements PMT1p, and that PMT3p complements PMT2p. PMT6p is highly homologous to PMT2p and PMT3p, although the type of composite that exhibits activity is not known. Also, each PMT protein is known to have selectivity for a substrate protein.

As PMT genes of other types of budding yeast, five genes highly homologous to the PMT1, 2, 4, 5, and 6 genes of *S. cerevisiae* in the case of *Candida albicans* (Mol. Microbiol., 55: 546-560, 2005), a gene highly homologous at least to the PMT4 gene of *S. cerevisiae* in the case of *Cryptococcus neoformans* (Eukaryot. Cell, 6: 222-234, 2007), and three genes (oma1, 2, and 4) highly homologous to the PMT1, 2, and 4 genes in the case of fission yeast, i.e., *Schizosaccharomyces pombe*, (Mol. Microbiol., 57: 156-170, 2005) have been discovered. Further, the existence of five genes that are highly homologous to the PMT1, 2, 4, 5, and 6 genes of *S. cerevisiae* was observed in methanol-assimilating yeast, *Ogataea minuta* (*O. minuta*).

The PMT gene is also found in mold. The PmtA gene and two other genes are found in *Aspergillus nidulans*, and the Pmt1 gene, which is highly homologous to the PMT2 gene of *S. cerevisiae*, is found in *Trichoderma reesei* (Curr. Genet., 43: 11-16, 2003).

PMT activity is said to have effects of acting on a peptide hydrophobic region, enhancing peptide hydrophilicity, and inhibiting peptide aggregation in ER cavity. When foreign proteins are produced, however, PMT activity occasionally adds an unnecessary O-sugar chain, which may result in insufficient formation of protein composites, lowered activity, or the like. For multimeric proteins, such as antibodies, in particular, formation of aggregates thereof (which refers to formation of light chain and heavy chain aggregates, in the case of antibodies) may be inhibited.

JP Patent No. 3630424 and JP Patent Publication (kohyo) No. H08-509867 (A) (1996) propose a method for producing a recombinant protein via inhibition of O-sugar chain addition resulting from modification of the PMT gene. These patent documents, however, do not describe the formation of aggregates of a light-chain and a heavy-chain of antibody.

An example in which PMT1 and PMT2 gene-deficient strains associated with formation of O-sugar chains are used to inhibit addition of O-sugar chains to promote aggregation of antibody light-chain and heavy-chain molecules by approximately 1.5 times is provided in WO 2002/046437. This data is the result of a pulse-labeling experiment using an RI-labeled amino acid, but it is not the result of observing the entire culture process. Also, a degree of inhibition of sugar chain addition is further lowered, and antibody productivity is deteriorated.

Although the HAC1 gene induces UPR, some of the UPR-inducible genes are known to be PMT genes that add yeast-specific O-sugar chains (Cell, 101: 249-258, 2000). Accordingly, introduction of the HAC1 gene may not be sufficient to produce high-quality multimeric proteins, such as antibodies.

As described above, a variety of methods have been proposed as methods for high-level secretory production of proteins in yeast. However, substantially no method is sufficient at a practical level. A method for efficiently producing proteins, in particular, high-molecular-weight proteins or protein aggregates, including antibodies, has not yet been discovered. When a trait is introduced into a cell via gene introduction, gene destruction, or the like, in general, the cell would experience a given sort of stress. Thus, other modification may be provided, or an opposite action may occur. When high-level protein expression is intended, for example, UPR becomes activated, which results in a negative element, such as sugar chain modification, degradation by a proteasome, or ER-associated degradation (ERAD). Accordingly, high-level secretory production of proteins having complicated structures, such as antibodies, are not achieved by a single process, such as introduction of a single gene. Also, mere combination of several conventional methods would not always yield synergistic effects.

Accordingly, the present invention is intended to provide a method for high-level secretory production of proteins and, more particularly, proteins having complicated structures, such as antibodies, in yeast or other host cells.

DISCLOSURE OF THE INVENTION

The present inventors have conducted concentrated studies in order to attain the above object. As a result, they discovered that genes associated with high-level secretory production of proteins, i.e., the activated HAC1 (the Hac1 protein, which is a transcription factor induced by splicing of mRNA by Ire1p upon application of endoplasmic reticulum stress) gene and the RRBP1 (ribosome-binding protein 1, ribosome receptor, p180 protein) gene, are coexpressed in methanol-assimilating yeast, *Ogataea minuta*, and the amount of antibody secretory production can be increased by approximately 10 times. Further, they discovered that activity of protein O-mannosyltransferase (PMT) associated with O-sugar chain addition to a yeast-specific protein, which inhibits aggregation of heteromultimers such as antibodies, may be inhibited to further improve productivity.

Also, they discovered that the gene associated with high-level secretory production of a protein, i.e., the activated HAC1 gene, may be expressed, and activity of protein O-mannosyltransferase (PMT) associated with O-sugar chain addition to a yeast-specific protein, which inhibits aggregation of heteromultimers such as antibodies, may be inhibited to realize synergistic improvement in productivity.

The present invention has been completed upon such findings (see FIG. 2).

Specifically, the present invention includes the following inventions.

[1] A transformed host cell comprising the activated HAC1 gene and the RRBP1 gene.

[2] The transformed host cell according to [1], which comprises the activated HAC1 gene (1) and the RRBP1 gene (2) below:

(1) the activated HAC1 gene selected from among (a) to (d) below:

(a) a gene encoding a protein which consists of the amino acid sequence as shown in SEQ ID NO: 23;

(b) a gene encoding a protein which consists of an amino acid sequence having at least 70% homology with the amino acid sequence as shown in SEQ ID NO: 23 and has the function of activating the unfolded protein response (UPR);

(c) a gene encoding a protein which consists of an amino acid sequence derived from the amino acid sequence as shown in SEQ ID NO: 23 by deletion, substitution, and/or addition of one or several amino acids and has the function of activating UPR; and (d) a gene which hybridizes under stringent conditions to a DNA consisting of the nucleotide sequence as shown in SEQ ID NO: 22 or a complementary nucleotide sequence thereof and encodes a protein having the function of activating UPR; and (2) the RRBP1 gene selected from among (e) to (h) below:

(e) a gene encoding human- or dog-derived RRBP1;

(f) a gene encoding a protein which consists of an amino acid sequence having at least 70% homology with the amino acid sequence of human- or dog-derived RRBP1 and has ribosome-binding activity;

(g) a gene encoding a protein which consists of an amino acid sequence derived from the amino acid sequence human- or dog-derived RRBP1 by deletion, substitution, and/or addition of one or several amino acids and has ribosome-binding activity; and (h) a gene which hybridizes under stringent conditions to a gene consisting of a nucleotide sequence of the human- or dog-derived RRBP1 gene or a complementary nucleotide sequence thereof and encodes a protein having ribosome-binding activity.

[3] The transformed cell according to [1] comprising the activated HAC1 gene (1) and the RRBP1 gene (2) below:

(1) the activated HAC1 gene selected from among (i) to (l) below:

(i) a gene encoding the activated HAC1 protein of *Saccharomyces cerevisiae, Trichoderma reesei,* or *Aspergillus nidulans;*

(j) a gene encoding a protein which consists of an amino acid sequence having at least 70% homology with the amino acid sequence of the activated HAC1 protein of *Saccharomyces cerevisiae, Trichoderma reesei,* or *Aspergillus nidulans* and has the function of activating UPR;

(k) a gene encoding a protein which consists of an amino acid sequence derived from the amino acid sequence of the activated HAC1 protein of *Saccharomyces cerevisiae, Trichoderma reesei,* or *Aspergillus nidulans* by deletion, substitution, and/or addition of one or several amino acids and has the function of activating UPR; and (l) a gene which hybridizes under stringent conditions to a gene consisting of a nucleotide sequence of the gene encoding the activated HAC1 protein of *Saccharomyces cerevisiae, Trichoderma reesei,* or *Aspergillus nidulans* or a complementary nucleotide sequence thereof and encodes a protein having the function of activating UPR; and (2) the RRBP1 gene selected from among (e) to (h) below:

(e) a gene encoding human- or dog-derived RRBP1;

(f) a gene encoding a protein which consists of an amino acid sequence having at least 70% homology with the amino acid sequence of human- or dog-derived RRBP1 and has ribosome-binding activity;

(g) a gene encoding a protein which consists of an amino acid sequence derived from the amino acid sequence human- or dog-derived RRBP1 by deletion, substitution, and/or addition of one or several amino acids and has ribosome-binding activity; and (h) a gene which hybridizes under stringent conditions to a gene consisting of a nucleotide sequence of the human- or dog-derived RRBP1 gene or a complementary nucleotide sequence thereof and encodes a protein having ribosome-binding activity.

[4] The transformed host cell according to any of [1] to [3], wherein the host cell is a eukaryotic cell.

[5] The transformed host cell according to [4], wherein the eukaryotic cell is yeast.

[6] The transformed host cell according to [5], wherein the yeast is methanol-assimilating yeast.

[7] The transformed host cell according to [6], wherein the methanol-assimilating yeast is *Ogataea minuta*.

[8] The transformed host cell according to [5], wherein the yeast is *Saccharomyces cerevisiae*.

[9] The transformed host cell according to any of [1] to [8], which comprises a gene encoding a foreign protein introduced therein.

[10] The transformed host cell according to [9], wherein the foreign protein is a multimeric protein.

[11] The transformed host cell according to [10], wherein the multimeric protein is a heteromultimer.

[12] The transformed host cell according to [11], wherein the heteromultimer is an antibody or a functional fragment thereof.

[13] A method for producing a protein comprising culturing the transformed host cell according to any of [9] to [12] in a medium and sampling a target protein from the culture product.

[14] The method according to [13], wherein culture is conducted under conditions in which protein O-mannosyltransferase (PMT) activity is inhibited.

[15] The method according to [14], wherein protein O-mannosyltransferase (PMT) activity is inhibited with the addition of an inhibitor of PMT activity to the medium.

[16] A gene encoding the activated HAC1 protein of methanol-assimilating yeast.

[17] A gene selected from among (a) to (d) below:

(a) a gene encoding a protein which consists of the amino acid sequence as shown in SEQ ID NO: 23;

(b) a gene encoding a protein which consists of an amino acid sequence having at least 70% homology with the amino acid sequence as shown in SEQ ID NO: 23 and has the function of activating the unfolded protein response (UPR);

(c) a gene encoding a protein which consists of an amino acid sequence derived from the amino acid sequence as shown in SEQ ID NO: 23 by deletion, substitution, and/or addition of one or several amino acids and has the function of activating UPR; and (d) a gene which hybridizes under stringent conditions to a DNA consisting of the nucleotide sequence as shown in SEQ ID NO: 22 or a complementary nucleotide sequence thereof and encodes a protein having the function of activating UPR.

[18] An expression vector comprising the gene according to [17].

[19] The expression vector according to [18], which is pOMexPGHy/Hac1.

[20] An expression vector comprising the activated HAC1 gene and the RRBP1 gene.

[21] The expression vector according to [20], wherein the activated HAC1 gene is the gene according to [17].

[22] The expression vector according to [20], wherein the activated HAC1 gene is a gene encoding the activated HAC1 protein of *Saccharomyces cerevisiae*, *Trichoderma reesei*, or *Aspergillus nidulans* or a homologous gene thereof.

[23] The vector according to [20], which is YEp351GAP-II-aHAC1/p180.

[24] The expression vector according to [20], wherein the RRBP1 gene is the human- or dog-derived RRBP1 gene or a homologous gene thereof.

[25] A transformed host cell into which the expression vector according to any of [18] to [24] has been introduced.

[26] A transformed host cell into which an expression vector comprising the activated HAC1 gene and an expression vector comprising the RRBP1 gene have been introduced.

[27] The transformed host cell according to [26], wherein the expression vector comprising the activated HAC1 gene is the expression vector according to [18] or [19].

[28] The transformed host cell according to [26], wherein the activated HAC1 gene is a gene encoding the activated HAC1 protein of *Saccharomyces cerevisiae*, *Trichoderma reesei*, or *Aspergillus nidulans* or a homologous gene thereof.

[29] The transformed cell according to [26], wherein the RRBP1 gene is the human- or dog-derived RRBP1 gene or a homologous gene thereof.

[30] A method for producing a transformed host cell comprising the steps of:
(A) introducing the activated HAC1 gene into a host cell; and
(B) introducing the RRBP1 gene into a host cell.

[31] The method according to [30], wherein the activated HAC1 gene is any of the following genes:
(1) the gene according to [17];
(2) a gene encoding the activated HAC1 protein of *Saccharomyces cerevisiae*, *Trichoderma reesei*, or *Aspergillus nidulans*;
(3) a gene encoding a protein which consists of an amino acid sequence having at least 70% homology with the amino acid sequence of the activated HAC1 protein of *Saccharomyces cerevisiae*, *Trichoderma reesei*, or *Aspergillus nidulans* and has the function of activating UPR;
(4) a gene encoding a protein which consists of an amino acid sequence derived from the amino acid sequence of the activated HAC1 protein of *Saccharomyces cerevisiae*, *Trichoderma reesei*, or *Aspergillus nidulans* by deletion, substitution, and/or addition of one or several amino acids and has the function of activating UPR; and
(5) a gene which hybridizes under stringent conditions to a gene consisting of a nucleotide sequence a gene encoding the activated HAC1 protein of *Saccharomyces cerevisiae*, *Trichoderma reesei*, or *Aspergillus nidulans* or a complementary nucleotide sequence thereof and encodes a protein having the function of activating UPR.

[32] The method according to [30], wherein the RRBP1 gene is any of the following genes:
(1) a gene encoding the human- or dog-derived RRBP1;
(2) a gene encoding a protein which consists of an amino acid sequence having at least 70% homology with the amino acid sequence of human- or dog-derived RRBP1 and has ribosome-binding activity;
(3) a gene encoding a protein which consists of an amino acid sequence derived from the amino acid sequence human- or dog-derived RRBP1 by deletion, substitution, and/or addition of one or several amino acids and has ribosome-binding activity; and
(4) a gene which hybridizes under stringent conditions to a gene consisting of a nucleotide sequence of the human- or dog-derived RRBP1 gene or a complementary nucleotide sequence thereof and encodes a protein having ribosome-binding activity.

[33] The method according to any of [30] to [32], wherein the host cell is a eukaryotic cell.

[34] The method according to [33], wherein the eukaryotic cell is yeast.

[35] The method according to [34], wherein the yeast is methanol-assimilating yeast.

[36] The method according to [35], wherein the methanol-assimilating yeast is *Ogataea minuta*.

[37] The method according to [34], wherein the yeast is *Saccharomyces cerevisiae*.

[38] A gene selected from among (a) to (d) below:
(a) a gene encoding a protein which consists of the amino acid sequence as shown in SEQ ID NO: 70;
(b) a gene encoding a protein which consists of an amino acid sequence having at least 70% homology with the amino acid sequence as shown in SEQ ID NO: 70 and has the function of activating the unfolded protein response (UPR);
(c) a gene encoding a protein which consists of an amino acid sequence derived from the amino acid sequence as shown in SEQ ID NO: 70 by deletion, substitution, and/or addition of one or several amino acids and has the function of activating UPR; and
(d) a gene which hybridizes under stringent conditions to a DNA consisting of the nucleotide sequence as shown in SEQ ID NO: 69a complementary nucleotide sequence thereof and encodes a protein having the function of activating UPR.

[39] An expression vector comprising the gene according to [38].

[40] The expression vector according to [39], which is pOMexPGHy/PpHac1.

[41] A method for producing a protein comprising culturing a transformed cell into which the activated HAC1 gene and/or the RRBP1 gene and a gene encoding a foreign protein have been introduced in a medium under conditions in which O-sugar chain synthesis is inhibited and sampling a target protein from the culture product.

[42] The method for producing a protein according to [41], wherein O-sugar chain synthesis is inhibited by insertionally inactivating the PMT gene.

[43] The method for producing a protein according to [41], wherein O-sugar chain synthesis is inhibited by adding the inhibitor of PMT activity to the medium.

[44] The method for producing a protein according to [41], wherein O-sugar chain synthesis is inhibited by insertionally inactivating the PMT gene and by adding the inhibitor of PMT activity to the medium.

[45] The method for producing a protein according to [43] or [44], wherein the inhibitor of PMT activity is 5-[[3,4-(1-phenylmethoxy)phenyl]methylene]-4-oxo-2-thioxo-3-thiazolidineacetic acid or {(5Z)-4-oxo-5-[3-(1-phenylethoxy)-4-(2-phenylethoxy)benzylidene]-2-thioxo-1,3-thiazolidin-3-yl}acetic acid.

[46] A transformed host cell with the insertionally inactivated PMT gene and with the activated HAC1 gene introduced therein.

[47] The transformed cell according to [46], wherein the host cell is *Ogataea minuta*.

BRIEF DESCRIPTION OF THE DRAWINGS

FIG. 8A shows a chart showing the results of a comparison of the abilities for antibody secretory production of antibody-producing yeast strains into which an expression vector for the activated HAC1 gene of *S. cerevisiae* and an expression vector for the human RRBP1 gene have been introduced. FIG. 8B shows a chart showing the results of a comparison of the abilities for antibody secretory production of antibody-producing yeast strains into which an expression vector for the activated HAC1 gene of *S. cerevisiae* and an expression vector for the human RRBP1 gene have been introduced under conditions in which O-sugar chain formation is inhibited. FIG. 8C shows a chart showing the results of a comparison of the abilities for antibody secretory production (absolute values) of antibody-producing yeast strains into which an expression vector for the activated HAC1 gene of *S. cerevisiae* and an expression vector for the human RRBP1 gene have been introduced with or without the addition of a PMT inhibitor.

FIG. 16A shows the results of Western analysis of culture supernatants of the PMT5 gene- or PMT6 gene-deficient antibody-producing strains. FIG. 16B shows the amount of antibody secretory production from the PMT5 gene- or PMT6 gene-deficient antibody-producing strains.

Figure 1:
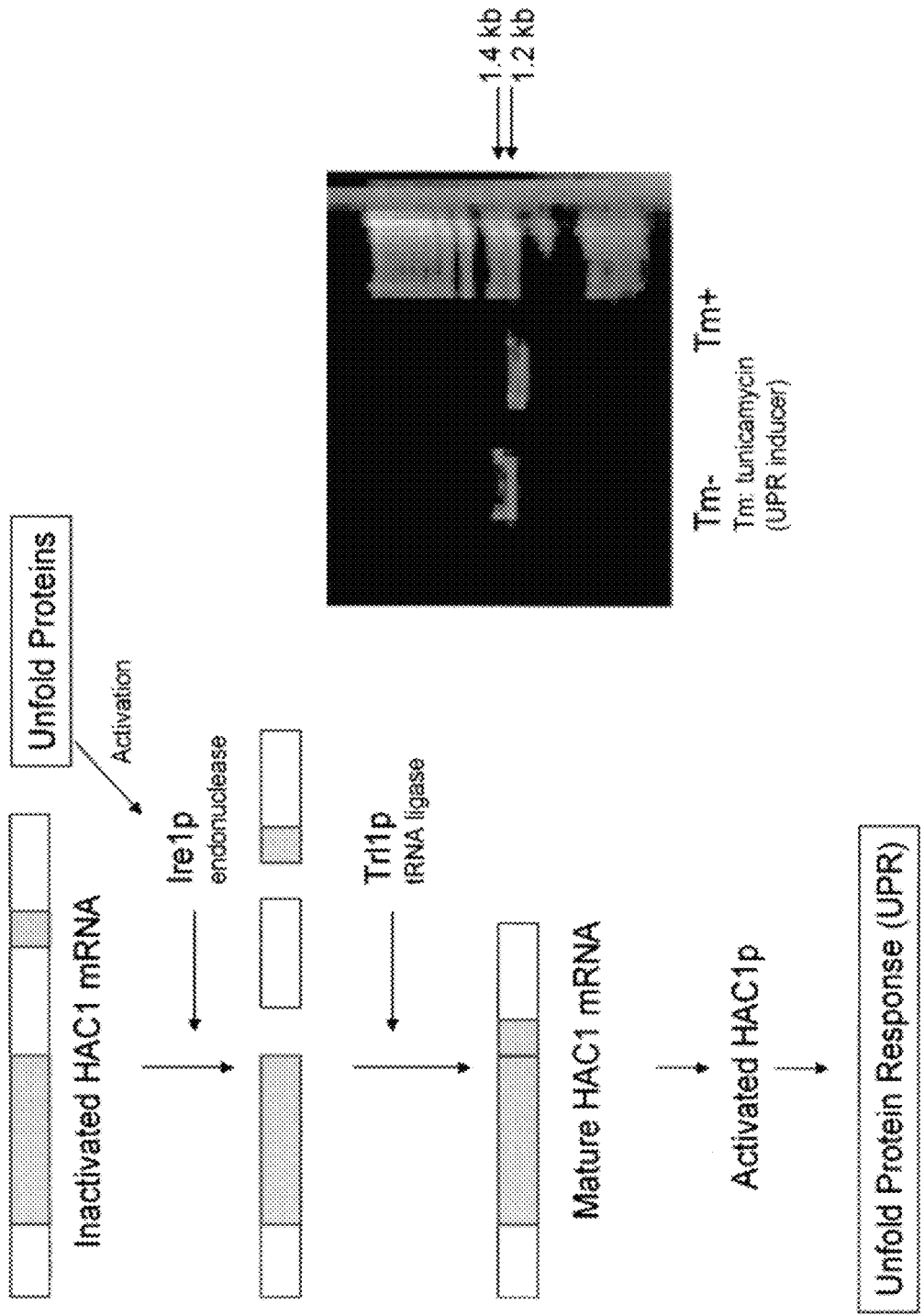
FIG. 1 shows a method for obtaining the activated HAC1 gene of *O. minuta* and the structure thereof.
Figure 2:
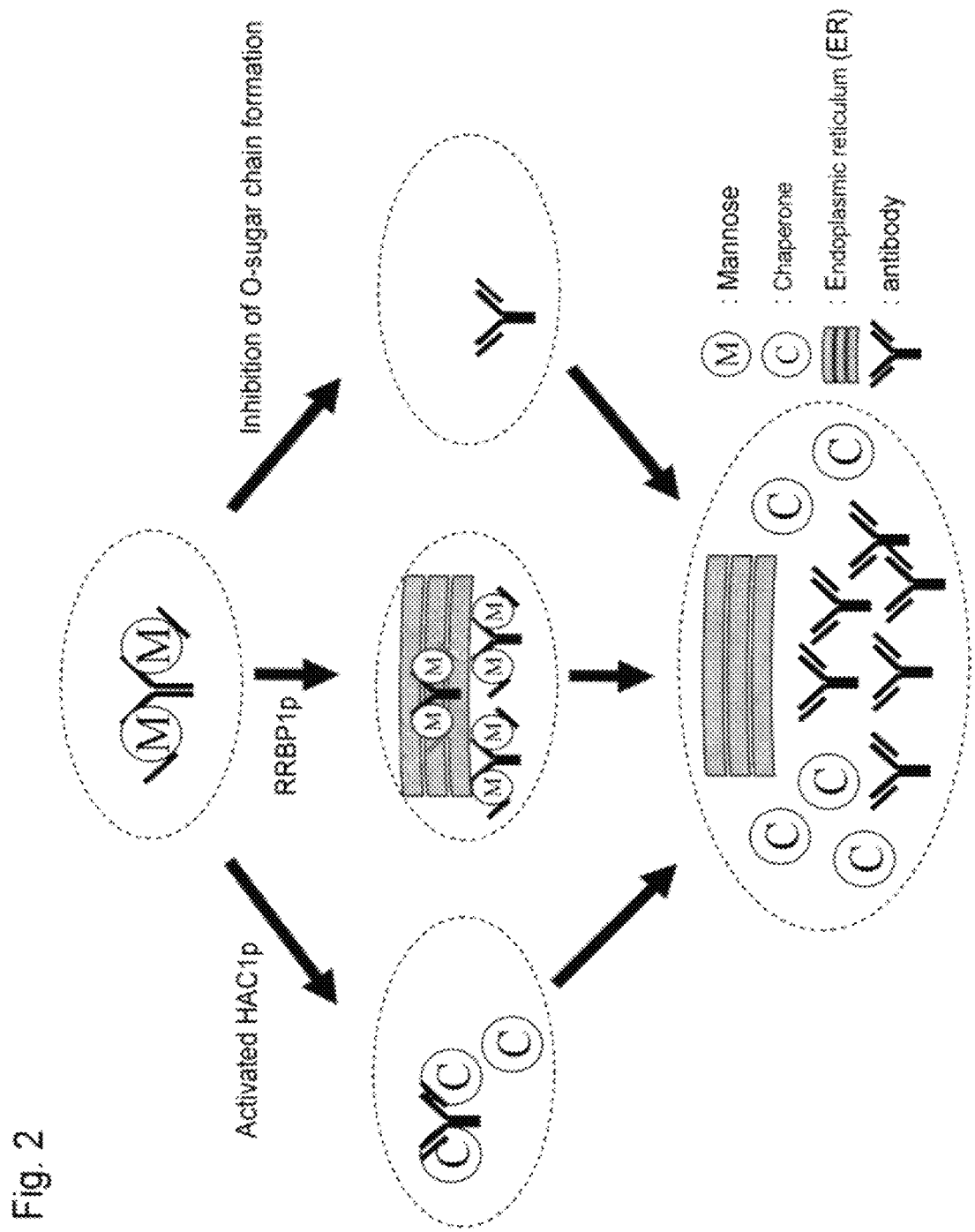
FIG. 2 schematically shows the technical scope of the present invention.

Hereafter, the present invention is described in detail. This patent application claims priority from Japanese Patent Application No. 2006-136993 filed on May 16, 2006, and includes part or all of the contents as disclosed in the description thereof.

The present invention is composed of the following two constituents. Specifically, a combination of (A) introduction of a gene associated with high-level secretory production of a protein and (B) inhibition of O-sugar chain addition inherent to yeast (and mold) can produce synergistic effects regarding high-level secretory production of a protein.

Hereafter, the present invention is described in detail.

The present invention provides a gene used for high-level secretory production of a protein, an expression vector comprising such gene, a transformed host cell into which such expression vector is introduced, and a method for producing a protein using such transformed host cell.

1. Gene Used for High-Level Secretory Production of a Protein (1) HAC1 Gene

In the present invention, a gene used for high-level secretory production of a protein is the HAC1 gene. The HAC1 gene is present as an inactive HAC1 gene on the genome; however, mRNA transcribed by the HAC1 gene upon endoplasmic reticulum stress application is subjected to splicing by Ire1p and converted into mRNA encoding a transcription factor, the HAC1 protein (Hac1p). The unfolded protein response (UPR) is then activated by the translated Hac1p. In the present invention, the activated HAC1 gene is defined as cDNA encoding the HAC1 protein (Hac1p) (i.e., complementary to mRNA).

Accordingly, it is preferable that the activated HAC1 gene be used in order to further improve the effects of the present invention. A given degree of effects can also be attained via introduction of the inactivated HAC1 gene.

Hereafter, the activated HAC1 gene encoding Hac1p that actually causes UPR to function is described. HAC1p is constituted by, from the N terminus, a DNA-binding domain that is highly conserved in organisms, the leucine zipper region, and an unknown active region in which mRNA is spliced and newly added by Ire1p at the C terminus.

The activated HAC1 gene used in the present invention is not particularly limited, provided that such gene encodes the activated HAC1 protein. Examples include DNA encoding a protein consisting of the amino acid sequence as shown in SEQ ID NO: 23 derived from *Ogataea minuta* (*O. minuta*), which was newly acquired in the present invention, and DNA encoding a protein consisting of the amino acid sequence derived from *Pichia pastoris* (*P. pastoris*) as shown in SEQ ID NO: 70. A functionally equivalent DNA homologous thereto may be employed.

The term "homologous DNAs" refers to, for example, a gene encoding a protein which consists of an amino acid sequence having at least 70% homology to the amino acid sequence as shown in SEQ ID NO: 23 or 70 and has the function of activating the unfolded protein response (UPR), a gene encoding a protein which consists of an amino acid sequence derived from the amino acid sequence as shown in SEQ ID NO: 23 or 70 by deletion, substitution, and/or addition of one or several amino acids and has the function of activating UPR, and a gene which hybridizes under stringent conditions to a DNA consisting of the nucleotide sequence as shown in SEQ ID NO: 22 or 69 or a complementary nucleotide sequence thereof and encodes a protein having the function of activating UPR.

The term "an amino acid sequence having at least 70% homology to the amino acid sequence as shown in SEQ ID NO: 23 or 70" refers to an amino acid sequence having preferably at least 80%, more preferably at least 90%, and most preferably at least 95% homology. Protein homology search can be carried out with the use of, for example, the DNA Databank of Japan (DDBJ) via FASTA, BLAST, or other programs.

The number indicated by the term "several" in the aforementioned "one or several amino acids in the amino acid sequence as shown in SEQ ID NO: 23 or 70" is not particularly limited. For example, the term "several" approximately refers to 20 or fewer, preferably 10 or fewer, more preferably 7 or fewer, and further preferably 5 or fewer.

Under the aforementioned "stringent conditions," a so-called specific hybrid is formed, but a non-specific hybrid is not formed. Under such conditions, for example, complementary strands of highly homologous DNA, i.e., DNA consisting of a nucleotide sequence having at least 80%, preferably at least 90%, and more preferably at least 95% homology to the nucleotide sequence as shown in SEQ ID NO: 22 or 69 undergo hybridization, but complementary strands of DNA having lower homology levels would not undergo hybridization. More specifically, the sodium concentration is 150 to 900 mM, and preferably 600 to 900 mM, and the temperature is 60° C. to 68° C., and preferably 65° C.

The mutation mentioned above, such as deletion, substitution, and/or addition, can be introduced via a technique known in the art, such as the Kunkel method or the Gapped duplex method, or a technique in accordance therewith. For example, mutagenesis kits utilizing site-directed mutagenesis, such as a Mutant-K (Takara Bio), Mutant-G (Takara Bio), or LA PCR in vitro Mutagenesis series kit (Takara Bio), can be used.

The term "function of activating UPR" refers to the function of activating the defense reactions of endoplasmic reticulum (ER) against accumulation of unfolded proteins (e.g., inhibition of transcription, acceleration of folding induced by molecular chaperons, degradation of denatured protein, or cell death caused by apoptosis). The function of activating UPR is substantially equivalent to the function of a gene encoding a protein consisting of the amino acid sequence as shown in SEQ ID NO: 23 or 70.

The activated HAC1 gene may be a gene of *O. minuta, P. pastoris,* or another methanol-assimilating yeast. Examples thereof include genes encoding activated HAC1 proteins derived from *Hansenulla polymorpha* (*Pichia angusta*), *Pichia methanolica,* and *Candida boidinii.* Also, it may be an activated HAC1 gene derived from another organism species, such as other types of yeast or mold. Examples thereof include a gene (YFL031W, GenBank accession number: DNA spliced from D26506 by Ire1p) encoding the activated HAC1 protein (GenBank accession number: NP_116622) derived from *Saccharomyces cerevisiae* (*S. cerevisiae*), a gene (GenBank accession number: AJ413272) encoding the activated HAC1 protein (GenBank accession number: CAC88374) derived from *Trichoderma reesei*, and a gene (GenBank accession number: AJ413273) encoding the active HacA protein (GenBank accession number: CAC88375) derived from *Aspergillus nidulans.*

The nucleotide sequences of genes encoding the activated HAC1 proteins derived from *S. cerevisiae, Trichoderma reesei,* and *Aspergillus nidulans* are shown in SEQ ID NOs: 39, 41, and 43, and the corresponding amino acid sequences are shown in SEQ ID NOs: 40, 42, and 44.

The activated HAC1 genes derived from *Ogataea minuta* and *Pichia pastoris* isolated herein were the first genes isolated from yeast strains other than *Saccharomyces cerevisiae*. This strongly suggests the presence of the gene of interest generally in yeast strains, such as methanol-assimilating yeast strains. Accordingly, these genes are within the scope of the activated HAC1 genes used in the present invention.

Further, a transcription factor that activates UPR may be used as an alternative to the aforementioned activated HAC1 gene. An example is a gene that is activated upon splicing, by Ire1p, from the XBP-1 gene (e.g., a human-derived gene with GenBank accession number: NM_005080), which is an HAC1 homolog derived from animal cells or other species. Artificial activation by Ire1, which also activates HAC1 (XBP-1), also corresponds to activation of UPR. Accordingly, it is considered to be equivalent to introduction of the activated HAC1 gene. Further, forced expression of the non-activated HAC1 gene is considered to yield equivalent effects to the case of introduction of activated HAC1 as described above.

The activated HAC1 gene can be obtained by any method, provided that UPR is induced. For example, mRNA may be obtained from a cell in which genes encoding proteins that are difficult to fold are expressed at high level or cells that are treated with a sugar chain modification inhibitor, such as tunicamycin, a redox agent, such as DTT or hydrogen peroxide, or a UPR inducer, following which cDNA is synthesized therefrom. Also, mRNA may be obtained from a sequence that is already disclosed by synthesizing a part of or the full length thereof with the use of a DNA synthesizer.

(2) RRBP1 Gene

In the present invention, an example of another gene used for high-level secretory production of a protein is the RRBP1 gene. The RRBP1 gene is a gene encoding a protein referred to as the ribosome-binding protein 1, and it is also referred to as the hES, ES130, ES/130, or DKFZp586A1420 gene. The mammalian RRBP1 gene is composed of the N-terminal transmembrane region, a subsequent region that is rich in basic amino acids, 54 repeats of a sequence comprising 10 amino acid residues, and the C-terminal region.

The RRBP1 gene used in the present invention is not particularly limited, provided that it encodes the ribosome-binding protein 1. Examples include the human-derived RRBP1 gene (encoding the KIAA 1398 protein; GenBank accession number: AB037819) and the dog-derived RRBP1 gene (encoding the ribosome receptor p180; GenBank accession number: X87224). As long as it is functionally equivalent to the aforementioned genes, a homologous gene thereof may be used. The nucleotide sequences of the human-derived RRBP1 gene and the dog-derived RRBP1 gene are shown in SEQ ID NOs: 45 and 47, and the corresponding amino acid sequences are shown in SEQ ID NOs: 46 and 48.

Examples of homologous genes include: a gene encoding a protein which consists of an amino acid sequence having at least 70% homology with the amino acid sequence of human- or dog-derived RRBP1 and has ribosome-binding activity; a gene encoding a protein which consists of an amino acid sequence derived from the amino acid sequence of human- or dog-derived RRBP1 by deletion, substitution, and/or addition of one or several amino acids and has ribosome-binding activity; and a gene which hybridizes under stringent conditions to a gene consisting of a nucleotide sequence of the human- or dog-derived RRBP1 gene or a complementary nucleotide sequence thereof and encodes a protein having ribosome-binding activity. The degree of homology, stringent conditions, and a method of mutagenesis are as described above.

Specific examples of such homologous genes include RRBP1 genes derived from mice (accession Nos: XM_622097, XM_91338, and XM_991888), a rat (accession No. XM_230637), a *Xenopus* (accession No: NM_001005671), and a zebra fish (zebra danio) (accession No: NM_199431).

The RRBP1 gene may also be obtained by a generally known technique. For example, mRNA may be prepared from a cell in which the RRBP1 gene is expressed, and cDNA may further be synthesized.

In the present invention, the aforementioned gene used for high-level secretory production of a protein and a gene encoding a foreign protein that is the target of high-level secretory production described below (hereafter these genes are referred to as "target genes") can be obtained by a general technique of preparing mRNA and synthesizing cDNA using reverse transcriptase. As an example of the aforementioned general technique, a cDNA library derived from a cell or tissue in which the target gene is expressed is subjected to screening with the use of a DNA probe synthesized from a fragment of the target gene, so as to isolate the gene of interest. mRNA can be prepared by a technique generally used in the art. For example, the aforementioned cell or tissue may be treated with a guanidine reagent or a phenol reagent to obtain total RNA, following which poly (A)+ RNA (mRNA) is then obtained via the affinity column method using oligo (dT) cellulose columns or poly U-sepharose using sepharose 2B as a carrier or a batch technique. Further, poly (A)+ RNA may be fractionated via sucrose density gradient centrifugation or via other means. Subsequently, the obtained mRNA is used as a template to synthesize single-stranded cDNA using oligo dT primers and reverse transcriptase, and double-stranded cDNA is synthesized from the single-stranded cDNA using DNA synthetase I, DNA ligase, RnaseH, and the like. The synthesized double-stranded cDNA is blunt-ended using T4 DNA synthetase, subjected to ligation of an adaptor (e.g., an EcoRI adaptor), phosphorylation, or the like, incorporated into a λ phage, such as λgt11, and then packaged in vitro to prepare a cDNA library. In addition to a λ phage, plasmid vectors may be used to prepare cDNA library. Thereafter, a strain having DNA of interest (i.e., a positive clone) may be selected from the cDNA library.

When the target gene is isolated from genomic DNA or when a fragment containing a promoter region and a terminator region is isolated, genomic DNA is extracted from a cell strain of a source organism, and the target gene is selected in accordance with a common technique (Molecular Cloning, 1989; Methods in enzymology 194, 1991). Genomic DNA can be extracted by the method of Cryer et al. (Methods in Cell Biology, 12, 39-44, 1975) or the method of P. Philippsen et al. (Methods Enzymol., 194, 169-182, 1991), for example. When the source is a yeast strain, for example, a yeast protoplast is prepared, and the yeast protoplast is then subjected to a conventional technique, such as known DNA extraction techniques, alcohol precipitation techniques after removal of cell residues at a high salt concentration, or alcohol precipitation techniques after phenol or chloroform extraction.

The target gene can be obtained by, for example, PCR (PCR Technology, Henry A. Erlich, Stockton Press, 1989). When amplifying the target gene via PCR, a synthesized 20mer to 30mer single-stranded DNA is used as a primer, and genomic DNA is used as a template. The nucleotide sequence of the amplified gene is confirmed and then used.

A fragment containing a target gene whose sequence is unknown can be obtained by (a) preparing a gene library by a conventional technique and (b) selecting a clone of interest from the resulting gene library to be amplified. A gene library can be prepared by obtaining chromosome DNA from a cell line of a source organism via a conventional technique, partially digesting the chromosome DNA with adequate restriction enzymes for fragmentation, ligating the resulting fragment to an adequate vector, and then introducing the vector into an adequate host cell. Alternatively, mRNA may be extracted from a cell, cDNA may be synthesized therefrom, the synthesized cDNA may be ligated to an adequate vector, and the vector may be introduced into an adequate host cell, so that a gene library can be prepared. In such a case, a plasmid that is known as a conventional vector for gene library preparation can be used, and phages, cosmids, or other vectors can be extensively used. A host cell that is subjected to transformation or transduction may be selected in accordance with vector type.

Clones that carry target gene fragments are selected from the above gene library via colony hybridization, plaque hybridization, or other means involving the use of label probes containing sequences specific to the target genes.

Also, the target genes can be subjected to chemical total synthesis. For example, two pairs of complementary oligonucleotides are prepared and then annealed, several annealed DNA strands are ligated with the aid of DNA ligase, or several partially complementary oligonucleotides are prepared and gaps are filled by PCR. Thus, genes can be synthesized.

DNA sequences of genes can be determined by a conventional technique, such as the dideoxy method (Sanger et al., Proc. Natl. Acad. Sci., U.S.A., 74, 5463-5467, 1977). Further, the above DNA nucleotide sequences can be easily determined with the use of a commercially available sequencing kit or the like.

2. Expression Vector

The present invention provides a vector comprising the activated HAC1 gene or the RRBP1 gene or a vector comprising both the activated HAC1 gene and the RRBP1 gene. In order to express the activated HAC1 gene and the RRBP1 gene in host cells, a vector comprising either the activated HAC1 gene or the RRBP1 gene may be used to carry out transformation. Alternatively, a vector comprising both such genes may be used to carry out transformation. Also, such expression vector may comprise a gene encoding a foreign protein. Alternatively, an expression vector comprising a gene encoding a foreign protein may be prepared separately. In such a case, vectors are cotransfected into a host cell.

A gene encoding a foreign protein is not particularly limited. Examples include: various enzyme genes, such as the α-amylase gene and the α-galactosidase gene; various interferon genes that are pharmaceutically useful and physiologically active proteins, such as interferon α and interferon γ; various interleukin genes, such as IL1 and IL2; various cytokine genes, such as the erythropoietin (EPO) gene and the granulocyte colony-stimulating factor (G-CSF) gene; and growth factor genes. These genes may be obtained via any means.

The present invention is particularly effective on a protein that is highly hydrophobic and a protein whose secretory production is insufficient due to composite formation. Thus, the aforementioned foreign protein includes a multimeric protein, such as an antibody or its functional fragment, i.e., a heteromultimer.

An expression regulation region may be adequately added to the activated HAC1 gene, the RRBP1 gene, or a gene encoding a foreign protein to constitute an expression vector as a protein expression unit. A protein expression unit comprises, in the direction of a reading frame of transcription, at least a promoter region, the above gene, and a transcription terminator region. A promoter that can be used herein may be an inducible expression promoter or constitutive expression promoter. Examples of inducible expression promoters include promoters involved in methanol metabolism of methanol-assimilating yeast, such as alcohol oxidase (AOX) gene promoters, dihydroxyacetone synthase (DAS) gene promoters, and formate dehydrogenase (FDH) promoters. An example of another inducible promoter that can be used is a copper-inducible (CUP) promoter. Examples of constitutive expression promoters include promoters of the glyceraldehyde-3-phosphate dehydrogenase (TDH, GAP) gene, the phosphoglycerokinase (PGK) gene, the phosphotriose isomerase (TPI) gene, the enolase (ENO) gene, the actin (ACT) gene, the cytochrome c (CYC) gene, the trehalose synthase (TPS) gene, and the alcohol dehydrogenase (ADH) gene. Also, a transcription terminator may be a sequence having activity of terminating transcription from a promoter. It may be a sequence of the same or a different gene of the promoter.

In order to realize high-level secretory production of foreign proteins, use of a potent promoter is necessary. When production of a protein that is less likely to fold or less likely to be secreted is attempted with the use of a highly active promoter, hyposecretion may disadvantageously occur. Such hyposecretion occurs due to the following reasons. That is, protein production exceeds the capacity of the ribosome where translation is performed and the endoplasmic reticulum wherein folding and secretion are performed. This causes excessively produced proteins to be denatured, accumulated, ubiquitinated in cells, and degraded by the proteosome. Accordingly, promoters that can attain an expression level to the extent that resulting proteins would be denatured and would not undergo aggregation or the resulting proteins would not exceed the secretion capacity may be adequately selected. Alternatively, activity of the promoters may be attenuated and the promoters of interest may then be used. Molecules that form heteromultimers are likely to be affected as described above among multimeric proteins. In particular, molecules such as antibodies are heterotetramers comprising two molecules each of the heavy chain and of the light chain being aggregated. Thus, the expression level is an important factor for realizing adequate aggregation. When the expression intensity of the activated HAC1 gene is excessively strong, excessive stress is applied to a cell, and this may disadvantageously inhibit growth. Thus, adjustment and optimization of promoter activity are required as described above.

The expression vector of the present invention can comprise a selection marker for selecting a transformant. For examples, expression vectors for yeast can comprise auxotrophic marker genes selected from among His1, His2, His3, His4, His5, His6, Leu2, Alg1, Alg2, Alg3, Trp1, Lys2, Ade1, Ade2, Ura3, and Ura5 genes.

As selection markers, drug-resistant markers that impart resistance to drugs such as cerulenin, aureobasidin, Zeocin, canavanine, cycloheximide, hygromycin, blasticidin, tetracycline, kanamycin, ampicillin, tetracycline, and neomycin can be used, in addition to the aforementioned auxotrophic markers. Thus, transformants can be selected. Also, genes that impart solvent resistance to ethanol, osmotic resistance to glycerol or salt, metal ion resistance to copper, and the like may be used as markers, so that transformants can be selected.

3. Transformed Host Cell

The transformed host cell of the present invention comprises the gene described in 1. above or the expression vector described in 2. above introduced therein.

An example of a host cell to be transformed is an eucaryotic cell, and preferably a yeast strain. Examples of yeast strains include methanol-assimilating yeast strains, such as *Ogataea minuta, Pichia pastoris, Hansenulla polymorpha* (*Pichia angusta*), and *Candida boidinii* and yeast strains, such as *Saccharomyces cerevisiae, Kluyveromyces lactis, Yarowia lipolytica*, and *Shizosaccharomyces pombe*. More specifically, the *Ogataea minuta* YK3 strain (Δoch1Δpep4Δprb1Δyps1Δura3Δade1) can be used as the *Ogataea minuta* strain, and the *Saccharomyces cerevisiae* BY4741 strain (MATaΔhis3Δleu2Δmet15Δura3) can be used as the *Saccharomyces cerevisiae* strain, although the yeast strains are not limited thereto.

Further, the present invention is intended to obtain a host cell in which the ER, which is essential for secretion, is enhanced. Accordingly, the present invention is applicable to animal cells or other cells.

In the present invention, an expression vector can be introduced into a host cell by any method, provided that an introduced gene is stably present and adequately expressed in a host. Examples of such methods that are generally employed include the calcium phosphate method (Ito et al., Agric. Biol. Chem., 48, 341, 1984), electroporation (Becker, D. M. et al., 1990; Methods. Enzymol., 194, 182-187), use of spheroplasts (Creggh et al., Mol. Cell. Biol., 5, 3376, 1985), the lithium acetate method (Itoh, H., 1983; J. Bacteriol. 153, 163-168), and lipofection.

4. Method for Producing Protein

In the present invention, proteins can be produced by culturing the transformed host cells via a conventional technique and sampling the proteins from the culture product, followed by purification. The term "culture product" used herein refers to culture cells, cultured strains, or disrupted cells or bacteria, in addition to a culture supernatant.

The transformed host cell can be cultured in a medium in accordance with a conventional method used for culture of the host cell.

When the transformed host cell is a microorganism, such as yeast, either a natural or synthetic medium may be used as a medium for culture, provided that it contains carbon sources, nitrogen sources, and inorganic salts assimilable by the microorganism and is capable of efficient culture of the transformant. Any carbon sources assimilable by the microorganism may be used, and examples thereof include: carbohydrates such as glucose, fructose, sucrose, and starch; organic acids such as acetic acid and propionic acid; and alcohols such as ethanol and propanol. Examples of nitrogen sources include: ammonia; ammonium salts of inorganic or organic acids such as ammonium chloride, ammonium sulfate, ammonium acetate, and ammonium phosphate; other nitrogen-containing compounds; peptone; meat extracts; and corn steep liquor. Examples of inorganic salts include: monopotassium phosphate, dipotassium phosphate, magnesium phosphate, magnesium sulfate, sodium chloride, iron(I) sulfate, manganese sulfate, copper sulfate, and calcium carbonate. In accordance with the type of selection marker, an antibiotic agent, such as aureobasidin, ampicillin, or tetracycline, may be adequately added to a medium. Alternatively, an amino acid that can be supplied by a gene complementing auxotrophy (e.g., Leu, Ura, or Trp) may be removed.

When culturing the transformed host cell, in the case of yeast, for example, the pH level of the medium is preferably adjusted to 4 to 7. The culture temperature is between 15° C. and 32° C., and preferably around 28° C. When a protein having a complicated steric structure as an antibody is expressed, culture may be preferably carried out at a low temperature, in order to more effectively fold such a protein in the cell. The culture duration is generally about 24 to 1,000 hours, and culture can be carried out via batch culture, such as static, shake, agitation, or aeration culture, or via continuous culture.

An expression product of a gene of a foreign protein from the culture product (i.e., a culture solution or cultured cells) can be confirmed via SDS-PAGE, Western blotting, ELISA, or the like.

The produced proteins may be isolated and purified via conventional techniques for protein isolation and purification. When target proteins are produced in the bacteria or cells after culture, the bacteria or cells may be pulverized using, for example, an ultrasonic pulverizer, a French press, a Manton-Gaulin homogenizer, Dinomil, or the like, to obtain target proteins. When the target proteins are produced outside the bacteria or cells, the culture solution is used as it is, or the bacteria or cells are removed via centrifugation or the like.

Thereafter, the target proteins are collected via extraction using an organic solvent, subjected to various chromatography techniques (e.g., hydrophobic, reversed-phase, affinity, or ion-exchange chromatography), gel filtration using molecular sieves, electrophoresis using polyacrylamide gel, or the like, according to need. These techniques may be employed solely or in combinations of two or more. Thus, the target proteins may be isolated and purified.

The above culture and purification techniques are examples, and methods are not limited thereto. The amino acid sequence of the purified gene product can be confirmed by a conventional method of amino acid analysis, such as automated amino acid sequencing via the Edman degradation technique.

5. Method for Inhibiting O-Sugar Chain (or Method for Inhibiting PMT Activity)

In the present invention, when yeast is used as a host cell, the aforementioned culture is preferably carried out under conditions in which protein O-mannosyltransferase (PMT) activity is inhibited.

An O-sugar chain is formed in a mammalian cell upon the addition of GalNAc by peptide O-GalNAc transferase, which is present mainly in the Golgi apparatus. Such sugar chain addition takes place after protein folding. In contrast, O-sugar chain formation in yeast and mold cells is initiated upon the addition of mannose to a serine or threonine residue of the protein by a protein-O-mannosyltransferase (PMT) encoded by the PMT gene. Such addition is referred to as PMT activity. The addition of mannose takes place in parallel with protein folding in the endoplasmic reticulum (ER) in the cell. Thus, an unnecessary sugar chain may be disadvantageously added to a site at which such addition would not take place in the case of expression of mammalian proteins. Consequently, such unnecessary modification would cause insufficient formation of aggregates and lower the activity.

By performing culture under conditions in which protein O-mannosyltransferase (PMT) activity is inhibited, accordingly, formation of an unnecessary 0 sugar chain can be inhibited. This also accelerates protein aggregation and enables maintenance of indigenous physical properties and activity of proteins. In the present invention, effects of high-level secretory production of proteins via introduction of the activated HAC1 gene and/or the RRBP gene can further produce synergistic effects by regulating the O-sugar chain formation enhanced by URP via inhibition of PMT activity.

Addition of an O-sugar chain peculiar to yeast or a mold can be inhibited by, for example, the two methods described below. These methods can be performed in combination.

(1) Culture and production are carried out under conditions in which PMT activity that undergoes addition of an O-sugar chain peculiar to yeast or a mold is inhibited.

(2) Cells in which PMT activity that undergoes addition of an O-sugar chain peculiar to yeast or a mold is inhibited are used.

The protein O-mannosyltransferase (PMT) activity of (1) above can be inhibited with the addition of an inhibitor of PMT activity (i.e., a PMT inhibitor) to the medium, for example. An example of an inhibitor of PMT activity that can be used is the rhodanine-3-acetic acid derivative (Bioorganic & Medicinal Chemistry Letters 14, pp. 3975-3978, 2004). Specific examples of the rhodanine-3-acetic acid derivative include 5-[[3,4-(1-phenylmethoxy)phenyl]methylene]-4-oxo-2-thioxo-3-thiazolidineacetic acid (compound (1c) described in Bioorganic & Medicinal Chemistry Letters, Vol. 14, p. 3975, 2004) and {(5Z)-4-oxo-5-[3-(1-phenylethoxy)-4-(2-phenylethoxy)benzylidene]-2-thioxo-1,3-thiazolidin-3-yl}acetic acid (compound (5a) described in Bioorganic &

Medicinal Chemistry Letters, Vol. 14, p. 3975, 2004). Such inhibitor of PMT activity (the rhodanine-3-acetic acid derivative) was first examined as an antibacterial agent, and it was not examined for the purpose of improving protein quality or productivity. The effects thereof were first discovered in the present invention. PMT is important for generation of mannoproteins that constitute the yeast strain wall. Excessively lowered PMT activity would adversely affect the growth of yeast. When inducible expression systems are used, accordingly, the addition of an inhibitor of PMT activity at the time of expression of genes of foreign proteins, following cell growth, would be more effective. Thus, high-quality target proteins in which O-sugar chain modification is inhibited can be produced at the maximum level.

The protein O-mannosyltransferase (PMT) activity described in (2) above can be inhibited by disrupting the PMT gene or inhibiting expression of such gene. In S. cerevisiae, PMT is encoded by at least 6 genes; i.e., the PMT1 gene (GenBank: L19169), the PMT2 gene (GenBank: L05146), the PMT3 gene (GenBank: X83797), the PMT4 gene (GenBank: X83798), the PMT5 gene (GenBank: X95644), and the PMT6 gene (GenBank: Z72984), and these genes independently form a homodimer (PMT4p) or a heterodimer (PMT1p/PMT2p) and exhibit activity. It is known that acting PMT varies in accordance with a glycoprotein. In the present invention, PMT proteins were found to have selectivity with regard to the addition of an O-sugar chain to an antibody. Specifically, the effects of inhibition of O-sugar chain addition were not found in the PMT5 or PMT6 gene-deficient strain, as described in the examples.

Thus, PMT is an important gene for the growth of yeast. When activity, such as disruption of the PMT gene, is eliminated or extremely lowered, the cell wall becomes fragile. Thus, the use of a PMT gene-deficient strain requires attention. Disruption of PMT genes as disclosed in WO 2002/046437 is not always effective. It may sometimes adversely affect the growth of a foreign protein due to growth inhibition, and inhibition of disruption or expression of PMT genes having optimal PMT activity, which can minimize O-sugar chain addition and modification to the target protein, is desired. Examples of methods for inhibiting PMT genes include a method involving the use of antisense RNA or RNAi and a method of attenuating a promoter. In the present invention, a method in which a DNA fragment is inserted into the PMT structural gene portion and the promoter region to cleave the gene (hereafter, such method may be referred to as "insertional inactivation of genes," and a plasmid vector for insertional inactivation of genes is referred to as a "insertional inactivation vector") is demonstrated as an example of a means for attenuating a promoter. Also, a method wherein a PMT gene fragment that does not have PMT activity but is generated as a protein or a gene whose activity-related amino acid residue has been mutated is introduced to inhibit PMT activity (i.e., a dominant-negative method) can also be employed.

BEST MODES FOR CARRYING OUT THE INVENTION

Hereafter, the present invention is described in detail with reference to the examples, although the technical scope of the present invention is not limited to the examples. Plasmids, restriction enzymes, DNA modifying enzymes, and the like that are used in the examples of the present invention are commercially available products, and these products can be used in accordance with conventional techniques. Also, procedures of DNA cloning, nucleotide sequencing, host cell transformation, culture of transformed host cells, sampling and purification of enzymes from culture products, and the like are well-known in the art or can be learned through existing publications.

EXAMPLE 1

Construction of Foreign Gene-Expressing Plasmid (1) Construction of Foreign Gene-Expressing Tandem Vector Comprising the AOX1 Gene Promoter Having the G418-Resistant Gene as the Marker, the Terminator Cassette and the GAP Gene Promoter, and the Terminator Cassette pOMex3G and pOMexGP1U disclosed in WO 2003/091431 were used as materials. pOMex3G was cleaved with XbaI and blunt-ended, followed by introduction of the SpeI linker. The resulting vector was designated as pOMex3GXS. Separately, pOMexGP1U was cleaved with EcoT22I and blunt-ended, followed by introduction of the ApaI linker. The resulting vector was designated as pOMexGP1UTA. pOMexGP1UTA was digested with HindIII and KpnI and blunt-ended. Thereafter, the isolated fragment of about 2.0 kb containing a GAP promoter and a terminator was digested with ApaI and then introduced into the blunt-ended pOMex3GXS. The resulting vector was designated as pOMexGAT-G. pOMexGAT-G is a tandem vector that comprises the SpeI-BamHI site within the AOX1 expression cassette and the SalI-ApaI site within the GAP expression cassette.

(2) Construction of a Foreign Gene-Expressing Vector with the Use of a Gap Gene Promoter and a Terminator Using the ADE1 Gene as a Selection Marker pOMex4A disclosed in WO 2003/091431 was used as a material. The aforementioned pOMexGP1U was treated with EcoT22I and blunt-ended, followed by introduction of the BamHI linker. The resulting vector was designated as pOMexGP2U. pOMexGP2U was treated with SalI and blunt-ended, followed by introduction of the SpeI linker. The resulting vector was designated as pOMexGP3U. pOMexGP3U was digested with HindIII and KpnI, and a fragment of approximately 2.0 kb containing the GAP expression cassette was isolated. The resulting fragment was ligated to a fragment of approximately 5.0 kb comprising the ADE1 marker isolated by treating pOMex4A with HindIII-KpnI. The resulting vector was designated as pOMexGP1A. pOMexGP1A is a foreign gene-expressing vector that comprises the SpeI-BamHI site within the GAP expression cassette.

(3) Construction of a Foreign Gene-Expressing Vector with a Phosphoglycerine Kinase (PGK1) Promoter and a Terminator Using a Hygromycin B-Resistant Gene as a Selection Marker The PGK1 gene encoding phosphoglycerine kinase was obtained from the *Ogataea minuta* IFO10746 strain, and the nucleotide sequence thereof was determined.

(3-1) Preparation of Probes

DNA degenerate primers comprising nucleotide sequences corresponding to the conserved amino acid sequences, i.e., RVDFNVPLD (SEQ ID NO: 123) and EGKELPGVA (SEQ ID NO: 124), derived from *Saccharomyces cerevisiae* (Gen Bank accession number: P00560) and *Candida maltosa* (GenBank accession number: P41757) were synthesized in the following manner.

PPG5:
(SEQ ID NO: 1)
5'-GN GTN GAY TTY AAY GTN CCN TTR GA-3'

-continued

PPG3:
                                        (SEQ ID NO: 2)
5'-GY NAC DCC NGG YAA YTC YTT DCC YTC-3'

The PPG5 primer (SEQ ID NO: 1) corresponds to the amino acid sequence, RVDFNVPLD (SEQ ID NO: 123), and the PPG3 primer (SEQ ID NO: 2) is a sequence of a complementary strand of a nucleotide sequence corresponding to the amino acid sequence, EGKELPGVA (SEQ ID NO: 124). Chromosome DNA of the *O. minuta* IFO10746 strain was used as a template, PCR was carried out using PPG5 and PPG3 primers at 94° C. for 30 seconds, 50° C. for 1 minute, and 72° C. for 1 minute, and this cycle was repeated 25 times. The amplified DNA fragment (approximately 1.2 kb) was recovered and cloned using the TOPO TA Cloning Kit. Plasmid DNA was isolated from the resulting clone, and the nucleotide sequence was determined. Thus, a clone having a nucleotide sequence encoding an amino acid sequence having high homology to the amino acid sequence of the PGK1 gene derived from *S. cerevisiae* and *C. maltosa* in the plasmid-inserted DNA fragment was selected. The 1.2-kb DNA-inserted fragment was recovered after the plasmid was cleaved with EcoRI, followed by agarose gel electrophoresis.
(3-2) Preparation and Screening of Library Chromosome DNA of the *O. minuta* IFO10746 strain was cleaved with various restriction enzymes and 0.8% agarose gel electrophoresis was performed. The separated DNA was transferred on the Hybond N+ nylon membrane (Amersham). The DNA fragment obtained in (1-3-1) above was labeled with the use of the AlkPhos DIRECT (Amersham), followed by Southern hybridization. Hybridization was carried out in accordance with a conventional technique (Molecular cloning 2nd edn., ed. Sambrook, J., et al., Cold Spring Harbor Laboratory U.S.A., 1989). As a result, the PGK1 gene was considered to be present in a BamHI fragment of approximately 9.0 kb. In order to clone the DNA fragment, genome library was prepared. Chromosome DNA of *O. minuta* was cleaved with BamHI and subjected to agarose electrophoresis, and a DNA fragment of approximately 9.0 kb was recovered from the gel. The recovered DNA fragment was ligated to the BamHI-cleaved pUC118 and transformed into the *E. coli* DH5α strain in accordance with the method of Hanahan (Gene, 10, 63, 1980) to prepare library. Approximately 4,000 clones were screened via colony hybridization using the aforementioned DNA fragments as probes. From among the obtained positive clones, the pOMPGK1 plasmids carrying PGK1 genes were selected.
(3-3) Nucleotide Sequencing The nucleotide sequence in the BamHI region in the pOMPGK1 plasmid was determined by the primer walking method, and the determined sequence was found to have the nucleotide sequence as shown in SEQ ID NO: 3. The nucleotide sequence as shown in SEQ ID NO: 3 comprises an open reading frame comprising 1,254 base pairs from nucleotides 4,766 to 6,016. Homology between the amino acid sequence as shown in SEQ ID NO: 4 that is deduced based on the open reading frame and phosphoglycerine kinases derived from *Saccharomyces cerevisiae* and *Candida maltosa* was inspected. As a result, the former homology was found to be 74%, and the latter homology was found to be 81%.
(3-4) Construction of Foreign Gene-Expressing Cassette Using PGK1 Gene Promoter and Terminator An expression cassette that introduces a foreign gene between a fragment containing the PGK1 gene promoter and a fragment containing a terminator of the *O. minuta* was prepared. In order to introduce the SpeI, BglII, and BamHI sites between the PGK1 gene promoter and the terminator, the following primers were synthesized.

OPGK-P-F:
                                                          (SEQ ID NO: 5)
5'-AAGCTTGACAATGTAGGAGATCATAAACACATCGTGCGCGTC-3'

OPGK-P-R:
                                                          (SEQ ID NO: 6)
5'-GGATCCAGATCTCATATGACTAGTTGCTAGTTCTATGCGGCGTTAGT

GTTTACACTACGACAGCT-3'

OPGK-T-F:
                                                          (SEQ ID NO: 7)
5'-GGATCCGTGGGATTTGCGTGATCTACGTAGTGGTTATTTT-3'

OPGK-T-R:
                                                          (SEQ ID NO: 8)
5'-GGTACCGCAGTGAAAGGCGATGCCACCATGTGCAAGGAGTTC-3'

Using pOMPGK1 above as a template, PCR was carried out using the OPGK-P-F primer (SEQ ID NO: 5) and the OPGK-P-R primer (SEQ ID NO: 6) at 94° C. for 30 seconds, 55° C. for 1 minute, and 72° C. for 1 minute, and this cycle was repeated 20 times. Also, PCR was carried out using the OPGK-T-F primer (SEQ ID NO: 7) and the OPGK-T-R primer (SEQ ID NO: 8) at 94° C. for 30 seconds, 55° C. for 1 minute, and 72° C. for 1 minute, and this cycle was repeated 20 times. The amplified 1.5-kb and 1.0-kb DNA fragments were recovered and cloned using the TOPO TA Cloning Kit. The nucleotide sequences of the insertion DNA fragments were determined to select clones having the correct nucleotide sequences. The 1.5-kb and 1.0-kb insertion DNA fragments were isolated as the HindIII-BamHI fragment and the BamHI-KpnI fragment, respectively.

The aforementioned 1.0-kb BamHI-KpnI fragment was introduced between BamHI and KpnI of pOMex5H described in WO 2003/091431. Thereafter, the aforementioned 1.5-kb HindIII-BamHI fragment was introduced between HindIII and BamHI of the obtained plasmid. The resulting plasmid was designated as pOMexPGHy. pOMexPGHy is a foreign gene-expressing vector comprising SpeI, BglII, and BamHI sites in the PGK1 gene expression cassette.

EXAMPLE 2

Construction of Antibody Gene Expression Vector

In order to clone a secretion signal of MF alpha1 (GenBank accession number: P01149) derived from *S. cerevisiae* (hereafter referred to as the "aMF secretion signal"), the following primers were synthesized.

Sp-aMFs-F:
5'-ACTAGTATGAGATTTCCTTCAATTT-3'      (SEQ ID NO: 9)

Sl-aMFs-F:
5'-GTCGACATGAGATTTCCTTCAATTT-3'      (SEQ ID NO: 10)

Xb-aMFs-R:
5'-AGCTTCAGCCTCTCTTTTATCTAGAGA-3'    (SEQ ID NO: 11)

Genome DNA of *S. cerevisiae* obtained in the same manner as described above was used as a template to carry out PCR using the Sp-aMFs-F primer (SEQ ID NO: 9) and Xb-aMFs-R primer (SEQ ID NO: 11) at 94° C. for 30 seconds, 55° C. for 1 minute, and 72° C. for 30 seconds, and this cycle was repeated 20 times. Also, PCR was carried out using the Sl-aMFs-F primer (SEQ ID NO: 10) and the Xb-aMFs-R primer (SEQ ID NO: 11) at 94° C. for 30 seconds, 55° C. for 1 minute, and 72° C. for 30 seconds, and this cycle was repeated 20 times. The amplified DNA fragments of approximately 0.3 kb in each PCR were recovered and cloned using the TOPO TA Cloning Kit. The nucleotide sequences of the insertion DNA sequences were confirmed, and the resulting plasmids were designated as TOPOaMFsSP and TOPOaMFsSL, respectively.

The anti-TRAIL receptor antibody gene (WO 2002/094880) was used as an antibody gene. In order to introduce restriction enzyme sites into sites at both terminuses of the light-chain and heavy-chain genes, the following primers were synthesized.

```
Xb-KREAEA-Hc-F:
                                  (SEQ ID NO: 12)
5'-TCTCTAGATAAAAGAGAGGCTGAAGCTCAGCTGCAGCTGCAGGAG

TC-3'

Hc-R-Bg:
                                  (SEQ ID NO: 13)
5'-CCAGATCTGGATCCTCATTTACCCGGAGACAGGGAGAGG-3'

Xb-KREAEA-Lc-F:
                                  (SEQ ID NO: 14)
5'-TCTCTAGATAAAAGAGAGGCTGAAGCTGAAATTGTGTTGACACAG

TC-3'

Lc-R-Ap:
                                  (SEQ ID NO: 15)
5'-AAAGGGCCCTCAACACTCTCCCCTGTTGAAGCTCT-3'
```

Using these DNA primers, PCR was carried out to amplify a light chain via 20 cycles of 94° C. for 30 seconds, 55° C. for 1 minute, and 72° C. for 1 minute and to amplify a heavy chain via 20 cycles of 94° C. for 30 seconds, 55° C. for 1 minute, and 72° C. for 1 minute and 30 seconds, and the amplified products were cloned into pCR2.1-TOPO. The nucleotide sequences of the insertion DNA sequences were confirmed, the resulting plasmids were designated as TOPOHc-Trail and TOPOLc-Trail, respectively. An aMF secretion signal isolated from TOPOaMFsSL via digestion with SalI and XbaI and an antibody light chain isolated from TOPOLc-Trail via digestion with XbaI and ApaI were introduced into the SalI-ApaI-digested pOMexGAT-G via 3 fragment ligation. The resulting plasmid was designated as pOMexGAT-G/L. Subsequently, an aMF secretion signal isolated from TOPOaMFsSP via digestion with SpeI and XbaI and an antibody heavy chain isolated from TOPOHc-Trail via digestion with XbaI and BglII were introduced into the SpeI-BamHI-digested pOMexGAT-G/L via 3 fragment ligation. The resulting vector was designated as pOMexGAT-G/Ab (FIG. 3). pOMexGAT-G/Ab is an antibody expression vector comprising both antibody heavy chain and light chain expression units.

EXAMPLE 3

Construction of Activated HAC1 Gene Expression Vector of *O. minuta*

The activated HAC1 gene was obtained by culturing cells (*O. minuta* YK2-3 strains) in YPD medium at 27° C. for 12 hours and adding tunicamycin to a concentration of 10 μg/ml in the medium so as to induce UPR. Culture was carried out in a tunicamycin-containing medium for an additional 12 hours. After the cells were collected, mRNA was prepared using the Yeastar RNA kit (ZYMO research).

The obtained mRNA was subjected to DNase treatment using DNase I Amplification Grade (Invitrogen). cDNA was synthesized from the mRNA using Super script III First-Strand Synthesis for RT (Invitrogen). The resulting cDNA was amplified via PCR using the HAC1-1 DNA primer (SEQ ID NO: 16) and the HAC1-12 primer (SEQ ID NO: 17) described below at 94° C. for 30 seconds, 52° C. for 30 seconds, and 72° C. for 1 minute, and this cycle was repeated 30 times. The amplified products were cloned into pCR2.1-TOPO (Invitrogen). Thereafter, the nucleotide sequences of the two types of PCR-amplified gene fragments were confirmed (SEQ ID NOs: 18 and 19).

```
HAC1-1:
5'-ATGACTTCCTTTTCAGCACCGCATC-3'   (SEQ ID NO: 16)

HAC1-12:
5'-CAAAATTGCAAGCAAGTTAACCG-3'     (SEQ ID NO: 17)
```

One of the two types of cDNA fragments obtained was consistent with the genome sequence; however, the other fragment was a shortened sequence lacking part thereof, i.e., a cDNA fragment spliced by Ire1p activated by UPR. In order to obtain cDNA of the activated HAC1, a PCR cycle of 94° C. for 30 seconds, 55° C. for 1 minute, and 72° C. for 30 seconds was repeated 20 times using cDNA pool, which is deduced to contain the speHAC1F DNA primer (SEQ ID NO: 20), the bglHAC1R primer (SEQ ID NO: 21), and cDNA of the activated HAC1.

```
speHAC1F:
                                  (SEQ ID NO: 20)
5'-gactagtATGACTTCCTTTTCAGCACCG-3' bglHAC1R:
                                  (SEQ ID NO: 21)
5'-cagatctTCATGACAAGAAATCATCGAAT-3'
```

Figure 3:
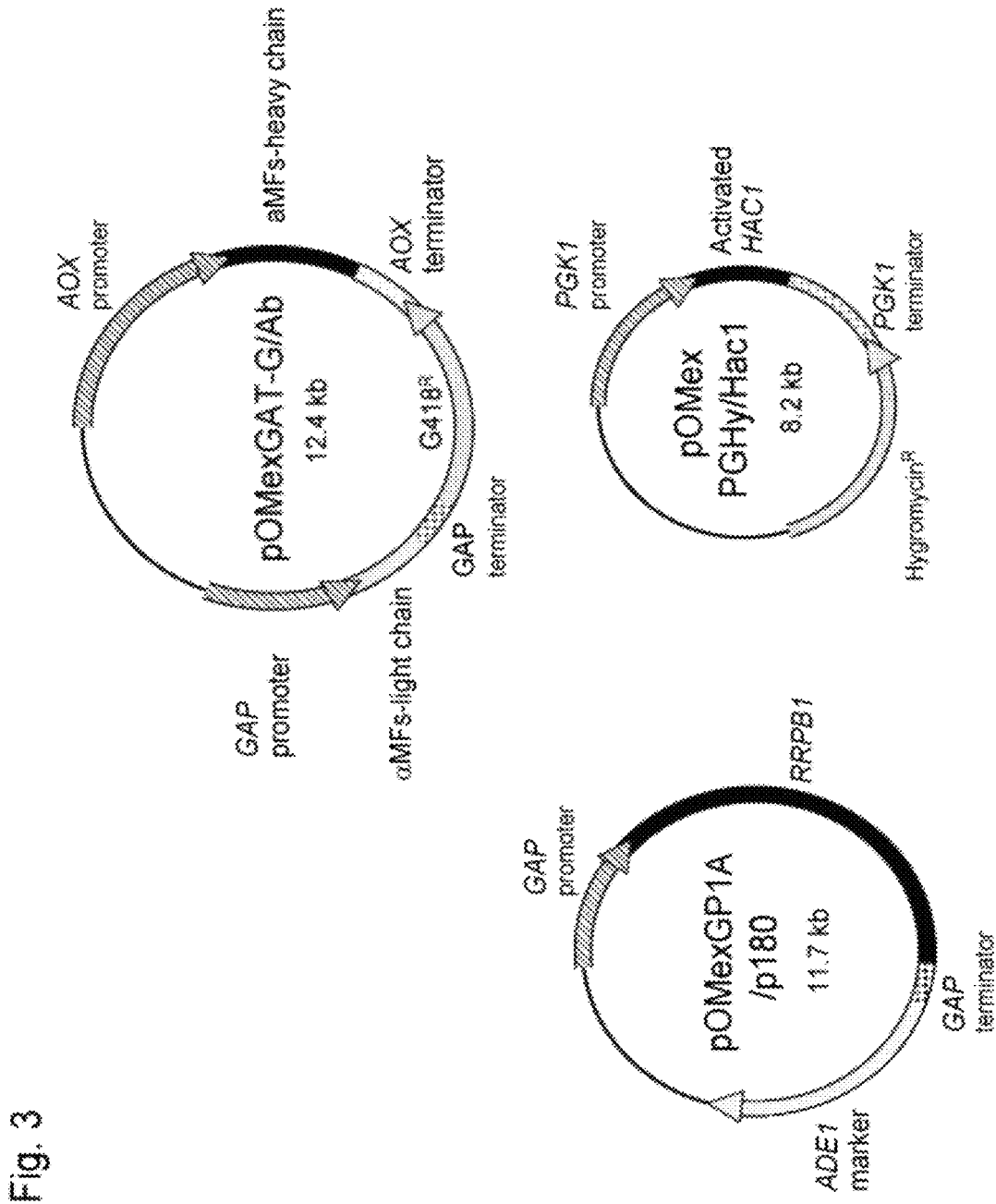
FIG. 3 shows the structures of an expression vector for the activated HAC1 gene of *O. minuta* (pOMexPGHy/Hac1), an expression vector for the human RRBP1 gene (pOMexGP1A/p180), and an expression vector for the human antibody gene (pOMexGAT-G/Ab).

The obtained fragment of approximately 1 kb comprised a sequence from the initiation codon to the termination codon of the activated HAC1 gene (SEQ ID NO: 22), which is equivalent to the amino acid sequence of activated Hac1p comprising 320 amino acid residues (SEQ ID NO: 23). This sequence was treated with SpeI and BglII, isolated, and then introduced into the SpeI-BglII-treated pOMexPGHy. The resulting vector was designated as pOMexPGHy/Hac1 (FIG. 3). This vector comprises an activated HAC1 gene expression unit.

EXAMPLE 4

Construction of Human RRBP1 Gene Expression Vector

The human RRBP1 gene (KIAA1398, GenBank Accession No. AB037819) provided by the Kazusa DNA Research Institute was used. In order to introduce restriction enzyme sites at both terminuses of the gene, the following DNA primers, p180 MSp-F and p180 UBg-R (SEQ ID NOs: 24 and 25), and the human RRBP1 gene were used to amplify the gene of interest by PCR via 20 cycles of 94° C. for 30 seconds, 55° C. for 1 minute, and 72° C. for 5 minutes.

```
p180 MSp-F:
                                  (SEQ ID NO: 24)
5'-ATACAATACAAAGTCGAGACTAGTATGGATATTTACGACACTCAAAC
CTT-3'
```

-continued p180 UBg-R:

(SEQ ID NO: 25)
5'-TCTATCCACACGGATCAGATCTTCAGACAGAGGTGCCCTCCTTTGAG
CTG-3'

The resulting fragment of approximately 4.5 kb was introduced into the SpeI-BamHI-digested pOMexGP1A using the BD In-Fusion Dry-Down PCR Cloning Kit (BD Science). A sequence of approximately 500 bp comprising a region encoding the initiation codon of the human RRBP1 gene was determined from the SpeI site, and a fragment of approximately 500 bp comprising a region encoding the termination codon of the human RRBP1 gene was determined from the BamHI site. The resulting vector was designated as pOMexGP1A/p180PCR. pOMexGP1A/p180PCR was digested with NdeI and AscI, and a fragment comprising a region from 110 bp to 4541 bp in ORF of the human RRBP1 gene was removed from the plasmid. Separately, the human RRBP1 gene provided by the Kazusa DNA Research Institute was digested with NdeI and AscI, a fragment comprising a region from 110 bp to 4541 bp in ORF was isolated, and the isolated fragment was introduced into the aforementioned NdeI-AscI-digested pOMexGP1A/p180PCR. The resulting vector was designated as pOMexGP1A/p180 (FIG. 3). pOMexGP1A/p180 is the human RRBP1 gene expression vector.

EXAMPLE 5

Preparation of Antibody-Expressing Yeast Strain (*O. minuta*)

Using the NotI-digested pOMexGAT-G/Ab vector, the *O. minuta* YK-3 strains (Δoch1Δpep4Δprb1Δyps1Δura3Δade1: described in WO 2003/091431) were transformed via electroporation. The conditions for electroporation described in WO 2003/091431 were employed. The transformed cells were selected in YPD agar plate medium containing 50 μg/ml of G418 and cultured. Thereafter, the genomes were extracted, introduction of a heavy chain was confirmed via PCR using the aforementioned Xb-KREAEA-Hc DNA primer (SEQ ID NO: 12) and Hc-R-Bg primer (SEQ ID NO: 13), and introduction of a light chain was confirmed via PCR using the aforementioned Xb-KREAEA-Lc-F primer (SEQ ID NO: 14) and Lc-R-Ap primer (SEQ ID NO: 15). The strain in which introduction of the heavy chain and the light chain genes had been observed was designated as the antibody-producing *O. minuta* AO1 strain.

EXAMPLE 6

Preparation of Antibody-Producing Yeast Strain (*O. minuta*) that Expresses the Activated HAC1 Gene and the RRBP1 Gene Sse8783I-digested pOMexGP1A/p180 was introduced into the antibody-producing *O. minuta* AO1 strain grown in Example 5 via electroporation. Transformed strain was obtained by selecting an ADE+ strain in SD agar plate medium, culturing the strain, extracting the genome, and confirming introduction of the RRBP1 gene via PCR using p180 MSp-F (SEQ ID NO: 24) and p180 UBg-R (SEQ ID NO: 25) mentioned above. The obtained transformed strain was designated as the *O. minuta* AK2R strain. At the same time, transformation was carried out using Sse8783I-digested pOMexGP1A to obtain the *O. minuta* AK2A strain as a control. Further, Aor51HI-digested pOMexPGHy-Hac1 was introduced into the *O. minuta* AK2R strain and the *O. minuta* AK2A strain via electroporation. Introduction of the activated HAC1 gene into the transformed strain was confirmed by selecting a strain in a YPD agar plate medium comprising hygromycin at 50 μg/ml, culturing the strain, extracting the genome, and confirming via PCR using the speHAC1F DNA primer (SEQ ID NO: 20) and the bglHAC1R primer (SEQ ID NO: 21). The resulting strains were designated as the *O. minuta* AK3RH strain and the *O. minuta* AK3AH strain. At the same time, Aor51 HI-digested pOMexPGHy was introduced into the *O. minuta* AK2R strain and the *O. minuta* AK2A strain to obtain the *O. minuta* AK3RHy strain and the *O. minuta* AK3AHy strain as controls.

EXAMPLE 7

Confirmation of Secretion of Antibody by Transformed Yeast Strain (*O. minuta*)

Figure 4:
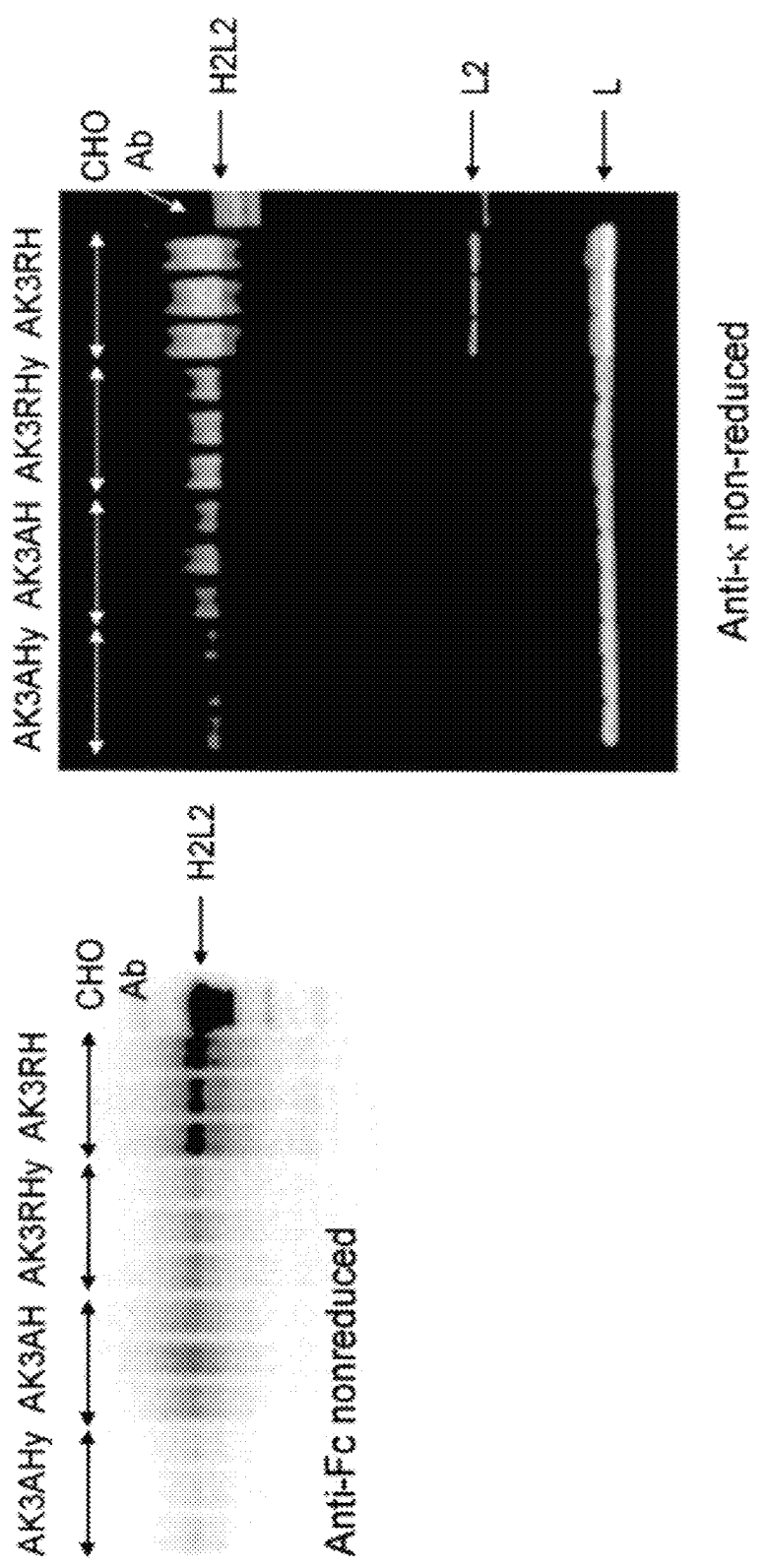
FIG. 4 shows the results of Western analysis of antibodies secreted in the culture supernatant of an antibody-producing yeast strain into which the activated HAC1 gene of *O. minuta* and the human RRBP1 gene have been introduced.

*O. minuta* AK3RH, *O. minuta* AK3AH, *O. minuta* AK3RHy, and *O. minuta* AK3AHy strains were cultured in BYPMG medium (1% yeast extract (Difco), 2% polypeptone (Difco), 1.5% methanol, 0.5% glycerol, and 0.1M phosphate buffer (pH 6.0)) at 28° C. for 4 days. A culture supernatant was prepared from the culture solution and subjected to SDS-PAGE. The separated protein was blotted on a PVDF membrane, and Western analysis was performed using labeled anti-human antibodies (anti-human Fc antibody and anti-human κ antibody). As a result, the strain into which the RRBP1 gene and the activated HAC1 gene had been introduced was found to secrete a significantly greater amount of antibodies than other strains, as shown in FIG. 4.

EXAMPLE 8

Productivity of Secretory Antibody by Transformed Yeast Strain (*O. minuta*)

Figure 5:
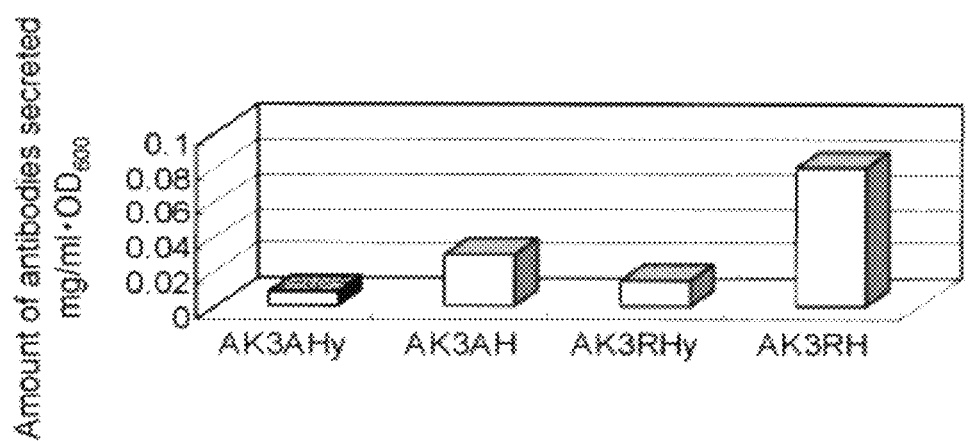
FIG. 5 shows a chart showing the results of measuring the amount of secreted antibodies of an antibody-producing yeast strain into which the activated HAC1 gene of *O. minuta* and the human RRBP1 gene have been introduced.

The culture solution prepared in Example 7 was subjected to HPLC using Protein A columns (Poros A 50 um 4.6 mm D/50 mml, Applied Biosystems) to measure the amount of antibody production (separation conditions: equilibration buffer: 10 mM phosphate buffer (pH 6.0); elution buffer: 10 mM phosphate buffer (pH 3.4); flow rate: 4 ml/min; detection: 210 nm). As a standard sample, an antibody produced in animal cells (CHO) was used. FIG. 5 shows the antibody productivity per OD 600=1. The amounts of antibodies secreted in the *O. minuta* AK3RHy strain into which only the RRBP1 gene had been introduced and in the *O. minuta* AK3AH strain into which only the activated HAC1 gene had been introduced tended to increase, compared with the amount in the control strain, i.e., the *O. minuta* AK3AHy strain. The amount of antibody production in the *O. minuta* AK3RH strain in which both the activated HAC1 gene and the RRBP1 gene were expressed, however, was significantly greater than that in the control strain, i.e., the *O. minuta* AK3AHy strain, and in the strain into which either the activated HAC1 gene or the RRBP1 gene had been solely introduced. It was thus confirmed that coexpression of the activated HAC1 gene and the RRBP1 gene would produce effects greater than the synergistic effects on antibody productivity.

EXAMPLE 9

Antibody Production Under Conditions in which O-Sugar Chain Formation Using the Transformed Yeast Strain (*O. minuta*) is Inhibited

Figure 6:
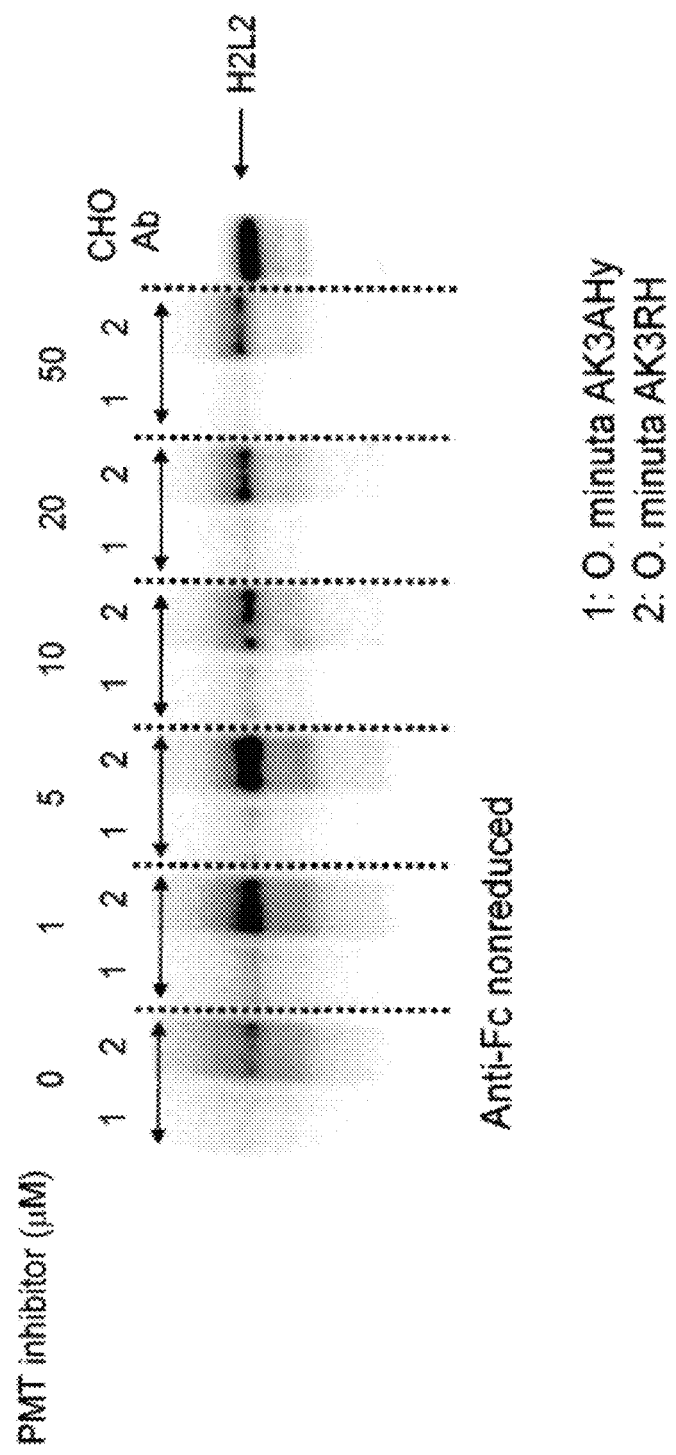
FIG. 6 shows the results of Western analysis of antibodies secreted in the culture supernatant of an antibody-producing yeast strain into which the activated HAC1 gene of *O. minuta* and the human RRBP1 gene have been introduced, which have been cultured under conditions in which O-sugar chain formation is inhibited.

*O. minuta* AK3RH and *O. minuta* AK3AHy were cultured in BYPG medium (1% yeast extract (Difco), 2% polypeptone (Difco), 0.5% glycerol, and 0.1M phosphate buffer (pH 6.0)) for 2 days, and these strain were cultured in BYPM media [1% yeast extract (Difco), 2% polypeptone (Difco), 1.5% methanol, and 0.1M phosphate buffer (pH 6.0)] to which 0 μM, 1 μM, 5 μM, 10 μM, 20 μM, and 50 μM PMT inhibitors (the rhodanine-3-acetic acid derivative: 5-[[3,4-(1-phenyl-methoxy)phenyl]methylene]-4-oxo-2-thioxo-3-thiazo-lidineacetic acid (compound (1c) described in Bioorganic & Medicinal Chemistry Letters, Vol. 14, p. 3975, 2004)) had been added at 28° C. for 2 days. A culture supernatant was prepared from the culture solution and subjected to SDS-PAGE. Thereafter, the separated protein was blotted on a PVDF membrane, and Western analysis was carried out using a labeled anti-human antibody (anti-human Fc antibody). FIG. 6 shows the results thereof. The adequate concentration of the PMT inhibitor to be added was 5 μM. In such a case, the amount of antibody secretion and the percentage of aggregate formation were increased.

EXAMPLE 10

Construction of Antibody Gene Expression Vector

In order to express a fusion protein of the secretion signal of S. cerevisiae-derived MF alpha1 (GenBank accession number: P01149) (hereafter referred to as a "aMF secretion signal"), the light chain of the anti-TRAIL receptor antibody, and the heavy chain thereof, the aMF secretion signal gene was ligated to the anti-TRAIL receptor antibody gene (WO 2001/083560) via overlap extension PCR using the following oligonucleotide primers.
For aMF Secretion Signal—a Heavy Chain of Anti-Trail Receptor Antibody

```
EcoALF:
                                      (SEQ ID NO: 26)
5'-GGAATTCATGAGATTTCCTTCAAT-3'

AlfH02:
                                      (SEQ ID NO: 27)
5'-CTCCACCAGCTGTACTTCTCTTTTCTCGAGAGATA-3'

AlfH03:
                                      (SEQ ID NO: 28)
5'-TATCTCTCGAGAAAAGAGAAGTACAGCTGGTGGAG-3'

AlfH04:
                                      (SEQ ID NO: 29)
5'-GGTCGACTCATTTACCCGGGGACAG-3'
```

For aMF Secretion Signal—a Light Chain of Anti-TRAIL Receptor Antibody

```
EcoALF:
                                      (SEQ ID NO: 26)
5'-GGAATTCATGAGATTTCCTTCAAT-3'

AlfL02:
                                      (SEQ ID NO: 30)
5'-TGGGTCATCTGAATGTCTCTTTTCTCGAGAGATA-3'

AlfL03:
                                      (SEQ ID NO: 31)
5'-TATCTCTCGAGAAAAGAGACATTCAGATGACCCA-3'

AlfL04:
                                      (SEQ ID NO: 32)
5'-GGTCGACCTAACACTCTCCCCTGT-3'
```

The aMF secretion signal gene region was amplified using, as a template, the genomic DNA of S. cerevisiae prepared using the Y-DER yeast DNA extraction reagent (PIERCE). The aMF secretion signal for the heavy chain was obtained via PCR using the EcoALF primer (SEQ ID NO: 26) and the AlfH02 primer (SEQ ID NO: 27) at 95° C. for 10 seconds, 55° C. for 30 seconds, and 68° C. for 60 seconds, and this cycle was repeated 30 times. The aMF secretion signal for the light chain was obtained via PCR using the EcoALF primer (SEQ ID NO: 26) and the AlfL02 primer (SEQ ID NO: 30) at 95° C. for 10 seconds, 55° C. for 30 seconds, and 68° C. for 60 seconds, and this cycle was repeated 30 times. The amplified target DNA fragments of approximately 0.26 kb were recovered.

The antibody gene region was amplified using cDNA of the anti-TRAIL receptor antibody (WO2001/083560) as a template. The heavy chain fragment was obtained via PCR using the AlfH03 primer (SEQ ID NO: 28) and the AlfH04 primer (SEQ ID NO: 29) at 95° C. for 10 seconds, 55° C. for 30 seconds, and 68° C. for 90 seconds, and this cycle was repeated 30 times. The light chain fragment was obtained via PCR using the AlfL03 primer (SEQ ID NO: 31) and the AlfL04 primer (SEQ ID NO: 32) at 95° C. for 10 seconds, 55° C. for 30 seconds, and 68° C. for 90 seconds, and this cycle was repeated 30 times. The target DNA fragment of the amplified heavy chain region of approximately 1.35 kb and that of the light chain region of approximately 0.65 kb were recovered.

Subsequently, aMF secretion signal region for the heavy chain and the heavy chain region of approximately 1.35 kb were used as templates to carry out PCR using the EcoALF primer (SEQ ID NO: 26) and the AlfH04 primer (SEQ ID NO: 29) at 95° C. for 10 seconds, 55° C. for 30 seconds, and 68° C. for 90 seconds, and this cycle was repeated 30 times. The amplified target DNA fragment of approximately 1.6 kb was recovered. Also, aMF secretion signal region for the light chain and the light chain region of approximately 0.65 kb were used as templates to carry out PCR using the EcoALF primer (SEQ ID NO: 26) and the AlfL04 primer (SEQ ID NO: 32) at 95° C. for 10 seconds, 55° C. for 30 seconds, and 68° C. for 60 seconds, and this cycle was repeated 30 times. The amplified target DNA fragment of approximately 0.9 kb was recovered. The recovered DNA fragments were cloned into pCR2.1-TOPO. Based on the nucleotide sequences of the insertion DNA fragments, these sequences were found to have the genes in which the aMF secretion signal had been fused in-frame to the antibody heavy chain and the aMF secretion signal had been fused in-frame to the antibody light chain, respectively. The obtained plasmids were designated as TOPO-alfHc and TOPO-alfLc, respectively. The EcoRI restriction enzyme site introduced into the EcoALF primer (SEQ ID NO: 26) and the SalI restriction enzyme sites introduced into the AlfH04 primer (SEQ ID NO: 29) and the AlfL04 primer (SEQ ID NO: 32) were used to recover DNA fragments encoding the fusion product of aMF secretion signal and the antibody heavy chain and that of the aMF secretion signal and the antibody light chain via EcoRI-SalI digestion from TOPO-alfHc and TOPO-alfLc.

Figure 7:
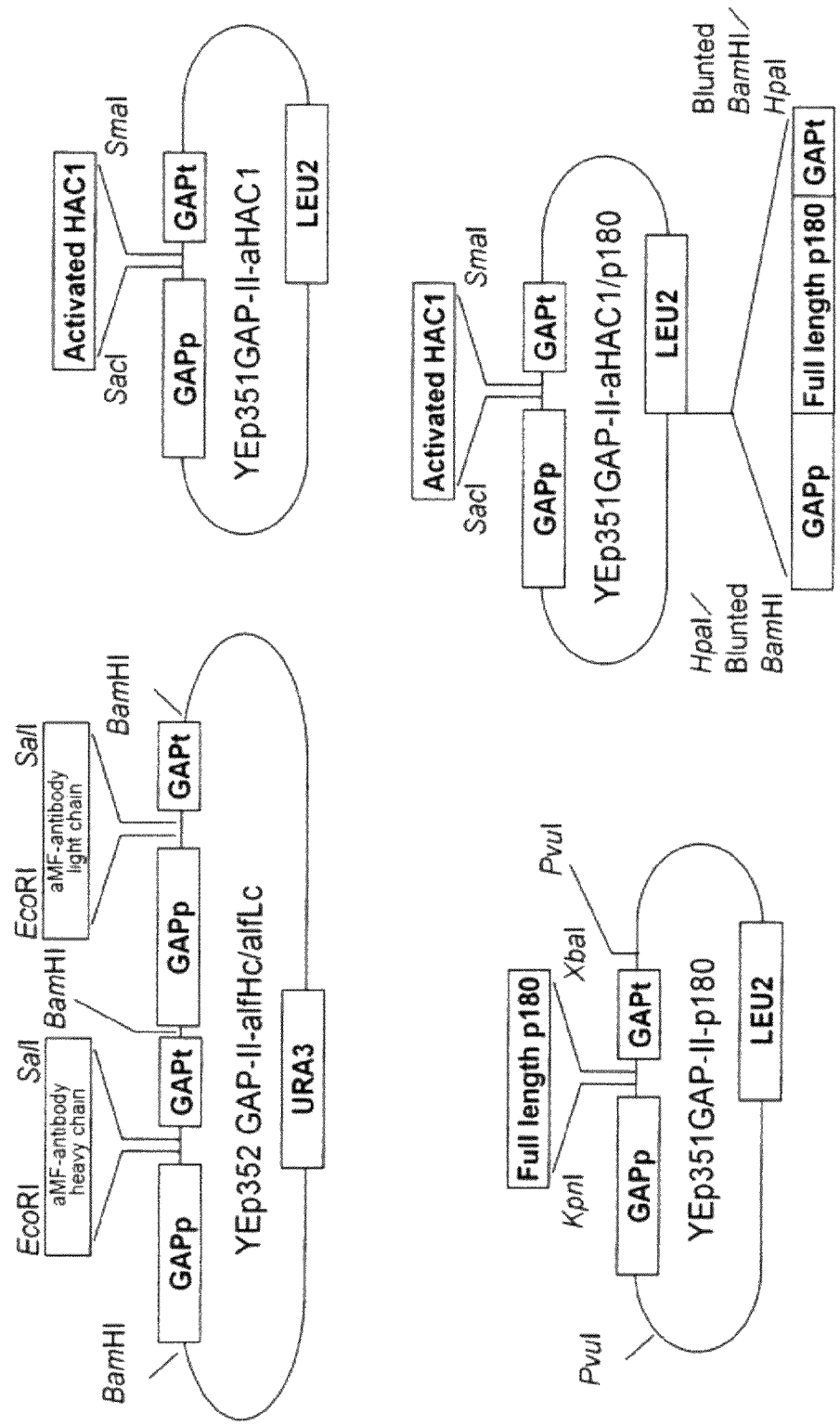
FIG. 7 shows an expression vector for active HAC1 of *S. cerevisiae* (YEp351GAP-II-aHAC1), an expression vector for the human RRBP1 gene (YEp351GAP-II-p180), an expression vector for the human antibody gene (YEp352GAP-II-alfHc/alfLc), and a coexpression vector for the activated HAC1 gene and the RRBP1 gene (YEp351GAP-II-aHAC1/p180).

In order to express the antibody heavy chain and the antibody light chain in S. cerevisiae, DNA fragments encoding the fusion product of aMF secretion signal and the antibody heavy chain and the fusion product of aMF secretion signal and the antibody light chain recovered via EcoRI-SalI digestion were ligated to the EcoRI-SalI site in the glyceraldehyde-3-phosphate dehydrogenase gene (TDH3, GAP) promoter-terminator cassette, which had been introduced into the YEp352 E. coli-yeast shuttle vector (Yeast 2, p. 163-167, 1986). The resulting plasmids were designated as YEp352GAP-II-alfHc and YEp352GAP-II-alfLc, respectively. Subsequently, the BamHI restriction enzyme sites at the both terminuses of the GAP promoter-terminator cassette were used to recover a gene fragment encoding BamHI-the GAP promoter-the aMF secretion signal-the antibody heavy chain-the GAP terminator-BamHI (fragment 1) and a gene fragment encoding BamHI-the GAP promoter-the aMF secretion signal-the antibody light chain-the GAP terminator-the BamHI (fragment 2) from YEp352GAP-II-alfHc and YEp352GAP-II-alfLc, respectively. Fragments 1 and 2 were introduced into the BamHI site of YEp352GAP-II-alfHc or Ep352GAP-II-alfLc via 3 fragment ligation, from which fragment 1 or 2 had been cleaved. The resulting vector was designated as YEp352 GAP-II-alfHc/alfLc (FIG. 7). Based on restriction enzyme cleavage patterns, tandem introduction of fragments 1 and 2 in the forward direction into YEp352 GAP-II-alfHc/alfLc was confirmed. YEp352 GAP-II-alfHc/alfLc is an antibody expression vector carrying both antibody heavy chain and light chain expression units.

EXAMPLE 11

Construction of S. cerevisiae Activated HAC1 Gene Expression Vector

RNase activity of activated IRE1 removes 252 nucleotides from HAC1 precursor mRNA of S. cerevisiae to form mature HAC1 mRNA. This mature HAC1 mRNA is translated into activated HAC1 from which 10 amino acid residues are removed from the C terminus and to which 18 amino acid residues are newly added (PNAS 97, pp. 4660-4665, 2000). Thus, a gene encoding activated HAC1 was constructed via overlap extension PCR using the following oligonucleotide primers.

```
HAC-Sac-ATG:
                                    (SEQ ID NO: 33)
5'-GGAGCTCATGGAAATGACTGATTTTG-3'

HAC-internalR:
                                    (SEQ ID NO: 34)
5'-GAATTCAAACCTGACTGCGCTTCTGGATTACGCCAATTGTCAAG-3'

HAC-internalF:
                                    (SEQ ID NO: 35)
5'-CTTGACAATTGGCGTAATCCAGAAGCGCAGTCAGGTTTGAATTC-3'

HAC-Sma-STOP:
                                    (SEQ ID NO: 36)
5'-GCCCGGGTCATGAAGTGATGAAGAAATC-3'
```

Genomic DNA of S. cerevisiae prepared with the use of the Y-DER yeast DNA extraction reagent (PIERCE) was used as a template. PCR was carried out using the HAC-Sac-ATG primer (SEQ ID NO: 33) and the HAC-internalR primer (SEQ ID NO: 34) at 95° C. for 10 seconds, 55° C. for 30 seconds, and 68° C. for 60 seconds, and this cycle was repeated 30 times. Separately, PCR was carried out using the HAC-internalF primer (SEQ ID NO: 35) and the HAC-Sma-STOP primer (SEQ ID NO: 36) at 95° C. for 10 seconds, 55° C. for 30 seconds, and 68° C. for 60 seconds, and this cycle was repeated 30 times. The amplified target DNA fragments of approximately 0.66 kb (fragment A) and of approximately 0.06 kb (fragment B) were recovered.

Subsequently, the amplified fragment A and fragment B were used as templates to carry out PCR using the HAC-Sac-ATG primer (SEQ ID NO: 33) and the HAC-Sma-STOP primer (SEQ ID NO: 36) at 95° C. for 10 seconds, 55° C. for 30 seconds, and 68° C. for 60 seconds, and this cycle was repeated 30 times to obtain the amplified target DNA fragment of approximately 0.7 kb. The recovered DNA fragment was cloned into pCR2.1-TOPO. Based on the nucleotide sequence of the insertion DNA fragment, the fragment was found to have a gene encoding activated HAC1 comprising 238 amino acid residues. The plasmid was designated as TOPO-aHac1. The SacI restriction enzyme site that had been introduced into the HAC-Sac-ATG primer (SEQ ID NO: 33) and the SmaI restriction enzyme site that had been introduced into the HAC-Sma-STOP primer (SEQ ID NO: 36) were used to recover a gene encoding activated HAC1 via SacI-SmaI digestion.

In order to express activated HAC1 in S. cerevisiae, a gene encoding activated HAC1 recovered via SacI-SmaI digestion was ligated to the SacI-SmaI site in the glyceraldehyde-3-phosphate dehydrogenase gene (TDH3, GAP) promoter-terminator cassette, which had been introduced into the YEp351 E. coli-yeast shuttle vector (Yeast 2, pp. 163-167, 1986). The resulting plasmid was designated as YEp351GAP-II-aHAC1 (FIG. 7). This vector comprises an activated HAC1 gene expression unit.

EXAMPLE 12

Construction of Human RRBP1 Gene Expression Vector

The human RRBP1 gene (KIAA1398, GenBank Accession No: AB037819) provided by the Kazusa DNA Research Institute was used. In order to introduce restriction enzyme sites at the both terminuses of the above gene, the gene was amplified via PCR using the following oligonucleotide primers, P180kpnatg and P180xbastop (SEQ ID NOs: 37 and 38) and the human RRBP1 gene at 95° C. for 10 seconds, 55° C. for 30 seconds, and 68° C. for 6 minutes, and this cycle was repeated 30 times.

```
P180kpnatg:
5'-GGGTACCATGGATATTTACGACACTC-3'      (SEQ ID NO: 37)

P180xbastop:
5'-GTCTAGATCAGACAGAGGTGCCCTCC-3'      (SEQ ID NO: 38)
```

The resulting fragment of approximately 4.7 kb was recovered and cloned into pCR2.1-TOPO. Based on the nucleotide sequence of the insertion DNA fragment, regions of approximately 600 bp at the both terminuses of the insertion fragment were confirmed to properly comprise the target nucleotide sequences. The resulting plasmid was designated as TOPO-P180. Subsequently, TOPO-P180 was digested with NdeI and HpaI restriction enzymes, and a fragment containing a region equivalent to a region between 110 bp and 4524 bp of KIAA1398 was removed. Into the removed region, a NdeI-HpaI fragment of approximately 4.4 kb of KIAA1398 was introduced to construct TOPO-P180N, and the XbaI restriction enzyme site was demethylated with the use of the E. coli SCS110 strain (Stratagene). The KpnI-XbaI restriction enzyme sites that had been introduced into the P180 kpnatg primer (SEQ ID NO: 37) and the P180xbastop primer (SEQ ID NO: 38) were used to recover a KpnI-XbaI fragment comprising a gene encoding RRBP1.

In order to express RRBP1 in S. cerevisiae, the KpnI-XbaI fragment recovered above was ligated to the KpnI-XbaI site in the glyceraldehyde-3-phosphate dehydrogenase gene (TDH3, GAP) promoter-terminator cassette, which had been introduced into the YEp352 E. coli-yeast shuttle vector (Yeast 2, pp. 163-167, 1986). The resulting plasmid was designated as YEp352GAP-II-p180. Subsequently, YEp352GAP-IIp180 was digested with the PvuI restriction enzyme, and a PvuI fragment containing the GAP promoter-the RRBP1 gene-GAP terminator was recovered. The PvuI fragment was ligated to a PvuI fragment comprising a marker gene, i.e., an essential region for replication of the YEp351 *E. coli*-yeast shuttle vector (Yeast 2, pp. 163-167, 1986) to construct YEp351GAP-II-p180 (FIG. 7). This vector comprises the RRBP1 gene expression unit.

EXAMPLE 13

Construction of Coexpression Vector for Activated HAC1 Gene and RRBP1 Gene

In order to introduce the activated HAC1 gene and the RRBP1 gene with the use of a single vector into *S. cerevisiae*, a coexpression vector for the activated HAC1 gene and the RRBP1 gene was constructed. YEp351GAP-II-aHAC1 constructed in Example 11 was digested with the HpaI restriction enzyme. Subsequently, a BamHI fragment containing the GAP promoter-the RRBP1 gene-GAP terminator was recovered from YEp352GAP-II-p180 constructed in Example 12, the both terminuses were blunt-ended using T4 DNA polymerase (Takara Bio), and the resultant was introduced into the HpaI site of YEp351GAP-II-aHAC1. The resulting plasmid was designated as YEp351GAP-II-aHAC1/p180 (FIG. 7). The nucleotide sequence was analyzed to determine the direction for introducing the BamHI fragment containing the introduced GAP promoter-the RRBP1 gene-GAP terminator. This vector comprises an expression unit for the activated HAC1 gene and the RRBP1 gene.

EXAMPLE 14

Construction of Antibody Expressing Yeast Strain and Antibody Expressing Yeast Strain (*S. cerevisiae*) that Expresses the Activated HAC1 Gene and the RRBP1 Gene Competent cells of the *S. cerevisiae* BY4741 strains (MATaΔhis3Δleu2Δmet15Δura3) were prepared using the Frozen-EZ yeast transformation II kit (ZYMO RESARCH). The *S. cerevisiae* BY4741 strains were inoculated into 5 ml of YPAD medium (YPD medium containing 0.04% of adenine (Sigma)), and yeast cells obtained via overnight culture (30° C. at 310 rpm) were used. The expression vectors constructed in Example 10 to Example 13 were introduced into the *S. cerevisiae* BY4741 strains using the Frozen-EZ yeast transformation II kit (ZYMO RESARCH). Transformants grown on ST agar medium comprising 2% agar (the yeast nitrogen base and ammonium sulfate medium comprising 2% glucose, 0.04% adenine, and 0.3 M KCl and lacking uracil and leucine (Sigma)) were selected as antibody expressing yeast strains.

YEp352 GAP-II-alfHc/alfLc comprising antibody heavy chain and light chain expression units has the URA3 marker gene that complements uracil-requiring mutation of a host. YEp351GAP-II (a control vector into which no gene has been introduced), YEp351GAP-II-aHAC1 (an activated HAC1 expression vector), YEp351GAP-II-p180 (an RRBP1 expression vector), and YEp351GAP-II-aHAC1/p180 (a coexpression vector for the activated HAC1 gene and RRBP1) each comprise a LEU2 marker gene that complements leucine-requiring mutation of a host. Thus, these vectors were transformed into a host, so that genes could be grown only when both vectors were introduced in combination as shown below to construct four types of antibody expressing yeast strains.

*S. cerevisiae* T2K01 YEp352 GAP-II-alfHc/alfLc (URA3) YEp351GAP-II (LEU2)
*S. cerevisiae* T2K02 YEp352 GAP-II-alfHc/alfLc (URA3) YEp351GAP-II-aHAC1 (LEU2)
*S. cerevisiae* T2K03 YEp352 GAP-II-alfHc/alfLc (URA3) YEp351GAP-II-p180 (LEU2)
*S. cerevisiae* T2K04 YEp352 GAP-II-alfHc/alfLc (URA3) YEp351GAP-II-aHAC1/p180 (LEU2)

EXAMPLE 15

Antibody Productivity by Transformed Yeast Strain (*S. cerevisiae*)

The *S. cerevisiae* T2K01, *S. cerevisiae* T2K02, *S. cerevisiae* T2K03, and *S. cerevisiae* T2K04 strains prepared in Example 14 were cultured using ST medium at 30° C. for 3 days. The culture solution was inoculated into YPAD medium to result in a final concentration of 5% therein, and culture was conducted at 30° C. for 3 days. A culture supernatant was prepared from the culture solution, and the resultant was designated as a sample containing antibodies secreted and produced by yeast. The secreted and produced antibodies were subjected to quantitative assay via sandwich ELISA. TRAIL receptor proteins that were antigens of the anti-TRAIL receptor antibodies were adsorbed on a 96-well plate, a yeast sample was added, and detection was carried out using a peroxidase-labeled human IgG specific Fc antibody (Peroxidase-labeled affinity purified antibody to human IgG (Fc) (KPL)) and the ABTS peroxidase substrate (KPL). Antibodies produced in animal cells (NS0) were used as standard samples.

As shown in FIG. 8A, the *S. cerevisiae* T2K03 strain into which only the RRBP1 gene had been introduced was not substantially different from a control strain, i.e., the *S. cerevisiae* T2K01 strain, in terms of productivity. In the case of the *S. cerevisiae* T2K02 strain into which only the activated HAC1 gene had been introduced, however, productivity was approximately twice that of the control strain, i.e., the *S. cerevisiae* T2K01 strain. Further, antibody productivity in the *S. cerevisiae* T2K04 strain in which the activated HAC1 gene and the RRBP1 gene were coexpressed was significantly higher than that in the control strain, i.e., the *S. cerevisiae* T2K01 strain, and a strain into which the activated HAC1 gene or RRBP1 gene had been solely introduced (i.e., approximately seven times higher than the control). This indicates that coexpression of the activated HAC1 gene and the RRBP1 gene would produce effects equivalent to or greater than synergistic effects on antibody productivity.

EXAMPLE 16

Antibody Productivity Under Conditions in which Formation of O-Sugar Chain Using Transformed Yeast Strain (*S. cerevisiae*) is Inhibited The *S. cerevisiae* T2K01, *S. cerevisiae* T2K02, *S. cerevisiae* T2K03, and *S. cerevisiae* T2K04 strains prepared in Example 14 were cultured using ST medium at 30° C. for 3 days. The culture solution was inoculated at a final concentration of 5% in YPAD medium to which 10 µM of PMT inhibitor (the rhodanine-3-acetic acid derivative: 5-[[3,4-(1-phenylmethoxy)phenyl]methylene]-4-oxo-2-thioxo-3-thia-zolidineacetic acid (compound (1c) described in Bioorganic & Medicinal Chemistry Letters, Vol. 14, p. 3975, 2004) had been initially added, and culture was conducted at 30° C. for 3 days. A culture supernatant was prepared from the culture solution, and the resultant was designated as a sample containing antibodies secreted and produced by yeast. In the same manner as in Example 15, the sample was subjected to quantitative assay via sandwich ELISA using antibodies produced in animal cells (NS0) as standard samples.

As shown in FIG. 8B, antibody productivity of the *S. cerevisiae* T2K02 strain into which the activated HAC1 gene had been introduced and that of the *S. cerevisiae* T2K03 strain into which the RRBP1 gene had been introduced were apparently higher than that in the control strain, i.e., the *S. cerevisiae* T2K01 strain. Further, the amount of antibodies produced by the *S. cerevisiae* T2K04 strain in which the activated HAC1 gene and the RRBP1 gene were coexpressed was significantly higher than that in the control strain, i.e., the *S. cerevisiae* T2K01 strain, and a strain into which the activated HAC1 gene or RRBP1 gene had been solely introduced (i.e., approximately eight times higher than the control). The synergistic effects of coexpression of the activated HAC1 gene and the RRBP1 gene on antibody production were further enhanced by inhibition of O-sugar chain formation.

EXAMPLE 17

Preparation of *Ogataea minuta* Protease YPS1 Gene-Deficient Strain (Δoch1Δyps1Δura3Δade1)

The YPS1 gene-deficient vector, pDOMYP1, disclosed in WO 2003/091431 was cleaved with BamHI and ClaI and transformed into the *O. minuta* TK5-3 strain (Δoch1Δura3Δade1) disclosed in WO 2003/091431 via an electric pulse method. In order to confirm that the YPS1 genes of such genes were disrupted, the following primers were synthesized.

```
DY5;
5'-CTCAAGGGCCTGGAGACTACG-3'      (SEQ ID NO: 49)

DY3;
5'-CGGGATTCCCGAGTCGCTCACC-3'     (SEQ ID NO: 50)
```

Chromosome DNA isolated from the transformed strain was used as a template to carry out PCR using the DY5 and DY3 primers at 94° C. for 30 seconds, 60° C. for 1 minute, and 72° C. for 2 minutes, and this cycle was repeated 25 times. An amplified 3.7-kb DNA fragment was detected from a strain into which the plasmid had been introduced in its YPS1 locus. The selected strain was designated as the *O. minuta* YK4 strain (Δoch1Δura3Δade1Δyps1::URA3). After the *O. minuta* YK4 strain was cultured in YPD medium to a stationary phase, strains exhibiting resistance to 5-fluoroorotic acid (5-FOA) were obtained. Chromosome DNA of the 5-FOA-resistant strain was used as a template to carry out PCR using the DY5 and DY3 primers at 94° C. for 30 seconds, 60° C. for 1 minute, and 72° C. for 3 minutes, and this cycle was repeated 25 times. An amplified 1.2-kb DNA fragment was detected from an URA3-lacking strain. This Δoch1Δura3Δade1Δyps1 strain was designated as *O. minuta* YK5 strain.

EXAMPLE 18

Preparation of Synthetic Antibody Gene Producing Strain (*O. minuta*) and Antibody Production (1) Construction of Synthetic Antibody Gene Expression Vector pOMexGP1U disclosed in WO 2003/091431 was cleaved with SpeI, blunt-ended, and then ligated. The SalI site and the EcoT22I site of the resulting plasmid were subjected to linker change with the SpeI site and the BamHI site, respectively. The resulting plasmid was designated as pOMexGP1UΔSp.

A gene was designed from the amino acid sequence of the anti-TRAIL receptor antibody gene (WO2002/094880) while taking the frequency of the use of codons of *O. minuta* into consideration, and an antibody gene was artificially synthesized therefrom (Takara Bio). The *S. cerevisiae* SUC2 signal or chicken lysozyme signal was added to the N-terminus of the light chain and heavy chain genes, and nucleotide sequences of the restriction enzyme sites (the XbaI site on the 5' side and the BamHI site on the 3' site) were added to the both terminuses (nucleotide sequences: SEQ ID NOs: 51, 53, 55, and 57; amino acid sequences: SEQ ID NOs: 52, 54, 56, and 58). Two types of light chain gene fragments having different signals that had been digested with XbaI and BamHI were introduced into the pOMexGP1A vector prepared in Example 1 (2). The resulting vectors were designated as pOMexGPA/AbSUC and pOMexGPA/AbLys. Two types of heavy chain gene fragments emitting different signals that had been digested with XbaI and BamH were introduced into the SpeI-BamHI site of the pOMexGP1UΔSp vector. The resulting vectors were designated as pOMexGPUΔSp/AbSUC and pOMexGPUΔSp/AbLys.

pOMexPGHy (Example 1 (3-4)) was used as a template to carry out PCR using the PGKHy-F DNA primer (SEQ ID NO: 59) and the PGKHy-R DNA primer (SEQ ID NO: 60) at 94° C. for 30 seconds, 55° C. for 30 seconds, and 72° C. for 1 minute, and this cycle was repeated 20 times. Thus, the hygromycin B-resistant gene was amplified.

```
PGKHy-F:
                                  (SEQ ID NO: 59)
5'-ATAGAACTAGCAACTAGATGAAAAAGCCTGAACTCAC-3'

PGKHy-R:
                                  (SEQ ID NO: 60)
5'-CAAATCCCACGGATCACTATTCCTTTGCCCTCGGAC-3'
```

The amplified gene fragment was introduced into SpeI-BglII-digested pOMexPGHy using the in-fusion kit (BD Bioscience), and the nucleotide sequence of the insertion fragment was determined. The resulting plasmid was used as a template to carry out PCR using the PGKpUC-p DNA primer (SEQ ID NO: 61) and the PGKpUC-t DNA primer (SEQ ID NO: 62) at 94° C. for 30 seconds, 55° C. for 30 seconds, and 72° C. for 2 minutes, and this cycle was repeated 20 times. Thus, a gene fragment containing the PGK promoter-hygromycin B-resistant gene-PGK terminator was amplified.

```
PGKpUC-p:
                                  (SEQ ID NO: 61)
5'-AATTCGAGCTCGGTACAGGGATACATGGGATACCAAAG-3'

PGKpUC-t:
                                  (SEQ ID NO: 62)
5'-GAGGATCCCCGGGTACCAGGGTCGATTTTCTTGGTCGA-3'
```

The amplified gene fragment was introduced into Asp718I-digested pUC118 (Takara Bio) using the in-fusion kit (BD Bioscience), and the nucleotide sequence of the insertion fragment was determined. The resulting plasmid was designated as PGKHyg/pUC118. pOMexGP1UΔSp was digested with HindIII and KpnI, a cassette comprising the GAP promoter-terminator was isolated, and the isolated cassette was inserted into the HindIII-KpnI-digested PGKHyg/pUC118. The resulting plasmid was designated as GAP/HyG/pUC118. Subsequently, pUC19 (Takara Bio) was digested with NdeI and EcoRI, blunt-ended, and then ligated to remove an NdeI- EcoRI region inside pUC19. This plasmid was digested with HindIII-SacI, and a gene fragment comprising the GAP promoter-terminator isolated from GAP/HyG/pUC118 via HindIII-SacI digestion and the PGK promoter-hygromycin B-resistant gene-PGK terminator was introduced. The resulting plasmid was designated as pOMexHy.

The antibody heavy chain gene fragment to which the XbaI-BamH-digested chicken lysozyme signal had been added was introduced into the SpeI-BamHI-treated pOMexHy, and the resulting vector was designated as pOMexHy/AbLys.

(2) Preparation of Antibody Gene Expressing Yeast Strain

Figure 9:
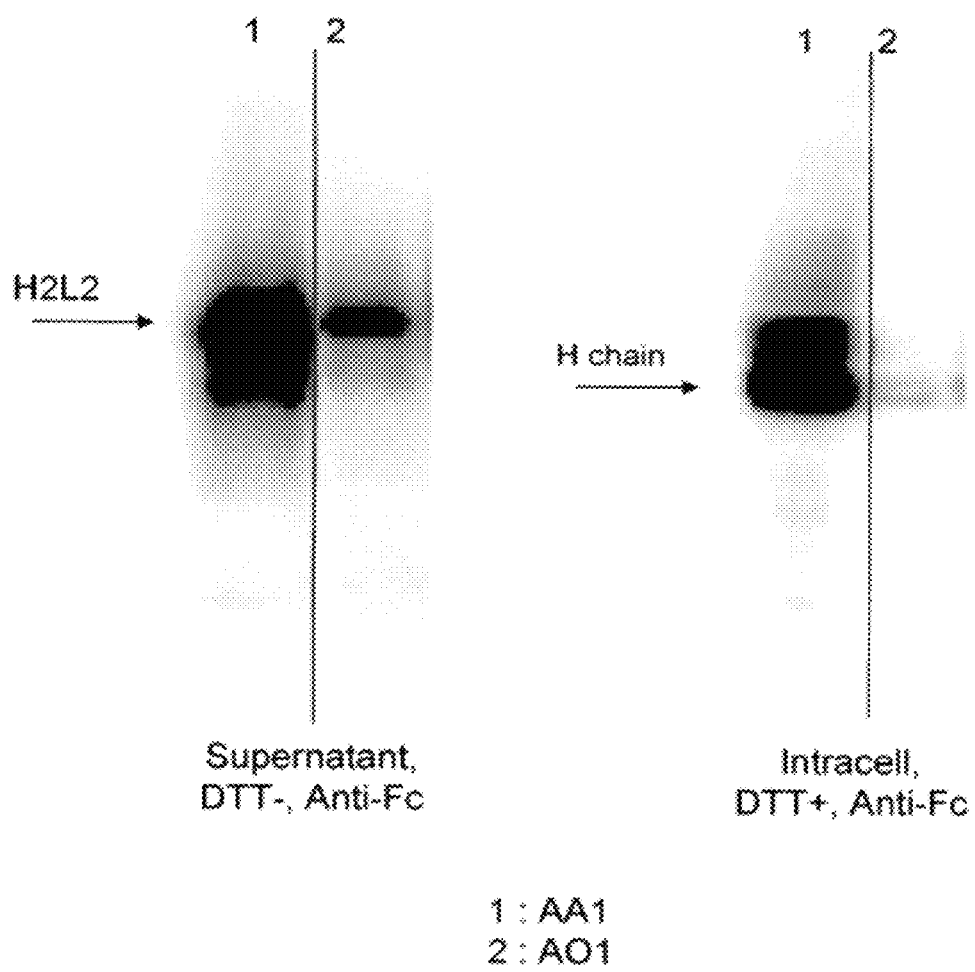
FIG. 9 shows the results of Western analysis of antibody production in antibody-producing strains into which a synthetic antibody gene, in which codons have been substituted, has been introduced.

The NotI-digested antibody expression vectors, i.e., pOMexGPA/AbLys and pOMexGPUΔSp/AbLys, were used to transform the *O. minuta* YK5 strain (Δoch1Δyps1Δura3Δade1) via electroporation. The conditions for electroporation described in WO 2003/091431 were employed. The transformed cells were selected in SD agar plate medium (2% glucose, 0.67% yeast nitrogen base (Difco)). A single colony was cultured in B2YP4G medium (1.34% yeast nitrogen base (Difco), 2% yeast extract (Difco), 4% polypeptone (Difco), 4% glycerol, and 0.1M phosphate buffer (pH 6.0)) at 27° C. for 4 days. A culture supernatant was prepared from the culture solution, Western analysis was carried out in the manner as described in Example 7 to select an antibody producing strain into which the antibody light chain and heavy chain genes had been introduced, and the resulting strain was designated as the *O. minuta* AA1 strain. As shown in FIG. 9, the amount of antibodies secreted by the *O. minuta* AA1 strain was significantly greater than that secreted by the *O. minuta* AO1 strain prepared in Example 5.

The NotI-digested antibody expression vectors, i.e., pOMexGPA/AbSUC and pOMexGPUΔSp/AbSUC, were introduced into the *O. minuta* TK5-3 strain (Δoch1Δura3Δade1) described in WO 2003/091431 to obtain an antibody expressing *O. minuta* YY1 strain. Methods of electroporation and strain selection described above were employed.

EXAMPLE 19

Acquisition of Activated HAC1 Gene of *P. pastoris* and Construction of Expression Vector The activated HAC1 gene of *P. pastoris* was obtained from the cells (GS115 strain of *P. pastoris*) in the same manner as in Example 3. cDNA was synthesized from the GS115 strain of *P. pastoris* in the same manner as in Example 3. This cDNA was amplified via PCR using the HACp1-1 DNA primer (SEQ ID NO: 63) and the HACp1-12 primer (SEQ ID NO: 64) shown below at 94° C. for 30 seconds, 52° C. for 30 seconds, and 72° C. for 1 minute, and this cycle was repeated 30 times. The amplified product was cloned into pCR2.1-TOPO (Invitrogen), and nucleotide sequences derived from the two types of PCR-amplified gene fragments were confirmed (SEQ ID NOs: 65 and 66).

```
                                    (SEQ ID NO: 63)
HACp1-1:   5'-ATGCCCGTAGATTCTTCTCATAAGACAGC-3'

(SEQ ID NO: 64)
HACp1-12:  5'-CAAAGTCATTTAAATCAAATGCATTAGCGG-3'
```

One (SEQ ID NO: 65) of the nucleotide sequences of the obtained two types of cDNA fragment was consistent with the genomic sequence; however, the other sequence (SEQ ID NO: 66) was partially deficient and shortened. This indicates that such deficient sequence was a cDNA fragment that had been spliced by UPR-activated Ire1p. In order to obtain full-length cDNA of activated HAC1, PCR was carried out at 94° C. for 30 seconds, 55° C. for 30 seconds, and 72° C. for 1 minute using the speHACp1F DNA primer (SEQ ID NO: 67) and the bglHACp1R DNA primer (SEQ ID NO: 68) shown below and a cDNA pool that was considered to contain the activated cDNA of HAC1 described above, and this cycle was repeated 20 times.

```
                                    (SEQ ID NO: 67)
speHACp1F:   5'-gactagtATGCCCGTAGATTCTTCTCATA-3'

(SEQ ID NO: 68)
bglHACp1R:   5'-cagatctCTATTCCTGGAAGAATACAAAGT-3'
```

The resulting fragment of approximately 1 kb contained a region between the initiation codon and the termination codon of the activated HAC1 gene of *P. pastoris* (SEQ ID NO: 69), which is equivalent to the amino acid sequence of activated Hac1p comprising 304 amino acid residues (SEQ ID NO: 70). The resultant was treated with SpeI and BglII, isolated, and then introduced into the SpeI-BglII-treated pOMexPGHy (Example 1 (3-4)). The resulting vector was designated as pOMexPGHy/PpHac1. This vector comprises the *P. pastoris*-derived activated HAC1 gene expression unit.

EXAMPLE 20

Construction of *S. cerevisiae* Activated HAC1 Gene Expression Vector

TOPO-aHac1 containing the activated HAC1 gene of *S. cerevisiae* prepared in Example 11 was used as a template to carry out PCR using the ScHAC-XbaF DNA primer (SEQ ID NO: 71) and the ScHAC-BamR DNA primer (SEQ ID NO: 72) at 94° C. for 30 seconds, 55° C. for 30 seconds, and 72° C. for 1 minute, and this cycle was repeated 20 times. Thus, the activated HAC1 gene of *S. cerevisiae* was amplified.

```
ScHAC-XbaF:
                                    (SEQ ID NO: 71)
5'-gtctagaATGGAAATGACTGATTTTGAACT-3'

ScHAC-BamR:
                                    (SEQ ID NO: 72)
5'-cggatccTCATGAAGTGATGAAGAAATCAT-3'
```

The resultant was digested with XbaI and BamHI, and a gene encoding *S. cerevisiae*-derived activated HAC1 was recovered. After isolation, the gene was introduced into the SpeI-BglII-treated pOMexPGHy (Example 1 (3-4)). The resulting vector was designated as pOMexPGHy/ScHac1. This vector comprises the *S. cerevisiae*-derived activated HAC1 gene expression unit.

EXAMPLE 21

Production of Antibody by the *O. minuta* Strain into which the *O. minuta, P. pastoris*, and *S. cerevisiae* Activated Hac1 Genes have been Introduced (1) Preparation of the *O. minuta* Strain into which the *O. minuta, P. pastoris*, and *S. cerevisiae* Activated HAC1 Genes have been Introduced The Aor51HI-digested *O. minuta*-derived activated HAC1 gene expression vector; i.e., pOMexPGHy/Hac1, the *P. pastoris*-derived activated HAC1 gene expression vector; i.e., pOMexPGHy/PpHac1, and the *S. cerevisiae*-derived activated HAC1 gene expression vector; i.e., pOMexPGHy/ScHac1, were introduced into the antibody-producing *O. minuta* AA1 strains grown in Example 18 via electroporation. Introduction of the activated HAC1 gene into the transformed strain was confirmed by selecting strains in YPD agar plate medium to which hygromycin B had been added at a concentration of 50 μg/ml, culturing the same, and then extracting the genome. The strain into which the *O. minuta*-derived activated HAC1 gene expression vector, pOMexPGHy/Hac1, had been introduced was subjected to PCR using the speHAC1F DNA primer (SEQ ID NO: 20) and the bglHAC1R DNA primer (SEQ ID NO: 21) described in Example 3. The strain into which the *P. pastoris*-derived activated HAC1 gene had been introduced was subjected to PCR using the speHACp1F DNA primer (SEQ ID NO: 67) and the bglHACp1R primer (SEQ ID NO: 68) at 94° C. for 30 seconds, 55° C. for 30 seconds, and 72° C. for 1 minute, and this cycle was repeated 30 times. The strain into which the *S. cerevisiae*-derived activated HAC1 gene had been introduced was subjected to PCR under the same conditions, except for the use of the ScHAC-XbaF DNA primer (SEQ ID NO: 71) and the ScHAC-BamR primer (SEQ ID NO: 72). The resulting strains were designated as the *O. minuta* AA2omH strain, the *O. minuta* AA2 ppH strain, and the *O. minuta* AA2scH strain. Simultaneously, Aor51HI-digested pOMexPGHy was introduced into the *O. minuta* AA1 strain to obtain the *O. minuta* AA2Hy strain as a control.

Figure 10:
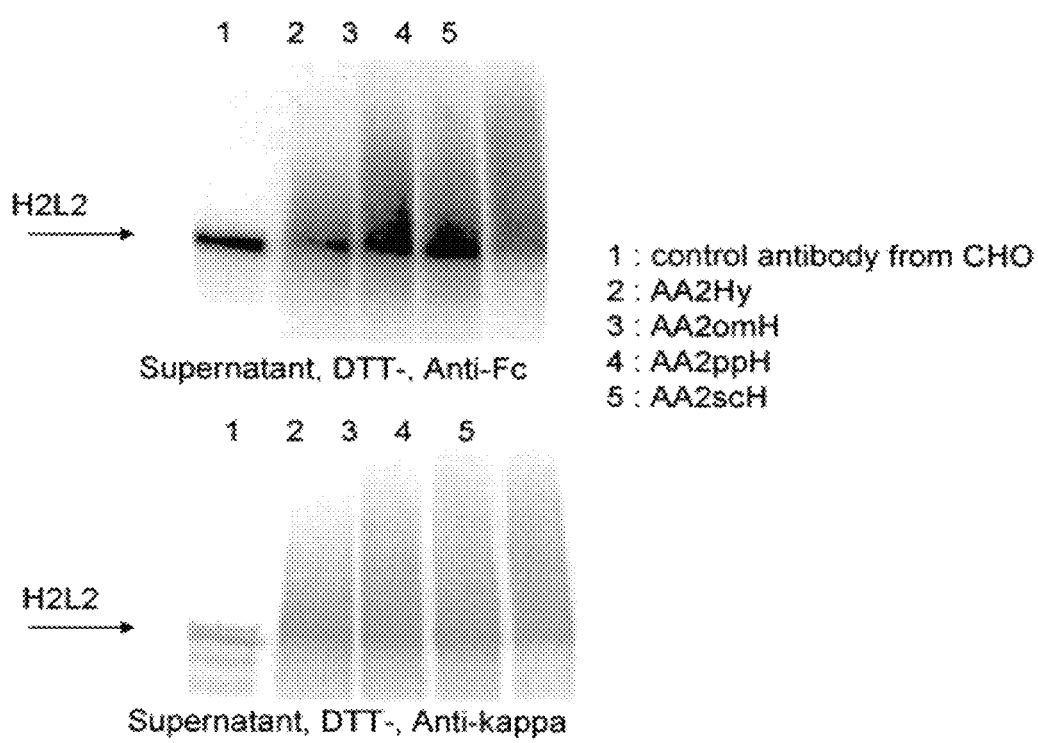
FIG. 10 shows the results of Western analysis of culture supernatants of antibody-producing strains into which the activated HAC1 genes derived from yeast strains have been introduced.

(2) Confirmation of Secretion of Antibody by Antibody Producing Strain into which HAC1 Gene had been Introduced The antibody producing strains into which the HAC1 genes had been introduced prepared in (1) above; i.e., the *O. minuta* AA2omH strain, the *O. minuta* AA2 ppH strain, the *O. minuta* AA2scH strain, and the *O. minuta* AA2Hy strain, were cultured in the manner described in Example 18 (2), and Western analysis was carried out under non-reducing conditions. The results are as shown in FIG. 10. That is, addition of a sugar chain to the antibody molecule was more significantly observed but the effects of remarkable acceleration of secretion of antibody-H2L2 aggregates were not observed in the *O. minuta* AA2omH strain, *O. minuta* AA2 ppH strain, and *O. minuta* AA2scH strains, compared with the control *O. minuta* AA2Hy strain prepared in (1) above. Thus, similar effects of production could be expected via introduction of the HAC1 gene derived from a species different from a host.

(3) Productivity of Secretory Antibody by Antibody-Producing *O. minuta* Strain into which the HAC1 Gene had been Introduced (Quantification via TR-FRET-Based Homogeneous Analysis)

Figure 11:
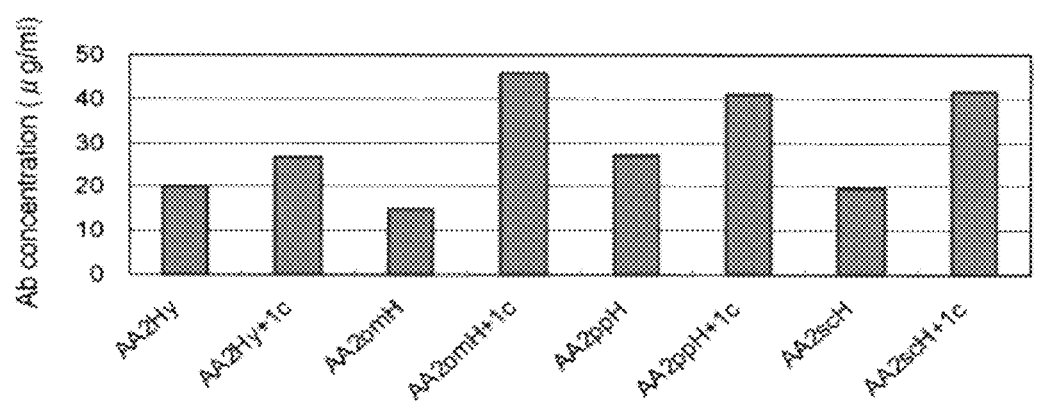
FIG. 11 shows the amount of antibody secretory production from antibody-producing strains into which the activated HAC1 genes derived from yeast strains have been introduced.

20 mM Tris-HCl buffer (pH 7.2) comprising 12 μl of 0.97 μg/ml LANCE Eu-W1024 labeled anti-human IgG (PerkinElmer), 8.3 ug/ml of biotin-conjugated mouse anti-human IgG (BD Bioscience), 16.7 ug/ml Surelight APC streptavidin (PerkinElmer), and 10% of Block Ace (Dainippon Pharmaceutical) was applied to a 96-well half area plate (Corning), and 2 μl of a sample solution prepared by adequately diluting the culture solution prepared in (2) above with 20 mM Tris-HCl buffer (pH 7.2) containing 10% of Block Ace was introduced therein, followed by agitation. The sample solution was subjected to the reaction at room temperature in the dark for 1 hour, and fluorescence was then assayed using EnVision (PerkinElmer). The amount of aggregate antibodies produced was determined based on the value at 665 nm/615 nm. Antibodies produced in animal cells (CHO) were used as standard samples. As shown in FIG. 11, no significant acceleration of antibody secretion was observed in the *O. minuta* AA2omH strain, the *O. minuta* AA2 ppH strain, and the *O. minuta* AA2scH strain into which the activated HAC1 genes had been introduced, compared with the *O. minuta* AA2Hy strain. However, similar effects of production could be expected even via introduction of the HAC1 gene derived from a species different from a host.

(4) Production of Antibody by the *O. minuta* Strain into which the HAC1 Gene had been Introduced Using PMT Inhibitor (1c)

A platinum loopful of the *O. minuta* AA2omH strain, the *O. minuta* AA2 ppH strain, the *O. minuta* AA2scH strain, and the *O. minuta* AA2Hy strain was inoculated into 5 ml of B2YP4G medium, cultured at 27° C. for 1 day, and then diluted with B2YP4G medium to adjust OD600 at 10. The PMT inhibitor described in Example 9 (1c: concentration of stock solution: 10 mM) was added thereto to a concentration of 2 μM therein. Culture was conducted at 27° C. for an additional 3 days, OD600 was assayed every 24 hours, and 0.04 μM each PMT inhibitor (1c) was added as the OD600 value increased by 1. A culture supernatant was prepared from the culture solution, and the amount of antibody production was measured by the method described in Example 21 (3). The results are shown in FIG. 11. It was found that the *O. minuta* AA2omH strain, the *O. minuta* AA2 ppH strain, and the *O. minuta* AA2scH strain into which the activated HAC1 gene had been introduced can exhibit more significant effects of accelerating antibody secretion by culturing them with the addition of the PMT inhibitor, compared with the control *O. minuta* AA2Hy strain.

Thus, effects of accelerating antibody secretion were found to be attained with the use of HAC1 genes of different species.

EXAMPLE 22

Isolation of *O. minuta*-Derived PMT Gene

The *O. minuta*-derived PMT1 gene was obtained via PCR using chromosome DNA of the *O. minuta* IFO10746 strain as a template and the PM1-5 DNA primer (SEQ ID NO: 73) and the PM1-3 DNA primer (SEQ ID NO: 74) at 94° C. for 30 seconds, 55° C. for 1 minute, and 72° C. for 2 minutes, and this cycle was repeated 25 times.

```
                                        (SEQ ID NO: 73)
PM1-5:    5'-ATGGCGGGCAAAAATCAGAAATCTAGCGCG-3'

(SEQ ID NO: 74)
PM1-3:    5'-TTACAACTCGTCTTTGACTAGAGGCGGGGA-3'
```

The amplified DNA fragment of approximately 2.4 kb was recovered and cloned using the TOPO TA Cloning Kit. Plasmid DNA was isolated from the resulting clone, and the nucleotide sequence of the insertion fragment (SEQ ID NO: 75) was determined. Thus, a clone having a nucleotide sequence encoding the amino acid sequence (SEQ ID NO: 76), which is highly homologous to the amino acid sequence of the *S. cerevisiae*-derived PMT1 gene was selected from the insertion DNA fragment of the plasmid. The isolated plasmid was designated as pOmPM1.

The *O. minuta*-derived PMT2 gene was obtained using the PM2-5 DNA primer (SEQ ID NO: 77) and the PM2-3 DNA primer (SEQ ID NO: 78), the PMT4 gene was obtained using the PM4-5 DNA primer (SEQ ID NO: 79) and the PM4-3 DNA primer (SEQ ID NO: 80), the PMT5 gene was obtained using the PM5-5 DNA primer (SEQ ID NO: 81) and the PM5-3 DNA primer (SEQ ID NO: 82), and the PMT6 gene was obtained using the PM6-5 DNA primer (SEQ ID NO: 83) and the PM6-3 DNA primer (SEQ ID NO: 84), in the same manner as in the case of the PMT1 gene. Plasmids comprising the PMT2 gene (nucleotide sequence: SEQ ID NO: 85; amino acid sequence: SEQ ID NO: 86), the PMT4 gene (nucleotide sequence: SEQ ID NO: 87; amino acid sequence: SEQ ID NO: 88), the PMT5 gene (nucleotide sequence: SEQ ID NO: 89; amino acid sequence: SEQ ID NO: 90) and the PMT6 gene (nucleotide sequence: SEQ ID NO: 91; amino acid sequence: SEQ ID NO: 92) were designated as pOmPM2, pOmPM4, pOmPM5, and pOmPM6, respectively.

```
                                            (SEQ ID NO: 77)
PM2-5:    5'-ATGGGCGAACGTACGGGCAAAAGTGCGCTC-3'

(SEQ ID NO: 78)
PM2-3:    5'-CTAATCGGAAATTCTCCACGTGCTCAAGAG-3'

(SEQ ID NO: 79)
PM4-5:    5'-ATGGGGCCCAAAATAAAGACCGGCAAGAAA-3'

(SEQ ID NO: 80)
PM4-3:    5'-CTATTTAGCAAAATGCAGTTTGATGTTGAG-3'

(SEQ ID NO: 81)
PM5-5:    5'-ATGGACGAGAAAAACATCTCTGGCTTAGAA-3'

(SEQ ID NO: 82)
PM5-3:    5'-CTACTCACTATAGACGGAGCAGTCGATCGA-3'

(SEQ ID NO: 83)
PM6-5:    5'-ATGTCCGAGTCAGAGCTGAGAAACCGCAAA-3'

(SEQ ID NO: 84)
PM6-3:    5'-CTAAGCTATACGCCAGGTGGAAACCCAGTT-3'
```

EXAMPLE 23

Preparation of PMT Gene-Insertionally Inactivating or Disrupting Vector for *O. minuta*

(1) Preparation of PMT Geneinsertional Inactivation Vector
(1-1) Preparation of PMT1 Gene-Insertional Inactivation Vector In order to isolate a partial sequence of the PMT1 gene with the use of pOmPM1 obtained in Example 22, the following PMT1hIII DNA primer (SEQ ID NO: 93) and the PMT1Kp DNA primer (SEQ ID NO: 94) were used to carry out PCR at 94° C. for 30 seconds, 55° C. for 30 seconds, and 72° C. for 2 minutes, and this cycle was repeated 15 times.

```
                                            (SEQ ID NO: 93)
PMT1hIII:  5'-caagcttGGACCTACAACACGTCCGAAGAA-3'

(SEQ ID NO: 94)
PMT1Kp:    5'-cggtaccGGTTTGATACCTTGGGTGGCACA-3'
```

The amplified DNA fragment of approximately 1.6 kb was digested with HindIII and KpnI and recovered. Subsequently, pPICZα (Invitrogen) was digested with BglII and blunt-ended. The HindIII linker was inserted therein, further digested with BamHI, and blunt-ended, followed by insertion of the KpnI linker. The resulting plasmid was designated as pZ-Hd-Kp. pZ-Hd-Kp was digested with HindIII and KpnI, a 2.0-kb DNA fragment containing a zeocine-resistant gene was isolated, and the PCR-amplified partial sequence of the PMT1 gene was inserted therein. The nucleotide sequence of the partial sequence of the inserted PMT1 gene was determined, and the resulting plasmid was then designated as pOmPM1dZ. pOmPM1dZ is capable of insertionally inactivating the structural gene (CDS) region and the promoter region of the *O. minuta* PMT1 gene and inhibiting transcription of the PMT1 gene. Separately, pOMexGPUΔSp prepared in Example 18 was digested with HindIII and KpnI, a gene fragment containing the GAP promoter and the terminator was recovered, and the recovered fragment was inserted into the HindIII-KpnI-digested 2.0-kb DNA fragment containing the zeocine-resistant gene. The resulting plasmid was designated as GAP/Z.

(1-2) Preparation of PMT2 Gene-Insertional Inactivation Vector

In order to isolate a partial sequence of the PMT2 gene with the use of pOmPM2 obtained in Example 22, the following PMT2hIII DNA primer (SEQ ID NO: 95) and the PMT2Kp DNA primer (SEQ ID NO: 96) were used to carry out PCR at 94° C. for 30 seconds, 55° C. for 30 seconds, and 72° C. for 2 minutes, and this cycle was repeated 15 times.

```
                                            (SEQ ID NO: 95)
PMT2hIII:  5'-gaagcttACTACATAATTCGTGTACGTGTTC-3'

(SEQ ID NO: 96)
PMT2Kp:    5'-cggtaccGTCGCCGTATTGGTCAGCAATCTC-3'
```

The amplified DNA fragment of approximately 1.5 kb was recovered and digested with HindIII and KpnI, and the digested fragment was then recovered. The obtained DNA fragment was inserted into a 2.0-kb DNA fragment containing a zeocine-resistant gene, which had been isolated from pZ-Hd-Kp via digestion with HindIII and KpnI, and the nucleotide sequence of the partial sequence of the inserted PMT2 gene was determined. The resulting plasmid was designated as pOmPM2dZ. pOmPM2dZ is capable of insertionally inactivating the structural gene (CDS) region and the promoter region of the *O. minuta* PMT2 gene and inhibiting transcription of the PMT2 gene.

(1-3) Preparation of PMT4 Gene-Insertional Inactivation Vector

In order to isolate a partial sequence of the PMT4 gene with the use of pOmPM4 obtained in Example 22, the following PMT4FHdinf DNA primer (SEQ ID NO: 97) and the PMT4RKpinf DNA primer (SEQ ID NO: 98) were used to carry out PCR at 94° C. for 30 seconds, 55° C. for 30 seconds, and 72° C. for 2 minutes, and this cycle was repeated 15 times.

```
PMT4FHdinf:
                                            (SEQ ID NO: 97)
5'-GTCATGAGATCCaagctGATCCCTCAATGGAGATCTACT-3'

PMT4RKpinf:
                                            (SEQ ID NO: 98)
5'-GGTGTGTGGGGGATCgGGATGCAAATGGATGGCTCGAAC-3'
```

The obtained DNA fragment of approximately 1.5 kb was inserted into a 2.0-kb DNA fragment containing a zeocine-resistant gene, which had been isolated from pZ-Hd-Kp via digestion with HindIII and KpnI using the in-fusion kit (BD Bioscience). The nucleotide sequence of the partial sequence of the inserted PMT4 gene was determined, and the resulting plasmid was then designated as pOmPM4dZ.

(2) Preparation of PMT Gene-Disrupting Vector
(2-1) Preparation of PMT5 Gene-Disrupting Vector pROMU1 containing a gene fragment having repeat sequences of approximately 0.8 kb upstream and downstream of the URA3 structural gene of *O. minuta* disclosed in WO 2003/091431 was digested with HindIII, and blunt-ended, followed by insertion of the BamHI linker. The resulting vector was digested with BamHI and BglII, and a fragment of approximately 3.3 kb containing repeat sequences and the URA3 gene of *O. minuta* was introduced into the BamHI-digested pBluescript KS- (Stratagene). The resulting vector was designated as rURApBKS.

Chromosome DNA of the *O. minuta* IFO10746 strain was used as a template, the PMT5maeF2 DNA primer (SEQ ID NO: 99) and the PMT5maeR DNA primer (SEQ ID NO: 100) were used to carry out PCR at 94° C. for 30 seconds, 55° C. for 1 minute, and 72° C. for 2 minutes, and this cycle was repeated 25 times. The amplified DNA fragment of approximately 1.5 kb was recovered and introduced into the BamHI-HindIII-digested rURApBKS using the in-fusion kit (BD Bioscience). The nucleotide sequence of the inserted gene fragment was determined. The resulting vector was designated as PMT5K/O/rURA3pre.

Chromosome DNA of the *O. minuta* IFO10746 strain was used as a template, the PMT5ushiroF DNA primer (SEQ ID NO: 101) and the PMT5ushiroR DNA primer (SEQ ID NO: 102) were used to carry out PCR at 94° C. for 30 seconds, 55° C. for 1 minute, and 72° C. for 2 minutes, and this cycle was repeated 25 times. The amplified DNA fragment of approximately 1.5 kb was recovered and introduced into the NotI-digested PMT5K/O/rURA3pre using the in-fusion kit (BD Bioscience). The nucleotide sequence of the inserted gene fragment was determined. The resulting vector was designated as PMT5K/O/rURA3.

```
PMT5maeF2:
                                          (SEQ ID NO: 99)
5'-GACGGTATCGATAAGCTTGATGCGCGGCCTTCCGACCTT-3'

PMT5maeR:
                                          (SEQ ID NO: 100)
5'-CTGGGGAAGCTCGGATCCGGCTCGAGGTCTTCGTTCAGA-3'

PMT5ushiroF:
                                          (SEQ ID NO: 101)
5'-CTAGTTCTAGAGCGGCCCAGGTCGCTTTCAGGCAGCAG-3'

PMT5ushiroR:
                                          (SEQ ID NO: 102)
5'-CACCGCGGTGGCGGCCAAGCTTGGGTACCGGCTCGCGTAG-3'
```

(2-2) Preparation of PMT6 Gene-Disrupting Vector

Chromosome DNA of the *O. minuta* IFO10746 strain was used as a template, the PMT6inf5'armF DNA primer (SEQ ID NO: 103) and the PMT6inf5'armR DNA primer (SEQ ID NO: 104) were used to carry out PCR at 94° C. for 30 seconds, 55° C. for 2 minutes, and 72° C. for 2 minutes, and this cycle was repeated for 25 times. The amplified DNA fragment of approximately 2.8 kb was recovered and introduced into the BamHI-digested rURApBKS using the in-fusion kit (BD Bioscience). The nucleotide sequence of the inserted gene fragment was determined. The resulting vector was designated as PMT6K/O/rURA3pre.

Chromosome DNA of the *O. minuta* IFO10746 strain was used as a template, the PMT6inf3'armF DNA primer (SEQ ID NO: 105) and the PMT6inf3'armR2DNA primer (SEQ ID NO: 106) were used to carry out PCR at 94° C. for 30 seconds, 55° C. for 2 minutes, and 72° C. for 2 minutes, and this cycle was repeated for 25 times. The amplified DNA fragment of approximately 2.5 kb was recovered and introduced into the NotI-SacII-digested PMT6K/O/rURA3pre using the in-fusion kit (BD Bioscience). The nucleotide sequence of the inserted gene fragment was determined. The resulting vector was designated as PMT6K/O/rURA3.

```
PMT6inf5'armF:
                                          (SEQ ID NO: 103)
5'-GCAGCCCGGGGgatccACGAAACCACGTCCTACT-3'

PMT6inf5'armR:
                                          (SEQ ID NO: 104)
5'-GGGGAAGCTcggatcGACTCATCTTGAAACGCA-3'

PMT6inf3'armF:
                                          (SEQ ID NO: 105)
5'-AGTTCTAGAGCGGCCTTACCACCATTACATGCC-3'

PMT6inf3'armR2:
                                          (SEQ ID NO: 106)
5'-AATTGGAGCTCCACCGCGGCCGCAACTTACTCGACGCTAA-3'
```

EXAMPLE 24

Preparation of Antibody Producing *O. minuta* Strain with an Insertionally Inactivated or Disrupted Pmt Gene and Evaluation Thereof (1) Preparation of Antibody Producing *O. minuta* Strain with an Insertionally Inactivated PMT Gene As for the PMT gene-insertional inactivation vectors prepared in Example 23, the PMT1 gene-insertional inactivation vector was digested with PstI, the PMT2 gene-insertional inactivation vector was digested with XhoI, and the PMT4 geneinsertional inactivation vector was digested with HindIII. These digestion products were introduced into the antibody producing *O. minuta* YY1 strain grown in Example 18 via electroporation. Interruption of PMT genes in the transformed strains was confirmed in the following manner. Strains were selected in YPD agar plate medium to which zeocine had been added to a concentration of 50 µg/ml therein and cultured, followed by extraction of the genomes. The PMT1 gene was subjected to PCR at 94° C. for 30 seconds, 55° C. for 30 seconds, and 72° C. for 1 minutes, and this cycle was repeated 30 times, with the use of a DNA primer pair of Zeo1 (SEQ ID NO: 107) and PMT1zeo1 (SEQ ID NO: 109) and a DNA primer pair of Zeo2 (SEQ ID NO: 108) and PMT1zeo2 (SEQ ID NO: 110). The PMT2 gene was subjected to PCR under the same conditions, with the use of a DNA primer pair of Zeo1 (SEQ ID NO: 107) and PMT2zeo1 (SEQ ID NO: 111) and a DNA primer pair of Zeo2 (SEQ ID NO: 108) and PMT2zeo2 (SEQ ID NO: 112). The PMT4 gene was subjected to PCR under the same conditions, with the use of a DNA primer pair of Zeo1 (SEQ ID NO: 107) and PMT4PCR3'armF (SEQ ID NO: 113) and a DNA primer pair of Zeo2 (SEQ ID NO: 108) and PMT4PCR5'armR3 (SEQ ID NO: 114). Thus, insertional inactivation of PMT genes upon introduction of insertional inactivation vectors was confirmed.

```
                                          (SEQ ID NO: 107)
Zeo1:            5'-GAACGGCACTGGTCAACTTGGCCAT-3'

(SEQ ID NO: 108)
Zeo2:            5'-CTTCGTGGCCGAGGAGCAGGACTGA-3'

(SEQ ID NO: 109)
PMT1zeo1:        5'-GAATTCTAGCCGAGCATGAGCTA-3'

(SEQ ID NO: 110)
PMT1zeo2:        5'-CGTTCAGACTCTTGTTGATTTTCCAC-3'

(SEQ ID NO: 111)
PMT2zeo1:        5'-GCTGTGCCACTGCACGCCTCGACTC-3'
```

```
                                         (SEQ ID NO: 112)
PMT2zeo2:         5'-CTTGTCCCTCTTGAATGGCGAGTG-3'

(SEQ ID NO: 113)
PMT4PCR3'armF:    5'-GGAACACGCCAAACATCATG-3'

(SEQ ID NO: 114)
PMT4PCR5'armR3:   5'-CACAAGCAGAATCAGGCAC-3'
```

The resulting strains were designated as the *O. minuta* YY2P1 strain (a strain with an insertionally inactivated PMT1 gene), the *O. minuta* YY2P2 strain (a strain with an insertionally inactivated PMT2 gene), and the *O. minuta* YY2P4 strain (a strain with an insertionally inactivated PMT4 gene). Also, Sse8387I-digested GAP/Z was introduced into the *O. minuta* YY1 strain, and a zeocine-resistant strain was selected to obtain the *O. minuta* YY2Z strain as a control strain.

Figure 12:
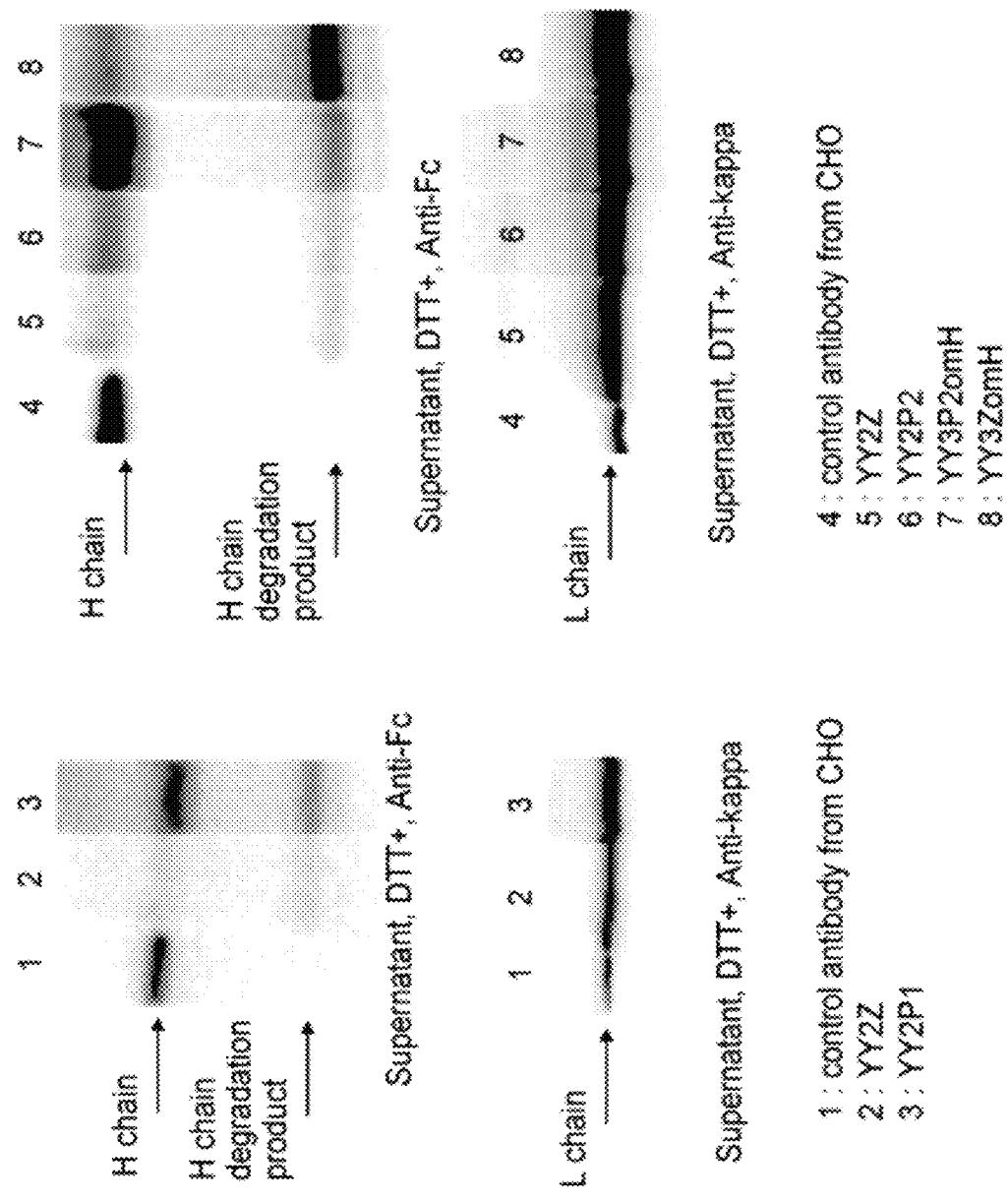
FIG. 12 shows the results of Western analysis of culture supernatants of antibody-producing strains with the insertionally inactivated PMT1 gene- or PMT2 gene and those of antibody-producing strains into which the activated HAC1 genes have been introduced.
Figure 14:
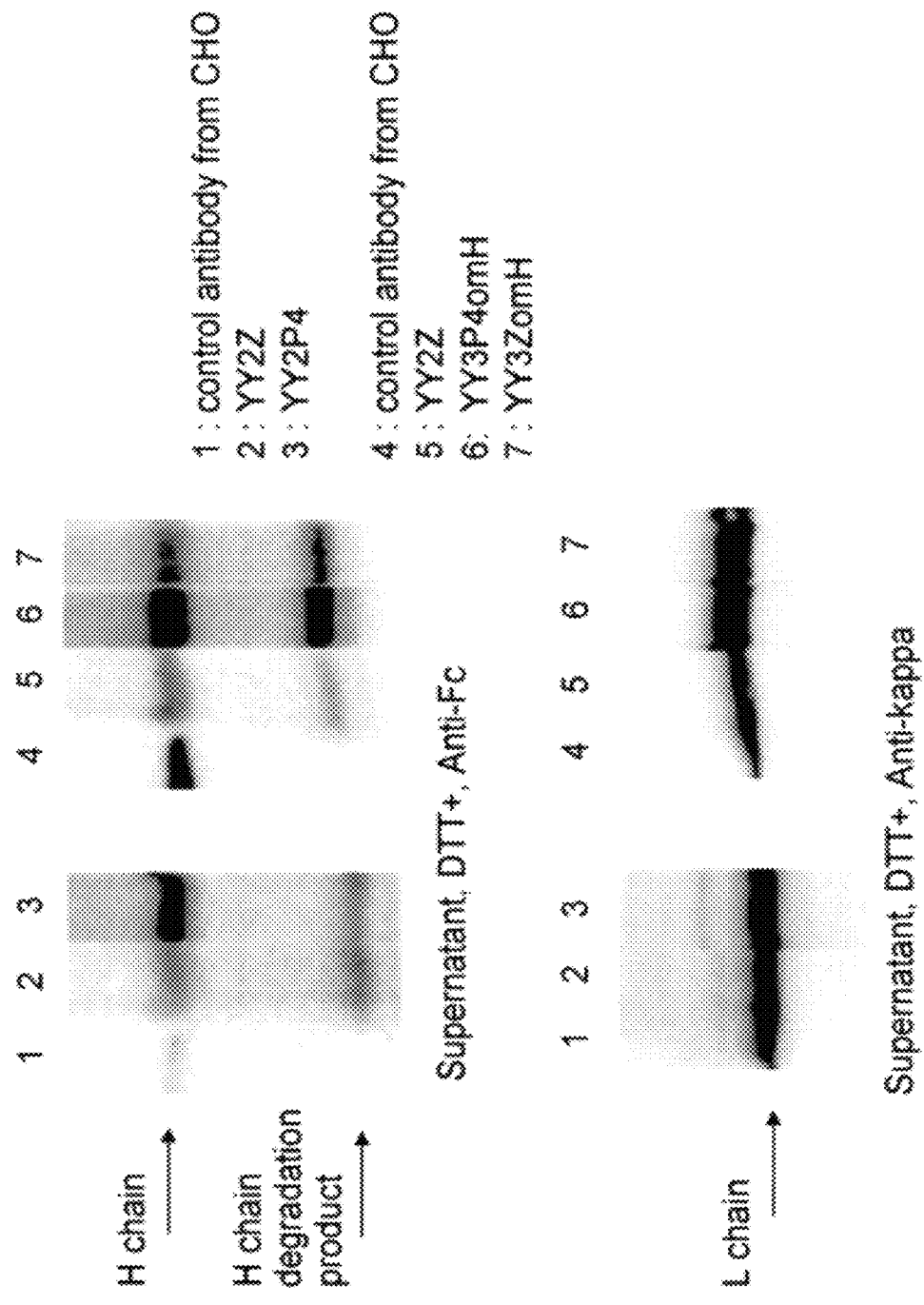
FIG. 14 shows the results of Western analysis of culture supernatants of antibody-producing strains with the insertionally inactivated PMT4 gene and those of antibody-producing strains into which the activated HAC1 genes have been introduced.

(2) Productivity of Secretory Antibody by Antibody Producing *O. minuta* Strain with an Insertionally Inactivated PMT Gene The antibody producing strains with an insertionally inactivated PMT genes prepared in (1) above were cultured in the manner as described in Example 18 (2), and Western analysis was then carried out. The results are shown in FIG. 12 and FIG. 14. That is, the amount of secretion of antibody aggregates was slightly increased from that attained by the *O. minuta* YY2P1 strain with an insertionally inactivated PMT1 gene, the *O. minuta* YY2P2 strain with an insertionally inactivated PMT2 gene, and the *O. minuta* YY2P4 strain with an insertionally inactivated PMT4 gene, compared with the *O. minuta* YY2Z strain prepared in (1) above (FIG. 12: lane 3 and lane 6; FIG. 14: lane 3).

(3) Productivity of Secretory Antibody by the Antibody Producing *O. minuta* Strain with an Insertionally Inactivated Pmt Gene (Quantification Via TR-FRET-Based Homogeneous Analysis)

Figure 13:
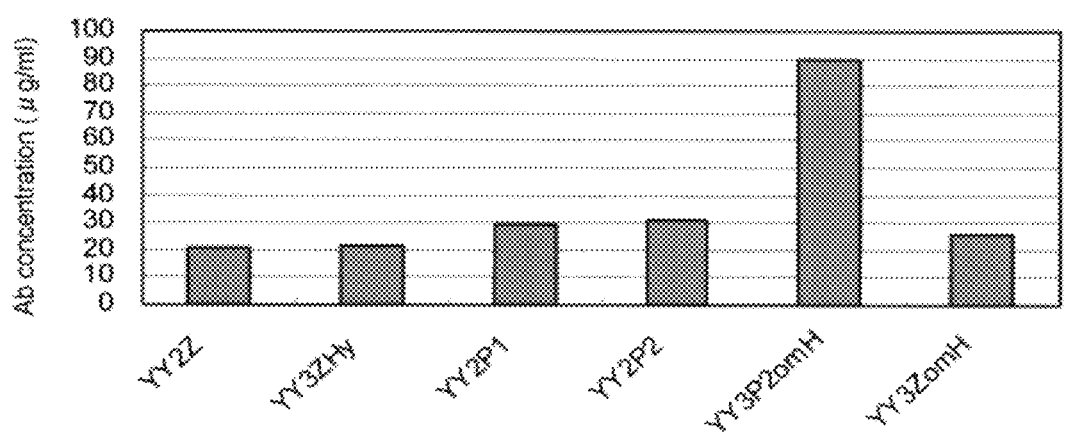
FIG. 13 shows the amount of antibody secretory production from antibody-producing strains with the insertionally inactivated PMT1 gene- or PMT2 gene and those of antibody-producing strains into which the activated HAC1 genes have been introduced.
Figure 15:
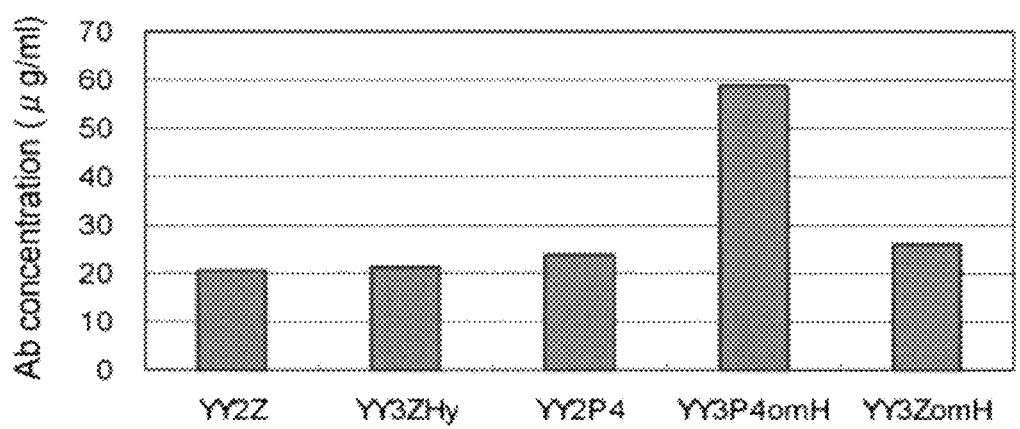
FIG. 15 shows the amount of antibody secretory production from antibody-producing strains with the insertionally inactivated PMT4 gene and antibody-producing strains into which the activated HAC1 genes have been introduced.

The amount of antibodies produced in the culture solution prepared in (2) above was measured by the method described in Example 21 (3). As a standard sample, antibodies produced in animal cells (CHO) were used. As shown in FIG. 13 and FIG. 15, the amounts of antibody aggregates secreted were slightly increased in the *O. minuta* YY2P1 strain with an an insertionally inactivated PMT1 gene, the *O. minuta* YY2P2 strain with an insertionally inactivated PMT2 gene, and the *O. minuta* YY2P4 strain with an insertionally inactivated PMT4 gene, compared with the *O. minuta* YY2Z strain prepared in (1) above (FIG. 13: YY2P1 and YY2P2; FIG. 15: YY2P4).

(4) Preparation of PMT5- and PMT6-Deficient Strains and Evaluation Thereof (4-1) Preparation of *O. minuta* PMT5 Gene-Deficient Strain (Δoch1Δyps1Δura3Δade1Δpmt5)

The PMT5 gene-disrupting vector, PMT5K/O/rURA3, prepared in Example 23 (2-1) was digested with HindIII and transformed into the *Ogataea minuta* YK5 strain (Δoch1Δura3Δade1Δyps1) prepared in Example 17 via the electric pulse method. In order to confirm that the PMT5 genes of these strains had been disrupted, the following primers were synthesized.

```
                                         (SEQ ID NO: 115)
gPMT5-5:    5'-CGGTGACGACTTCGACTAGTCGAG-3'

(SEQ ID NO: 116)
gPMT5-2:    5'-CGGTGCTGTTGGCGTCGTCATGGGTG-3'

(SEQ ID NO: 117)
gPMT5-3:    5'-GGCGCGTTCCAATTCCACTCTGCTG-3'

(SEQ ID NO: 118)
gPMT5-4:    5'-CGACGAGTCCTCTCACCAGGAGGTTG-3'
```

Chromosome DNA isolated from the transformed strain was used as a template to carry out PCR using the gPMT5-5 primer (SEQ ID NO: 115) and the gPMT5-2 primer (SEQ ID NO: 116) at 94° C. for 30 seconds, 60° C. for 1 minute, and 72° C. for 2 minutes, and this cycle was repeated 25 times. A 4.9-kb amplified DNA fragment was detected from a strain into which a plasmid had been incorporated in its PMT5 locus. Similarly, chromosome DNA isolated from the transformed strain was used as a template to carry out PCR using the gPMT5-3 primer (SEQ ID NO: 117) and the gPMT5-4 primer (SEQ ID NO: 118) at 94° C. for 30 seconds, 60° C. for 1 minute, and 72° C. for 2 minutes, and this cycle was repeated 25 times. A 4.9-kb amplified DNA fragment was detected from a strain into which a plasmid had been incorporated in its PMT5 locus. The selected strain was designated as the *O. minuta* YK6 strain (Δoch1Δura3Δade1Δyps1Δpmt5::URA3).

(4-2) Preparation of *O. minuta* PMT6 Gene Deficient Strain (Δoch1Δyps1Δura3Δade1Δpmt6)

The PMT6 gene-disrupting vector, PMT6K/O/rURA3, prepared in Example 23 (2-2) was digested with BamHI and NotI and then transformed into the *O. minuta* YK5 strain (Δoch1Δura3Δade1Δyps1) prepared in Example 17 via the electric pulse method. In order to confirm that the PMT6 genes of these strains had been disrupted, the following primers were synthesized.

```
                                         (SEQ ID NO: 119)
PMT6 PCR3'armF:    5'-TGTGGGTGCGATCCTGAG-3'

(SEQ ID NO: 120)
PMT6 PCR3'armR:    5'-GCCGTCGTTGGAGCAAAACT-3'

(SEQ ID NO: 121)
PMT6 PCR5'armF:    5'-GCATGTGCCACTGCTAAA-3'

(SEQ ID NO: 122)
PMT6 PCR5'armR:    5'-GACCAACTTTCCCGTGTAA-3'
```

Chromosome DNA isolated from the transformed strain was used as a template, the PMT6 PCR3'armF primer (SEQ ID NO: 119) and the PMT6 PCR3'armR primer (SEQ ID NO: 120) were used to carry out PCR at 94° C. for 30 seconds, 60° C. for 1 minute, and 72° C. for 2 minutes, and this cycle was repeated for 25 times. A 5.8-kb amplified DNA fragment was detected from a strain into which a plasmid had been incorporated in its PMT6 locus. Similarly, chromosome DNA isolated from the transformed strain was used as a template to carry out PCR using the PMT6 PCR5'armF primer (SEQ ID NO: 121) and the PMT6 PCR5'armR primer (SEQ ID NO: 122) at 94° C. for 30 seconds, 60° C. for 1 minute, and 72° C. for 2 minutes, and this cycle was repeated 25 times. A 6.3-kb amplified DNA fragment was detected from a strain into which a plasmid had been incorporated in its PMT6 locus. The selected strain was designated as the *O. minuta* YK7 strain (Δoch1Δura3Δade1Δyps1Δpmt6::URA3).

(5) Preparation of Antibody Producing *O. minuta* Strain in which the PMT5 and PMT6 Genes had been Disrupted The NotI-digested antibody expression vector, pOMexGPA/AbLys, (prepared in Example 18 (1)) and the Sse8387I-digested antibody expression vector, pOMexHy/AbLys, (prepared in Example 18 (1)) were used to transform the *O. minuta* YK6 strain (Δoch1Δyps1Δura3Δade1Δpmt5::rURA3) and the *O. minuta* YK7 strain (Δoch1Δyps1Δura3Δade1Δpmt6::rURA3) via electroporation. The transformed cells were selected in SD agar plate medium (2% glucose, 0.67% yeast nitrogen base (Difco)) to which hygromycin B had been added at a concentration of 50 μg/ml therein. A single colony was cultured in B2YP4G medium (1.34% yeast nitrogen base (Difco), 2% yeast extract (Difco), 4% polypeptone (Difco), 4% glycerol, 0.1M phosphate buffer (pH 6.0)) at 27° C. for 4 days. A culture supernatant was prepared from the culture solution, Western analysis was carried out by the method described in Example 7, and antibody-producing strains into which the antibody light chain and heavy chain genes had been introduced were selected. The resulting strains were designated as the *O. minuta* AP5 strain (the PMT5 gene-deficient strain) and the *O. minuta* AP6 strain (the PMT6 gene-deficient strain). Separately, the NotI-digested antibody expression vector, pOMexGPA/AbLys, and the Sse8387I-digested pOMexHy/AbLys were introduced into the *O. minuta* YK4 strain (Δoch1Δura3Δade1Δyps1::rURA3) via electroporation, and antibody producing strains were prepared and selected as control strains in the manner described above. The obtained strains were designated as *O. minuta* Acon strains.

(6) Productivity of Secretory Antibody by an Antibody Producing *O. minuta* Strain in which the PMT5 and PMT6 Genes had been Disrupted The *O. minuta* AP5 strain in which the PMT5 gene had been disrupted and the *O. minuta* AP6 strain and the *O. minuta* Acon strain in which the PMT6 gene had been disrupted were cultured in the manner described in Example 18 (2), and non-reducing Western analysis was carried out. The amount of antibodies produced in the culture solution was measured in the manner described in Example 21 (3). As a standard sample, antibodies produced in animal cells (CHO) were used. The results are shown in FIG. 16. That is, there was no significant difference in productivity of antibody aggregates between the *O. minuta* AP5 strain or *O. minuta* AP6 strain and the control *O. minuta* Acon strain.

EXAMPLE 25

Preparation of the *O. minuta* Strain with an Insertionally Inactivated PMT Gene and with the HAC1 Gene Introduced Therein and Evaluation Thereof (1) Preparation of the *O. minuta* Strain with an Insertionally Inactivated PMT Gene the HAC1 Gene had been Introduced The *O. minuta*-derived activated HAC1 gene expression vector, pOMexPGHy/Hac1, prepared in Example 3 was digested with Aor51HI and introduced into the *O. minuta* YY2P2 strain (a strain with an insertionally inactivated PMT2 gene), the *O. minuta* YY2P4 strain (a strain with an insertionally inactivated PMT4 gene), and the *O. minuta* YY2Z strain (the control strain), which had been prepared in Example 24 (1), via electroporation. In order to confirm that the activated HAC1 gene had been introduced into the transformed strain, strains were selected in YPD agar plate medium to which hygromycin B had been added at a concentration of 50 μg/ml therein, the strains were cultured, the genomes were extracted, and PCR was carried out, in accordance with the method of Example 6. The obtained strains were designated as the *O. minuta* YY3P2omH strain (the strain with an insertionally inactivated PMT2 gene and with the HAC1 gene introduced therein), the *O. minuta* YY3P4omH strain (the strain with an insertionally inactivated PMT4 gene and with the HAC1 gene introduced therein), and the *O. minuta* YY3ZomH strain (the control strain into which the HAC1 gene had been introduced). Simultaneously, Aor51HI-digested pOMexPGHy was introduced into the *O. minuta* YY2Z strain, and the *O. minuta* YY3ZHy strain (the control strain into which a vector had been introduced) was obtained as a control strain.

(2) Productivity of Secretory Antibody by *O. minuta* Strain with an Insertionally Inactivated PMT Gene and with the HAC1 Gene Introduced Therein The antibody producing strains with an insertionally inactivated PMT gene and with the HAC1 gene introduced therein prepared in (1) above were cultured by the method described in Example 18 (2), and Western analysis was carried out. The results are shown in FIG. 12 and FIG. 14. The *O. minuta* YY3P2omH strain with an insertionally inactivated PMT2 gene and with the HAC1 gene introduced therein was found to secrete a significantly greater amount of antibodies than the *O. minuta* YY3ZomH strain into which only the HAC1 gene had been introduced and the *O. minuta* YY2P2 strain with an insertionally inactivated PMT2 gene (FIG. 12: lane 7). The *O. minuta* YY3P4omH strain with an insertionally inactivated PMT4 gene and with the HAC1 gene introduced therein was found to secrete a significantly greater amount of antibodies than the *O. minuta* YY3ZomH strain into which only the HAC1 gene had been introduced and the *O. minuta* YY2P4 strain with an insertionally inactivated PMT4 gene (FIG. 14: lane 6).

The amount of antibodies produced in the culture solution was measured by the methods described in Example 8 and in Example 21 (3). As a standard sample, antibodies produced in animal cells (CHO) were used. The results are shown in FIG. 13 and in FIG. 15. The *O. minuta* YY3P2omH strain with an insertionally inactivated PMT2 gene and with the HAC1 gene introduced therein was found to secrete a significantly greater amount of antibody aggregates than the control strains, i.e., the *O. minuta* YY3ZomH strain (a strain into which only the HAC1 gene had been introduced), the *O. minuta* YY2P2 strain (a strain with an insertionally inactivated PMT2 gene), and the *O. minuta* YY3ZHy strain (a control strain into which a vector had been introduced) (FIG. 13: *O. minuta* YY3P2omH strain). Also, the *O. minuta* YY3P4omH strain with an insertionally inactivated PMT4 gene and with the HAC1 gene introduced therein was found to secrete a significantly greater amount of antibodies than the control strains, i.e., the *O. minuta* YY3ZomH strain (a strain into which only the HAC1 gene had been introduced), the *O. minuta* YY2P4 strain (a strain with an insertionally inactivated PMT4 gene), and the *O. minuta* YY3ZHy strain (a control strain into which a vector had been introduced) (FIG. 15: the *O. minuta* YY3P4omH strain).

EXAMPLE 26

Antibody Production by *O. minuta* Strain with an Insertionally Inactivated PMT Gene and with the HAC1 Gene Introduced Therein Using the PMT Inhibitor (1c)

Figure 17:
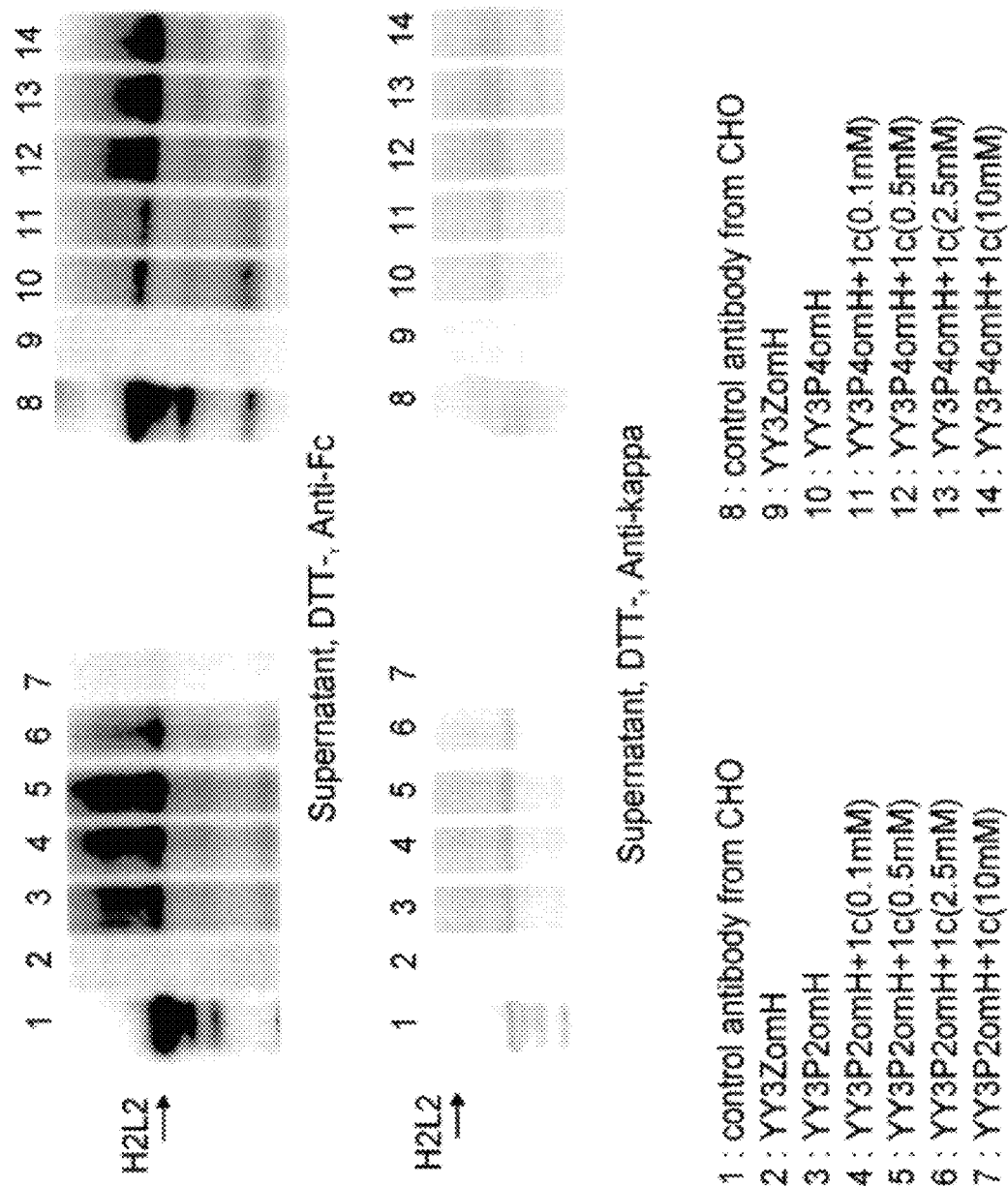
FIG. 17 shows the results of Western analysis of culture supernatants obtained by culturing antibody-producing strains with the insertionally inactivated PMT2 or PMT4 gene and with the activated HAC1 gene introduced therein with the addition of a PMT inhibitor (1c).
Figure 18:
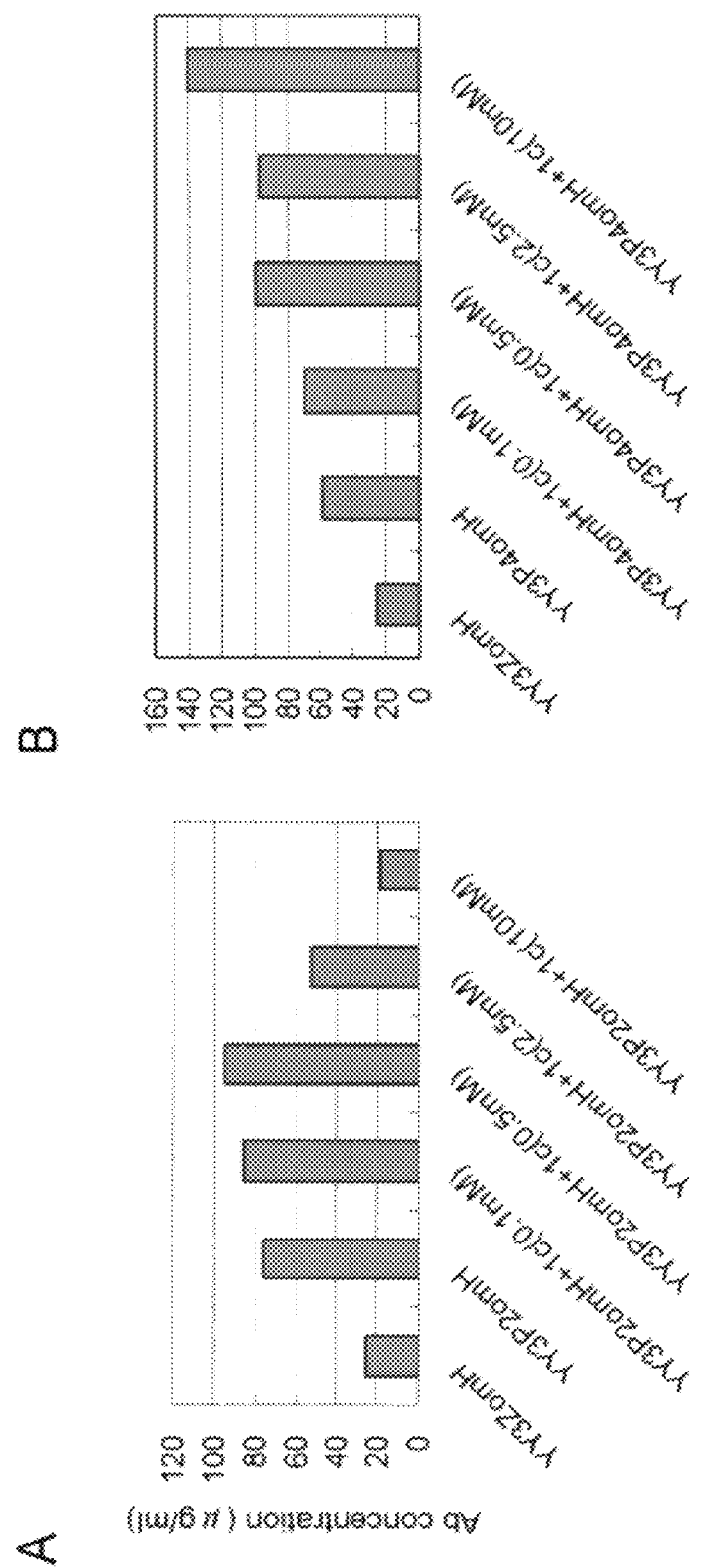
FIG. 18A shows the amount of antibody secretory production in culture supernatants obtained by culturing antibody-producing strains with the insertionally inactivated PMT2 gene and with the activated HAC1 gene introduced therein with the addition of a PMT inhibitor (1c).
FIG. 18B shows the amount of antibody secretory production in a culture supernatant obtained by culturing antibody-producing strains with the insertionally inactivated PMT4 gene and with the activated HAC1 gene introduced therein with the addition of a PMT inhibitor (1c).

A platinum loopful of antibody-producing strains with an insertionally inactivated PMT gene and with the HAC1 gene introduced therein prepared in Example 25 (1) was inoculated into 5 ml of B2YP4G medium, cultured at 27° C. for 1 day, and diluted with B2YP4G medium to adjust OD600 to 10. The resultant was added to the PMT inhibitors described in Example 9 (1c; concentrations of stock solutions: 0.1 mM, 0.5 mM, 2.5 mM, and 10 mM) to concentrations of 0.016 µM, 0.08 µM, 0.4 µM, and 2.0 µM, respectively. Culture was conducted at 27° C. for an additional 3 days, OD600 was measured every 24 hours, and PMT inhibitors (1c) were added in amounts of 0.00032 µM, 0.0016 µM, 0.008 µM, and 0.04 µM, respectively, as the OD600 value increased by 1. A culture supernatant was prepared from the culture solution, and Western analysis was carried out by the method described in Example 18 (2). The results are shown in FIG. 17. Further, productivity of secretory antibodies was quantified by the method described in Example 21 (3). The results are shown in FIG. 18. The highest antibody productivity in the *O. minuta* YY3P2omH strain (a strain with an insertionally inactivated PMT2 gene and with the HAC1 gene introduced therein) was attained when approximately 0.008 µM PMT inhibitor (concentration of stock solution: 2.5 mM) was added as the OD600 value increased by 1. The highest antibody productivity in the *O. minuta* YY3P4omH strain (a strain with an insertionally inactivated PMT4 gene and with the HAC1 gene introduced therein) was attained when approximately 0.04 µM PMT inhibitor (concentration of stock solution: 10 mM) was added as the OD600 value increased by 1. It can be deduced that sugar chain addition is strongly inhibited by inhibition of PMT gene expression and use of PMT inhibitors in combination. In order to inhibit sugar chain addition regarding the strain into which HAC1 had been introduced, a higher productivity of aggregate antibodies can be expected by inhibition of PMT protein activity with inhibition of PMT gene expression and use of PMT inhibitors in combination.

EXAMPLE 27

Evaluation of PMT Inhibitor (5a)

Figure 19:
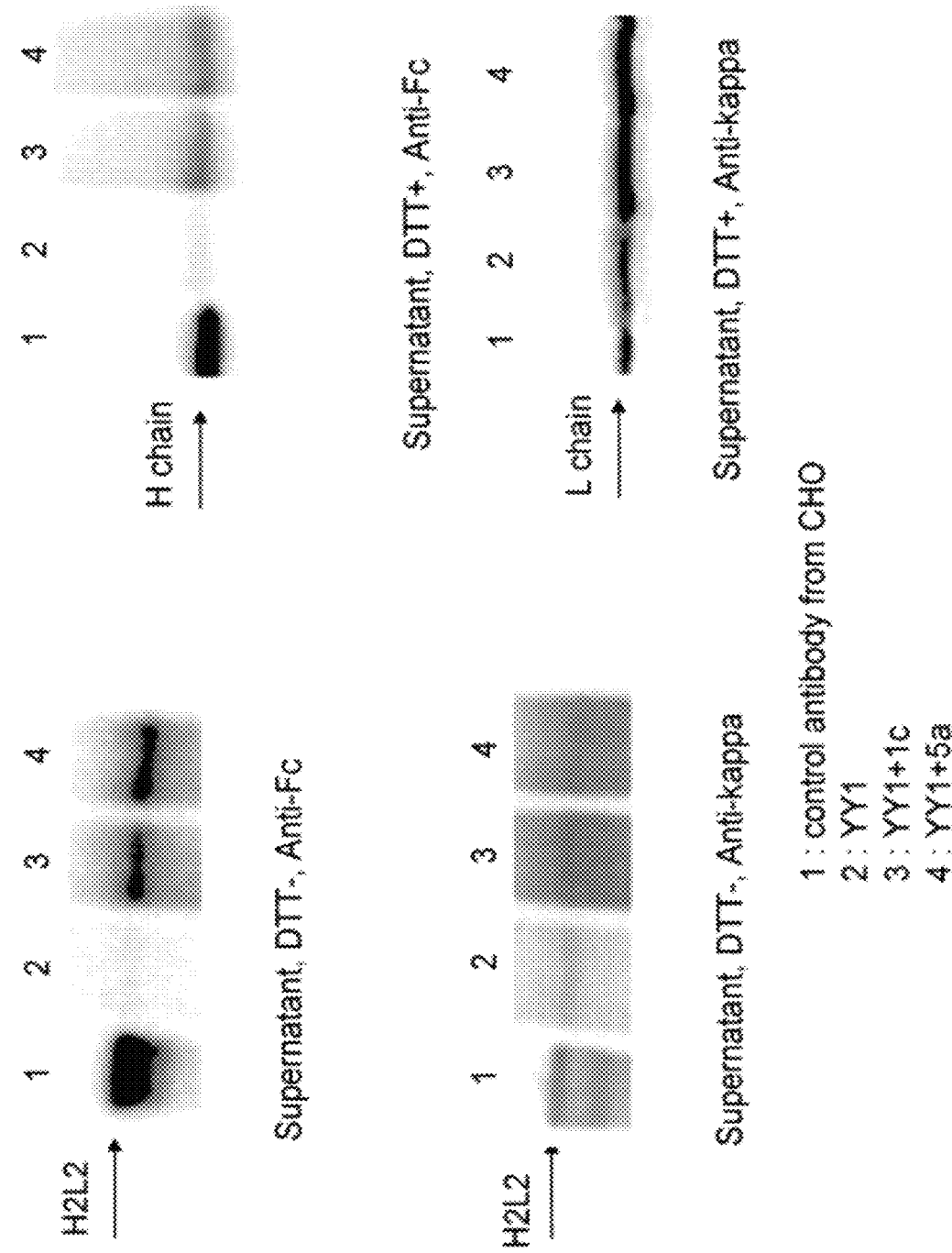
FIG. 19 shows the results of Western analysis of culture supernatants, which have been cultured with the addition of a variety of PMT inhibitors (rhodanine-3-acetic acid derivatives).
Figure 20:
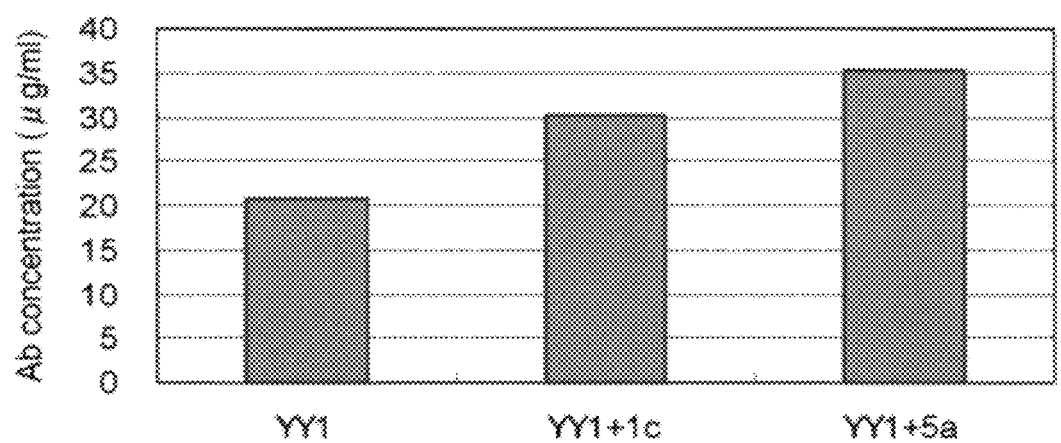
FIG. 20 shows the amount of antibody secretory production in culture supernatants, which have been cultured with the addition of a variety of PMT inhibitors (rhodanine-3-acetic acid derivatives).

A platinum loopful of the *O. minuta* YY1 strains into which antibody genes had been introduced was inoculated into 5 ml of B2YP4G medium, cultured at 27° C. for 1 day, and diluted with B2YP4G medium to adjust OD600 at 10. A PMT inhibitor ({(5Z)-4-oxo-5-[3-(1-phenylethoxy)-4-(2-phenylethoxy)benzylidene]-2-thioxo-1,3-thiazolidin-3-yl}acetic acid (compound 5a described in Bioorganic & Medicinal Chemistry Letters, Vol. 14, p. 3975, 2004) that is different from the PMT inhibitor (1c) described in Example 9 was added thereto to result in a concentration of 1 µm therein. Culture was conducted at 27° C. for an additional 3 days, OD600 was measured every 24 hours, and the PMT inhibitor was added in amounts of 0.02 µM as the OD600 value increased by 1. A culture supernatant was prepared from the culture solution, Western analysis was carried out by the method described in Example 18 (2), and productivity of secretory antibodies was quantified by the method described in Example 21 (3). The results are shown in FIG. 19 and in FIG. 20. Productivity of antibody aggregates was considered to tend to increase via the addition of the PMT inhibitor (5a), which had been newly examined. Thus, the PMT inhibitor (5a) was considered to have effects equivalent to those of the PMT inhibitor (1c) described in Example 9.

INDUSTRIAL APPLICABILITY

The present invention enables high-level secretory production of proteins having complicated structures, such as antibodies, as well as general proteins, in yeast.

---

The invention claimed is:

1. An isolated polynucleotide encoding an activated Homologous to atf/Creb 1 (HAC 1)-protein, wherein the isolated polynucleotide is selected from (a) and (b):
   (a) a polynucleotide comprising a cDNA sequence that encodes a polypeptide comprising the amino acid sequence of SEQ ID NO: 23; and
   (b) a polynucleotide comprising a cDNA sequence that encodes a polypeptide having at least 80% amino acid sequence identity to the amino acid sequence of SEQ ID NO: 23, wherein said polypeptide having at least 80% amino acid identity to the amino acid sequence of SEQ ID NO: 23 has function of activating the unfolded protein response (UPR).

2. A method for producing a transformed yeast cell, comprising the step of introducing the isolated polynucleotide according to claim 1 into a yeast cell.

3. The method according to claim 2, wherein the yeast cell is a methanol-assimilating yeast cell.

4. The method according to claim 3, wherein the methanol-assimilating yeast cell is *Ogataea minuta*.

5. The method according to claim 2, wherein the yeast cell is *Saccharomyces cerevisiae*.

6. An expression vector comprising the polynucleotide according to claim 1.

7. The expression vector according to claim 6, which is pOMexPGHy/Hac1.

8. The expression vector according to claim 6, which further comprises a polynucleotide encoding a mammalian ribosome-binding protein 1 (RRBP 1) protein.

9. The expression vector according to claim 8, wherein the polynucleotide encoding a mammalian RRBP 1 protein is selected from (a) and (b):
   (a) a polynucleotide encoding human RRBP 1 or dog RRBP 1; and
   (b) a polynucleotide encoding a polypeptide having at least 80% amino acid sequence identity to the amino acid sequence of human RRBP 1 or dog RRBP 1, wherein said polypeptide having at least 80% amino acid identity to the amino acid sequence of human RRBP 1 or dog RRBP 1 has a function of stabilizing mRNA.

10. A transformed yeast cell comprising the expression vector according to claim 6.

11. The transformed yeast cell according to claim 10, wherein the endogenous protein-O-mannosyltransferase (PMT) gene of said transformed yeast cell is further insertionally inactivated.

12. The transformed cell according to claim 11, wherein the yeast cell is *Ogataea minuta*.

13. A method for producing a protein, comprising the step of culturing the transformed yeast cell according to claim 10 in a medium under conditions in which O-sugar chain synthesis is inhibited, wherein said transformed yeast cell further expresses a polynucleotide encoding a foreign protein to produce the foreign protein; and isolating the produced foreign protein from the culture medium.

14. The method for producing a protein according to claim 13, wherein O-sugar chain synthesis is inhibited by insertionally inactivating the endogenous protein O-mannosyltransferase (PMT) gene of said yeast cell.

15. The method for producing a protein according to claim 13, wherein O-sugar chain synthesis is inhibited by adding an inhibitor of the endogenous PMT protein of said yeast cell to the medium.

16. The method according to claim 15, wherein the inhibitor is 5-[[3,4-(1-phenylmethoxy)phenyl]methylene]-4-oxo-2-thioxo-3-thiazolidineacetic acid or {(5Z)-4-oxo-5-3-(1-phenylethoxy)-4-(2-phenylethoxy)benzylidene]-2-thioxo-1,3-thiazolidin-3-yl}acetic acid.

17. The method for producing a protein according to claim 13, wherein O-sugar chain synthesis is inhibited by insertionally inactivating the endogenous PMT gene of said yeast cell, and further adding an inhibitor of the endogenous PMT protein of said yeast cell to the medium.

18. A transformed yeast cell comprising the expression vector according to claim 8.

19. A method for producing a protein, comprising the step of culturing the transformed yeast cell according to claim 18 in a medium under conditions in which O-sugar chain synthesis is inhibited, wherein said transformed yeast cell further expresses a polynucleotide encoding a foreign protein to produce the foreign protein; and isolating the produced foreign protein from the culture medium.

20. A transformed yeast cell comprising the expression vector of claim 9.

21. A method for producing a protein, comprising the step of culturing the transformed yeast cell according to claim 20 in a medium under conditions in which O-sugar chain synthesis is inhibited, wherein said transformed yeast cell further expresses a polynucleotide encoding a foreign protein to produce the foreign protein; and isolating the produced foreign protein from the culture medium.

22. A transformed yeast cell comprising a first isolated polynucleotide encoding an activated HAC1 protein selected from (a) and (b):
  (a) a polynucleotide comprising a cDNA sequence that encodes a polypeptide comprising the amino acid sequence of SEQ ID NO: 23; and
  (b) a polynucleotide comprising a cDNA sequence that encodes a polypeptide having at least 80% amino acid sequence identity to the amino acid sequence of SEQ ID NO: 23, wherein said polypeptide having at least 80% amino acid identity to the amino acid sequence of SEQ ID NO: 23 has a function of activating the unfolded protein response (UPR); and
  wherein said transformed yeast cell further comprises a second isolated polynucleotide selected from (c) and (d):
  (c) a polynucleotide encoding human RRBP 1 or dog RRBP 1; and
  (d) a polynucleotide encoding a polypeptide having at least 80% amino acid sequence identity to the amino acid sequence of human RRBP 1 or dog RRBP1, wherein said polypeptide having at least 80% amino acid identity to the amino acid sequence of human RRBP1 or dog RRBP1 has a function of stabilizing mRNA.

23. The transformed yeast cell according to claim 22, wherein the yeast cell is a methanol-assimilating yeast cell.

24. The transformed yeast cell according to claim 23, wherein the methanol-assimilating yeast cell is *Ogataea minuta*.

25. The transformed yeast cell according to claim 22, wherein the yeast cell is *Saccharomyces cerevisiae*.

26. The transformed yeast cell according to claim 22, wherein said yeast cell further comprises a polynucleotide encoding a foreign protein.

27. The transformed yeast cell according to claim 26, wherein the foreign protein is a multimeric protein.

28. The transformed yeast cell according to claim 27, wherein the multimeric protein is a heteromultimer.

29. The transformed yeast cell according to claim 28, wherein the heteromultimer is an antibody or a functional fragment thereof.

30. A method for producing a foreign protein, comprising culturing the transformed yeast cell according to claim 26 in a medium to express the foreign protein, and isolating the produced foreign protein from the culture medium.

31. The method according to claim 30, wherein the culturing step is conducted under conditions in which the transferase activity of endogenous protein O-mannosyltransferase (PMT) of said transformed yeast cell is inhibited.

32. The method according to claim 31, wherein said transferase activity is inhibited by addition of an inhibitor of said transferase activity to the medium.

* * * * *